(12) United States Patent
Pekari et al.

(10) Patent No.: US 7,741,488 B2
(45) Date of Patent: Jun. 22, 2010

(54) TETRAHYDROPYRIDOTHIOPHENES AS ANTIPROLIFERATIVE AGENTS FOR THE TREATMENT OF CANCER

(75) Inventors: Klaus Pekari, Radolfzell (DE); Mathias Schmidt, Constance (DE); Thomas Bär, Reichenau (DE); Thomas Beckers, Constance (DE); Björn Bartels, Radolfzell (DE)

(73) Assignee: 4SC AG, Planegg, Martinsrid (DE)

( * ) Notice: Subject to any disclaimer, the term of this patent is extended or adjusted under 35 U.S.C. 154(b) by 465 days.

(21) Appl. No.: 11/883,624

(22) PCT Filed: Feb. 10, 2006

(86) PCT No.: PCT/EP2006/050859

§ 371 (c)(1),
(2), (4) Date: Sep. 18, 2007

(87) PCT Pub. No.: WO2006/084904

PCT Pub. Date: Aug. 17, 2006

(65) Prior Publication Data
US 2009/0098133 A1   Apr. 16, 2009

(30) Foreign Application Priority Data

Feb. 11, 2005 (EP) ................... 05101007
May 25, 2005 (EP) ................... 05104493
Dec. 14, 2005 (EP) ................... 05112159

(51) Int. Cl.
C07D 471/02 (2006.01)
(52) U.S. Cl. .................................... 546/114
(58) Field of Classification Search ................. 546/114
See application file for complete search history.

(56) References Cited

U.S. PATENT DOCUMENTS

| 3,449,439 | A | 6/1969 | Kuhnen et al. |
| 4,963,559 | A | 10/1990 | Suzuki |
| 5,422,335 | A | 6/1995 | Hagen et al. |
| 6,069,620 | A | 5/2000 | Nakamura et al. |
| 7,138,529 | B2 * | 11/2006 | Erickson et al. ............... 549/61 |
| 2003/0218593 | A1 | 11/2003 | Inoue et al. |
| 2003/0232994 | A1 | 12/2003 | Lu et al. |
| 2004/0171603 | A1 | 9/2004 | Pato et al. |
| 2004/0209943 | A1 | 10/2004 | Erickson et al. |
| 2005/0154024 | A1 | 7/2005 | Bryans |

FOREIGN PATENT DOCUMENTS

| DE | 272 078 | 9/1989 |
| DE | 40 39 734 | 6/1992 |
| WO | WO 9427969 | 12/1994 |
| WO | WO 98/02440 | 1/1998 |
| WO | 99/46267 | 9/1999 |
| WO | WO 0014090 | 3/2000 |
| WO | WO 0247762 | 6/2002 |
| WO | WO 02/092076 | 11/2002 |
| WO | WO 03080607 | 10/2003 |
| WO | WO 03084947 | 10/2003 |
| WO | WO 03102153 | 12/2003 |
| WO | 2004/024065 | 3/2004 |
| WO | 2004/024066 | 3/2004 |
| WO | WO 2004/065351 | 8/2004 |
| WO | WO 2004/069149 | 8/2004 |
| WO | 2004/092156 | 10/2004 |
| WO | WO 2005023818 | 3/2005 |
| WO | 2005/033102 | 4/2005 |
| WO | WO 2005030770 | 4/2005 |
| WO | WO 2005/044008 | 5/2005 |
| WO | 2005/060711 | 7/2005 |
| WO | WO 2006/014135 | 2/2006 |
| WO | WO 2006/084869 | 8/2006 |
| WO | WO 2006/084904 | 8/2006 |
| WO | WO 2006/125813 | 11/2006 |
| WO | WO 2006/125815 | 11/2006 |
| WO | WO 2008020045 | 12/2008 |

OTHER PUBLICATIONS

Database Chemcats, Columbus, Ohio, U.S., XP 002377744, 2 pages, which is the same as Sep. 3, 2007—SciFinder pp. 1 and 2.
Chemical Abstracts, CAS RN 724704-04-5 CAS RN 724704-02-3 XP 002336416, 10 pages.
Fujita, M. et al., "Synthesis and Bioactivities of Novel Bicyclic Thiophenes and 4,5,6,7-Tetrahydrothieno[2,3-c]pyridines as Inhibitors of Tumor Necrosis Factor-alpha (TNF-alpha) Production," Bioorganic & Medicinal Chemistry Letters, vol. 12, pp. 1897-1900 (2002).
Database Chemcats, Chemical Abstracts Service, Columbus, Ohio, U.S.; XP002303659; Abstract and "Ambinter Screening Library", Jan. 1, 2004.
Database Chemcats, Chemical Abstracts Service, Columbus, Ohio, U.S.; XP002369767; Abstract and "Interchim Intermediates", Jan. 18, 2005.
Database Chemcats, Chemical Abstracts Service, Columbus, Ohio, U.S.; XP002369768; Abstract and "Ambinter Stock Screening Collection", Jul. 3, 2005.
Database Chemcats, Chemical Abstracts Service, Columbus, Ohio, U.S.; XP002303660; Abstract and "TimTec Overseas Stock", Jun. 1, 2004.

(Continued)

Primary Examiner—D. Margaret Seaman
Assistant Examiner—Nizal S Chandrakumar
(74) Attorney, Agent, or Firm—Millen, White, Zelano & Branigan, P.C.

(57) ABSTRACT

Compounds of a certain formula (I),

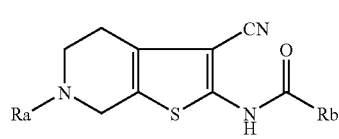

in which Ra and Rb have the meanings indicated in the description, are novel effective compounds with anti-proliferative and apoptosis inducing activity.

17 Claims, No Drawings

OTHER PUBLICATIONS

Database Chemcats, Chemical Abstracts Service, Columbus, Ohio, U.S.; XP002361377 Abstract and "Ambinter Screening Library", Jan. 1, 2004.

Sensfuss, U. et al., "2-Aminothiophenes from Triacetonamine: A Convenient Way to Novel Sterically Hindered Piperidine Deriviatives," Heteroatom Chemistry, vol. 9, No. 6, pp. 529-536 (1998).

Sensfuss, U. et al., "An unusual Cascade Reaction Yielding Ortho-Peri-Fused Thienopyridopyrimidines," Heterocycles, vol. 55, No. 1, pp. 171-180 (2001).

Castanedo, G. And Sutherlin, D. "Synthesis of tetrasubstituted thiphenes on solid-support using the Gewald reaction," Tetrahedron Letters, vol. 42, pp. 7181-7184 (2001).

Charette, A. Janes, M. Lebel, H., "Bis(oxazoline) copper(I)-catalyzed enantioselective cyclopropanation of cinnamate esters with diazomethane," Tetrahedron: Asymmetry, vol. 14, pp. 867-872 (2003).

Ezquerra, J., Prieto, L., Avendano, C., Martos, J., and De la Cuesta, E., "Asymmetric Michael Addition Reactions Using Ethyl (S)-4,4-Dimethylpyroglutamate as a Chiral Auxiliary," Tetrahedron Letters, vol. 40, pp. 1575-1578 (1999).

Huang, K., Huang, Z., "A practical and Controllable Enantioselective Synthesis of 2-Phenyl-cyclopropanecarboxylates via a Camphor-Derived Sulfonium Ylide," Synlett, No. 10, pp. 1621-1623 (2005).

Lipshutz, B., Servesko, J., and Taft, B., "Asymmetric 1,4-Hydrosilylations of alpha, beta-Unsaturated Esters," J. Am. Chem. Soc., vol. 126, pp. 8352-8353 (2004).

Lyle, M., Wilson, P., "Synthesis of a New Chiral Nonracemic C2-Symmetric 2,2'-Bipyridyl Ligand and Its Application in Copper (I)-Catalyzed Enantioselective Cyclopropanation Reactions," Organic Letters, vol. 6, No. 5, pp. 855-857.

Sakuma, S., Sakai, M, Itooka, R., and Miyaura, N. "Asymmetric Conjugate 1,4-Addition of Arylboronic Acids to alpha, beta-Unsaturated Esters Catalyzed by Rhodium(I)(S)-binap," J. Org. Chem., vol. 65, pp. 5951-5955 (2000).

Lindstedt, E. and Nilsson, M., "2-Thienyl as Auxiliary Group in Mixed Lithium Diorganocuprates," Acta Chemica Scandinavica, B 40, pp. 466-469 (1986).

Sainsbury, M., Weerasinghe, D., and Dolman, D., Chemistry of 6H-pyridol[4,3-b]carbazoles, Part 9. An Efficient route to 3-[1-(3-Ethylpyridyl)] indoles and the Synthesis of Some New Ellipticines. J.C.S. Perkin I, pp. 587-590.

Tang, W., Wang, W., and Zhang, X., "Phospholane-Oxazoline Ligands for Ir-Catalyzed Asymmetric Hydrogenation," Angew. Chem. Int. Ed., vol. 42, No. 8, pp. 943-946 (2003).

Chemcats, Interchim Intermediates—XP-002361378—"Thieno[2,3-c]pyridine-6(5H)-carboxylic acid, 2-[(3-chlorobenzoyl)amino]-3-cyano-4,7-dihydroethyl ester" pp. 1-5.

Non-Final Office Action dated Jun. 19, 2008 in related U.S. Appl. No. 11/597,556 filed Nov. 26, 2007. (US-2007-0213360-A1).

Non-Final Office Action dated Oct. 8, 2008 in related U.S. Appl. 11/883,596 filed Sep. 17, 2007. (US-2008-0096914-A1).

Non-Final Office Action dated Oct. 8, 2008 in related U.S. Appl. No. 11/628,369 filed Dec. 4, 2006. (US-2007-0259911-A1).

Non-Final Office Action dated Jun. 25, 2008 in related U.S. Appl. No. 11/597,142 filed Nov. 20, 2006. (US-2007-0244112-A1).

Non-Final Office Action dated Jun. 3, 2009 in related U.S. Appl. No. 12/411,486 filed Mar. 26, 2009.

Non-Final Office Action dated Jun. 4, 2009 in related U.S. Appl. No. 12/390,827 filed Feb. 23, 2009.

Ashimori et al., "Novel 1,4-Dihydropyridine Calcium Antagonists. I. Synthesis and Hypotensive Activity of 4-(Substituted Pyridel)-1,4-dihydropyridine Derivatives." Chem. Pharm. Bull., v.38(9), pp. 2446-2458, 1990.

Srikrishna et al., "A Simple Strategy for Spirocyclopentannulation of Cyclic Ketones. Formal Total Synthesis of (+)-Acorone." Tetrahedron Letters, v.37(10, pp. 1683-1686, 1996.

Uemura et al., "Highly Efficient Enantioselective Synthesis of Optically Active Carboxylic Acids by $Ru(OCOCH_3)_2[(S)-H_8-BINAP]$." J. Org. Chem., v.61, pp. 5510-5516, 1996.

\* cited by examiner

TETRAHYDROPYRIDOTHIOPHENES AS ANTIPROLIFERATIVE AGENTS FOR THE TREATMENT OF CANCER

This application was filed under 35 U.S.C. 371 as a national stage of PCT/EP2006/050859, filed Feb. 10, 2006.

FIELD OF APPLICATION OF THE INVENTION

The invention relates to tetrahydropyridothiophene derivatives, which can be used in the pharmaceutical industry for the production of pharmaceutical compositions.

The invention further relates to the contribution made to the art by the finding, that said tetrahydropyridothiophene derivatives display cell-cycle dependent, anti-proliferative and apoptosis inducing activity.

The invention also relates to the use of these compounds for the therapy of hyperproliferative diseases, in particular human cancer.

KNOWN TECHNICAL BACKGROUND

Cancer chemotherapy was established with the alkylating agent Cyclophosphamide (Endoxan®), an oxazaphosphorin pro-drug activated preferentially in the tumor. The target of alkylating agents like Cyclophosphamide is DNA and the concept, that cancer cells with uncontrolled proliferation and a high mitotic index are killed preferentially, proved to be very successful. Standard cancer chemotherapeutic drugs finally kill cancer cells upon induction of programmed cell death ("apoptosis") by targeting basic cellular processes and molecules. These basic cellular processes and molecules include RNA/DNA (alkylating and carbamylating agents, platin analogs and topoisomerase inhibitors), metabolism (drugs of this class are named anti-metabolites and examples are folic acid, purin and pyrimidine antagonist) as well as the mitotic spindle apparatus with αβ-tubulin heterodimers as the essential component (drugs are categorized into stabilizing and destabilizing tubulin inhibitors; examples are Taxol/Paclitaxel®, Docetaxel/Taxotere® and vinca alkaloids).

A subgroup of proapoptotic anticancer agents target cells preferentially in mitosis. In general these agents do not induce apoptosis in non-dividing cells, arrested in the G0, G1 or G2 phase of the cell division cycle. In contrast, dividing cells going through mitosis (M-phase of the cell division cycle), are killed efficiently by induction of apoptosis by this subgroup agents. Therefore, this subgroup or class of anti-cancer agents is described as cell-cycle specific or cell-cycle dependent. Tubulin inhibitors, with Taxol (Paclitaxel®) as a prominent example, belong to this class of cell-cycle specific, apoptosis inducing anti-cancer agents.

The international application WO2004/024065 describes, inter alia, tetrahydropyridothiophene derivatives as glucagons antagonists for the treatment of diabetes.

The german document DE4039734 describes, inter alia, N-alkylated tetrahydropyridothiophene derivatives as components of herbicidal agents.

The german document DD272078 describes, inter alia, N-alkylated tetrahydropyridothiophene derivatives with anti-anaphylactic und antihistaminergic properties.

The international application WO2005/033102 describes thiophene-based compounds exhibiting ATP-utilizing enzyme inhibitory activity.

The international application WO2004/092156 describes substituted 3-cyanothiophene acetamides as glucagon receptor antagonists.

The international application WO9946267 describes 2-aminothiophene derivatives as modulators of protein tyrosine phosphatases.

The international application WO2005/060711 describes a method of treating diseases mediated by sirtuin, e.g. SirT1 mediated deacetylation, using substituted thiophene compounds.

The international application WO2005/033102 describes a method of combating phytopathogenic diseases on plants using 2-aminothiophene derivatives.

DESCRIPTION OF THE INVENTION

It has now been found that the tetrahydropyridothiophene derivatives, which are described in greater details below, differ from prior art compounds by unanticipated and originative structural alterations and have surprising and particularly advantageous properties.

Thus, for example, the compounds according to this invention are potent and highly efficacious inhibitors of cellular (hyper)proliferation and/or cell-cycle specific inducers of apoptosis in cancer cells. Therefore, unanticipatedly, these compounds can be useful for treating (hyper)proliferative diseases and/or disorders responsive to the induction of apoptosis, in particular cancer. By having a cell-cycle specific mode of action, these derivates should have a higher therapeutic index compared to standard chemotherapeutic drugs targeting basic cellular processes like DNA replication or interfering with basic cellular molecules like DNA.

Thus, for example, the compounds according to this invention are expected to be useful in targeted cancer therapy.

The invention thus relates, in a first aspect (aspect a), to compounds of formula I

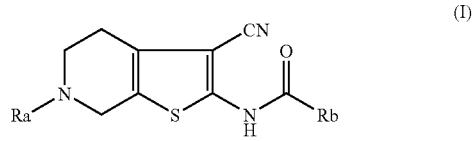

wherein
Ra is —C(O)OR1, in which
R1 is 1-7C-alkyl, 3-7C-cycloalkyl, 1-7C-alkyl substituted by Raa, or 2-7C-alkyl substituted by Rab and Rac on different carbon atoms,
Rb is -T-Q, in which
T is 1-6C-alkylene or 3-7C-cycloalkylene, and
Q is substituted by Rba and Rbb and Rbc, and is phenyl,
wherein
Raa is selected from the group consisting of:
  3-7C-cycloalkyl,
  halogen, trifluoromethyl, cyano, hydroxyl,
  Har, morpholino,
  —C(O)R2, —C(O)OR3, —C(O)N(R4)R5,
  —N(R6)C(O)R7, —OC(O)R8,
  completely or predominantly fluorine-substituted 1-4C-alkoxy, and
  —OR9,
  wherein said Har may be optionally substituted by one or two substituents independently selected from R10,
  in which
R2, R3, R4, R5, R6, R7 and R8 may be the same or different and are independently selected from the group consisting of:
  hydrogen and 1-7C-alkyl, R9 is selected from the group consisting of:
1-4C-alkyl, 3-7C-cycloalkyl, 3-7C-cycloalkyl-1-4C-alkyl, hydroxy-2-4C-alkyl, 1-4C-alkoxy-2-4C-alkyl, phenyl-1-4C-alkyl, pyridyl-1-4C-alkyl, and (1-4C-alkoxy-2-4C-alkoxy)-2-4C-alkyl, either Har is bonded to the parent molecular group via a ring carbon or a ring nitrogen atom, and is a 5-membered monocyclic unsaturated, aromatic heteroaryl ring comprising one to four heteroatoms independently selected from nitrogen, oxygen and sulphur, or Har is bonded to the parent molecular group via a ring carbon atom, and is a 6-membered monocyclic unsaturated, aromatic heteroaryl ring comprising one or two nitrogen atoms, or Har is bonded to the parent molecular group via a ring carbon or a ring nitrogen atom, and is a 9- or 10-membered fused bicyclic unsaturated, aromatic heteroaryl ring comprising one to three heteroatoms independently selected from nitrogen, oxygen and sulphur, each R10 may be the same or different is each independently selected from the group consisting of:
1-4C-alkyl, halogen and 1-4C-alkoxy, Rab is hydroxyl, Rac is hydroxyl, or Rab and Rac bonded to adjacent carbon atoms form together an 1-2C-alkylenedioxy bridge which is optionally substituted by one or two substituents independently selected from fluorine and methyl, or Rab and Rac bonded to carbon atoms two bonds distant from each other form together a methylenedioxy bridge which is optionally substituted by one or two substituents independently selected from fluorine and methyl, Rba is selected from the group consisting of:
1-4C-alkoxy, 3-7C-cycloalkoxy, 3-7C-cycloalkyl-1-4C-alkoxy, 1-4C-alkoxy-2-4C-alkoxy, phenyl-1-4C-alkoxy, cyano-1-4C-alkoxy, 3-6C-alkinyloxy, nitro, and completely or predominantly fluorine-substituted 1-4C-alkoxy, Rbb is selected from the group consisting of:
hydrogen, 1-4C-alkyl, halogen, trifluoromethyl, and 1-4C-alkoxy, Rbc is selected from the group consisting of:
hydrogen, 1-4C-alkyl, halogen, trifluoromethyl, and 1-4C-alkoxy, or Rbb and Rbc bounded in ortho position to each other form together an 1-2C-alkylenedioxy bridge, or a completely or partially fluorine-substituted 1-2C-alkylenedioxy bridge;

under the provisio, that those compounds, in which T is methylene substituted by 1-5C-alkyl, are thereof disclaimed;

and the salts thereof.

The invention further relates, in a second aspect (aspect b), which is an embodiment of aspect a, to compounds of formula I wherein Ra is —C(O)OR1, in which R1 is 1-7C-alkyl, 3-7C-cycloalkyl, or 1-7C-alkyl substituted by Raa, Rb is -T-Q, in which T is 1-6C-alkylene or 3-7C-cycloalkylene, and Q is Rba- and Rbb-substituted phenyl, wherein Raa is selected from the group consisting of:
3-7C-cycloalkyl,
halogen, trifluoromethyl, cyano, hydroxyl,
Har, morpholino,
—C(O)R2, —C(O)OR3, —C(O)N(R4)R5,
—N(R6)C(O)R7, —OC(O)R8,
completely or predominantly fluorine-substituted 1-4C-alkoxy, and
—OR9,
wherein said Har may be optionally substituted by one or two substituents independently selected from R10, in which R2, R3, R4, R5, R6, R7 and R8 may be the same or different and are independently selected from the group consisting of:
hydrogen and 1-7C-alkyl, R9 is selected from the group consisting of:
1-4C-alkyl, 3-7C-cycloalkyl, 3-7C-cycloalkyl-1-4C-alkyl, hydroxy-2-4C-alkyl, 1-4C-alkoxy-2-4C-alkyl, phenyl-1-4C-alkyl, pyridyl-1-4C-alkyl, and (1-4C-alkoxy-2-4C-alkoxy)-2-4C-alkyl, either Har is bonded to the parent molecular group via a ring carbon or a ring nitrogen atom, and is a 5-membered monocyclic unsaturated, aromatic heteroaryl ring comprising one to four heteroatoms independently selected from nitrogen, oxygen and sulphur, or Har is bonded to the parent molecular group via a ring carbon atom, and is a 6-membered monocyclic unsaturated, aromatic heteroaryl ring comprising one or two nitrogen atoms, or Har is bonded to the parent molecular group via a ring carbon or a ring nitrogen atom, and is a 9- or 10-membered fused bicyclic unsaturated, aromatic heteroaryl ring comprising one to three heteroatoms independently selected from nitrogen, oxygen and sulphur, each R10 may be the same or different is each independently selected from the group consisting of:
1-4C-alkyl, halogen and 1-4C-alkoxy, Rba is selected from the group consisting of:
1-4C-alkoxy, 3-7C-cycloalkoxy, 3-7C-cycloalkyl-1-4C-alkoxy, cyano-1-4C-alkoxy, 3-6C-alkinyloxy, nitro, and completely or predominantly fluorine-substituted 1-4C-alkoxy, Rbb is selected from the group consisting of:
hydrogen, 1-4C-alkyl, halogen, trifluoromethyl, and 1-4C-alkoxy;

under the provisio, that those compounds, in which T is methylene substituted by 1-5C-alkyl, are thereof disclaimed;

and the salts thereof.

1-4C-Alkyl is a straight-chain or branched alkyl radical having 1 to 4 carbon atoms. Examples are the butyl, isobutyl, sec-butyl, tert-butyl, propyl, isopropyl, and, particularly, the ethyl and methyl radicals.

1-5C-Alkyl is a straight-chain or branched alkyl radical having 1 to 5 carbon atoms. Examples are the pentyl, butyl, isobutyl, sec-butyl, tert-butyl, propyl, isopropyl, ethyl and methyl radicals.

2-4C-Alkyl represents a straight-chain or branched alkyl radical having 2 to 4 carbon atoms. Examples which may be mentioned are the butyl, isobutyl, sec-butyl, tert-butyl, isopropyl and preferably the propyl and ethyl radicals.

1-7C-Alkyl is a straight-chain or branched alkyl radical having 1 to 7 carbon atoms. Examples are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, isopropyl, and, in particular, the propyl, ethyl and methyl radicals.

1-6C-Alkylene is a straight chain or branched alkylene radical having 1 to 4 carbon atoms. Examples which may be mentioned in this context are the methylene (—$CH_2$—), ethylene (—$CH_2$—$CH_2$—), trimethylene (—$CH_2$—$CH_2$—$CH_2$—), tetramethylene (—$CH_2$—$CH_2$—$CH_2$—$CH_2$—), 1,2-dimethylethylene [—CH($CH_3$)—CH($CH_3$)—], 1,1-dimethylethylene [—C($CH_3$)$_2$—$CH_2$—], 2,2-dimethylethylene [—$CH_2$—C($CH_3$)$_2$—], isopropylidene [—C($CH_3$)$_2$—], 1-methylethylene radical [—CH($CH_3$)—$CH_2$—], 2-methylethylene radical [—$CH_2$—CH($CH_3$)—], pentamethylene (—$CH_2$—$CH_2$—$CH_2$—$CH_2$—$CH_2$—) and the hexamethylene radicals (—$CH_2$—$CH_2$—$CH_2$—$CH_2$—$CH_2$—$CH_2$—), of which the 1-4C-alkylene radicals, in particular the ethylene, the 2,2-dimethylethylene, the 1-methylethylene and the 2-methylethylene radicals, are more worthy to be mentioned. In more particular worthy to be mentioned are the ethylene and the 2-methylethylene [—$CH_2$—CH($CH_3$)—] radicals. It is to be understood, that, when T is one of those 1-6C-alkylene radicals drawn above, said radical is attached with its right terminus to the moiety Q.

3-7C-Cycloalkyl stands for cyclopropyl, cyclobutyl, cyclopentyl, cyclohexyl and cycloheptyl, of which cyclopropyl and cyclopentyl are to be emphasized.

3-7C-Cycloalkylene represents cycloalkylene radicals having 3 to 7 carbon atoms, such as cyclopropylene, cyclobutylene, cyclopentylene, cyclohexylene and cycloheptylene, of which cyclopropylene is more worthy to be mentioned, where the 1,2-cyclopropylene radical is to be emphasized.

Phenyl-1-4C-alkyl represents one of the abovementioned 1-4C-alkyl radicals, which is substituted by a phenyl radical. Examples which may be mentioned are the phenethyl and the benzyl radicals.

Pyridyl-1-4C-alkyl represents one of the abovementioned 1-4C-alkyl radicals, which is substituted by a pyridyl radical. Examples which may be mentioned are the 2-pyridyl-ethyl and the pyridylmethyl radicals.

Pyridyl includes pyridin-2-yl, pyridin-3-yl and pyridin-4-yl.

Halogen within the meaning of the present invention is iodine, or, particularly, bromine, chlorine and fluorine.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

2-4C-Alkoxy represents radicals which, in addition to the oxygen atom, contain a straight-chain or branched alkyl radical having 2 to 4 carbon atoms. Examples which may be mentioned are the butoxy, isobutoxy, sec-butoxy, tert-butoxy, isopropoxy and preferably the propoxy and ethoxy radicals.

1-2C-Alkylenedioxy represents, for example, the methylenedioxy [—O—$CH_2$—O—] and the ethylenedioxy [—O—$CH_2$—$CH_2$—O—] radicals.

As completely or partially fluorine-substituted 1-2C-alkylenedioxy bridge, for example, the difluoromethylenedioxy [—O—$CF_2$—O—] or the tetrafluoroethylenedioxy [—O—$CF_2$—$CF_2$—O—] radical may be mentioned.

An 1-2C-alkylenedioxy bridge which is optionally substituted by one or two substituents independently selected from fluorine and methyl refers, for example, to the methylenedioxy [—O—$CH_2$—O—], the ethylenedioxy [—O—$CH_2$—$CH_2$—O—], the dimethylmethylenedioxy [—O—C($CH_3$)$_2$—O—] or the difluoromethylenedioxy [—O—$CF_2$—O—] radicals.

A methylenedioxy bridge which is optionally substituted by one or two substituents independently selected from fluorine and methyl refers, for example, to the methylenedioxy [—O—$CH_2$—O—], the dimethylmethylenedioxy [—O—C($CH_3$)$_2$—O—] or the difluoromethylenedioxy [—O—$CF_2$—O—] radicals.

3-6C-Alkinyloxy represents radicals which, in addition to the oxygen atom, contain a straight-chain or branched alkinyl radical having 3 to 6 carbon atoms. Examples are the 2-pentinyloxy, 2-butinyloxy, 3-butinyloxy and, particularly, the 2-propinyloxy (propargyloxy) radicals.

3-7C-Cycloalkoxy stands for cyclopropyloxy, cyclobutyloxy, cyclopentyloxy, cyclohexyloxy or cycloheptyloxy, of which cyclopropyloxy, cyclobutyloxy and cyclopentyloxy are to be emphasized.

Cyano-1-4C-alkoxy represents 1-4C-alkoxy radicals, which are substituted by one cyano radical. Examples which may be mentioned are the cyanomethoxy and the 2-cyanoyethoxy radicals.

As completely or predominantly fluorine-substituted 1-4C-alkoxy, for example, the 2,2,3,3,3-penta-fluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radicals may be mentioned. "Predominantly" in this connection means that more than half of the hydrogen atoms of the 1-4C-alkoxy radicals are replaced by fluorine atoms.

1-4C-Alkoxy-2-4C-alkoxy represents 2-4C-alkoxy radicals, which are substituted by one of the abovementioned 1-4C-alkoxy radicals. Examples which may be mentioned are the methoxyethoxy, ethoxyethoxy and the isopropoxyethoxy radicals, particularly the 2-methoxyethoxy, 2-ethoxyethoxy and the 2-isopropoxyethoxy radicals.

3-7C-Cycloalkyl-1-4C-alkoxy stands for one of the abovementioned 1-4C-alkoxy radicals substituted by one of the abovementioned 3-7C-cycloalkyl radicals. Examples which may be mentioned are the 3-7C-cycloalkylmethoxy radicals, such as cyclopropylmethoxy, cyclobutylmethoxy, cyclopentylmethoxy, cyclohexylmethoxy or cycloheptylmethoxy, of which cyclopropylmethoxy, cyclobutylmethoxy or cyclopentylmethoxy are in particular to be mentioned.

Phenyl-1-4C-alkoxy represents one of the abovementioned 1-4C-alkoxy radicals, which is substituted by a phenyl radical. Examples which may be mentioned are the phenethoxy and the benzyloxy radicals.

1-4C-Alkoxy-2-4C-alkyl represents 2-4C-alkyl radicals, which are substituted by one of the abovementioned 1-4C-alkoxy radicals. Examples which may be mentioned are the methoxyethyl, ethoxyethyl and the isopropoxyethyl radicals, particularly the 2-methoxyethyl, 2-ethoxyethyl and the 2-isopropoxyethyl radicals.

(1-4C-Alkoxy-2-4C-alkoxy)-2-4C-alkyl represents 2-4C-alkyl radicals, which are substituted by one of the abovementioned 1-4C-alkoxy-2-4C-alkoxy radicals. Examples which may be mentioned are the 2-(2-methoxyethoxy)-ethyl and the 2-(2-ethoxyethoxy)-ethyl radicals.

Hydroxy-2-4C-alkyl represents 2-4C-alkyl radicals, which are substituted by a hydroxyl group. Examples which may be mentioned are the 2-hydroxyethyl and the 3-hydroxypropyl radicals.

3-7C-Cycloalkyl-1-4C-alkyl stands for one of the abovementioned 1-4C-alkyl radicals, which is substituted by one of the abovementioned 3-7C-cycloalkyl radicals. Examples which may be mentioned are the cyclohexylethyl radical and, particularly, the 3-7C-cycloalkylmethyl radicals, such as cyclopropylmethyl, cyclobutylmethyl, cyclopentylmethyl, cyclohexylmethyl or cycloheptylmethyl, in particular the cyclopropylmethyl, cyclobutylmethyl and the cyclopentylmethyl radical.

1-4C-Alkoxycarbonyl represents a radical which, in addition to the carbonyl group, contains one of the abovementioned 1-4C-alkoxy radicals. Examples which may be mentioned are the methoxycarbonyl, the ethoxycarbonyl and the tertbutoxycarbonyl radicals.

In addition to the nitrogen atom, mono- or di-1-4C-alkylamino radicals contain one or two of the abovementioned 1-4C-alkyl radicals. Di-1-4C-alkylamino is preferred and here, in particular, dimethyl-, diethyl- or diisopropylamino.

Mono- or Di-1-4C-alkylaminocarbonyl radicals contain in addition to the carbonyl group one of the abovementioned mono- or di-1-4C-alkylamino radicals. Examples which may be mentioned are the N-methyl- the N,N-dimethyl-, the N-ethyl-, the N-propyl-, the N,N-diethyl- and the N-isopropylaminocarbonyl radical.

An 1-4C-Alkylcarbonylamino radical is, for example, the propionylamino ($C_3H_7C(O)NH$—) and the acetylamino radical ($CH_3C(O)NH$—).

1-4C-Alkylcarbonyloxy stands for a carbonyloxy group to which one of the abovementioned 1-4C-alkyl radicals is bonded. An example is the acetoxy radical ($CH_3C(O)$—O—).

(1-4C-Alkoxy-2-4C-alkoxy)-2-4C-alkoxy represents 2-4C-alkoxy radicals, which are substituted by one of the abovementioned 1-4C-alkoxy-2-4C-alkoxy radicals. Examples which may be mentioned are the 2-(2-methoxyethoxy)-ethoxy and the 2-(2-ethoxyethoxy)-ethoxy radicals.

1-4C-Alkylcarbonyl is a carbonyl group to which one of the abovementioned 1-4C-alkyl radicals is bonded. An example is the acetyl radical ($CH_3CO$—).

In a first embodiment Har is bonded to the parent molecular group via a ring carbon or a ring nitrogen atom, and is a 5-membered monocyclic unsaturated, aromatic heteroaryl ring comprising one to four heteroatoms independently selected from nitrogen, oxygen and sulphur.

Examples for Har according to this first embodiment may include, but are not limited to, furanyl, thiophenyl, pyrrolyl, oxazolyl, isoxazolyl, thiazolyl, isothiazolyl, imidazolyl, pyrazolyl, triazolyl, thiadiazolyl, or oxadiazolyl.

A more detailed example for Har according to this first embodiment includes imidazolyl.

A further more detailed example for Har according to this first embodiment includes imidazol-1-yl. Another further more detailed example for Har according to this first embodiment includes imidazol-4-yl and, particularly, imidazol-5-yl and imidazol-2-yl.

In a second embodiment Har is bonded to the parent molecular group via a ring carbon atom, and is a 6-membered monocyclic unsaturated, aromatic heteroaryl ring comprising one or two nitrogen atoms. Examples for Har according to this second embodiment may include pyridinyl, pyrimidinyl, pyrazinyl or pyridazinyl.

A more detailed example for Har according to this second embodiment includes pyridinyl.

A further more detailed example for Har according to this second embodiment includes pyridin-2-yl. Another further more detailed example for Har according to this second embodiment includes pyridin-3-yl.

Another further more detailed example for Har according to this second embodiment includes pyridin-4-yl.

In a third embodiment Har is bonded to the parent molecular group via a ring carbon or a ring nitrogen atom, and is a 9- or 10-membered fused bicyclic unsaturated, aromatic heteroaryl ring comprising one to three heteroatoms independently selected from nitrogen, oxygen and sulphur.

Examples for Har according to this third embodiment may include, but are not limited to, the benzo-fused derivatives of the Har radicals according to the abovementioned first and second embodiment, such as e.g. quinazolinyl, quinoxalinyl, cinnolinyl, quinolinyl, isoquinolinyl, indolyl, isoindolyl, indazolyl, phthalazinyl, benzothiophenyl, benzofuranyl, isobenzofuranyl, benzoxazolyl, benzothiazolyl or benzimidazolyl, as well as naphthyridinyl or indolizinyl.

Mono- or di-(R101)-substituted imidazol-1-yl or pyrazol-1-yl stands for an imidazol-1-yl or pyrazol-1-yl radical, respectively, which is substituted by one or two radicals independently selected from R101, such as mono- or di-methyl-substituted imidazol-1-yl or pyrazol-1-yl, respectively, like 2-methyl-imidazol-1-yl, 4-methyl-imidazol-1-yl or 5-methyl-imidazol-1-yl, or 2,4-dimethyl-imidazol-1-yl; in particular 2-methyl-imidazol-1-yl, 4-methyl-imidazol-1-yl or 2,4-dimethyl-imidazol-1-yl.

R101- and/or R102-substituted pyridyl or pyrimidinyl, respectively, may include, for example, methoxy-substituted pyridyl or pyrimidinyl, respectively, like 4-methoxy-pyridin-2-yl or 4-methoxy-pyridin-3-yl or 3-methoxy-pyridin-2-yl; or methyl-substituted pyridyl or pyrimidinyl, respectively, like 4-methyl-pyridin-2-yl or 4-methyl-pyridin-3-yl; or methoxy- and methyl-substituted pyridyl or pyrimidinyl, respectively.

1N-(1-4C-alkyl)-imidazolyl or 1N-(1-4C-alkyl)-pyrazolyl, respectively, refers to imidazolyl or pyrazolyl, respectively, which is substituted by 1-4C-alkyl on the nitrogen atom in position 1, such as e.g. 1N-methyl-imidazolyl or 1N-ethyl-imidazolyl, e.g. 1-methyl-imidazol-2-yl, 1-methyl-imidazol-5-yl or 1-ethyl-imidazol-2-yl; in particular 1-methyl-imidazol-2-yl or 1-methyl-imidazol-5-yl. R101-substituted 1N-(1-4C-alkyl)-imidazolyl or R101-substituted 1N-(1-4C-alkyl)-pyrazolyl, respectively, may include, for example, methyl- or ethyl-substituted 1N-(1-4C-alkyl)-imidazolyl or 1N-(1-4C-alkyl)-pyrazolyl, respectively, like methyl-substituted 1N-methyl-imidazolyl, e.g. 1,4-dimethyl-imidazol-2-yl or 1,5-dimethylimidazol-2-yl.

1N—(H)-imidazolyl or 1N—(H)-pyrazolyl, respectively, refers to imidazolyl or pyrazolyl, respectively, which is substituted by hydrogen on the nitrogen atom in position 1, such as e.g. 1H-imidazol-2-yl or 1H-imidazol-5-yl. R101-substituted 1N—(H)-imidazolyl or R101-substituted 1N—(H)-pyrazolyl, respectively, may include, for example, methyl- or ethyl-substituted 1N—(H)-imidazolyl or 1N—(H)-pyrazolyl, respectively, like methyl-substituted 1N—(H)-imidazolyl, e.g. 4-methyl-1H-imidazol-2-yl or 5-methyl-1H-imidazol-2-yl.

It is to be understood, that, if a radical Har contains quaternizable imino-type ring nitrogen atoms (—N=), said Har radical is not attached via said quaternizable imino-type ring nitrogen atom to the parent molecular group.

The expression (Rba)-phenyl means that the phenyl radical is substituted by Rba, which is attached to any of the positions of the phenyl ring; the expression 2-(Rba)-phenyl means that the phenyl radical is substituted by Rba, which is attached in the 2-position to the phenyl radical (i.e. the ortho position with respect to the binding position in which the phenyl ring is bonded to the parent molecular group); the expression Rbb-substituted 2-(Rba)-phenyl means that the phenyl radical is substituted by both Rbb and Rba, whereby the substituent Rba is bonded in the 2-position to the phenyl radical, and the substituent Rbb is bonded in any other position to the phenyl ring; the expression 2-(Rba)-5-(Rbb)-phenyl means, that the phenyl radical is substituted by both Rba and Rbb, whereby the substituent Rba is bonded in the 2-position to the phenyl radical, and the substituent Rbb is bonded in the 5-position to the phenyl ring; and the expression Rbb- and Rbc-substituted 2-(Rba)-phenyl means that the phenyl radical is substituted by Rba, Rbb and Rbc, whereby the substituent Rba is bonded in the 2-position to the phenyl radical, and the substituents Rbb and Rbc are bonded in any other positions to the phenyl ring; In this connection, further similar expressions mentioned herein indicating in short form the positions in which substituents are bonded to a ring radical (e.g. phenyl radical) are to be understood similarly, mutatis mutandis, as specified exemplarily and representatively for the foregoing expressions.

The term (Raa)-methyl stands for methyl which is substituted by Raa. The term 2-(Raa)-ethyl stands for ethyl which is substituted in 2-position by Raa. The term 3-(Raa)-propyl stands for propyl which is substituted in 3-position by Raa.

In general, unless otherwise mentioned, the radicals Har include all the possible isomeric forms thereof, particularly the positional isomers thereof. Thus, for example, the term pyridinyl or pyridyl includes pyridin-2-yl, pyridin-3-yl and pyridin-4-yl.

Constituents which are optionally substituted as stated herein, may be substituted, unless otherwise noted, at any possible position.

Unless otherwise mentioned, the phenyl radical may be substituted by its substituents or parent molecular groups at any possible position.

The heterocyclic groups, alone or as part of other groups, mentioned herein may be substituted by their given substituents or parent molecular groups, unless otherwise noted, at any possible position, such as e.g. at any substitutable ring carbon or ring nitrogen atom.

Unless otherwise noted, rings containing quaternizable imino-type ring nitrogen atoms (—N═) may be preferably not quaternized on these imino-type ring nitrogen atoms by the mentioned substituents or parent molecular groups.

Unless otherwise noted, any heteroatom of a heterocyclic ring with unsatisfied valences mentioned herein is assumed to have the hydrogen atom(s) to satisfy the valences.

When any variable occurs more than one time in any constituent, each definition is independent.

The person skilled in the art is aware on account of his/her expert knowledge that certain combinations of the variable characteristics mentioned in the description of this invention lead to chemically less stable compounds. This can apply, for example, to certain compounds, in which—in a manner being disadvantageous for chemical stability—two heteroatoms (S, N or O) would directly meet or would only be separated by one carbon atom. Those compounds according to this invention, in which the combination of the abovementioned variable substituents does not lead to chemically less stable compounds, are therefore preferred.

Suitable salts for compounds of formula I according to this invention—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to this invention on an industrial scale, are converted into pharmacologically tolerable salts by processes known to the person skilled in the art.

According to expert's knowledge the compounds of formula I according to this invention as well as their salts may contain, e.g. when isolated in crystalline form, varying amounts of solvents. Included within the scope of the invention are therefore all solvates and in particular all hydrates of the compounds of formula I according to this invention as well as all solvates and in particular all hydrates of the salts of the compounds of formula I according to this invention.

In the context of this invention, hyperproliferation and analogous terms are used to describe aberrant/dysregulated cellular growth, a hallmark of diseases like cancer. This hyperproliferation might be caused by single or multiple cellular/molecular alterations in respective cells and can be, in context of a whole organism, of benign or malignant behaviour. Inhibition of cell proliferation and analogous terms is used herein to denote an ability of the compound to retard the growth of and/or kill a cell contacted with that compound as compared to cells not contacted with that compound. Most preferable this inhibition of cell proliferation is 100%, meaning that proliferation of all cells is stopped and/or cells undergo programmed cell death. In some preferred embodiments the contacted cell is a neoplastic cell. A neoplastic cell is defined as a cell with aberrant cell proliferation. A benign neoplasia is described by hyperproliferation of cells, incapable of forming an aggressive, metastasizing tumor in-vivo. In contrast, a malignant neoplasia is described by cells with different cellular and biochemical abnormalities, e.g. capable of forming tumor metastasis. The acquired functional abnormalities of malignant neoplastic cells (also defined as "hallmarks of cancer") are replicative potential ("hyperproliferation"), self-sufficiency in growth signals, insensitivity to anti-growth signals, evasion from apoptosis, sustained angiogenesis and tissue invasion and metastasis.

Inducer of apoptosis and analogous terms are used herein to identify a compound which executes programmed cell death in cells contacted with that compound. Apoptosis is defined by complex biochemical events within the contacted cell, such as the activation of cystein specific proteinases ("caspases") and the fragmentation of chromatin. Induction of apoptosis in cells contacted with the compound might not necessarily be coupled with inhibition of cell proliferation. Preferably, the inhibition of cell proliferation and/or induction of apoptosis is specific to cells with aberrant cell growth (hyperproliferation). Thus, compared to cells with aberrant cell growth, normal proliferating or arrested cells are less sensitive or even insensitive to the proliferation inhibiting or apoptosis inducing activity of the compound. Finally, cytotoxic is used in a more general sense to identify compounds which kill cells by various mechanisms, including the induction of apoptosis/programmed cell death in a cell cycle dependent or cell-cycle independent manner.

Cell cycle specific and analogous terms are used herein to identify a compound as inducing apoptosis only in continuously proliferating cells actively passing a specific phase of the cell cycle, but not in resting, non-dividing cells. Continuously proliferating cells are typical for diseases like cancer and characterized by cells in all phases of the cell division cycle, namely in the G ("gap") 1, S ("DNA synthesis"), G2 and M ("mitosis") phase.

Compounds according to aspect a of the present invention more worthy to be mentioned include those compounds of formula I as defined at the outset, or, particularly, of formulae Ia, Ib, Ic, Id or Id' as shown below wherein
Ra is —C(O)OR1, in which
R1 is 1-4C-alkyl, 1-7C-alkyl substituted by Raa, or 2-7C-alkyl substituted by Rab and Rac on different carbon atoms,
Rb is -T-Q, in which
T is 1-6C-alkylene or 3-7C-cycloalkylene, and
Q is substituted by Rba and Rbb and Rbc, and is phenyl,
wherein
Raa is selected from the group consisting of:
  hydroxyl,
  Har, morpholino,
  —C(O)R2, —C(O)OR3, —C(O)N(R4)R5,
  —N(R6)C(O)R7, —OC(O)R8, and
  —OR9,
  wherein said Har may be optionally substituted by one or two substituents independently selected from R10,
  in which
R2, R3, R4, R5, R6, R7 and R8 may be the same or different and are independently selected from the group consisting of:
  hydrogen and 1-4C-alkyl,
R9 is selected from the group consisting of:
  1-4C-alkyl, hydroxy-2-4C-alkyl, 1-4C-alkoxy-2-4C-alkyl, phenyl-1-4C-alkyl, pyridyl-1-4C-alkyl, and (1-4C-alkoxy-2-4C-alkoxy)-2-4C-alkyl,
either
Har is bonded to the parent molecular group via a ring carbon or a ring nitrogen atom, and is a 5-membered monocyclic unsaturated, aromatic heteroaryl ring comprising one to four heteroatoms independently selected from nitrogen, oxygen and sulphur,
  such as e.g. any one selected from furanyl, thiophenyl, pyrrolyl, oxazolyl, isoxazolyl, thiazolyl, isothiazolyl, imidazolyl, pyrazolyl, triazolyl, thiadiazolyl and oxadiazolyl,
or
Har is bonded to the parent molecular group via a ring carbon atom, and is a 6-membered monocyclic unsaturated, aromatic heteroaryl ring comprising one or two nitrogen atoms, such as e.g. any one selected from pyridinyl, pyrazinyl, pyridazinyl and pyrimidinyl,
each R10 may be the same or different is each independently selected from the group consisting of:
  1-4C-alkyl, halogen and 1-4C-alkoxy,
Rab is hydroxyl,
Rac is hydroxyl,
or Rab and Rac bonded to adjacent carbon atoms form together a dimethylmethylenedioxy bridge,
Rba is selected from the group consisting of:
  1-4C-alkoxy, 3-5C-cycloalkoxy, 3-5C-cycloalkyl-1-4C-alkoxy, cyano-2-4C-alkoxy, 3-5C-alkinyloxy, nitro, and completely or predominantly fluorine-substituted 1-4C-alkoxy,
Rbb is selected from the group consisting of:
  hydrogen, 1-4C-alkyl, halogen, trifluoromethyl, and 1-4C-alkoxy,
Rbc is selected from the group consisting of:
  hydrogen, halogen, and 1-4C-alkoxy,
or Rbb and Rbc bounded in ortho position to each other form together a methylenedioxy, ethylenedioxy, difluoromethylenedioxy or tetrafluoroethylenedioxy bridge;

under the provisio, that those compounds, in which T is methylene substituted by 1-5C-alkyl, are thereof disclaimed;
and the salts thereof.

In another embodiment, compounds according to aspect a of the present invention more worthy to be mentioned include those compounds of formula I as defined at the outset, or, particularly, of formulae Ia, Ib, Ic or Id as shown below, wherein
Ra is —C(O)OR1, in which
R1 is 1-4C-alkyl, 1-7C-alkyl substituted by Raa, or 2-7C-alkyl substituted by Rab and Rac on different carbon atoms,
Rb is -T-Q, in which
T is 1-6C-alkylene or 3-7C-cycloalkylene, and
Q is substituted by Rba and Rbb and Rbc, and is phenyl,
wherein
Raa is selected from the group consisting of:
  hydroxyl,
  Har, morpholino,
  —C(O)R2, —C(O)OR3, —C(O)N(R4)R5,
  —N(R6)C(O)R7, —OC(O)R8, and
  —OR9,
  wherein said Har may be optionally substituted by one or two substituents independently selected from R10,
  in which
R2, R3, R4, R5, R6, R7 and R8 may be the same or different and are independently selected from the group consisting of:
  hydrogen and 1-4C-alkyl,
R9 is selected from the group consisting of:
  1-4C-alkyl, hydroxy-2-4C-alkyl, 1-4C-alkoxy-2-4C-alkyl, phenyl-1-4C-alkyl, pyridyl-1-4C-alkyl, and (1-4C-alkoxy-2-4C-alkoxy)-2-4C-alkyl,
either
Har is bonded to the parent molecular group via a ring carbon or a ring nitrogen atom, and is a 5-membered monocyclic unsaturated, aromatic heteroaryl ring comprising one to four heteroatoms independently selected from nitrogen, oxygen and sulphur, such as e.g. any one selected from furanyl, thiophenyl, pyrrolyl, oxazolyl, isoxazolyl, thiazolyl, isothiazolyl, imidazolyl, pyrazolyl, triazolyl, thiadiazolyl and oxadiazolyl,
or
Har is bonded to the parent molecular group via a ring carbon atom, and is a 6-membered monocyclic unsaturated, aromatic heteroaryl ring comprising one or two nitrogen atoms, such as e.g. any one selected from pyridinyl, pyrazinyl, pyridazinyl and pyrimidinyl,
each R10 may be the same or different is each independently selected from the group consisting of:
1-4C-alkyl, halogen and 1-4C-alkoxy,
Rab is hydroxyl,
Rac is hydroxyl,
or Rab and Rac bonded to adjacent carbon atoms form together a dimethylmethylenedioxy bridge,
Rba is selected from the group consisting of:
1-4C-alkoxy, 3-5C-cycloalkoxy, 3-5C-cycloalkyl-1-4C-alkoxy, cyano-2-4C-alkoxy, 3-5C-alkinyloxy, nitro, and completely or predominantly fluorine-substituted 1-4C-alkoxy,
Rbb is selected from the group consisting of:
hydrogen, 1-4C-alkyl, halogen, trifluoromethyl, and 1-4C-alkoxy,
Rbc is selected from the group consisting of:
hydrogen, halogen, and 1-4C-alkoxy,
or Rbb and Rbc bounded in ortho position to each other form together a methylenedioxy, ethylenedioxy, difluoromethylenedioxy or tetrafluoroethylenedioxy bridge;

under the provisio, that those compounds, in which T is methylene substituted by 1-5C-alkyl, are thereof disclaimed;

and the salts thereof.

Compounds according to aspect a of the present invention in particular worthy to be mentioned include those compounds of formulae Ia, Ib, Ic, Id or Id' as shown below wherein
Ra is —C(O)OR1, in which
R1 is 1-4C-alkyl, 1-4C-alkyl substituted by Raa, or 3-4C-alkyl substituted by Rab and Rac on different carbon atoms, and
Q is substituted by Rba and Rbb and Rbc, and is phenyl, wherein
Raa is selected from the group consisting of:
hydroxyl,
Har, morpholino,
—C(O)R2, —C(O)OR3, —C(O)N(R4)R5,
—N(R6)C(O)R7, —OC(O)R8, and
—OR9,
wherein said Har may be optionally substituted by one or two substituents independently selected from R10,
in which
R2, R3, R4, R5, R6, R7 and R8 may be the same or different and are independently selected from the group consisting of:
hydrogen and 1-4C-alkyl,
R9 is selected from the group consisting of:
1-4C-alkyl, hydroxy-2-4C-alkyl, 1-4C-alkoxy-2-4C-alkyl, phenyl-1-4C-alkyl, pyridyl-1-4C-alkyl, and (1-4C-alkoxy-2-4C-alkoxy)-2-4C-alkyl, either
Har is bonded to the parent molecular group via a ring carbon or a ring nitrogen atom, and is imidazolyl, pyrazolyl or triazolyl, or
Har is bonded to the parent molecular group via a ring carbon atom, and is pyridinyl, pyrazinyl or pyrimidinyl,
each R10 may be the same or different is each independently selected from the group consisting of:
1-4C-alkyl and 1-4C-alkoxy,
Rab is hydroxyl,
Rac is hydroxyl,
or Rab and Rac bonded to adjacent carbon atoms form together a dimethylmethylenedioxy bridge,
Rba is selected from the group consisting of:
1-4C-alkoxy, and completely or predominantly fluorine-substituted 1-4C-alkoxy,
Rbb is selected from the group consisting of:
hydrogen, 1-4C-alkyl, and 1-4C-alkoxy,
Rbc is selected from the group consisting of:
hydrogen, and halogen,
or Rbb and Rbc bounded in ortho position to each other form together a methylenedioxy, ethylenedioxy, difluoromethylenedioxy or tetrafluoroethylenedioxy bridge, and the salts thereof.

In another embodiment, compounds according to aspect a of the present invention in particular worthy to be mentioned include those compounds of formulae Ia, Ib, Ic or Id as shown below wherein
Ra is —C(O)OR1, in which
R1 is 1-4C-alkyl, or 1-4C-alkyl substituted by Raa, or 3-4C-alkyl substituted by Rab and Rac on different carbon atoms, and
Q is substituted by Rba and Rbb and Rbc, and is phenyl, wherein
Raa is selected from the group consisting of:
hydroxyl,
pyridinyl, pyrimidinyl, pyrazinyl, triazol-1-yl, imidazol-1-yl, pyrazol-1-yl, morpholino, 1N-(1-4C-alkyl)-imidazolyl, 1N-(1-4C-alkyl)-pyrazolyl,
—C(O)R2, —C(O)OR3, —C(O)N(R4)R5,
—N(R6)C(O)R7, —OC(O)R8, and
—OR9,
in which
R2, R3, R4, R5, R6, R7 and R8 may be the same or different and are independently selected from the group consisting of:
hydrogen and 1-4C-alkyl,
R9 is selected from the group consisting of:
1-4C-alkyl, hydroxy-2-4C-alkyl, 1-4C-alkoxy-2-4C-alkyl, phenyl-1-4C-alkyl, pyridyl-1-4C-alkyl, and (1-4C-alkoxy-2-4C-alkoxy)-2-4C-alkyl,
Rab is hydroxyl,
Rac is hydroxyl,
or Rab and Rac bonded to adjacent carbon atoms form together a dimethylmethylenedioxy bridge,
Rba is selected from the group consisting of:
1-4C-alkoxy, and completely or predominantly fluorine-substituted 1-4C-alkoxy,
Rbb is selected from the group consisting of:
hydrogen, 1-4C-alkyl, and 1-4C-alkoxy,
Rbc is selected from the group consisting of:
hydrogen, and halogen,
or Rbb and Rbc bounded in ortho position to each other form together a methylenedioxy, ethylenedioxy, difluoromethylenedioxy or tetrafluoroethylenedioxy bridge, and the salts thereof.

In one embodiment of aspect a (embodiment a1), compounds according to aspect a of the present invention in more particular worthy to be mentioned include those compounds of formula Ia, Ib or Ic as shown below wherein
Ra is —C(O)OR1, in which
either
R1 is 1-4C-alkyl such as e.g. methyl, ethyl or propyl, or
R1 is 1-4C-alkyl, such as e.g. methyl, ethyl or propyl, which is substituted by Raa, in which
Raa is pyridyl, pyrimidinyl, R101- and/or R102-substituted pyridyl, or R101- and/or R102-substituted pyrimidinyl, or
R1 is 1-4C-alkyl, such as e.g. methyl, ethyl or propyl, which is substituted by Raa, in which
Raa is 1N-(1-4C-alkyl)-imidazolyl, 1N-(1-4C-alkyl)-pyrazolyl, R101-substituted 1N-(1-4C-alkyl)-imidazolyl, or R101-substituted 1N-(1-4C-alkyl)-pyrazolyl, or
R1 is 1-4C-alkyl, such as e.g. methyl, ethyl or propyl, which is substituted by Raa, in which
Raa is 1N—(H)-imidazolyl, 1N—(H)-pyrazolyl, R101-substituted 1N—(H)-imidazolyl, or R101-substituted 1N—(H)-pyrazolyl, or
R1 is 3-4C-alkyl, such as e.g. propyl or butyl, which is substituted by Rab and Rac on different carbon atoms, in which
Rab is hydroxyl,
Rac is hydroxyl,
or Rab and Rac bonded to adjacent carbon atoms form together a dimethylmethylenedioxy bridge, or
R1 is 1-4C-alkyl, such as e.g. methyl, ethyl or propyl, which is substituted by Raa, in which
Raa is —C(O)OR3, or
R1 is 2-4C-alkyl, such as e.g. ethyl or propyl, which is substituted by Raa, in which
Raa is hydroxyl, morpholino, —OC(O)R8, or —OR9, or
R1 is 2-4C-alkyl, such as e.g. ethyl or propyl, which is substituted by Raa, in which
Raa is imidazol-1-yl, pyrazol-1-yl, mono- or di-(R101)-substituted imidazol-1-yl, or mono- or di-(R101)-substituted pyrazol-1-yl, and
Q is substituted by Rba and Rbb and Rbc, and is phenyl,
wherein
R3 is selected from the group consisting of:
hydrogen, and 1-4C-alkyl such as e.g. methyl or ethyl,
R8 is 1-4C-alkyl such as e.g. methyl,
R9 is selected from the group consisting of:
1-4C-alkyl such as e.g. methyl or ethyl,
phenyl-1-2C-alkyl such as e.g. benzyl,
1-2C-alkoxy-2-3C-alkyl such as e.g. 2-methoxyethyl, and
(1-2C-alkoxy-2-3C-alkoxy)-2-3C-alkyl such as e.g. 2-(2-methoxyethoxy)-ethyl,
R101 is 1-4C-alkyl such as e.g. methyl or ethyl,
R102 is 1-4C-alkoxy such as e.g. methoxy or ethoxy, or 1-4C-alkyl such as e.g. methyl or ethyl,
Rba is selected from the group consisting of:
methoxy, ethoxy, trifluoromethoxy, and difluoromethoxy,
Rbb is selected from the group consisting of:
hydrogen, methyl, ethyl, methoxy, and ethoxy,
Rbc is hydrogen,
especially
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
methoxy, ethoxy, trifluoromethoxy, and difluoromethoxy,
Rbb is selected from the group consisting of:
methyl, ethyl, methoxy, and ethoxy;

in a particular subembodiment
Rba is selected from the group consisting of:
methoxy, and ethoxy,
Rbb is selected from the group consisting of:
hydrogen, methyl, and methoxy,
Rbc is hydrogen,
especially
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
methoxy and ethoxy,
Rbb is selected from the group consisting of:
methyl and methoxy;

in a more particular subembodiment
Rba is selected from the group consisting of:
methoxy, and ethoxy,
Rbb is selected from the group consisting of:
hydrogen, and methyl,
Rbc is hydrogen,
especially
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
methoxy and ethoxy,
Rbb is methyl;

and the salts thereof.
In another embodiment of aspect a (embodiment a2), compounds according to aspect a of the present invention in more particular worthy to be mentioned include those compounds of formula Ia as shown below
wherein
Ra is —C(O)OR1, in which
R1 is 1-4C-alkyl such as e.g. methyl, ethyl or propyl,
or
pyridyl-1-4C-alkyl such as e.g. pyridylmethyl, 2-pyridylethyl or 3-pyridylpropyl,
or
2-4C-alkyl, such as e.g. ethyl or propyl, which is substituted by Raa,
or
3-4C-alkyl, such as e.g. propyl or butyl, which is substituted by Rab and Rac on different carbon atoms, and
Q is substituted by Rba and Rbb and Rbc, and is phenyl,
wherein
Raa is selected from the group consisting of:
hydroxyl,
morpholino,
—C(O)OR3, —OC(O)R8, and
—OR9,
in which
R3 is selected from the group consisting of:
hydrogen, and 1-4C-alkyl such as e.g. methyl or ethyl,
R8 is 1-4C-alkyl such as e.g. methyl,
R9 is selected from the group consisting of:

1-4C-alkyl such as e.g. methyl or ethyl, phenyl-1-2C-alkyl such as e.g. benzyl,
1-2C-alkoxy-2-3C-alkyl such as e.g. 2-methoxyethyl, and
(1-2C-alkoxy-2-3C-alkoxy)-2-3C-alkyl such as e.g. 2-(2-methoxyethoxy)-ethyl, Rab is hydroxyl,
Rac is hydroxyl,
or Rab and Rac bonded to adjacent carbon atoms form together a dimethylmethylenedioxy bridge,
Rba is selected from the group consisting of:
  methoxy, ethoxy, trifluoromethoxy, and difluoromethoxy,
Rbb is selected from the group consisting of:
  hydrogen, methyl, methoxy, and ethoxy,
Rbc is selected from the group consisting of:
  hydrogen, fluorine, chlorine, and bromine,
or Rbb and Rbc bounded in ortho position to each other form together a tetrafluoroethylenedioxy bridge;

in a particular subembodiment
Rba is selected from the group consisting of:
  methoxy, and ethoxy,
Rbb is selected from the group consisting of:
  hydrogen, methyl, and methoxy,
Rbc is hydrogen, especially
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
  methoxy and ethoxy,
Rbb is selected from the group consisting of:
  methyl and methoxy;

in a more particular subembodiment
Rba is selected from the group consisting of:
  methoxy, and ethoxy,
Rbb is selected from the group consisting of:
  hydrogen, and methyl,
Rbc is hydrogen, especially
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
  methoxy and ethoxy,
Rbb is methyl;

and the salts thereof.

In another embodiment of aspect a (embodiment a3), compounds according to aspect a of the present invention in more particular worthy to be mentioned include those compounds of formula Ia as shown below wherein
Ra is —C(O)OR1, in which either
R1 is methyl, ethyl or propyl, or
R1 is (Raa)-methyl, 2-(Raa)-ethyl or 3-(Raa)-propyl, in which
Raa is pyridyl, pyrimidinyl or pyrazinyl, or
R1 is 2-(Raa)-ethyl or 3-(Raa)-propyl, in which
Raa is hydroxyl, imidazol-1-yl, pyrazol-1-yl, methoxy, ethoxy, 2-methoxyethoxy or methylcarbonyloxy, or
R1 is 2,3-dihydroxypropyl;

and wherein
either
Q is 2-methoxyphenyl, or
Q is 2-ethoxyphenyl, or
Q is 2-(Rba)-3-(Rbb)-phenyl, in which
Rba is methoxy or ethoxy,
Rbb is methoxy or methyl, or
Q is 2-(Rba)-5-(Rbb)-phenyl, in which
Rba is methoxy or ethoxy,
Rbb is methoxy or methyl, or
Q is 2-(Rba)-3-(Rbc)-phenyl, in which
Rba is methoxy or ethoxy,
Rbc is chlorine or fluorine, or
Q is 2-(Rba)-5-(Rbc)-phenyl, in which
Rba is methoxy or ethoxy,
Rbb is chlorine or fluorine;

in a particular subembodiment
either
Q is 2-methoxyphenyl, or
Q is 2-ethoxyphenyl, or
Q is 2-(Rba)-3-(Rbb)-phenyl, in which
Rba is methoxy or ethoxy,
Rbb is methoxy or methyl, or
Q is 2-(Rba)-5-(Rbb)-phenyl, in which
Rba is methoxy or ethoxy,
Rbb is methoxy or methyl, in a more particular subembodiment
either
Q is 2-methoxyphenyl, or
Q is 2-ethoxyphenyl, or
Q is 2-(Rba)-3-(Rbb)-phenyl, in which
Rba is methoxy or ethoxy,
Rbb is methyl, or
Q is 2-(Rba)-5-(Rbb)-phenyl, in which
Rba is methoxy or ethoxy,
Rbb is methyl;

and the salts thereof.

In a more detailed embodiment of aspect a (embodiment a1'i), compounds according to aspect a of the present invention in further more particular worthy to be mentioned include those compounds of formula Ia, Ib or Ic as shown below wherein
Ra is —C(O)OR1, in which either
R1 is methyl, ethyl or propyl, or
R1 is (Raa)-methyl, 2-(Raa)-ethyl, or 3-(Raa)-propyl, in which
Raa is pyridyl, pyrimidinyl, methyl-substituted pyridyl, or methoxy-substituted pyridyl, or
R1 is 2,3-dihydroxy-propyl, or
R1 is (Raa)-methyl, 2-(Raa)-ethyl, or 3-(Raa)-propyl, in which
Raa is carboxyl or methoxycarbonyl, or
R1 is 2-(Raa)-ethyl, or 3-(Raa)-propyl, in which
Raa is hydroxyl, methylcarbonyloxy, methoxy, ethoxy, benzyloxy, or 2-methoxyethoxy, or
R1 is 2-(Raa)-ethyl, or 3-(Raa)-propyl, in which
Raa is imidazol-1-yl, or mono- or di-methyl-substituted imidazol-1-yl;

and wherein
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
  methoxy and ethoxy,
Rbb is selected from the group consisting of:
  methyl and methoxy, especially
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
  methoxy and ethoxy,
Rbb is methyl;

in a particular subembodiment
either
Q is 2-methoxyphenyl, or
Q is 2-ethoxyphenyl, or
Q is 3-methoxyphenyl, or
Q is 3-ethoxyphenyl, or
Q is 2-(Rba)-3-(Rbb)-phenyl, in which
Rba is methoxy or ethoxy,
Rbb is methyl, or
Q is 2-(Rba)-5-(Rbb)-phenyl, in which
Rba is methoxy or ethoxy,
Rbb is methyl;

in a more particular subembodiment
either
Q is 2-methoxyphenyl, or
Q is 2-ethoxyphenyl, or
Q is 3-methoxyphenyl, or
Q is 3-ethoxyphenyl, or
Q is 2-(Rba)-5-(Rbb)-phenyl, in which
Rba is methoxy,
Rbb is methyl;

and the salts thereof.

Yet in a more detailed embodiment of aspect a (embodiment a1'ii), compounds according to aspect a of the present invention in further more particular worthy to be mentioned include those compounds of formula Ia, Ib or Ic as shown below wherein
Ra is —C(O)OR1, in which either
R1 is methyl, ethyl or propyl, or
R1 is (Raa)-methyl, 2-(Raa)-ethyl, or 3-(Raa)-propyl, in which
Raa is pyridyl, pyrimidinyl, methyl-substituted pyridyl, or methoxy-substituted pyridyl, or
R1 is (Raa)-methyl, 2-(Raa)-ethyl, or 3-(Raa)-propyl, in which
Raa is 1N-methyl-imidazolyl, or
R1 is 2,3-dihydroxy-propyl, or
R1 is (Raa)-methyl, 2-(Raa)-ethyl, or 3-(Raa)-propyl, in which
Raa is carboxyl or methoxycarbonyl, or
R1 is 2-(Raa)-ethyl, or 3-(Raa)-propyl, in which
Raa is hydroxyl, methylcarbonyloxy, methoxy, ethoxy, benzyloxy, or 2-methoxyethoxy, or
R1 is 2-(Raa)-ethyl, or 3-(Raa)-propyl, in which
Raa is imidazol-1-yl, or mono- or di-methyl-substituted imidazol-1-yl;

and wherein
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
  methoxy and ethoxy,
Rbb is selected from the group consisting of:
  methyl and methoxy, especially
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl, in which
Rba is selected from the group consisting of:
  methoxy and ethoxy,
Rbb is methyl;

in a particular subembodiment either
Q is 2-methoxyphenyl, or
Q is 2-ethoxyphenyl, or
Q is 3-methoxyphenyl, or
Q is 3-ethoxyphenyl, or
Q is 2-(Rba)-3-(Rbb)-phenyl, in which
Rba is methoxy or ethoxy,
Rbb is methyl, or
Q is 2-(Rba)-5-(Rbb)-phenyl, in which
Rba is methoxy or ethoxy,
Rbb is methyl;

in a more particular subembodiment either
Q is 2-methoxyphenyl, or
Q is 2-ethoxyphenyl, or
Q is 3-methoxyphenyl, or
Q is 3-ethoxyphenyl, or
Q is 2-(Rba)-5-(Rbb)-phenyl, in which
Rba is methoxy,
Rbb is methyl;

and the salts thereof.

In another more detailed embodiment of aspect a (embodiment a2'), compounds according to aspect a of the present invention in further more particular worthy to be mentioned include those compounds of formula Ia as shown below
wherein
Ra is —C(O)OR1, in which
either
R1 is methyl, ethyl or propyl, or
R1 is pyridylmethyl, 2-pyridylethyl or 3-pyridylpropyl, or
R1 is 2-(Raa)-ethyl, or 3-(Raa)-propyl, in which
Raa is hydroxyl, methoxycarbonyl, methylcarbonyloxy, methoxy, ethoxy, benzyloxy or 2-methoxyethoxy, or
R1 is 2,3-dihydroxy-propyl or 2,2-dimethyl-[1,3]dioxolan-4-ylmethyl;

and wherein
Q is 2-(Rba)-phenyl, 3-(Rba)-phenyl, 4-(Rba)-phenyl, Rbb-substituted 2-(Rba)-phenyl, Rbb-substituted 3-(Rba)-phenyl, Rbb-substituted 4-(Rba)-phenyl, Rbc-substituted 2-(Rba)-phenyl, Rbc-substituted 3-(Rba)-phenyl, Rbc-substituted 4-(Rba)-phenyl, Rbb- and Rbc-substituted 2-(Rba)-phenyl, Rbb- and Rbc-substituted 3-(Rba)-phenyl, or Rbb- and Rbc-substituted 4-(Rba)-phenyl,
in which
Rba is selected from the group consisting of:
  methoxy, ethoxy, and difluoromethoxy,
Rbb is selected from the group consisting of:
  methyl, methoxy, and ethoxy,
Rbc is bromine,
or Rbb and Rbc bounded in ortho position to each other form together a tetrafluoroethylenedioxy bridge, especially
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
  methoxy and ethoxy,
Rbb is selected from the group consisting of:
  methyl and methoxy;

in a particular subembodiment
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
  methoxy and ethoxy,
Rbb is methyl;

in a more particular subembodiment either
Q is 2-methoxyphenyl, or
Q is 2-ethoxyphenyl, or
Q is 3-methoxyphenyl, or
Q is 3-ethoxyphenyl, or
Q is 2-(Rba)-3-(Rbb)-phenyl, in which
Rba is methoxy or ethoxy,
Rbb is methyl, or
Q is 2-(Rba)-5-(Rbb)-phenyl, in which
Rba is methoxy or ethoxy,
Rbb is methyl;

in a further more particular subembodiment either
Q is 2-methoxyphenyl, or
Q is 2-ethoxyphenyl, or
Q is 3-methoxyphenyl, or
Q is 3-ethoxyphenyl, or
Q is 2-(Rba)-5-(Rbb)-phenyl, in which
Rba is methoxy,
Rbb is methyl;

and the salts thereof.

In another more detailed embodiment of aspect a (embodiment a3'), compounds according to aspect a of the present invention in further more particular worthy to be mentioned include those compounds of formula Ia as shown below wherein
Ra is —C(O)OR1, in which either
R1 is methyl, ethyl or propyl, or
R1 is pyridylmethyl or 2-pyridylethyl, or
R1 is 2-(Raa)-ethyl, in which
Raa is hydroxyl, methoxy or 2-methoxyethoxy, or
R1 is 2,3-dihydroxypropyl;

and wherein either
Q is 2-ethoxyphenyl, or
Q is 2-(Rba)-5-(Rbb)-phenyl, in which
Rba is methoxy,
Rbb is methoxy or methyl, or
Q is 2-(Rba)-5-(Rbb)-phenyl, in which
Rba is ethoxy,
Rbb is methoxy or methyl;

in a particular subembodiment either
Q is 2-ethoxyphenyl, or
Q is 2-(Rba)-5-(Rbb)-phenyl, in which
Rba is methoxy,
Rbb is methyl, or
Q is 2-(Rba)-5-(Rbb)-phenyl, in which
Rba is ethoxy,
Rbb is methyl, in a more particular subembodiment either
Q is 2-ethoxyphenyl, or
Q is 2-(Rba)-5-(Rbb)-phenyl, in which
Rba is methoxy,
Rbb is methyl;

and the salts thereof.

Compounds according to aspect a of the present invention to be emphasized include those compounds of formula Ia or Ic as shown below wherein
Ra is —C(O)OR1, in which either
R1 is (Raa)-methyl, or 2-(Raa)-ethyl, in which
Raa is pyridyl, or
R1 is 2,3-dihydroxy-propyl, or
R1 is 2-(Raa)-ethyl, in which
Raa is hydroxyl or methoxy, or
R1 is 2-(Raa)-ethyl, in which
Raa is imidazol-1-yl;

and wherein
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
methoxy and ethoxy,
Rbb is selected from the group consisting of:
methyl and methoxy;

in a subembodiment
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
methoxy and ethoxy,
Rbb is methyl;

in a particular subembodiment either
Q is 2-methoxyphenyl, or
Q is 2-ethoxyphenyl, or
Q is 3-methoxyphenyl, or
Q is 3-ethoxyphenyl, or
Q is 2-(Rba)-3-(Rbb)-phenyl, in which
Rba is methoxy or ethoxy,
Rbb is methyl, or
Q is 2-(Rba)-5-(Rbb)-phenyl, in which
Rba is methoxy or ethoxy,
Rbb is methyl;

in a more particular subembodiment either
Q is 2-methoxyphenyl, or
Q is 2-ethoxyphenyl, or
Q is 3-methoxyphenyl, or
Q is 3-ethoxyphenyl, or
Q is 2-(Rba)-5-(Rbb)-phenyl, in which
Rba is methoxy,
Rbb is methyl;

in a further more particular subembodiment either
Q is 2-methoxyphenyl, or
Q is 2-ethoxyphenyl, or
Q is 3-methoxyphenyl, or
Q is 2-(Rba)-5-(Rbb)-phenyl, in which
Rba is methoxy,
Rbb is methyl;

and the salts thereof.

Yet compounds according to aspect a of the present invention to be emphasized include those compounds of formula Ia or Ic as shown below
wherein
Ra is —C(O)OR1, in which either
R1 is (Raa)-methyl, or 2-(Raa)-ethyl, in which
Raa is pyridyl, or
R1 is (Raa)-methyl, in which
Raa is 1N-methyl-imidazolyl, or
R1 is 2,3-dihydroxy-propyl, or
R1 is (Raa)-methyl, in which
Raa is carboxyl or methoxycarbonyl, or
R1 is 2-(Raa)-ethyl, in which
Raa is hydroxyl or methoxy, or
R1 is 2-(Raa)-ethyl, in which
Raa is imidazol-1-yl, or mono- or di-methyl-substituted imidazol-1-yl;

and wherein
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
methoxy and ethoxy,
Rbb is selected from the group consisting of:
methyl and methoxy;

in a subembodiment
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
methoxy and ethoxy,
Rbb is methyl;

in a particular subembodiment
either
Q is 2-methoxyphenyl, or
Q is 2-ethoxyphenyl, or
Q is 3-methoxyphenyl, or
Q is 3-ethoxyphenyl, or
Q is 2-(Rba)-3-(Rbb)-phenyl, in which
Rba is methoxy or ethoxy,
Rbb is methyl, or
Q is 2-(Rba)-5-(Rbb)-phenyl, in which
Rba is methoxy or ethoxy,
Rbb is methyl;

in a more particular subembodiment
either
Q is 2-methoxyphenyl, or
Q is 2-ethoxyphenyl, or
Q is 3-methoxyphenyl, or
Q is 3-ethoxyphenyl, or
Q is 2-(Rba)-5-(Rbb)-phenyl, in which
Rba is methoxy,
Rbb is methyl;

in a further more particular subembodiment
either
Q is 2-methoxyphenyl, or
Q is 2-ethoxyphenyl, or
Q is 3-methoxyphenyl, or
Q is 2-(Rba)-5-(Rbb)-phenyl, in which
Rba is methoxy,
Rbb is methyl;

and the salts thereof.

Compounds according to aspect a of the present invention to be more emphasized include those compounds of formula Ia or Ic as shown below
wherein
Ra is —C(O)OR1, in which either
R1 is (Raa)-methyl, or 2-(Raa)-ethyl, in which
Raa is pyridyl, or
R1 is 2,3-dihydroxy-propyl, or
R1 is 2-(Raa)-ethyl, in which
Raa is hydroxyl, or
R1 is 2-(Raa)-ethyl, in which
Raa is imidazol-1-yl;

and wherein
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
methoxy and ethoxy,
Rbb is methyl;

in a subembodiment either
Q is 2-methoxyphenyl, or
Q is 2-ethoxyphenyl, or
Q is 3-methoxyphenyl, or
Q is 3-ethoxyphenyl, or
Q is 2-(Rba)-3-(Rbb)-phenyl, in which
Rba is methoxy or ethoxy,
Rbb is methyl, or
Q is 2-(Rba)-5-(Rbb)-phenyl, in which
Rba is methoxy or ethoxy,
Rbb is methyl;

in a particular subembodiment either
Q is 2-methoxyphenyl, or
Q is 2-ethoxyphenyl, or
Q is 3-methoxyphenyl, or
Q is 3-ethoxyphenyl, or
Q is 2-(Rba)-5-(Rbb)-phenyl, in which
Rba is methoxy,
Rbb is methyl;

in a more particular subembodiment either
Q is 2-methoxyphenyl, or
Q is 2-ethoxyphenyl, or
Q is 3-methoxyphenyl, or
Q is 2-(Rba)-5-(Rbb)-phenyl, in which
Rba is methoxy,
Rbb is methyl;

and the salts thereof.

Yet compounds according to aspect a of the present invention to be more emphasized include those compounds of formula Ia or Ic as shown below wherein
Ra is —C(O)OR1, in which either
R1 is (Raa)-methyl, or 2-(Raa)-ethyl, in which
Raa is pyridin-2-yl, pyridin-3-yl or pyridin-4-yl, or
R1 is (Raa)-methyl, in which
Raa is 1-methyl-imidazol-2-yl or 1-methyl-imidazol-5-yl, or
R1 is 2,3-dihydroxy-propyl, or
R1 is (Raa)-methyl, in which
Raa is carboxyl or methoxycarbonyl, or
R1 is 2-(Raa)-ethyl, in which
Raa is hydroxyl or methoxy, or
R1 is 2-(Raa)-ethyl, in which
Raa is imidazol-1-yl, 2-methyl-imidazol-1-yl or 4-methyl-imidazol-1-yl;

and wherein
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is selected from the group consisting of:
methoxy and ethoxy,
Rbb is methyl;

in a subembodiment either
Q is 2-methoxyphenyl, or
Q is 2-ethoxyphenyl, or
Q is 3-methoxyphenyl, or
Q is 3-ethoxyphenyl, or
Q is 2-(Rba)-3-(Rbb)-phenyl, in which
Rba is methoxy or ethoxy,
Rbb is methyl, or
Q is 2-(Rba)-5-(Rbb)-phenyl, in which
Rba is methoxy or ethoxy,
Rbb is methyl;

in a particular subembodiment either
Q is 2-methoxyphenyl, or
Q is 2-ethoxyphenyl, or
Q is 3-methoxyphenyl, or
Q is 3-ethoxyphenyl, or
Q is 2-(Rba)-5-(Rbb)-phenyl, in which
Rba is methoxy,
Rbb is methyl;

in a more particular subembodiment either
Q is 2-methoxyphenyl, or
Q is 2-ethoxyphenyl, or
Q is 3-methoxyphenyl, or
Q is 2-(Rba)-5-(Rbb)-phenyl, in which
Rba is methoxy,
Rbb is methyl;

and the salts thereof.

Compounds according to aspect b of the present invention more worthy to be mentioned include those compounds of formula I as defined at the outset, or, particularly, of formulae Ia, Ib, Ic or Id as shown below wherein
Ra is —C(O)OR1, in which
R1 is 1-4C-alkyl, or 1-7C-alkyl substituted by Raa,
Rb is -T-Q, in which
T is 1-6C-alkylene or 3-7C-cycloalkylene, and
Q is Rba- and Rbb-substituted phenyl, wherein
Raa is selected from the group consisting of:
  hydroxyl,
  Har, morpholino,
  —C(O)R2, —C(O)OR3, —C(O)N(R4)R5,
  —N(R6)C(O)R7, —OC(O)R8, and
  —OR9,
  wherein said Har may be optionally substituted by one or two substituents independently selected from R10,
  in which
R2, R3, R4, R5, R6, R7 and R8 may be the same or different and are independently selected from the group consisting of:
  hydrogen and 1-4C-alkyl,
R9 is selected from the group consisting of:
  1-4C-alkyl, hydroxy-2-4C-alkyl, 1-4C-alkoxy-2-4C-alkyl, phenyl-1-4C-alkyl, pyridyl-1-4C-alkyl, and (1-4C-alkoxy-2-4C-alkoxy)-2-4C-alkyl, either
Har is bonded to the parent molecular group via a ring carbon or a ring nitrogen atom, and is a 5-membered monocyclic unsaturated, aromatic heteroaryl ring comprising one to four heteroatoms independently selected from nitrogen, oxygen and sulphur, such as e.g. any one selected from furanyl, thiophenyl, pyrrolyl, oxazolyl, isoxazolyl, thiazolyl, isothiazolyl, imidazolyl, pyrazolyl, triazolyl, thiadiazolyl and oxadiazolyl, or
Har is bonded to the parent molecular group via a ring carbon atom, and is a 6-membered monocyclic unsaturated, aromatic heteroaryl ring comprising one or two nitrogen atoms, such as e.g. any one selected from pyridinyl, pyrazinyl, pyridazinyl and pyrimidinyl,
each R10 may be the same or different is each independently selected from the group consisting of:
  1-4C-alkyl, halogen and 1-4C-alkoxy,
Rba is selected from the group consisting of:
  1-4C-alkoxy, 3-5C-cycloalkoxy, 3-5C-cycloalkyl-1-4C-alkoxy, cyano-2-4C-alkoxy, 3-5C-alkinyloxy, nitro, and completely or predominantly fluorine-substituted 1-4C-alkoxy,
Rbb is selected from the group consisting of:
  hydrogen, 1-4C-alkyl, halogen, trifluoromethyl, and 1-4C-alkoxy;

under the provisio, that those compounds, in which T is methylene substituted by 1-5C-alkyl, are thereof disclaimed;

and the salts thereof.

Compounds according to aspect b of the present invention in particular worthy to be mentioned include those compounds of formulae Ia, Ib, Ic or Id as shown below wherein
Ra is —C(O)OR1, in which
R1 is 1-4C-alkyl, or 2-4C-alkyl substituted by Raa, and
Q is Rba- and Rbb-substituted phenyl, wherein
Raa is selected from the group consisting of:
  hydroxyl,
  pyridinyl, triazol-1-yl, imidazol-1-yl, pyrazol-1-yl, morpholino,
  —C(O)R2, —C(O)OR3, —C(O)N(R4)R5,
  —N(R6)C(O)R7, —OC(O)R8, and
  —OR9,
  in which
R2, R3, R4, R5, R6, R7 and R8 may be the same or different and are independently selected from the group consisting of:
  hydrogen and 1-4C-alkyl,
R9 is selected from the group consisting of:
  1-4C-alkyl, hydroxy-2-4C-alkyl, 1-4C-alkoxy-2-4C-alkyl, pyridyl-1-4C-alkyl, and (1-4C-alkoxy-2-4C-alkoxy)-2-4C-alkyl,
Rba is selected from the group consisting of:
  1-4C-alkoxy and 3-4C-alkinyloxy,
Rbb is selected from the group consisting of:
  hydrogen and 1-4C-alkoxy, and the salts thereof.

Compounds according to aspect b of the present invention in more particular worthy to be mentioned include those compounds of formula Ia as shown below wherein
Ra is —C(O)OR1, in which
R1 is 1-4C-alkyl, such as e.g. ethyl,
  or
  2-4C-alkyl, such as e.g. ethyl or propyl, which is substituted by Raa, and
Q is Rba- and Rbb-substituted phenyl, wherein
Raa is selected from the group consisting of:
  hydroxyl,
  pyridinyl, morpholino,
  —C(O)OR3, —OC(O)R8, and
  —OR9,
  in which
R3 is selected from the group consisting of:
  hydrogen and 1-4C-alkyl,
R8 is 1-4C-alkyl,
R9 is selected from the group consisting of:
  1-4C-alkyl, such as e.g. methyl or ethyl,
  1-2C-alkoxy-2-3C-alkyl, such as e.g. 2-methoxyethyl, and
  (1-2C-alkoxy-2-3C-alkoxy)-2-3C-alkyl, such as e.g. 2-(2-methoxyethoxy)-ethyl,
Rba is selected from the group consisting of:
  methoxy, ethoxy and proparyloxy,
Rbb is selected from the group consisting of:
  hydrogen, methoxy and ethoxy, and the salts thereof.

Compounds according to aspect b of the present invention in further more particular worthy to be mentioned include those compounds of formula Ia as shown below wherein
Ra is —C(O)OR1, in which
R1 is 1-4C-alkyl, such as e.g. ethyl, and
Q is Rba- and Rbb-substituted phenyl, wherein
Rba is selected from the group consisting of:
  methoxy and ethoxy,
Rbb is selected from the group consisting of:
  hydrogen and methoxy, and the salts thereof.

In the compounds of formula I according to the present invention, the significances mentioned in the following details/subdetails and/or variants/subvariants are of concern individually or in any possible single or multiple combination thereof:

A first embodimental detail (detail a) of the compounds of formula I according to this invention includes those compounds of formula I, in which
Ra is —C(O)OR1, in which
R1 is 1-4C-alkyl, such as e.g. methyl, ethyl or propyl, particularly ethyl.

A second embodimental detail (detail b) of the compounds of formula I according to this invention includes those compounds of formula I,
in which
Ra is —C(O)OR1, in which
R1 is 1-4C-alkyl, such as e.g. methyl, ethyl or propyl, which is substituted by Raa, in which Raa has one of the meanings as defined in the compounds mentioned above.

A subdetail (detail b1) of the compounds according to detail b of this invention include those compounds of formula I,
in which
R1 is 1-4C-alkyl, such as e.g. methyl, ethyl or propyl, which is substituted by Raa, in which
Raa is 1-4C-alkoxy, 1-4C-alkoxy-2-4C-alkoxy, (1-4C-alkoxy-2-4C-alkoxy)-2-4C-alkoxy, hydroxyl, 1-4C-alkoxycarbonyl, phenyl-1-4C-alkoxy, 1-4C-alkylcarbonyloxy, carboxyl, mono- or di-1-4C-alkylaminocarbonyl, carbamoyl, 1-4C-alkylcarbonylamino, 1-4C-alkylcarbonyl, or Har, in which
Har has one of the meanings as defined in the compounds mentioned above.

A further subdetail (detail b2) of the compounds according to detail b of this invention include those compounds of formula I,
in which
R1 is 1-4C-alkyl, such as e.g. ethyl or propyl, which is substituted by Raa, in which
Raa is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, 1-4C-alkylcarbonyloxy, or 1-4C-alkylcarbonylamino.

Another subdetail (detail b2') of the compounds according to detail b of this invention include those compounds of formula I,
in which
R1 is 1-4C-alkyl, such as e.g. methyl, ethyl or propyl, which is substituted by Raa, in which
Raa is 1-4C-alkoxycarbonyl, carboxyl, mono- or di-1-4C-alkylaminocarbonyl, or carbamoyl.

A further subdetail (detail b3) of the compounds according to detail b of this invention include those compounds of formula I,
in which
either
R1 is 1-4C-alkyl, such as e.g. ethyl or propyl, which is substituted by Raa, in which
Raa is 1-4C-alkoxy, 1-4C-alkoxy-2-4C-alkoxy, (1-4C-alkoxy-2-4C-alkoxy)-2-4C-alkoxy, hydroxyl, or 1-4C-alkylcarbonyloxy,
or
R1 is 1-4C-alkyl, such as e.g. methyl, ethyl or propyl, which is substituted by Raa, in which
Raa is 1-4C-alkoxycarbonyl, or carboxyl.

Another subdetail (detail b3') of the compounds according to detail b of this invention include those compounds of formula I,
in which
either
R1 is 1-4C-alkyl, such as e.g. ethyl or propyl, which is substituted by Raa, in which
Raa is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, or 1-4C-alkylcarbonyloxy,
or
R1 is 1-4C-alkyl, such as e.g. methyl, ethyl or propyl, which is substituted by Raa, in which
Raa is 1-4C-alkoxycarbonyl, or carboxyl.

A further subdetail (detail b4) of the compounds according to detail b of this invention include those compounds of formula I,
in which
either
R1 is 1-4C-alkyl, such as e.g. ethyl or propyl, which is substituted by Raa, in which
Raa is 1-2C-alkoxy, 1-2C-alkoxy-ethoxy, (1-2C-alkoxy-ethoxy)-ethoxy, hydroxyl or 1-2C-alkylcarbonyloxy,
or
R1 is 1-4C-alkyl, such as e.g. methyl, ethyl or propyl, which is substituted by Raa, in which
Raa is 1-2C-alkoxycarbonyl or carboxyl.

A further subdetail (detail b5) of the compounds according to detail b of this invention include those compounds of formula I,
in which
R1 is 1-4C-alkyl, such as e.g. ethyl or propyl, which is substituted by Raa, in which
Raa is Har, in which
Har is optionally substituted by one or two substituents independently selected from R10 as defined in the compounds mentioned above, and is
  a 5-membered monocyclic heteroaryl radical comprising one to four heteroatoms independently selected from nitrogen, oxygen and sulphur, such as e.g. any one selected from furanyl, thiophenyl, pyrrolyl, oxazolyl, isoxazolyl, thiazolyl, isothiazolyl, imidazolyl, pyrazolyl, triazolyl, thiadiazolyl and oxadiazolyl,
whereby said Har radical is attached to the adjacent 1-4C-alkyl radical via a ring carbon or ring nitrogen atom.

A further subdetail (detail b6) of the compounds according to detail b of this invention include those compounds of formula I,
in which
R1 is 1-4C-alkyl, such as e.g. methyl, ethyl or propyl, which is substituted by Raa, in which Raa is Har, in which
Har is optionally substituted by one or two substituents independently selected from R10 as defined in the compounds mentioned above, and is
a 6-membered monocyclic heteroaryl radical comprising one or two nitrogen atoms, such as e.g. any one selected from pyridinyl, pyrazinyl, pyridazinyl and pyrimidinyl,
whereby said Har radical is attached to the adjacent 1-4C-alkyl radical via a ring carbon atom.

A further subdetail (detail b7) of the compounds according to detail b of this invention include those compounds of formula I,
in which
R1 is 1-4C-alkyl, such as e.g. ethyl or propyl, which is substituted by Raa, in which
Raa is morpholino.

A further subdetail (detail b8) of the compounds according to detail b of this invention include those compounds of formula I,
in which
R1 is 1-4C-alkyl, such as e.g. methyl, ethyl or propyl, which is substituted by Raa, in which
Raa is Har, in which
Har is optionally substituted by one or two substituents independently selected from R10 as defined in the compounds mentioned above, and is pyridinyl.

A further subdetail (detail b9) of the compounds according to detail b of this invention include those compounds of formula I,
in which
R1 is 1-4C-alkyl, such as e.g. ethyl or propyl, which is substituted by Raa, in which
Raa is Har, in which
Har is optionally mono-substituted by R10, and is pyridinyl, imidazolyl (e.g. imidazol-1-yl) or pyrazolyl (e.g. pyrazol-1-yl), in which
R10 is 1-4C-alkyl,
such as e.g.
Har is pyridinyl, imidazol-1-yl, pyrazol-1-yl, 1N-(methyl)-imidazolyl or 1N-(methyl)-pyrazolyl.

A further subdetail (detail b10) of the compounds according to detail b of this invention include those compounds of formula I,
in which
R1 is 1-4C-alkyl, such as e.g. methyl, ethyl or propyl, which is substituted by Raa, in which
Raa is Har, in which
Har is unsubstituted, and is pyridinyl.

A further subdetail (detail b11) of the compounds according to detail b of this invention include those compounds of formula I,
in which
either
R1 is 1-4C-alkyl, such as e.g. ethyl or propyl, which is substituted by Raa, in which
Raa is 1-4C-alkoxy, such as e.g. methoxy or ethoxy, or hydroxyl,
or
R1 is 1-4C-alkyl, such as e.g. methyl, ethyl or propyl, which is substituted by Raa, in which
Raa is 1-4C-alkoxycarbonyl, such as e.g. methoxycarbonyl, or carboxyl.

A further subdetail (detail b12) of the compounds according to detail b of this invention include those compounds of formula I,
in which
either
R1 is 1-4C-alkyl, such as e.g. ethyl or propyl, which is substituted by Raa, in which
Raa is methoxy, ethoxy, hydroxyl, 2-methoxyethoxy or methylcarbonyloxy,
or
R1 is 1-4C-alkyl, such as e.g. methyl, ethyl or propyl, which is substituted by Raa, in which
Raa is methoxycarbonyl.

A further subdetail (detail b13) of the compounds according to detail b of this invention include those compounds of formula I,
in which
R1 is 1-4C-alkyl, such as e.g. ethyl or propyl, which is substituted by Raa, in which
Raa is 1-4C-alkoxy, such as e.g. methoxy or ethoxy, or hydroxyl.

Another subdetail (detail b13') of the compounds according to detail b of this invention include those compounds of formula I,
in which
R1 is 1-4C-alkyl, such as e.g. ethyl or propyl, which is substituted by Raa, in which
Raa is 2-methoxyethoxy.

A further subdetail (detail b14) of the compounds according to detail b of this invention include those compounds of formula I,
in which
R1 is 2-(Raa)-ethyl, or 3-(Raa)-propyl, in which
Raa is methoxy, ethoxy, hydroxyl, methylcarbonyloxy, or 2-methoxyethoxy.

Another subdetail (detail b14') of the compounds according to detail b of this invention includes those compounds of formula I,
in which
R1 is 2-(Raa)-ethyl, or 3-(Raa)-propyl, in which
R2 is methoxy, hydroxyl, methoxycarbonyl, methylcarbonyloxy, or 2-methoxyethoxy.

A further subdetail (detail b15) of the compounds according to detail b of this invention include those compounds of formula I,
in which
R1 is 2-(Raa)-ethyl, in which
Raa is methoxy, hydroxyl, or 2-methoxyethoxy.

A further subdetail (detail b16) of the compounds according to detail b of this invention include those compounds of formula I,
in which
R1 is propyl or butyl, each of which is bisubstituted by hydroxyl on different carbon atoms, such as e.g. 2,3-dihydroxy-propyl.

A further subdetail (detail b17) of the compounds according to detail b of this invention include those compounds of formula I,
in which
R1 is 2,3-dihydroxypropyl.

A further subdetail (detail b18) of the compounds according to detail b of this invention include those compounds of formula I,
in which
R1 is 2-methoxyethyl.

A further subdetail (detail b19) of the compounds according to detail b of this invention include those compounds of formula I, in which
R1 is 2-hydroxyethyl.

A further subdetail (detail b20) of the compounds according to detail b of this invention include those compounds of formula I,
in which
R1 is pyridylmethyl, 2-pyridylethyl or 3-pyridylpropyl, such as e.g. pyridin-2-yl-methyl, pyridin-3-yl-methyl, pyridin-4-yl-methyl, 2-(pyridin-2-yl)-ethyl, 2-(pyridin-3-yl)-ethyl or 2-(pyridin-4-yl)-ethyl.

A further subdetail (detail b21) of the compounds according to detail b of this invention include those compounds of formula I,
in which
R1 is pyridylmethyl, such as e.g. pyridin-2-yl-methyl, pyridin-3-yl-methyl or pyridin-4-yl-methyl.

A further subdetail (detail b22) of the compounds according to detail b of this invention include those compounds of formula I,
in which
R1 is 2-pyridylethyl, such as e.g. 2-(pyridin-2-yl)-ethyl, 2-(pyridin-3-yl)-ethyl or 2-(pyridin-4-yl)-ethyl.

A further subdetail (detail b23) of the compounds according to detail b of this invention include those compounds of formula I,
in which
R1 is (Raa)-methyl, 2-(Raa)-ethyl or 3-(Raa)-propyl, in which
Raa is R101- and/or R102-substituted pyridyl, in which
R101 is methyl,
R102 is methoxy or methyl.

A further subdetail (detail b24) of the compounds according to detail b of this invention include those compounds of formula I,
in which
R1 is 2-(Raa)-ethyl or 3-(Raa)-propyl, in which
Raa is imidazol-1-yl.

A further subdetail (detail b25) of the compounds according to detail b of this invention include those compounds of formula I,
in which
R1 is 2-(Raa)-ethyl or 3-(Raa)-propyl, in which
Raa is mono- or di-methyl-substituted imidazol-1-yl.

A further subdetail (detail b26) of the compounds according to detail b of this invention include those compounds of formula I,
in which
R1 is (Raa)-methyl, 2-(Raa)-ethyl or 3-(Raa)-propyl, in which
Raa is 1N-methyl-imidazolyl.

A further subdetail (detail b27) of the compounds according to detail b of this invention include those compounds of formula I,
in which
R1 is 2-(Raa)-ethyl, in which
Raa is mono- or di-methyl-substituted imidazol-1-yl, such as e.g. 2-methyl-imidazol-1-yl, 4-methyl-imidazol-1-yl or 2,4-dimethyl-imidazol-1-yl.

A further subdetail (detail b28) of the compounds according to detail b of this invention include those compounds of formula I,
in which
R1 is 2-(2-methyl-imidazol-1-yl)-ethyl or 2-(4-methyl-imidazol-1-yl)-ethyl.

A further subdetail (detail b29) of the compounds according to detail b of this invention include those compounds of formula I,
in which
R1 is (Raa)-methyl or 2-(Raa)-ethyl, in which
Raa is 1N-methyl-imidazolyl, such as e.g. 1-methyl-imidazol-2-yl or 1-methyl-imidazol-5-yl.

A further subdetail (detail b30) of the compounds according to detail b of this invention include those compounds of formula I,
in which
R1 is (1-methyl-imidazol-2-yl)-methyl or (1-methyl-imidazol-5-yl)-methyl.

A further subdetail (detail b31) of the compounds according to detail b of this invention include those compounds of formula I,
in which
R1 is 2-(imidazol-1-yl)-ethyl.

A third embodimental detail (detail c) of the compounds of formula I according to this invention includes those compounds of formula Ia, in which R1 is any one of the meanings indicated in Table 1 given below.

A fourth embodimental detail (detail d) of the compounds of formula I according to this invention includes those compounds of formula Ic*, in which R1 is any one of the meanings indicated in Table 1 given below.

A fifth embodimental detail (detail e) of the compounds of formula I according to this invention includes those compounds of formula Ic**, in which R1 is any one of the meanings indicated in Table 1 given below.

A first embodimental variant (variant a) of the compounds of formula I according to this invention includes those compounds of formula I, which are from formula Ia

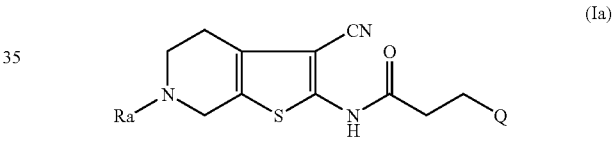
(Ia)

A second embodimental variant (variant b) of the compounds of formula I according to this invention includes those compounds of formula I, which are from formula Ib

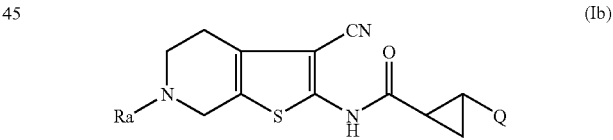
(Ib)

In the context of variant b, one subvariant of variant b includes compounds of formula Ib, in which the radicals —N(H)—C(O)— and Q are located at the opposite side of the plane defined by the cyclopropane ring.

A third embodimental variant (variant c) of the compounds of formula I according to this invention includes those compounds of formula I, which are from formula Ic

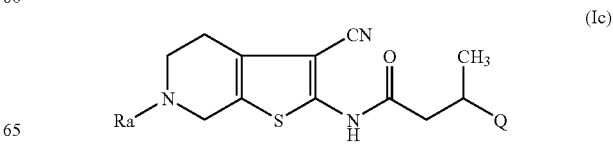
(Ic)

In the context of variant c, one subvariant of variant c includes compounds of formula Ic*, another subvariant of variant c includes compounds of formula Ic**

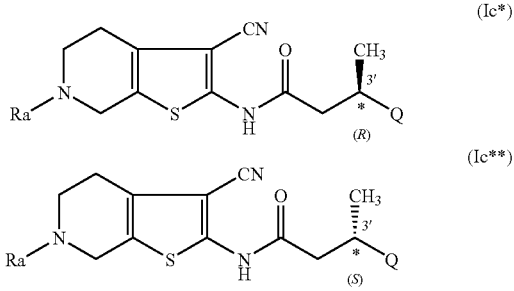

If, for example, in compounds of formula Ic* Q has one of the meanings given above, then the configuration-according the rules of Cahn, Ingold and Prelog- is R in the position 3' indicated in formula Ic* above.

If, for example, in compounds of formula Ic Q has one of the meanings given above, then the configuration-according the rules of Cahn, Ingold and Prelog- is S in the position 3' indicated in formula Ic above.

A fourth embodimental variant (variant d) of the compounds of formula I according to this invention includes those compounds of formula I, which are from formulae Id or Id'

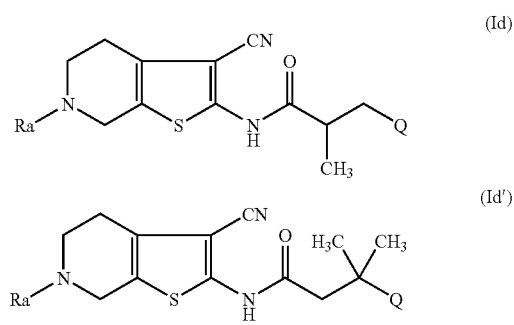

In the meaning of this invention, among the variants a to d, the variants a and c are to be emphasized.

A fifth embodimental variant (variant e) of the compounds of formula I according to this invention includes those compounds of any of the formulae Ia, Ib, Ic, Id and Id',
in which
Q is Rba- and Rbb-substituted phenyl, in which
Rba has one of the meanings as defined in the compounds mentioned above,
Rbb has one of the meanings as defined in the compounds mentioned above,
Rbc is hydrogen.

A subvariant (variant e1) of the compounds according to variant e of this invention include those compounds of any of the formulae Ia, Ib, Ic, Id and Id',
in which
Q is Rba- and Rbb-substituted phenyl, in which
Rba is 1-4C-alkoxy,
Rbb is hydrogen, halogen, 1-4C-alkyl or 1-4C-alkoxy,
Rbc is hydrogen.

A further subvariant (variant e2) of the compounds according to variant e of this invention include those compounds of any of the formulae Ia, Ib, Ic, Id and Id',
in which
Q is Rba- and Rbb-substituted phenyl, in which
Rba is 1-4C-alkoxy, such as e.g. methoxy or ethoxy,
Rbb is hydrogen,
Rbc is hydrogen.

A further subvariant (variant e3) of the compounds according to variant e of this invention include those compounds of any of the formulae Ia, Ib, Ic, Id and Id',
in which
Q is Rba- and Rbb-substituted phenyl, in which
Rba is methoxy,
Rbb is hydrogen,
Rbc is hydrogen.

A further subvariant (variant e4) of the compounds according to variant e of this invention include those compounds of any of the formulae Ia, Ib, Ic, Id and Id',
in which
Q is Rba- and Rbb-substituted phenyl, in which
Rba is ethoxy,
Rbb is hydrogen,
Rbc is hydrogen.

A further subvariant (variant e5) of the compounds according to variant e of this invention include those compounds of any of the formulae Ia, Ib, Ic, Id and Id',
in which
Q is Rba- and Rbb-substituted phenyl, in which
Rba is 1-4C-alkoxy, such as e.g. 1-2C-alkoxy,
Rbb is 1-4C-alkoxy, such as e.g. 1-2C-alkoxy,
Rbc is hydrogen.

A further subvariant (variant e6) of the compounds according to variant e of this invention include those compounds of any of the formulae Ia, Ib, Ic, Id and Id',
in which
Q is Rba- and Rbb-substituted phenyl, in which
Rba is methoxy or ethoxy,
Rbb is methoxy,
Rbc is hydrogen.

A further subvariant (variant e7) of the compounds according to variant e of this invention include those compounds of any of the formulae Ia, Ib, Ic, Id and Id',
in which
Q is Rba- and Rbb-substituted phenyl, in which
Rba is methoxy,
Rbb is methoxy,
Rbc is hydrogen.

A further subvariant (variant e8) of the compounds according to variant e of this invention include those compounds of any of the formulae Ia, Ib, Ic, Id and Id',
in which
Q is Rba- and Rbb-substituted phenyl, in which
Rba is ethoxy,
Rbb is ethoxy,
Rbc is hydrogen.

A further subvariant (variant e9) of the compounds according to variant e of this invention include those compounds of any of the formulae Ia, Ib, Ic, Id and Id',
in which
Q is Rba- and Rbb-substituted phenyl, in which
Rba is methoxy,
Rbb is ethoxy,
Rbc is hydrogen.

A further subvariant (variant e10) of the compounds according to variant e of this invention include those compounds of any of the formulae Ia, Ib, Ic, Id and Id',
in which
Q is Rba- and Rbb-substituted phenyl, in which Rba is completely or predominantly fluorine-substituted 1-4C-alkoxy, such as e.g. difluoromethoxy or trifluoromethoxy,
Rbb is hydrogen,
Rbc is hydrogen.

A further subvariant (variant e11) of the compounds according to variant e of this invention include those compounds of any of the formulae Ia, Ib, Ic, Id and Id',
in which
Q is any one selected from the group consisting of 2-methoxyphenyl, 3-methoxyphenyl, 4-methoxyphenyl, 2-ethoxyphenyl, 3-ethoxyphenyl, 4-ethoxyphenyl, 2-difluoromethoxy-phenyl, 3-difluoromethoxy-phenyl, 4-difluoromethoxy-phenyl, dimethoxyphenyl such as e.g. 3,5-dimethoxyphenyl, 2,5-dimethoxyphenyl, 2,6-dimethoxyphenyl or 2,3-dimethoxyphenyl, and diethoxyphenyl such as e.g. 2,3-diethoxyphenyl.

A further subvariant (variant e12) of the compounds according to variant e of this invention include those compounds of any of the formulae Ia, Ib, Ic, Id and Id',
in which
Q is any one selected from the group consisting of 2-methoxyphenyl, 3-methoxyphenyl, 4-methoxyphenyl, 2-ethoxyphenyl, 3-ethoxyphenyl, 4-ethoxyphenyl, and dimethoxyphenyl such as e.g. 2,5-dimethoxyphenyl or 2,3-dimethoxyphenyl.

A further subvariant (variant e13) of the compounds according to variant e of this invention include those compounds of any of the formulae Ia, Ib, Ic, Id and Id',
in which
Q is any one selected from the group consisting of 2-methoxyphenyl, 3-methoxyphenyl, 4-methoxyphenyl, 2-ethoxyphenyl, 3-ethoxyphenyl and 4-ethoxyphenyl.

A further subvariant (variant e14) of the compounds according to variant e of this invention include those compounds of any of the formulae Ia, Ib, Ic, Id and Id',
in which
Q is any one selected from the group consisting of 2-methoxyphenyl, 3-methoxyphenyl, 2-ethoxyphenyl and 3-ethoxyphenyl.

A further subvariant (variant e15) of the compounds according to variant e of this invention include those compounds of any of the formulae Ia, Ib, Ic, Id and Id',
in which
Q is any one selected from the group consisting of 2,6-dimethoxyphenyl, 2,5-dimethoxyphenyl and 2,3-dimethoxyphenyl.

A further subvariant (variant e16) of the compounds according to variant e of this invention include those compounds of any of the formulae Ia, Ib, Ic, Id and Id',
in which
Q is any one selected from the group consisting of 2,5-dimethoxyphenyl and 2,3-dimethoxyphenyl.

A sixth embodimental variant (variant f) of the compounds of formula I according to this invention includes those compounds of any of the formulae Ia, Ib, Ic, Id and Id',
in which
Q is Rba- and Rbb- and Rbc-substituted phenyl, in which
Rba has one of the meanings as defined in the compounds mentioned above,
Rbb has one of the meanings as defined in the compounds mentioned above,
Rbc has one of the meanings as defined in the compounds mentioned above.

A subvariant (variant f1) of the compounds according to variant f of this invention include those compounds of any of the formulae Ia, Ib, Ic, Id and Id',
in which
Q is Rba- and Rbb- and Rbc-substituted phenyl, in which
Rbb is hydrogen,
Rbc is hydrogen.

A further subvariant (variant f2) of the compounds according to variant f of this invention include those compounds of any of the formulae Ia, Ib, Ic, Id and Id',
in which
Q is Rba- and Rbb- and Rbc-substituted phenyl, in which
Rbb is hydrogen.

A further subvariant (variant f3) of the compounds according to variant f of this invention include those compounds of any of the formulae Ia, Ib, Ic, Id and Id',
in which
Q is Rba- and Rbb- and Rbc-substituted phenyl, in which
Rbc is hydrogen.

A subvariant (variant f4) of the compounds according to variant f of this invention include those compounds of any of the formulae Ia, Ib, Ic, Id and Id',
in which
Q is Rba- and Rbb- and Rbc-substituted phenyl, in which
Rba is 1-4C-alkoxy,
Rbb is hydrogen, halogen, 1-4C-alkyl or 1-4C-alkoxy,
Rbc is hydrogen or halogen.

A further subvariant (variant f5) of the compounds according to variant f of this invention include those compounds of any of the formulae Ia, Ib, Ic, Id and Id',
in which
Q is Rba- and Rbb- and Rbc-substituted phenyl, in which
Rba is 1-4C-alkoxy, such as e.g. methoxy or ethoxy,
Rbb is 1-4C-alkoxy, such as e.g. methoxy or ethoxy,
Rcc is halogen.

A further subvariant (variant f6) of the compounds according to variant f of this invention include those compounds of any of the formulae Ia, Ib, Ic, Id and Id',
in which
Q is Rba- and Rbb- and Rbc-substituted phenyl, in which
Rba is 1-4C-alkoxy, such as e.g. methoxy or ethoxy,
Rbb is hydrogen,
Rcc is halogen.

A further subvariant (variant f7) of the compounds according to variant f of this invention include those compounds of any of the formulae Ia, Ib, Ic, Id and Id',
in which
Q is Rba- and Rbb- and Rbc-substituted phenyl, in which
Rba is 1-4C-alkoxy, such as e.g. methoxy or ethoxy,
Rbb is 1-4C-alkyl, such as e.g. methyl or ethyl,
Rcc is hydrogen.

A further subvariant (variant f8) of the compounds according to variant f of this invention include those compounds of any of the formulae Ia, Ib, Ic, Id and Id',
in which
Q is Rba- and Rbb- and Rbc-substituted phenyl, in which
Rba is methoxy,
Rbb is methyl,
Rcc is hydrogen.

A further subvariant (variant f9) of the compounds according to variant f of this invention include those compounds of any of the formulae Ia, Ib, Ic, Id and Id',
in which
Q is Rba- and Rbb- and Rbc-substituted phenyl, in which
Rba is ethoxy,
Rbb is methyl,
Rcc is hydrogen.

A further subvariant (variant f10) of the compounds according to variant f of this invention include those compounds of any of the formulae Ia, Ib, Ic, Id and Id', in which
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is methoxy or ethoxy,
Rbb is methyl, ethyl, methoxy or ethoxy.

A further subvariant (variant f11) of the compounds according to variant f of this invention include those compounds of any of the formulae Ia, Ib, Ic, Id and Id',
in which
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is methoxy or ethoxy,
Rbb is methyl or methoxy.

A further subvariant (variant f12) of the compounds according to variant f of this invention include those compounds of any of the formulae Ia, Ib, Ic, Id and Id',
in which
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
in which
Rba is methoxy or ethoxy,
Rbb is methyl.

A further subvariant (variant f13) of the compounds according to variant f of this invention include those compounds of any of the formulae Ia, Ib, Ic, Id and Id',
in which
Q is Rbb-substituted 2-(Rba)-phenyl.

A further subvariant (variant f14) of the compounds according to variant f of this invention include those compounds of any of the formulae Ia, Ib, Ic, Id and Id',
in which
Q is Rbb-substituted 3-(Rba)-phenyl.

A further subvariant (variant f15) of the compounds according to variant f of this invention include those compounds of any of the formulae Ia, Ib, Ic, Id and Id',
in which
Q is Rbb-substituted 4-(Rba)-phenyl.

A further subvariant (variant f16) of the compounds according to variant e of this invention include those compounds of any of the formulae Ia, Ib, Ic, Id and Id',
in which
Q is 2-(Rba)-phenyl.

A further subvariant (variant f117) of the compounds according to variant f of this invention include those compounds of any of the formulae Ia, Ib, Ic, Id and Id',
in which
Q is 3-(Rba)-phenyl.

A further subvariant (variant f18) of the compounds according to variant f of this invention include those compounds of any of the formulae Ia, Ib, Ic, Id and Id',
in which
Q is 4-(Rba)-phenyl.

A further subvariant (variant f19) of the compounds according to variant f of this invention include those compounds of any of the formulae Ia, Ib, Ic, Id and Id',
in which
Q is 2-(Rba)-5-(Rbb)-phenyl.

A further subvariant (variant f20) of the compounds according to variant f of this invention include those compounds of any of the formulae Ia, Ib, Ic, Id and Id',
in which
Q is 2-(Rba)-3-(Rbb)-phenyl.

A further subvariant (variant f21) of the compounds according to variant f of this invention include those compounds of any of the formulae Ia, Ib, Ic, Id and Id',
in which
Q is 2-(Rba)-6-(Rbb)-phenyl.

A further subvariant (variant f22) of the compounds according to variant f of this invention include those compounds of any of the formulae Ia, Ib, Ic, Id and Id',
in which
Q is 2-(Rbb)-3-(Rba)-phenyl.

A further subvariant (variant f23) of the compounds according to variant f of this invention include those compounds of any of the formulae Ia, Ib, Ic, Id and Id',
in which
Q is 2-(Rbb)-5-(Rba)-phenyl.

A further subvariant (variant f24) of the compounds according to variant f of this invention include those compounds of any of the formulae Ia, Ib and Ic,
in which
Q is 2-(Rba)-5-(Rbb)-phenyl, in which
Rba is methoxy,
Rbb is methoxy or methyl.

A further subvariant (variant f25) of the compounds according to variant f of this invention include those compounds of any of the formulae Ia, Ib and Ic,
in which
Q is 2-(Rba)-5-(Rbb)-phenyl, in which
Rba is ethoxy,
Rbb is methoxy or methyl.

A further subvariant (variant f26) of the compounds according to variant f of this invention include those compounds of any of the formulae Ia, Ib and Ic,
in which
Q is 2-(Rba)-5-(Rbb)-phenyl, in which
Rba is methoxy or ethoxy,
Rbb is methyl.

A further subvariant (variant f27) of the compounds according to variant f of this invention include those compounds of any of the formulae Ia, Ib and Ic,
in which
Q is 2-(Rba)-3-(Rbb)-phenyl, in which
Rba is methoxy or ethoxy,
Rbb is methyl.

A further subvariant (variant f28) of the compounds according to variant f of this invention include those compounds of any of the formulae Ia, Ib and Ic,
in which
Q is 2-(Rba)-6-(Rbb)-phenyl, in which
Rba is methoxy or ethoxy,
Rbb is methyl.

A further subvariant (variant f29) of the compounds according to variant f of this invention include those compounds of any of the formulae Ia, Ib and Ic,
in which
Q is any one selected from the group consisting of 2-methoxy-3-methyl-phenyl, 2-methoxy-5-methyl-phenyl, 2-methoxy-6-methyl-phenyl, 2-ethoxy-3-methyl-phenyl, 2-ethoxy-5-methyl-phenyl, 2-ethoxy-6-methyl-phenyl, 2-methyl-3-methoxy-phenyl, 2-methyl-5-methoxy-phenyl, 2-methyl-3-ethoxy-phenyl and 2-methyl-5-ethoxy-phenyl.

A further subvariant (variant f30) of the compounds according to variant f of this invention include those compounds of any of the formulae Ia, Ib and Ic, in which
Q is any one selected from the group consisting of 2-ethoxy-3-methyl-phenyl, 2-ethoxy-5-methyl-phenyl and 2-ethoxy-6-methyl-phenyl.

A further subvariant (variant f31) of the compounds according to variant f of this invention include those compounds of any of the formulae Ia, Ib and Ic,
in which
Q is any one selected from the group consisting of 2-methoxy-3-methyl-phenyl, 2-methoxy-5-methyl-phenyl and 2-methoxy-6-methyl-phenyl.

A further subvariant (variant f32) of the compounds according to variant f of this invention include those compounds of any of the formulae Ia, Ib and Ic,
in which
Q is 2-methoxy-5-methyl-phenyl.

A further subvariant (variant f33) of the compounds according to variant f of this invention include those compounds of any of the formulae Ia, Ib and Ic,
in which
Q is 2-ethoxy-5-methyl-phenyl.

A further subvariant (variant f34) of the compounds according to variant f of this invention include those compounds of any of the formulae Ia, Ib and Ic,
in which
Q is 2-ethoxyphenyl.

A further subvariant (variant f35) of the compounds according to variant f of this invention include those compounds of any of the formulae Ia, Ib and Ic,
in which
Q is 2-methoxyphenyl.

A further subvariant (variant f36) of the compounds according to variant f of this invention include those compounds of any of the formulae Ia, Ib and Ic,
in which
Q is 3-methoxyphenyl.

A further subvariant (variant f37) of the compounds according to variant f of this invention include those compounds of any of the formulae Ia, Ib and Ic,
in which
Q is 3-ethoxyphenyl.

A further subvariant (variant f32) of the compounds according to variant f of this invention include those compounds of any of the formulae Ia, Ib and Ic,
in which
Q is 2-methoxy-5-methyl-phenyl.

A further subvariant (variant f33) of the compounds according to variant f of this invention include those compounds of any of the formulae Ia, Ib and Ic,
in which
Q is 2-ethoxy-5-methyl-phenyl.

A further subvariant (variant f34) of the compounds according to variant f of this invention include those compounds of any of the formulae Ia, Ib and Ic,
in which
Q is 2-ethoxyphenyl.

A further subvariant (variant f35) of the compounds according to variant f of this invention include those compounds of any of the formulae Ia, Ib and Ic,
in which
Q is 2-methoxyphenyl.

A further subvariant (variant f36) of the compounds according to variant f of this invention include those compounds of any of the formulae Ia, Ib and Ic,
in which
Q is 3-methoxyphenyl.

A further subvariant (variant f37) of the compounds according to variant f of this invention include those compounds of any of the formulae Ia, Ib and Ic,
in which
Q is 3-ethoxyphenyl.

A further subvariant (variant f38) of the compounds according to variant f of this invention include those compounds of formula Ia,
in which
Q is 2-methoxy-5-methyl-phenyl.

A further subvariant (variant f39) of the compounds according to variant f of this invention include those compounds of formula Ia,
in which
Q is 2-ethoxy-5-methyl-phenyl.

A further subvariant (variant f40) of the compounds according to variant f of this invention include those compounds of formula Ia,
in which
Q is 2-ethoxyphenyl.

A further subvariant (variant f41) of the compounds according to variant f of this invention include those compounds of formula Ia,
in which
Q is 2-methoxyphenyl.

A further subvariant (variant f42) of the compounds according to variant f of this invention include those compounds of formula Ia,
in which
Q is 3-methoxyphenyl.

A further subvariant (variant f43) of the compounds according to variant f of this invention include those compounds of formula Ia,
in which
Q is 3-ethoxyphenyl.

A further subvariant (variant f44) of the compounds according to variant f of this invention include those compounds of formula Ic,
in which
Q is 2-methoxy-5-methyl-phenyl.

A further subvariant (variant f45) of the compounds according to variant f of this invention include those compounds of formula Ic,
in which
Q is 2-ethoxy-5-methyl-phenyl.

A further subvariant (variant f46) of the compounds according to variant f of this invention include those compounds of formula Ic,
in which
Q is 2-ethoxyphenyl.

A further subvariant (variant f47) of the compounds according to variant f of this invention include those compounds of formula Ic,
in which
Q is 2-methoxyphenyl.

A further subvariant (variant f48) of the compounds according to variant f of this invention include those compounds of formula Ic,
in which
Q is 3-methoxyphenyl.

A further subvariant (variant f49) of the compounds according to variant f of this invention include those compounds of formula Ic,
in which
Q is 3-ethoxyphenyl.

A further subvariant (variant f50) of the compounds according to variant f of this invention include those compounds of any of the formulae Ia and Ic,
in which
either
Q is 2-methoxyphenyl, or
Q is 2-ethoxyphenyl, or
Q is 3-methoxyphenyl, or
Q is 3-ethoxyphenyl, or
Q is 2-(Rba)-3-(Rbb)-phenyl, in which
Rba is methoxy or ethoxy,
Rbb is methyl, or
Q is 2-(Rba)-5-(Rbb)-phenyl, in which
Rba is methoxy or ethoxy,
Rbb is methyl.

A further subvariant (variant f51) of the compounds according to variant f of this invention include those compounds of any of the formulae Ia and Ic,
in which
either
Q is 2-methoxyphenyl, or
Q is 2-ethoxyphenyl, or
Q is 3-methoxyphenyl, or
Q is 3-ethoxyphenyl, or
Q is 2-(Rba)-5-(Rbb)-phenyl, in which
Rba is methoxy,
Rbb is methyl.

A further subvariant (variant f52) of the compounds according to variant f of this invention include those compounds of any of the formulae Ia and Ic,
in which
either
Q is 2-methoxyphenyl, or
Q is 2-ethoxyphenyl, or
Q is 3-methoxyphenyl, or
Q is 2-(Rba)-5-(Rbb)-phenyl, in which
Rba is methoxy,
Rbb is methyl.

A seventh embodimental variant (variant g) of the compounds of formula I according to this invention includes those compounds of formula Ia, in which Q is any one of the meanings indicated in Table 1 given below.

An eighth embodimental variant (variant h) of the compounds of formula I according to this invention includes those compounds of formula Ic*, in which Q is any one of the meanings indicated in Table 1 given below.

A ninth embodimental variant (variant i) of the compounds of formula I according to this invention includes those compounds of formula Ic**, in which Q is any one of the meanings indicated in Table 1 given below.

It is to be understood that the present invention includes any or all possible combinations and subsets of the details, variants, subdetails and subvariants defined hereinabove.

When the compounds of formula I are chiral compounds (e.g. by having one or more chiral centers), the invention refers to all conceivable stereoisomers, like e.g. diastereomers and enantiomers, in substantially pure form as well as in any mixing ratio, including the racemates, as well as the salts thereof.

Accordingly, the stereoisomers of formula Ic* and of formula Ic** and the salts thereof are part of the invention.

In general, enantiomerically pure compounds of this invention can be prepared according to art-known processes, such as e.g. via asymmetric syntheses, for example, by preparation and separation of appropriate diastereoisomeric compounds or by using chiral synthons or chiral reagents; by chromatographic separation on chiral separating columns; by means of salt formation of the racemic compounds with optically active acids or bases, subsequent resolution of the salts and release of the desired compound from the salt; by derivatization with chiral auxiliary reagents, subsequent diastereomer separation and removal of the chiral auxiliary group; or by (fractional) crystallization from a suitable solvent.

Exemplary compounds according to the present invention may include, without being restricted thereto, any compound selected from those compounds of formula I mentioned in the following examples, the enantiomers (e.g., when the compound is from formula Ic, in one special embodiment, the enantiomer having the formula Ic* and, in another special embodiment, the enantiomer having the formula Ic**) as well as the salts of these compounds and enantiomers.

As interesting exemplary compounds according to this invention any or all of the following compounds of formula Ia, in which Ra is —C(O)OR1, are more worthy to be mentioned by means of the substituent meanings for R1 and Q in the Table 1 given below, as well as the salts thereof.

As other interesting exemplary compounds according to this invention any or all of the following compounds of formula Ic, in which Ra is —C(O)OR1, are more worthy to be mentioned by means of the substituent meanings for R1 and Q in the Table 1 given below, as well as the enantiomers and the salts of these compounds and enantiomers.

As other interesting exemplary compounds according to this invention any or all of the following compounds of formula Ic*, in which Ra is —C(O)OR1, are more worthy to be mentioned by means of the substituent meanings for R1 and Q in the Table 1 given below, as well as the salts thereof.

As other interesting exemplary compounds according to this invention any or all of the following compounds of formula Ic**, in which Ra is —C(O)OR1, are more worthy to be mentioned by means of the substituent meanings for R1 and Q in the Table 1 given below, as well as the salts thereof.

TABLE 1

| | R1 | Q |
|---|---|---|
| 1.) | 2-hydroxyethyl | 2-methoxyphenyl |
| 2.) | 2,3-dihydroxy-propyl | 2-methoxyphenyl |
| 3.) | 2-(imidazol-1-yl)-ethyl | 2-methoxyphenyl |
| 4.) | pyridin-2-yl-methyl | 2-methoxyphenyl |
| 5.) | pyridin-3-yl-methyl | 2-methoxyphenyl |
| 6.) | pyridin-4-yl-methyl | 2-methoxyphenyl |
| 7.) | 2-(pyridin-2-yl)-ethyl | 2-methoxyphenyl |

TABLE 1-continued

| | R1 | Q |
|---|---|---|
| 8.) | 2-(pyridin-3-yl)-ethyl | 2-methoxyphenyl |
| 9.) | 2-(pyridin-4-yl)-ethyl | 2-methoxyphenyl |
| 10.) | 2-hydroxyethyl | 2-ethoxyphenyl |
| 11.) | 2,3-dihydroxy-propyl | 2-ethoxyphenyl |
| 12.) | 2-(imidazol-1-yl)-ethyl | 2-ethoxyphenyl |
| 13.) | pyridin-2-yl-methyl | 2-ethoxyphenyl |
| 14.) | pyridin-3-yl-methyl | 2-ethoxyphenyl |
| 15.) | pyridin-4-yl-methyl | 2-ethoxyphenyl |
| 16.) | 2-(pyridin-2-yl)-ethyl | 2-ethoxyphenyl |
| 17.) | 2-(pyridin-3-yl)-ethyl | 2-ethoxyphenyl |
| 18.) | 2-(pyridin-4-yl)-ethyl | 2-ethoxyphenyl |
| 19.) | 2-hydroxyethyl | 3-methoxyphenyl |
| 20.) | 2,3-dihydroxy-propyl | 3-methoxyphenyl |
| 21.) | 2-(imidazol-1-yl)-ethyl | 3-methoxyphenyl |
| 22.) | pyridin-2-yl-methyl | 3-methoxyphenyl |
| 23.) | pyridin-3-yl-methyl | 3-methoxyphenyl |
| 24.) | pyridin-4-yl-methyl | 3-methoxyphenyl |
| 25.) | 2-(pyridin-2-yl)-ethyl | 3-methoxyphenyl |
| 26.) | 2-(pyridin-3-yl)-ethyl | 3-methoxyphenyl |
| 27.) | 2-(pyridin-4-yl)-ethyl | 3-methoxyphenyl |
| 28.) | 2-hydroxyethyl | 3-ethoxyphenyl |
| 29.) | 2,3-dihydroxy-propyl | 3-ethoxyphenyl |
| 30.) | 2-(imidazol-1-yl)-ethyl | 3-ethoxyphenyl |
| 31.) | pyridin-2-yl-methyl | 3-ethoxyphenyl |
| 32.) | pyridin-3-yl-methyl | 3-ethoxyphenyl |
| 33.) | pyridin-4-yl-methyl | 3-ethoxyphenyl |
| 34.) | 2-(pyridin-2-yl)-ethyl | 3-ethoxyphenyl |
| 35.) | 2-(pyridin-3-yl)-ethyl | 3-ethoxyphenyl |
| 36.) | 2-(pyridin-4-yl)-ethyl | 3-ethoxyphenyl |
| 37.) | 2-hydroxyethyl | 2-methoxy-5-methyl-phenyl |
| 38.) | 2,3-dihydroxy-propyl | 2-methoxy-5-methyl-phenyl |
| 39.) | 2-(imidazol-1-yl)-ethyl | 2-methoxy-5-methyl-phenyl |
| 40.) | pyridin-2-yl-methyl | 2-methoxy-5-methyl-phenyl |
| 41.) | pyridin-3-yl-methyl | 2-methoxy-5-methyl-phenyl |
| 42.) | pyridin-4-yl-methyl | 2-methoxy-5-methyl-phenyl |
| 43.) | 2-(pyridin-2-yl)-ethyl | 2-methoxy-5-methyl-phenyl |
| 44.) | 2-(pyridin-3-yl)-ethyl | 2-methoxy-5-methyl-phenyl |
| 45.) | 2-(pyridin-4-yl)-ethyl | 2-methoxy-5-methyl-phenyl |

Compounds of formula I according to the present invention can be prepared as described below or as shown in the following reaction schemes, or as disclosed in WO2004/024066 or, particularly, WO2004/024065, the disclosure of which is incorporated herein, or similarly or analogously thereto according to preparation procedures or synthesis strategies known to the person skilled in the art. Accordingly, compounds of formula I according to the present invention can be obtained as specified by way of example in the following examples, or similarly or analogously thereto.

Thus, as shown in reaction scheme below, a compound of formula III, in which Ra has the meanings given above, can be condensed with malonitrile in the presence of sulfur and a suitable base, such as for example an amine (e.g. diethyl amine or morpholine) to give corresponding compounds of formula II in a manner known to the person skilled in the art (e.g. according to a Gewald reaction) or as described in the following examples.

Compounds of formula III are known or can be obtained in an art-known manner, or analogously or similarly thereto.

Compounds of formula II can be reacted with compounds of formula Rb—C(O)—X, in which Rb has the meanings mentioned above and X is a suitable leaving group, preferably a chlorine atom, in an acylation reaction under conditions habitual per se to give the desired compounds of formula I, in which Ra and Rb have the meanings given above.

Alternatively, compounds of the formula I can also be prepared from the corresponding compounds of formula II and corresponding compounds of formula Rb—C(O)—X, in which X is hydroxyl, by reaction with amide bond linking reagents known to the person skilled in the art. Exemplary amide bond linking reagents known to the person skilled in the art which may be mentioned are, for example, the carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N,N,N',N'-tetramethyluronium tetrafluoroborate or O-(benzotriazol-1-yl)-N,N,N',N'-tetramthyl-uronium-hexafluorophosphate] and N,N'-carbonyldiimidazole. In the scope of this invention preferred amide bond linking reagents are uronium salts and, particularly, carbodiimides, preferably, 1-ethyl-3-(3-dimethylaminopropyl)carbodiimide hydrochloride (EDC).

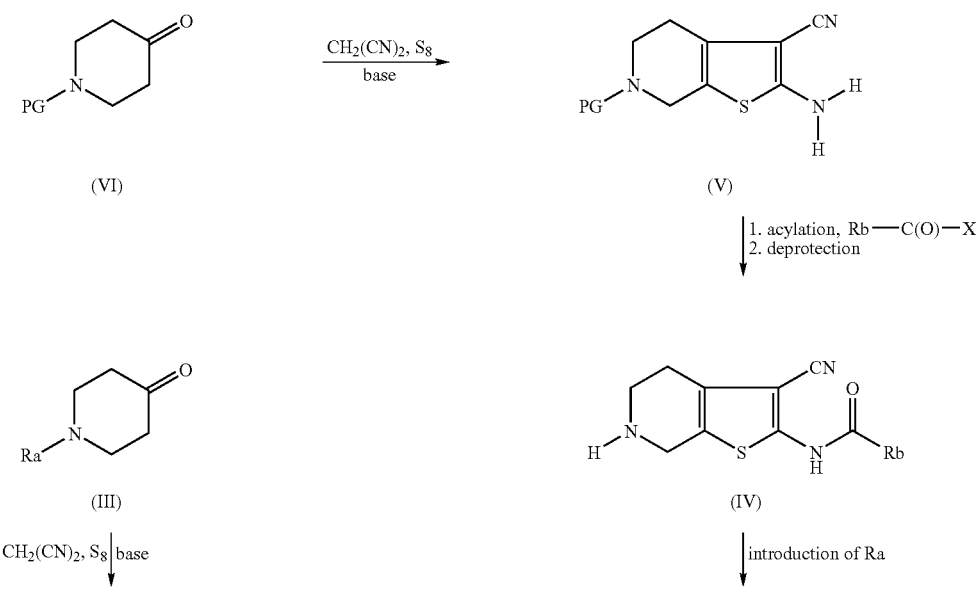

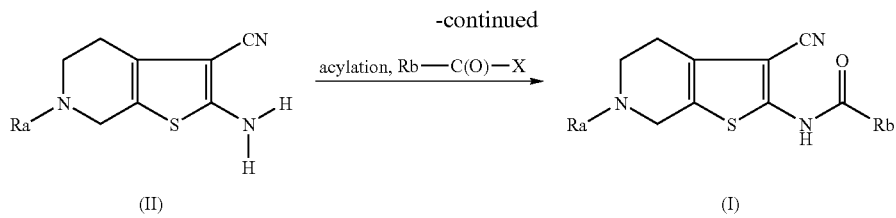

(II) → (I)

Acid derivatives of formula Rb—C(O)—X are known, commercially available or can be prepared as it is known for the skilled person, e.g. from the corresponding carboxylic acids.

Carboxylic acids of formula Rb—C(O)—OH are known, commercially available or can be obtained as it is habitual for the skilled person, e.g. analogously or similarly to standard procedures.

Thus, for example, carboxylic acids of formula Rb—C(O)—OH, in which Rb is -T-Q, in which T is 1-6C-alkylene, as defined above, especially those, in which Rb is —CH$_2$—CH$_2$-Q or —CH$_2$—CH(CH$_3$)-Q, in which Q has the meanings given above, can be obtained via CC-coupling reactions, such as e.g. by Heck or Knoevenagel reaction or, in particular, starting from aldehydes of the formula Q-CHO or ketones, especially methylketones, of the formula Q-C(O)CH$_3$, respectively, by Horner-Wadsworth-Emmons reaction, and then hydration reaction and, if necessary, hydrolysis of the corresponding esters obtained.

β-Methyl-propionic acids can be also obtained as given in J. Org. Chem. 61, 16, 1996, 5510-5516 and Tetrahedron Lett. 37, 10, 1996, 1683-1686 and subsequent hydration, such as e.g. described in the following examples, or analogously or similarly thereto.

In this context, there are several options for the synthesis of enantiomerically pure β-methyl-propionic acids known in literature, e.g.:

- asymmetric addition of phenylboronic acids to (α-,β-unsaturated esters using chiral catalysts (see e.g. S. Sakuma, M. Sakai, R. Itooka, N. Miyaura J. Org. Chem. 2000, 65, 5951-5955),
- asymmetric Michael addition to α-,β-unsaturated esters using chiral auxiliaries (see e.g. J. Ezquerra, L. Prieto, C. Avendano, J. L. Martos, E. dela Cuesta, Tetrahedr. Lett. 1999, 40, 1575-1578),
- asymmetric hydrogenation of α-,β-unsaturated esters and acids (see e.g. T. Uemura, X. Zhang, K. Matsumura, et al., J. Org. Chem. 1996, 61, 5510-5516; or W. Tang, W. Wang, X. Zhang Angew. Chem. Int. Ed 2003, 42(8), 943-946), or
- asymmetric hydrosilylation of α-,β-unsaturated esters (see e.g. B. Lipshutz, J. M. Servesko, B. R. Taft: J. Am. Chem. Soc. 2004, 126(27), 8352-8353).

For more specific example of preparation of propionic or butyric acids of formula Rb—C(O)—OH, 3-(2-methoxyphenyl)propanoic acid is described e.g. in U.S. Pat. No. 4,567,053 or in J. Org. Chem. 69, 11, 2004, 3610-3619; 3-(3-methoxyphenyl)propanoic acid is described e.g. in J. Heterocycl. Chem. 26, 1989, 365-369; 3-(2-ethoxyphenyl)propanoic acid is described e.g. in Justus Liebigs Ann. Chem., 226, 1884, 351; 3-(3-ethoxyphenyl)propanoic acid is described e.g. in Justus Liebigs Ann. Chem. 736, 1970, 110-125; 3-(2-methoxy-phenyl)-butyric acid is described e.g. in J. Am. Chem. Soc., 61, 1939, 3039; and 3-(3-methoxy-phenyl)-butyric acid is described e.g. in J. Chem. Soc. Perkin Trans. 1, 1972, 1186, 1190.

Further on, for example, carboxylic acids of formula Rb—C(O)—OH, in which Rb is -T-Q, in which T is 1,2-cyclopropylene and Q has the meanings given above, can be obtained, starting from aldehydes of the formula Q-CHO, via Knoevenagel or Horner-Wadsworth-Emmons reaction, and then cyclopropanation reaction of the double bond (e.g. by Simmons-Smith reaction or, in particular, by Corey-Chaykovsky reaction using dimethylsulfoxonium methylide) and, if necessary, hydrolysis of the corresponding esters obtained.

Aldehydes of formula Q-CHO and methylketones of formula Q-C(O)CH$_3$, in which Q has the meanings given above, are known or can be obtained in a manner customary for the skilled person analogously or similarly to known compounds.

In an alternative synthesis route, compounds of formula VI, in which PG is a suitable temporary protective group, such as for example tertbutoxycarbonyl (Boc) or one of those mentioned in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000), can be condensed with malonitrile in the presence of sulfur and a suitable base as described above to give corresponding compounds of formula V.

Compounds of formula VI are known or can be obtained in an art-known manner.

Compounds of formula V can be acylated with compounds of formula Rb—C(O)—X analogously as mentioned above. Optionally, said amide bond formation can be obtained under microwave assistance. Subsequential deprotection of the protective group PG in a manner customary per se for the skilled person gives compounds of formula IV, in which Rb has the meanings as mentioned above.

Compounds of formula IV can be converted into desired compounds of formula I by introduction of the group Ra via carbamate formation reaction. This carbamate formation reaction can be carried out analogously to the methods known to the person skilled in the art or as described by way of example in the following examples. The appropriate starting compounds for this carbamate formation reaction are art-known or can be obtained according to art-known procedures or analogously or similarly as disclosed for known compounds.

Thus, for example, when Har-substituted alcohols, in which Har has the meanings given above (e.g. substituted or unsubstituted pyridyl or imidazolyl), are used as starting compounds in the carbamate formation reaction, these alcohols can be obtained via CC-coupling reaction or nucleophilic substitution reaction of appropriate building blocks. Thus, e.g. Har-CH$_2$—OH or Har-CH$_2$—CH$_2$—OH, respectively, can be obtained from the corresponding heteroaromatic compounds by hydroxymethylation (e.g. metallation/ reaction with formaldehyde) or hydroxyethylation (e.g. metallation/reaction with ethylene oxide) reaction, respectively.

Compounds of formula Har-CH$_2$—OH, in which Har is attached via a ring carbon atom to the methylene moiety and has the meanings given above (e.g. substituted or unsubstituted pyridyl, or 1N-methyl-imidazolyl), can be also obtained from the corresponding aldehydes of the formula Har-CHO by art-known reduction reaction.

Aldehydes of the formula Har-CHO are known or can be obtained as it is known for the skilled person, such as e.g. from the corresponding heteroaromatic compounds by formylation reaction. Some aldehydes can be obtained as described e.g. for 4-methoxy-pyridin-2-carbaldehyde in Ashimori et al, Chem Pharm Bull 38, 2446-2458 (1990) or analogously or similarly thereto.

It is to be understood for the skilled worker, that certain compounds of this invention can be converted into further compounds of this invention by art-known synthesis strategies and reactions habitual per se to a person of ordinary skill in the art.

Therefore, optionally, compounds of formula I can be converted into further compounds of formula I by methods known to one of ordinary skill in the art. More specifically, for example, from compounds of the formula I in which
a) Raa is acyloxy, such as e.g. acetoxy, the corresponding free hydroxyl compounds can be obtained by removal of the acyl group, such as e.g. by saponification reaction;
b) Rab and Rac taken together form a cyclic acetal or ketal, such as e.g. the 2,2-dimethyl-[1,3]dioxolan acetal, the corresponding free dihydroxy compounds can be obtained by cleavage of the acetal or ketal, such as e.g. by deacetalization reaction;
c) Raa is an ester group, such as e.g. methoxycarbonyl, the corresponding free carboxyl compounds can be obtained by deesterification, such as e.g. by saponification reaction.

The methods mentioned under a) to c) can be expediently carried out analogously to the methods known to the person skilled in the art or as described by way of example in the following examples.

Optionally, compounds of the formula I can be converted into their salts, or, optionally, salts of the compounds of the formula I can be converted into the free compounds. Corresponding processes are habitual per se to the skilled person.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000).

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as methanol, ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds of formula I. All these other possible synthesis routes are also part of this invention.

The present invention also relates to intermediates, including their salts, methods and processes useful in synthesizing compounds according to this invention.

Having described the invention in detail, the scope of the present invention is not limited only to those described characteristics or embodiments. As will be apparent to persons skilled in the art, modifications, analogies, variations, derivations, homologisations, alternatives and adaptations to the described invention can be made on the base of art-known knowledge and/or, particularly, on the base of the disclosure (e.g. the explicite, implicite or inherent disclosure) of the present invention without departing from the spirit and scope of this invention as defined by the scope of the appended claims.

The following examples serve to illustrate the invention further without restricting it. Likewise, further compounds of formula I, whose preparation is not explicitly described, can be prepared in an analogous or similar manner or in a manner familiar per se to the person skilled in the art using customary process techniques.

Any or all of the compounds of formula I according to the present invention which are mentioned in the following examples as final compounds as well as their salts, stereoisomers and salts of the stereoisomers are a preferred subject of the present invention.

In the examples, MS stands for mass spectrum, M is the molecular ion in mass spectroscopy, calc. for calculated, fnd. for found, Boc for the tertbutoxycarbonyl group, EDC for 1-ethyl-3-(3-dimethylaminopropyl)carbodiimide hydrochloride and other abbreviations have their meanings customary per se to the skilled person.

Further on, according to common practice in stereochemistry, the term "(RS)" characterizes a racemate comprising the one enantiomer having the configuration R and the other enantiomer having the configuration S; each of these enantiomers in pure form as well as their mixtures including the racemic mixtures is part of this invention.

EXAMPLES

Final Compounds

A. General Procedure for Amide Bond Formation

In a sealable test tube, the corresponding acid (1.5 mmol) is suspended in a mixture of DMF (0.15 mmol) and dichloromethane (7.5 mL). A solution of oxalyl chloride (3.0 mmol) in dichloromethane (7.5 mL) is then added and the mixture stirred for 1 h at room temperature. After that, the solvents and excess of oxalyl chloride are removed in vacuo, the residue is dissolved in toulene (7.5 mL) and added to the corresponding amine (1 mmol) in a vial suitable for microwave technology. Diisopropyl ethyl amine (1.5 mmol) is added, the vial capped and the mixture is heated for 30 min at 150° C. using microwave technology. Purification is achieved either by filtration followed by washing (water) and crystallization (ethanol) or removal of solvents in vacuo and subsequent column chromatography on silica gel, using mixtures of dichloromethane, methanol and triethyl amine as eluents.

The following compounds can be prepared according to general procedure A starting from 2-amino-3-cyano-4,7-dihydro-5H-thieno[2,3-c]pyridine-6-carboxylic acid ethyl ester (compound A1) and the appropriate art-known carboxylic acid.

1. 3-Cyano-2-[3-(4-methoxy-phenyl)-propanoylamino]-4,7-dihydro-5H-thieno[2,3-c]pyridine-6-carboxylic acid ethyl ester

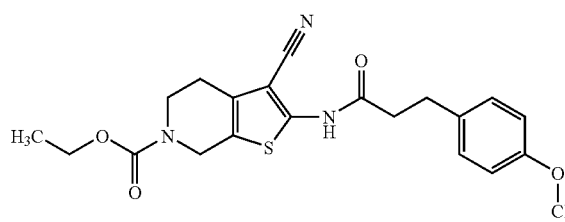

MS: calc.: C,21; H,23; N,3; O,4; S, (413.5) fnd.: 414.1 [M+H]..

2. 3-Cyano-2-[3-(3-methoxy-phenyl)-propanoylamino]-4,7-dihydro-5H-thieno[2,3-c]pyridine-6-carboxylic acid ethyl ester

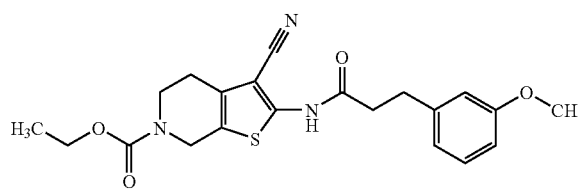

MS: calc.: C,21; H,23; N,3; O,4; S, (413.5) fnd.: 414.0 [M+H]..

3. 3-Cyano-2-[3-(2-methoxy-phenyl)-propanoylamino]-4,7-dihydro-5H-thieno[2,3-c]pyridine-6-carboxylic acid ethyl ester

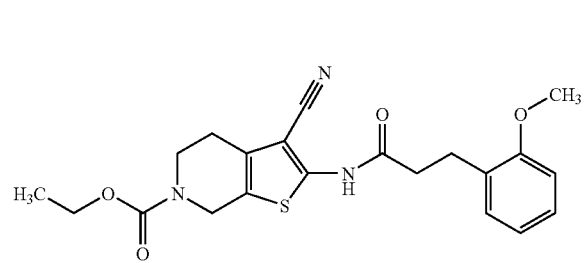

MS: calc.: C,21; H,23; N,3; O,4; S, (413.5) fnd.: 414.0 [M+H]..

4. 3-Cyano-2-[3-(3-nitro-phenyl)-propanoylamino]-4,7-dihydro-5H-thieno[2,3-c]pyridine-6-carboxylic acid ethyl ester

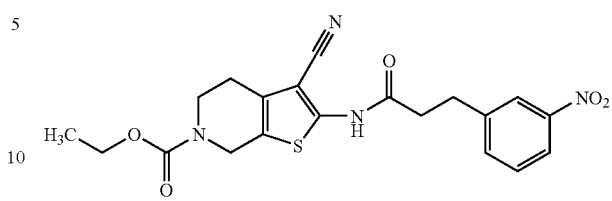

MS: calc.: C,20; H,20; N,4; O,5; S, (428.47) fnd.: 429.0 [M+H].

5. 3-Cyano-2-[3-(4-ethoxy-phenyl)-propanoylamino]-4,7-dihydro-5H-thieno[2,3-c]pyridine-6-carboxylic acid ethyl ester

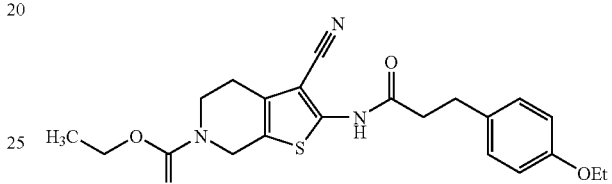

MS: calc.: C,22; H,25; N,3; O,4; S, (427.53) fnd.: 428.0 [M+H].

6. 3-Cyano-2-[3-(2,3-dimethoxy-phenyl)-propanoylamino]-4,7-dihydro-5H-thieno[2,3-c]pyridine-6-carboxylic acid ethyl ester

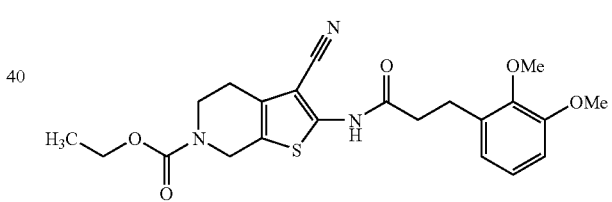

MS: calc.: C,22; H,25; N,3; O,5; S, (443.53) fnd.: 444.0 [M+H].

7. 3-Cyano-2-[3-(2,5-dimethoxy-phenyl)-propanoylamino]-4,7-dihydro-5H-thieno[2,3-c]pyridine-6-carboxylic acid ethyl ester

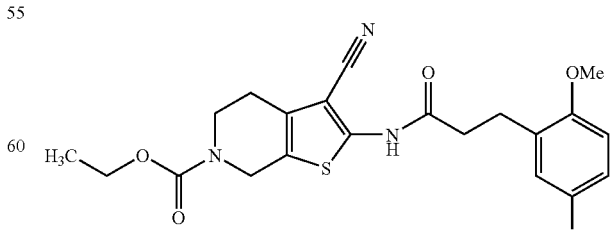

MS: calc.: C,22; H,25; N,3; O,5; S, (443.53) fnd.: 444.0 [M+H].

8. 3-Cyano-2-[3-(3-ethoxy-phenyl)-propanoylamino]-4,7-dihydro-5H-thieno[2,3-c]pyridine-6-carboxylic acid ethyl ester

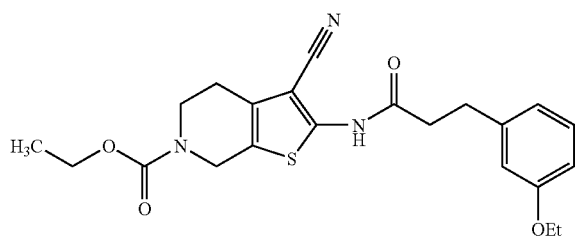

MS: calc.: C,22; H,25; N,3; O,4; S, (427.53) fnd.: 428.0 [M+H].

AA. General Procedures for Amide Bond Formation a) Starting from the trifluoroacetate Salt:

To a solution of the appropriate acid (1.5 mmol) in dichloromethane (5 ml), carbonyldiimidazole (CDI, 1.78 mmol) is added. The reaction vessel is equipped with a bubbler, the mixture is stirred until the gas evolution is completed (30 min, approximately). Then, a mixture of the suspension of the appropriate starting trifluoroacetate salt in dichloromethane (10 ml) and triethylamine (0.2 g, 2 mmole) is added to the reaction mixture. Stirring is continued for 18 to 24 hours at room temperature, the reaction is monitored by TLC.

Work up a1: if the reaction mixture is a solution, it is extracted by three portions of 5% sodium hydrogencarbonate (10 ml each) and once by water (10 ml), the organic layer is evaporated and the residue subjected to purification.

Work up a2: if the reaction mixture is a suspension, the solid product is filtered off. If the amount of this solid product is not sufficient, the mother liquour is further worked up as procedure A.

Purification: The majority of the products can be recrystallized from acetonitrile or ethanol, in some cases by simple trituration of the organic residue with acetonitrile or ethanol. After filtration, the crystals are washed with diethyl ether. In case this procedure does not yield clean products, flash chromatography is performed using mixtures of dichloromethane and methanol as eluent.

b) Starting from the Free Amine using EDCI

A mixture of the appropriate starting base (1 mmol), the appropriate acid (1.5 mmol), ethyl-dimethylaminopropylcarbodiimide (EDCI, 0.29 g, 1.5 mmol), 4-dimethylaminopyridine (DMAP, 0.25 g, 0.2 mmol) and water-free dichloromethane (10 ml) are stirred at room temperature for 18 to 24 hours. The reaction mixture is monitored by TLC. The reaction mixture is worked up as in the reactions carried out with CDI.

c) Using Acid chlorides

To a suspension of the appropriate starting trifluoroacetate salt (1 mmol) in dichloromethane (10 ml) triethylamine (0.4 g, 4 mmol) is added. The formed solution is added to a solution of the appropriate acid chloride (1.2 mmol) in dichloromethane (10 ml) dropwise at 0° C. with stirring and, then, stirring is continued for 24 h at room temperature. The mixture is evaporated and the residue dissolved in dichloromethane. This solution is extracted twice by water (15 ml) and once by saturated sodium chloride solution (15 ml). Purification is carried out as described in procedures a) and b).

d) Using CDI under Microwave Assistance 3.5 eq of the appropriate acid are dissolved in dichloromethane and 2.5 eq CDI is added. After the gas evolution has subsided, a solution of the appropriate amino building block in dichloromethane containing 5 eq triethylamine is added. The reaction mixture is heated in a sealed tube for 3 hours at 75° C. under microwave assistance. Purification is carried out as described in procedures a) and b).

The following compounds can be prepared according to general procedure AA d) starting from 2-amino-3-cyano-4,7-dihydro-5H-thieno[2,3-c]pyridine-6-carboxylic acid tertbutyl ester (compound A2) and the appropriate art-known carboxylic acid.

9. 3-Cyano-2-[3-(2-ethoxy-phenyl)-propanoylamino]-4,7-dihydro-5H-thieno[2,3-c]pyridine-6-carboxylic acid tert-butyl ester

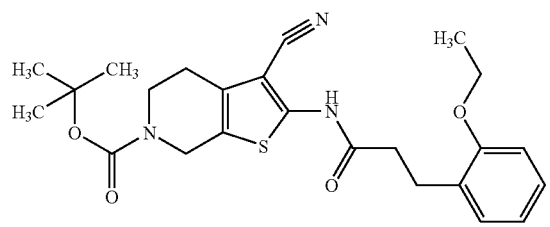

MS: calc.: C,24; H,29; N,3; O,4; S, (455,58) fnd.: 455,9 [M+H].

10. 3-Cyano-2-[3-(2-methoxy-phenyl)-propanoylamino]-4,7-dihydro-5H-thieno[2,3-c]pyridine-6-carboxylic acid tert-butyl ester

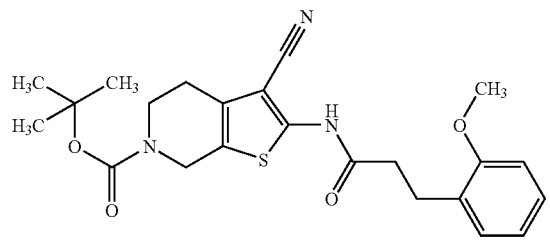

MS: calc.: C,23; H,27; N,3; O,4; S, (441,55) fnd.: 441,8 [M+H].

11. 3-Cyano-2-[3-(3-methoxy-phenyl)-propanoylamino]-4,7-dihydro-5H-thieno[2,3-c]pyridine-6-carboxylic acid tert-butyl ester

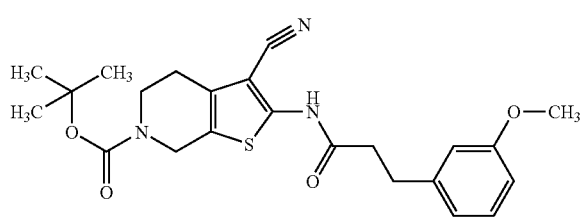

MS: calc.: C,23; H,27; N,3; O,4; S, (441,55) fnd.: 442 [M+H].

Using the appropriate carboxylic acids, further relevant compounds can be prepared similarly to Example 9, 10 or 11.

The following compounds can be prepared according to general procedure M b) or d) starting from 2-amino-3-cyano-4,7-dihydro-5H-thieno[2,3-c]pyridine-6-carboxylic acid ethyl ester (compound A1) and the appropriate art-known carboxylic acid.

12. 3-Cyano-2-{3-[2-(1,1-difluoro-methoxy)-phenyl]-propanoylamino}-4,7-dihydro-5H-thieno[2,3-c]pyridine-6-carboxylic acid ethyl ester

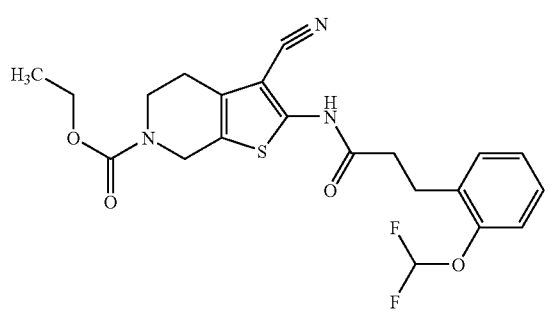

MS: calc.: C,21; H,21; F,2; N,3; O,4; S, (449,48) fnd.: 450 [M+H].

13. 3-Cyano-2-[3-(3,5-dimethoxy-phenyl)-propanoylamino]-4,7-dihydro-5H-thieno[2,3-c]pyridine-6-carboxylic acid ethyl ester

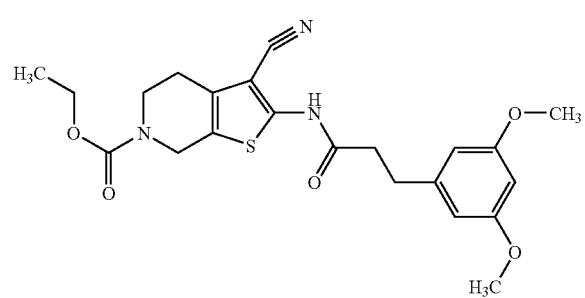

MS: calc.: C,22; H,25; N,3; O,5; S, (443,53) fnd.: 444,2 [M+H].

14. 2-[3-(5-Bromo-2,3-dimethoxy-phenyl)-propanoylamino]-3-cyano-4,7-dihydro-5H-thieno[2,3-c]pyridine-6-carboxylic acid ethyl ester

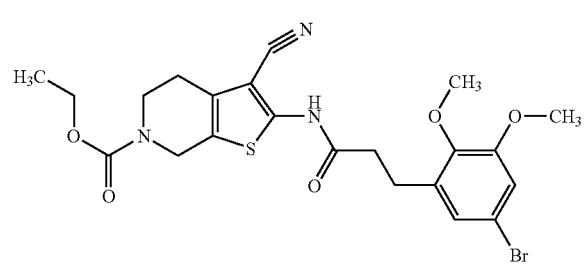

MS: calc.: C,22; H,24; Br N,3; O,5; S, (522,42) fnd.: 519,9 [M−H].

15. 2-[3-(5-Bromo-2-methoxy-phenyl)-propanoylamino]-3-cyano-4,7-dihydro-5H-thieno[2,3-c]pyridine-6-carboxylic acid ethyl ester

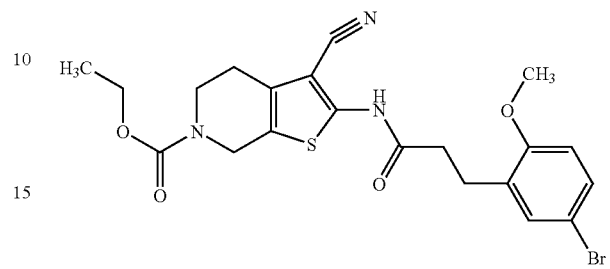

MS: calc.: C,21; H,22, Br N,3; O,4; S, (492,4) fnd.: 492 [M+H].

16. 3-Cyano-2-[3-(2,3-diethoxy-phenyl)-propanoylamino]-4,7-dihydro-5H-thieno[2,3-c]pyridine-6-carboxylic acid ethyl ester

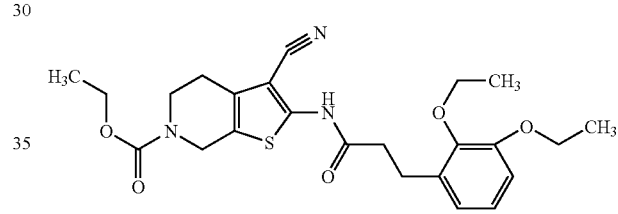

MS: calc.: C,24; H,29; N,3; O,5; S, (471,58) fnd.: 472,1 [M+H].

17. 3-Cyano-2-[3-(2-methoxy-5-methyl-phenyl)-propanoylamino]-4,7-dihydro-5H-thieno[2,3-c]pyridine-6-carboxylic acid ethyl ester

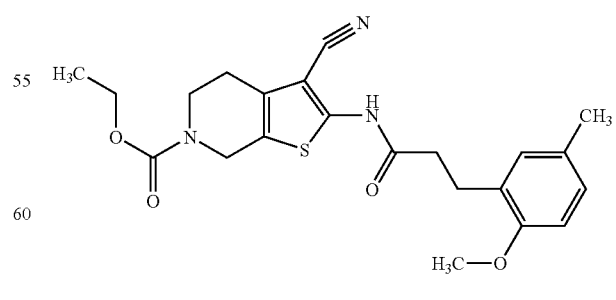

MS: calc.: C,22; H,25; N,3; O,4; S, (427,53) fnd.: 428,1 [M+H].

18. 3-Cyano-2-[3-(2,2,3,3-tetrafluoro-6-methoxy-2,
3-dihydro-benzo[1,4]dioxin-5-yl)-propanoylamino]-
4,7-dihydro-5H-thieno[2,3-c]pyridine-6-carboxylic
acid ethyl ester

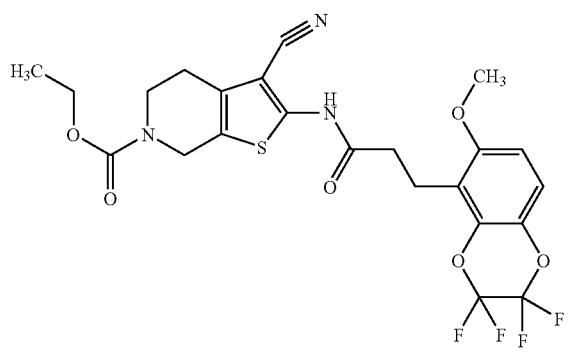

MS: calc.: C,23; H,21; F,4; N,3; O,6; S, (543,5) fnd.: 544 [M+H].

19. 3-Cyano-2-[3-(2-ethoxyphenyl)-propanoy-
lamino]-4,7-dihydro-5H-thieno[2,3-c]-pyridine-6-
carboxylic acid ethyl ester

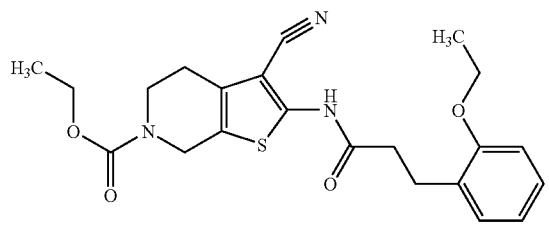

MS: calc.: C,22; H,25; N,3; O,4; S, (427,53) fnd.: 428 [M+H].

The following compounds can be prepared according to the carbamate preparation described in the general procedure D starting from N-(3-cyano-4,5,6,7-tetrahydro-thieno[2,3-c]pyridine-2-yl)-3-(2-ethoxy-phenyl)-propionamide (compound A4) and the appropriate art-known alcohol or chloroformiate.

20. 3-Cyano-2-[3-(2-ethoxy-phenyl)-propanoy-
lamino]-4,7-dihydro-5H-thieno[2,3-c]pyridine-6-
carboxylic acid 2,2-dimethyl-[1,3]dioxolan-4-ylm-
ethyl ester

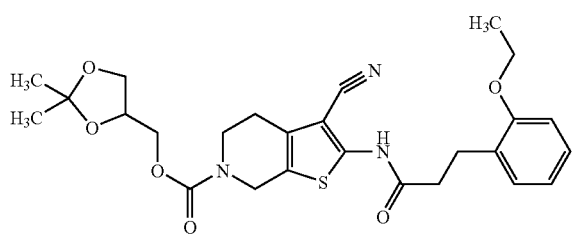

MS: calc.: C,26; H,31; N,3; O,6; S, (513,62) fnd.: 513,8 [M+H].

21. 3-Cyano-2-[3-(2-ethoxy-phenyl)-propanoy-
lamino]-4,7-dihydro-5H-thieno[2,3-c]pyridine-6-
carboxylic acid 2-benzyloxy-ethyl ester

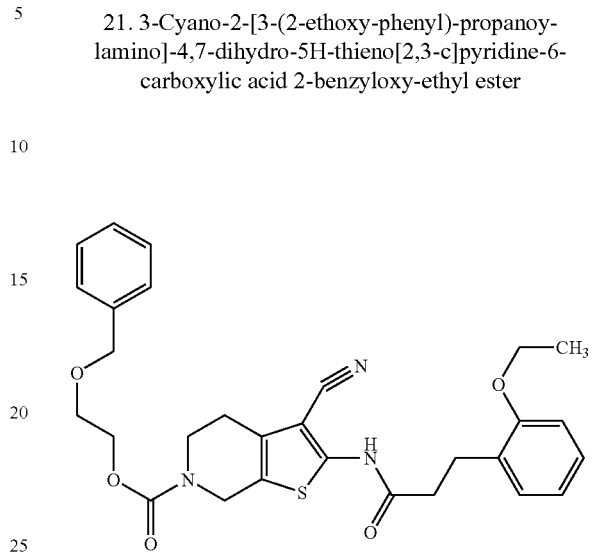

MS: calc.: C,29; H,31; N,3; O,5; S, (533,65) fnd.: 534 [M+H].

22. 3-Cyano-2-[3-(2-ethoxy-phenyl)-propiony-
lamino]-4,7-dihydro-5H-thieno[2,3-c]pyridine-6-
carboxylic acid 2-acetoxy-ethyl ester The following compounds can be prepared according to the carbamate preparation described in the general procedure D starting from N-(3-cyano-4,5,6,7-tetrahydro-thieno[2,3-c]pyridine-2-yl)-3-(2-methoxy-phenyl)-propionamide (compound A3) and the appropriate art-known alcohol or chloroformiate.

23. 3-Cyano-2-[3-(2-methoxy-phenyl)-propanoy-
lamino]-4,7-dihydro-5H-thieno[2,3-c]pyridine-6-
carboxylic acid 2-methoxy-ethyl ester

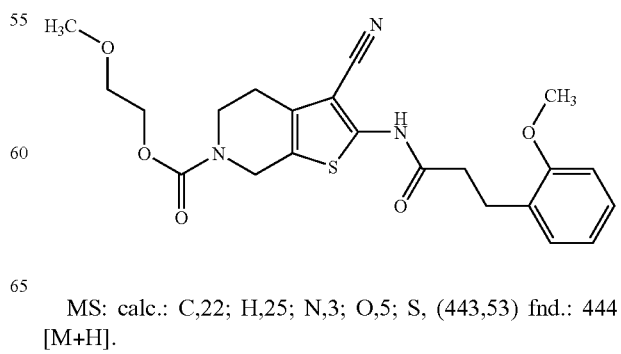

MS: calc.: C,22; H,25; N,3; O,5; S, (443,53) fnd.: 444 [M+H].

24. 3-Cyano-2-[3-(2-methoxy-phenyl)-propanoylamino]-4,7-dihydro-5H-thieno[2,3-c]pyridine-6-carboxylic acid 2-benzyloxy-ethyl ester

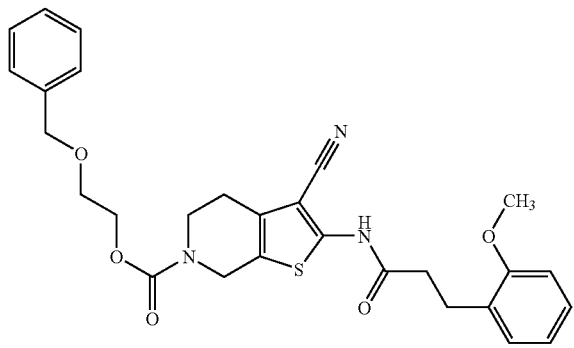

MS: calc.: C,28; H,29; N,3; O,5; S, (519,62) fnd.: 520,2 [M+H].

25. 3-Cyano-2-[3-(2-methoxy-phenyl)-propanoylamino]-4,7-dihydro-5H-thieno[2,3-c]pyridine-6-carboxylic acid 2-pyridin-2-yl-ethyl ester

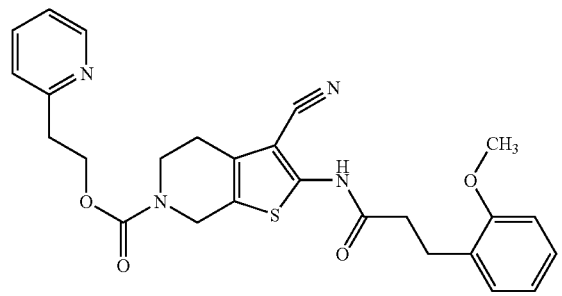

MS: calc.: C,26; H,26; N,4; O,4; S, (490,59) fnd.: 491,2 [M+H].

26. 3-Cyano-2-[3-(2-methoxy-phenyl)-propanoylamino]-4,7-dihydro-5H-thieno[2,3-c]pyridine-6-carboxylic acid pyridin-2-ylmethyl ester

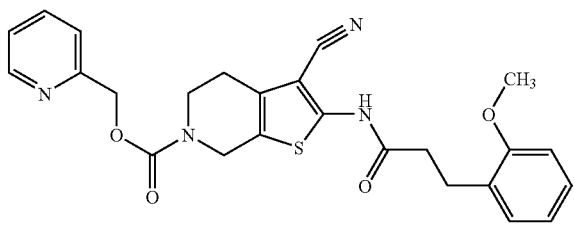

MS: calc.: C,25; H,24; N,4; O,4; S, (476,56) fnd.: 477,1 [M+H].

27. 3-Cyano-2-[3-(2-methoxy-phenyl)-propanoylamino]-4,7-dihydro-5H-thieno[2,3-c]pyridine-6-carboxylic acid pyridin-3-ylmethyl ester

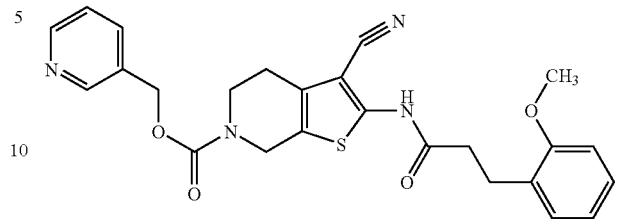

MS: calc.: C,25; H,24; N,4; O,4; S, (476,56) fnd.: 477,2 [M+H].

28. 3-Cyano-2-[3-(2-methoxy-phenyl)-propanoylamino]-4,7-dihydro-5H-thieno[2,3-c]pyridine-6-carboxylic acid pyridin-4-ylmethyl ester

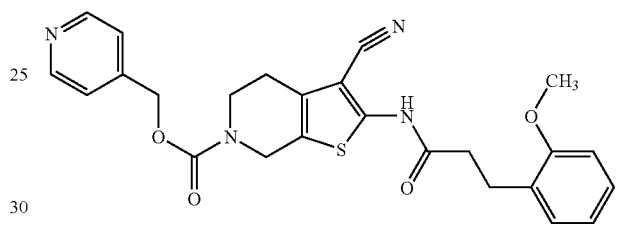

MS: calc.: C,25; H,24; N,4; O,4; S, (476,56) fnd.: 477,2 [M+H].

29. 3-Cyano-2-[3-(3-methoxy-phenyl)-propanoylamino]-4,7-dihydro-5H-thieno[2,3-c]pyridine-6-carboxylic acid pyridin-2-ylmethyl ester

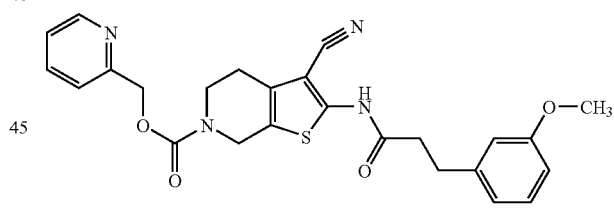

MS: calc.: C,25; H,24; N,4; O,4; S, (476,56) fnd.: 476,9 [M+H].

30. 3-Cyano-2-[3-(2-methoxy-phenyl)-propanoylamino]-4,7-dihydro-5H-thieno[2,3-c]pyridine-6-carboxylic acid 2,2-dimethyl-[1,3]dioxolan-4-ylmethyl ester

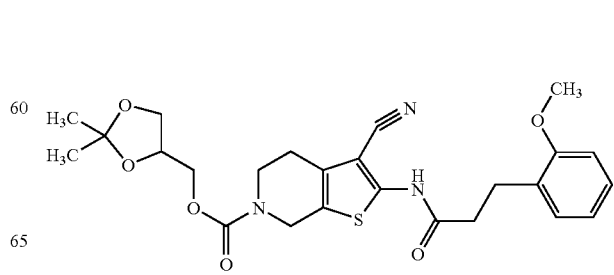

MS: calc.: C,25; H,29; N,3; O,6; S, (499,59) fnd.: 499,8 [M+H].

31. 3-Cyano-2-[3-(2-methoxy-phenyl)-propionylamino]-4,7-dihydro-5H-thieno[2,3-c]pyridine-6-carboxylic acid 2-acetoxy-ethyl ester

32. 3-Cyano-2-[3-(2-methoxy-phenyl)-propanoylamino]-4,7-dihydro-5H-thieno[2,3-c]pyridine-6-carboxylic acid 2,3-dihydroxy-propyl ester

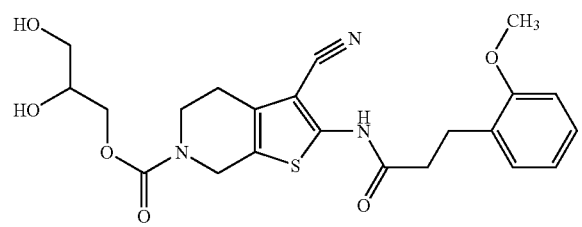

0,26 mmol of 3-Cyano-2-[3-(2-methoxy-phenyl)-propanoylamino]-4,7-dihydro-5H-thieno[2,3-c]pyridine-6-carboxylic acid 2,2-dimethyl-[1,3]dioxolan-4-ylmethyl ester (Example 30) are dissolved in 10 ml AcCN/H$_2$O (2/1) and 0.1 eq PTSA is added. After stirring over night, some triethylamine is added and the solvent removed. Recrystallization from ethanol gives the desired product in 80% yield.

MS: calc.: C,22; H,25; N,3; O,6; S, (459,53)fnd.: 460 [M+H].

33. 3-Cyano-2-[3-(2-ethoxy-phenyl)-propanoylamino]-4,7-dihydro-5H-thieno[2,3-c]pyridine-6-carboxylic acid 2,3-dihydroxy-propyl ester

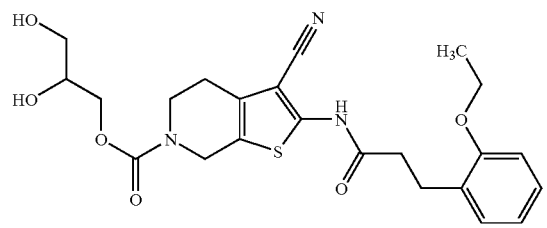

This compound is prepared similarly as Example 32 starting from 3-Cyano-2-[3-(2-ethoxy-phenyl)-propanoylamino]-4,7-dihydro-5H-thieno[2,3-c]pyridine-6-carboxylic acid 2,2-dimethyl-[1,3]dioxolan-4-ylmethyl ester (Example 20).

MS: calc.: C,23; H,27; N,3; O,6; S, (473,55) fnd.: 474 [M+H].

34. 3-Cyano-2-[3-(2-methoxy-phenyl)-propanoylamino]-4,7-dihydro-5H-thieno[2,3-c]pyridine-6-carboxylic acid 2-hydroxy-ethyl ester

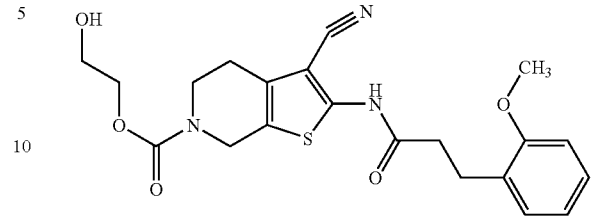

3-Cyano-2-[3-(2-methoxy-phenyl)-propionylamino]-4,7-dihydro-5H-thieno[2,3-c]pyridine-6-carboxylic acid 2-acetoxy-ethyl ester (Example 31) is stirred in 1N NaOH over night at room temperature. After acidification with aqueous HCl the precipitated product is filtered off and recristalized from ethanol.

MS: calc.: C,21; H,23; N,3; O,5; S, (429,5) fnd.: 430,1 [M+H].

35. 3-Cyano-2-[3-(2-ethoxy-phenyl)-propanoylamino]-4,7-dihydro-5H-thieno[2,3-c]pyridine-6-carboxylic acid 2-hydroxy-ethyl ester

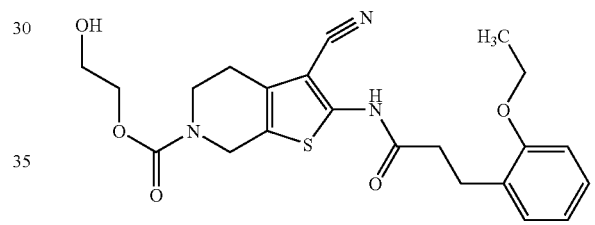

This compound is prepared similarly as Example 34 starting from 3-Cyano-2-[3-(2-ethoxy-phenyl)-propionylamino]-4,7-dihydro-5H-thieno[2,3-c]pyridine-6-carboxylic acid 2-acetoxy-ethyl ester (Example 22).

MS: calc.: C,22; H,25; N,3; O,5; S, (443,53) fnd.: 444 [M+H].

Using similar procedures to those described herein but with suitable choice of starting materials (which are known or which can be obtained according to procedures customary to the skilled person or described herein, or analogously or similarly thereto), the following compounds can be prepared.

36. 3-Cyano-2-[3-(3-methoxy-phenyl)-propanoylamino]-4,7-dihydro-5H-thieno[2,3-c]pyridine-6-carboxylic acid pyridin-3-ylmethyl ester

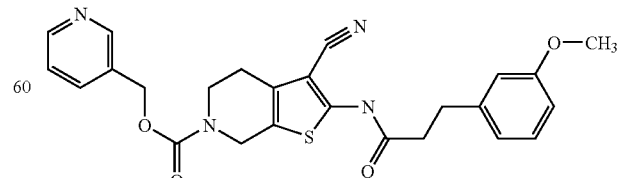

MS: calc.: C,25; H,24; N,4; O,4; S, (476,56) fnd.: 477,3 [M+H].

37. 3-Cyano-2-[3-(3-methoxy-phenyl)-propanoylamino]-4,7-dihydro-5H-thieno[2,3-c]pyridine-6-carboxylic acid pyridin-4-ylmethyl ester

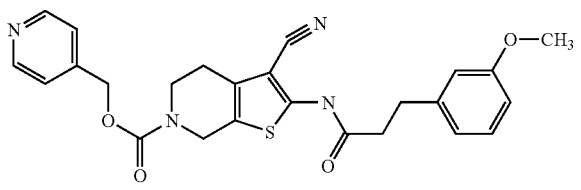

MS: calc.: C,25; H,24; N,4; O,4; S, (476,56) fnd.: 477,3 [M+H].

38. 3-Cyano-2-[3-(3-methoxy-phenyl)-propanoylamino]-4,7-dihydro-5H-thieno[2,3-c]pyridine-6-carboxylic acid 2-pyridin-2-yl-ethyl ester

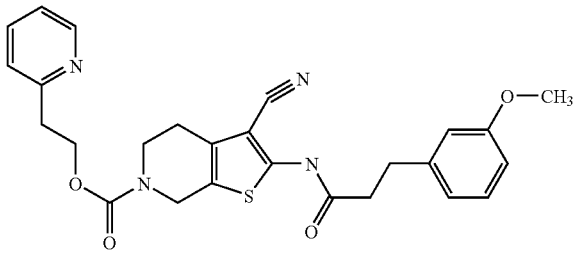

MS: calc.: C,26; H,26; N,4; O,4; S, (490,59) fnd.: 491,2 [M+H].

39. 3-Cyano-2-[3-(2-trifluoromethoxy-phenyl)-propanoylamino]-4,7-dihydro-5H-thieno[2,3-c]pyridine-6-carboxylic acid ethyl ester

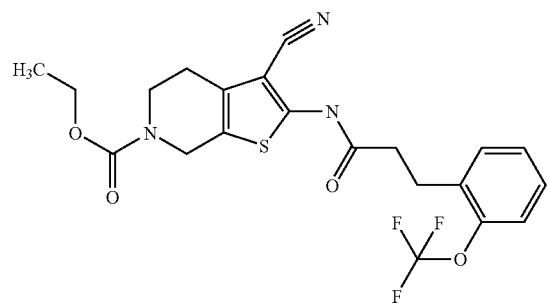

MS: calc.: C,21; H,20; F,3; N,3; O,4; S, (467,47) fnd.: 468 [M+H].

40. 3-Cyano-2-[3-(2-ethoxy-phenyl)-propanoylamino]-4,7-dihydro-5H-thieno[2,3-c]pyridine-6-carboxylic acid 2-methoxy-ethyl ester

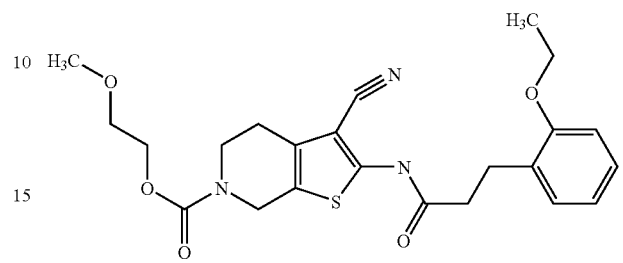

MS: calc.: C,23; H,27; N,3; O,5; S, (457,55) fnd.: 458,1 [M+H].

41. 3-Cyano-2-[3-(2-ethoxy-phenyl)-propanoylamino]-4,7-dihydro-5H-thieno[2,3-c]pyridine-6-carboxylic acid pyridin-2-ylmethyl ester

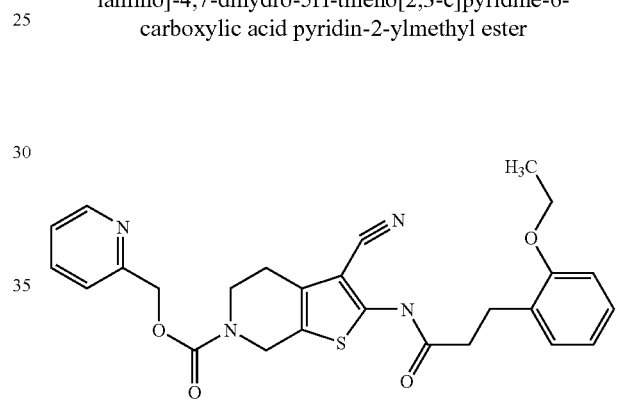

MS: calc.: C,26; H,26; N,4; O,4; S, (490,59) fnd.: 491,3 [M+H].

42. 3-Cyano-2-[3-(2-ethoxy-phenyl)-propanoylamino]-4,7-dihydro-5H-thieno[2,3-c]pyridine-6-carboxylic acid pyridin-3-ylmethyl ester

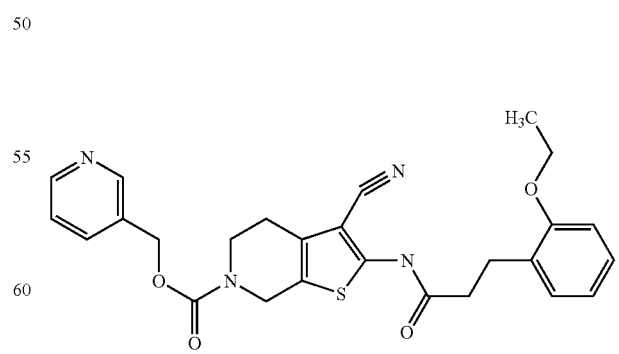

MS: calc.: C,26; H,26; N,4; O,4; S, (490,59) fnd.: 491,3 [M+H].

43. 3-Cyano-2-[3-(2-ethoxy-phenyl)-propanoylamino]-4,7-dihydro-5H-thieno[2,3-c]pyridine-6-carboxylic acid pyridin-4-ylmethyl ester

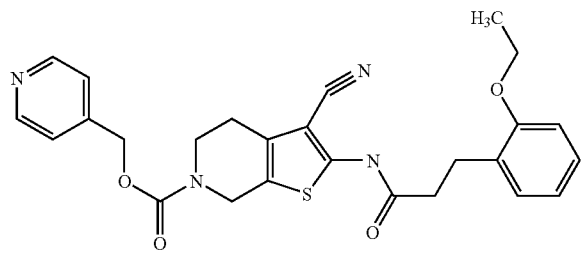

MS: calc.: C,26; H,26; N,4; O,4; S, (490,59) fnd.: 491,4 [M+H].

44. 3-Cyano-2-[3-(2-ethoxy-phenyl)-propanoylamino]-4,7-dihydro-5H-thieno[2,3-c]pyridine-6-carboxylic acid 2-pyridin-2-yl-ethyl ester

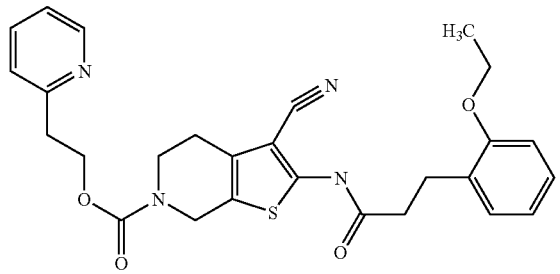

MS: calc.: C,27; H,28; N,4; O,4; S, (504,61) fnd.: 505,3 [M+H].

45. 3-Cyano-2-[3-(3-methoxy-phenyl)-propanoylamino]-4,7-dihydro-5H-thieno[2,3-c]pyridine-6-carboxylic acid 2-methoxy-ethyl ester

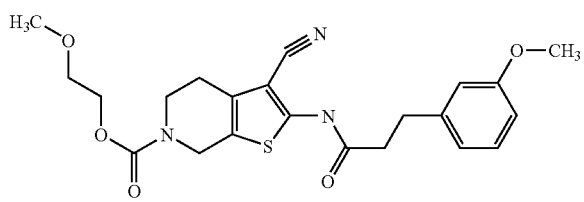

MS: calc.: C,22; H,25; N,3; O,5; S, (443,53) fnd.: 444,1 [M+H].

46. 3-Cyano-2-[3-(2,5-dimethoxy-phenyl)-propanoylamino]-4,7-dihydro-5H-thieno[2,3-c]pyridine-6-carboxylic acid 2-hydroxy-ethyl ester

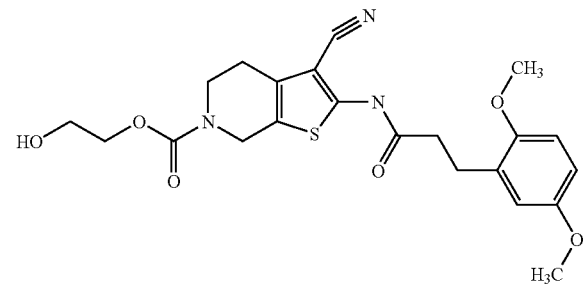

MS: calc.: C,22; H,25; N,3; O,6; S, (459,53) fnd.: 460,2 [M+H].

47. 3-Cyano-2-[3-(5-methoxy-2-methyl-phenyl)-propanoylamino]-4,7-dihydro-5H-thieno[2,3-c]pyridine-6-carboxylic acid 2-hydroxy-ethyl ester

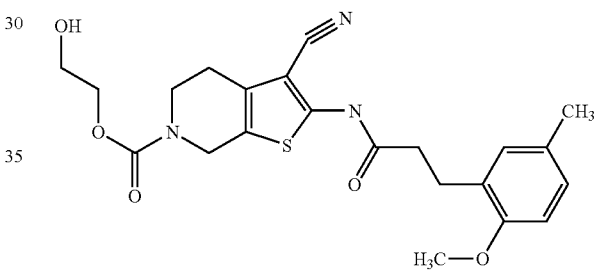

MS: calc.: C,22; H,25; N,3; O,5; S, (443,53) fnd.: 444,2 [M+H].

48. 3-Cyano-2-[3-(2-methoxy-5-methyl-phenyl)-propanoylamino]-4,7-dihydro-5H-thieno[2,3-c]pyridine-6-carboxylic acid 2-pyridin-2-yl-ethyl ester

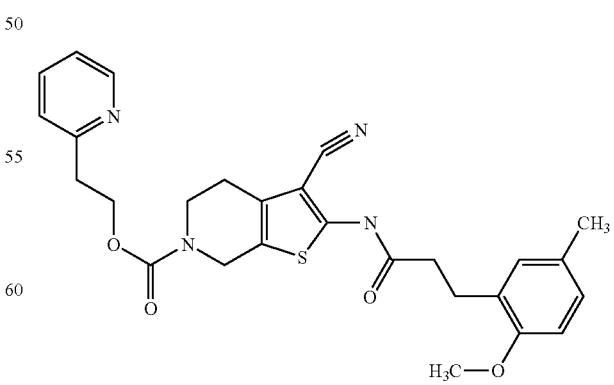

MS: calc.: C,27; H,28; N,4; O,4; S, (504,61) fnd.: 505,4 [M+H].

49. 3-Cyano-2-[(RS)-3-(2-methoxy-phenyl)-butanoylamino]-4,7-dihydro-5H-thieno[2,3-c]pyridine-6-carboxylic acid ethyl ester

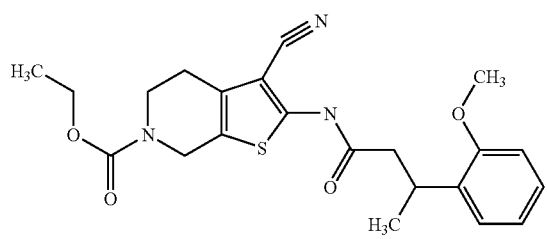

MS: calc.: C,22; H,25; N,3; O,4; S, (427,53) fnd.: 427,9 [M+H].

50. 3-Cyano-2-[3-(2,5-dimethoxy-phenyl)-propanoylamino]-4,7-dihydro-5H-thieno[2,3-c]pyridine-6-carboxylic acid pyridin-3-ylmethyl ester

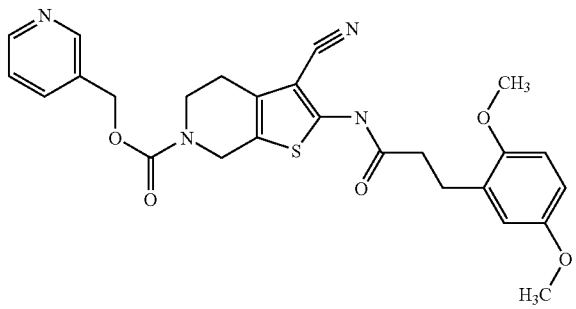

MS: calc.: C,26; H,26; N,4; O,5; S, (506,58) fnd.: 507,2 [M+H].

51. 3-Cyano-2-[3-(2-methoxy-5-methyl-phenyl)-propanoylamino]-4,7-dihydro-5H-thieno[2,3-c]pyridine-6-carboxylic acid pyridin-3-ylmethyl ester

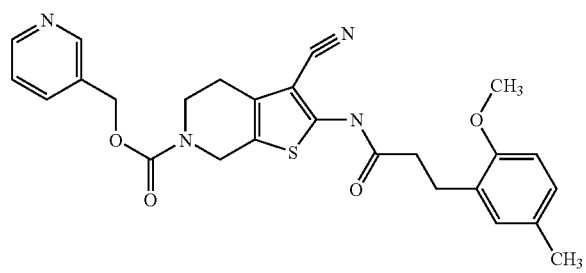

MS: calc.: C,26; H,26; N,4; O,4; S, (490,59) fnd.: 491,2 [M+H].

52. 3-Cyano-2-[3-(2-methoxy-5-methyl-phenyl)-propanoylamino]-4,7-dihydro-5H-thieno[2,3-c]pyridine-6-carboxylic acid 2,3-dihydroxy-propyl ester

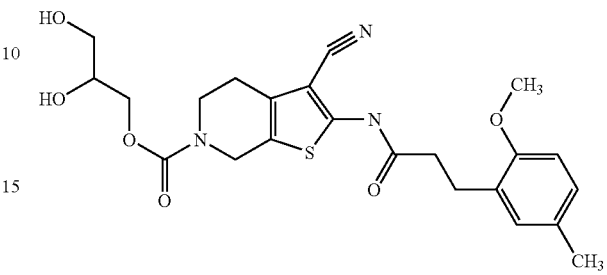

MS: calc.: C,23; H,27; N,3; O,6; S, (473,55) fnd.: 474 [M+H].

53. 3-Cyano-2-[3-(3-methoxy-phenyl)-propanoylamino]-4,7-dihydro-5H-thieno[2,3-c]pyridine-6-carboxylic acid 2-hydroxy-ethyl ester

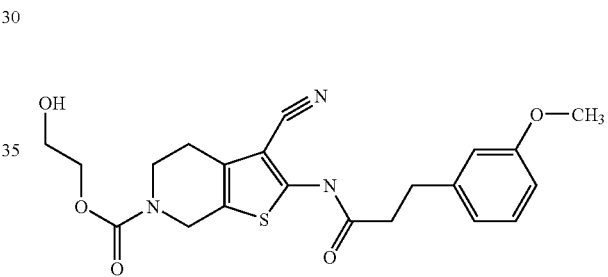

MS: calc.: C,21; H,3; N,3; O,5; S, (429,5) fnd.: 430 [M+H].

54. 3-Cyano-2-({1-[2-(2-methoxy-5-methyl-phenyl)-cyclopropyl]-methanoyl}-amino)-4,7-dihydro-5H-thieno[2,3-c]pyridine-6-carboxylic acid ethyl ester

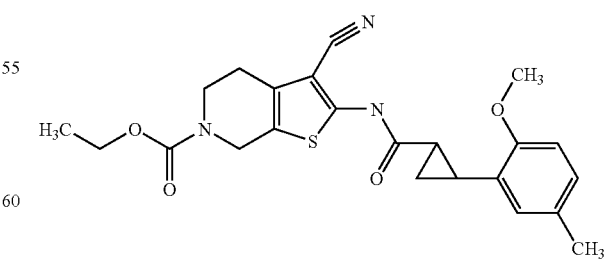

MS: calc.: C,23; H,25; N,3; O,4; S, (439,54) fnd.: 439,9 [M+H].

55. 3-Cyano-2-[3-(2,5-dimethoxy-phenyl)-propanoylamino]-4,7-dihydro-5H-thieno[2,3-c]pyridine-6-carboxylic acid 2-pyridin-2-yl-ethyl ester

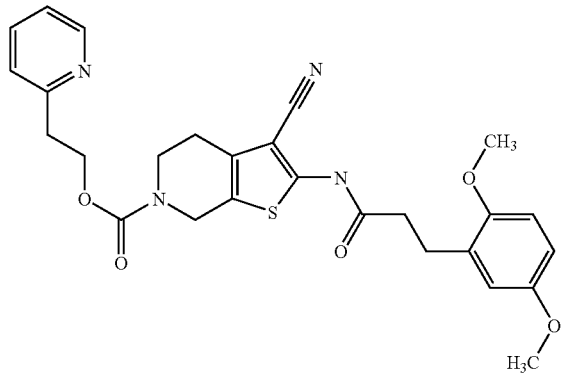

MS: calc.: C,27; H,28; N,4; O,5; S, (520,61) fnd.: 521,2 [M+H].

56. 3-Cyano-2-[3-(2-methoxy-5-methyl-phenyl)-propanoylamino]-4,7-dihydro-5H-thieno[2,3-c]pyridine-6-carboxylic acid 2-morpholin-4-yl-ethyl ester

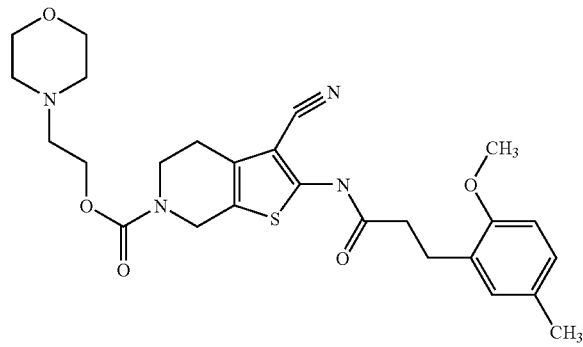

MS: calc.: C,26; H,32; N,4; O,5; S, (512,63) fnd.: 513,2 [M+H].

57. 3-Cyano-2-[3-(2-methoxy-5-methyl-phenyl)-propanoylamino]-4,7-dihydro-5H-thieno[2,3-c]pyridine-6-carboxylic acid 4-methoxy-pyridin-3-ylmethyl ester

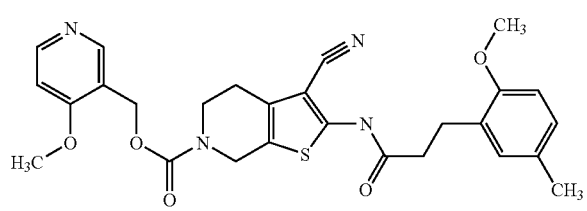

MS: calc.: C,27; H,28; N,4; O,5; S, (520,61) fnd.: 521,2 [M+H].

58. 3-Cyano-2-[3-(3-methoxy-phenyl)-propanoylamino]-4,7-dihydro-5H-thieno[2,3-c]pyridine-6-carboxylic acid 2-imidazol-1-yl-ethyl ester

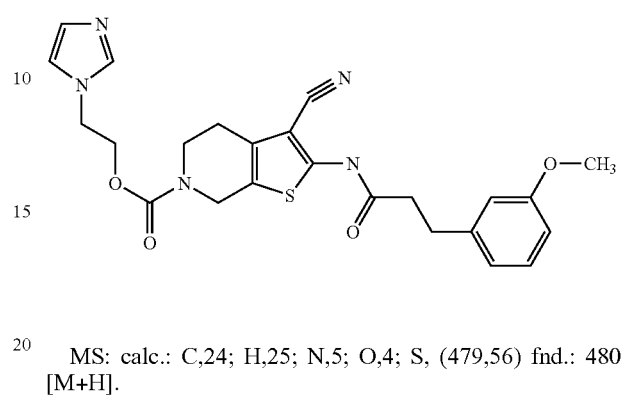

MS: calc.: C,24; H,25; N,5; O,4; S, (479,56) fnd.: 480 [M+H].

59. 3-Cyano-2-[3-(3-ethoxy-phenyl)-propanoylamino]-4,7-dihydro-5H-thieno[2,3-c]pyridine-6-carboxylic acid methoxycarbonylmethyl ester

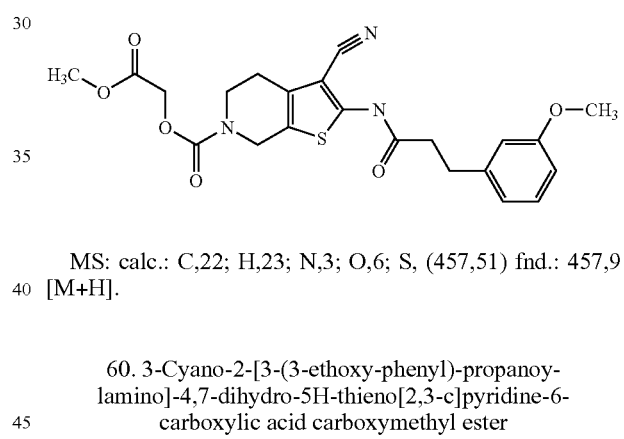

MS: calc.: C,22; H,23; N,3; O,6; S, (457,51) fnd.: 457,9 [M+H].

60. 3-Cyano-2-[3-(3-ethoxy-phenyl)-propanoylamino]-4,7-dihydro-5H-thieno[2,3-c]pyridine-6-carboxylic acid carboxymethyl ester

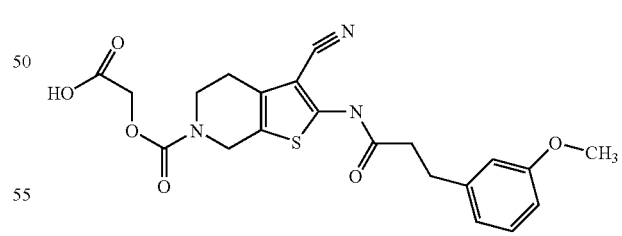

The title compound is prepared from Example 59 by art-known saponification reaction.

MS: calc.: C,21; H,21; N,3; O,6; S, (443,48) fnd.: 443,9 [M+H].

The following compounds 61 to 66, 73, 74, 76 to 103, 104 to 148, 156 to 158, 169 to 180, 182, and 185 to 204 are prepared according to general procedure D' starting from the appropriate starting compounds A3 to A42 and the appropriate alcohols, which are known or which can be obtained according to procedures customary to the skilled person or described herein, or analogously or similarly thereto.

Using similar procedures to those described herein but with suitable choice of starting materials (which are known or which can be obtained according to procedures customary to the skilled person or described herein, or analogously or similarly thereto), the following compounds 67 to 72, and 75 may be prepared.

The following compounds 149 to 155, and 181 can be obtained from the corresponding methyl esters by art-known saponification reaction using for example LiOH or NaOH.

The following compounds 159 to 164, and 183 can be obtained from the corresponding acetonides by art-known deacetalization reaction using for example PTSA or CSA in AcCN/water. After neutralization of the reaction mixture, the solvent is removed and the remaining residue subjected to chromatography (flash or HPLC).

The following compounds 165 to 168, and 184 can be obtained from the corresponding acetates by art-known removal of the acetyl function using for example LiOH or NaOH.

61. 3-Cyano-2-[3-(2-methoxy-phenyl)-propanoy-lamino]-4,7-dihydro-5H-thieno[2,3-c]pyridine-6-carboxylic acid 2-pyridin-3-yl-ethyl ester

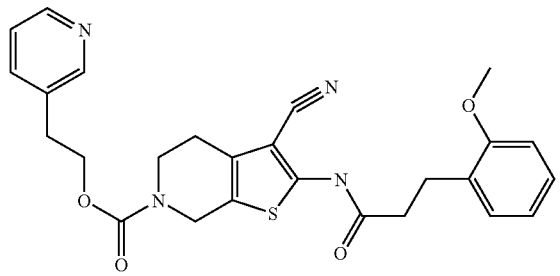

MS: calc.: C,26; H,26; N,4; O,4; S, (490.59) fnd.: 491,0 [M+H].

62. 3-Cyano-2-[3-(2-methoxy-phenyl)-propanoy-lamino]-4,7-dihydro-5H-thieno[2,3-c]pyridine-6-carboxylic acid 2-pyridin-4-yl-ethyl ester

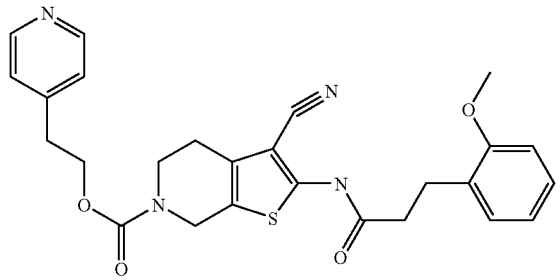

MS: calc.: C,26; H,26; N,4; O,4; S, (490.59) fnd.: 491,2 [M+H].

63. 3-Cyano-2-[3-(3-methoxy-phenyl)-propanoy-lamino]-4,7-dihydro-5H-thieno[2,3-c]pyridine-6-carboxylic acid 2-pyridin-3-yl-ethyl ester

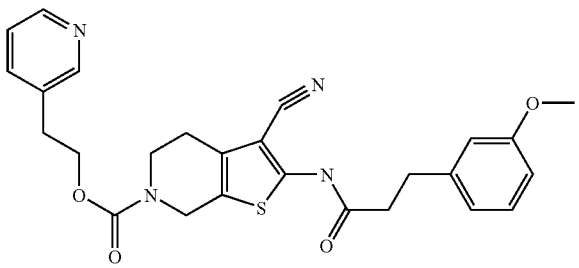

MS: calc.: C,26; H,26; N,4; O,4; S, (490.59) fnd.: 491,0 [M+H].

64. 3-Cyano-2-[3-(3-methoxy-phenyl)-propanoy-lamino]-4,7-dihydro-5H-thieno[2,3-c]pyridine-6-carboxylic acid 2-pyridin-4-yl-ethyl ester

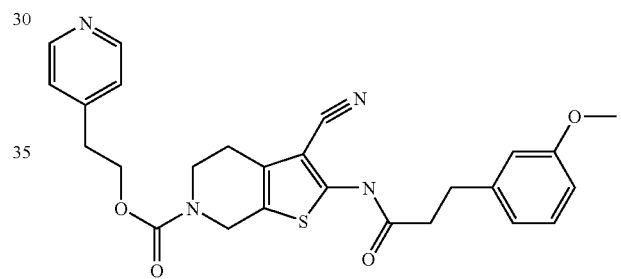

MS: calc.: C,26; H,26; N,4; O,4; S, (490.59) fnd.: 491,0 [M+H].

65. 3-Cyano-2-[3-(2-ethoxy-phenyl)-propanoy-lamino]-4,7-dihydro-5H-thieno[2,3-c]pyridine-6-carboxylic acid 2-pyridin-3-yl-ethyl ester

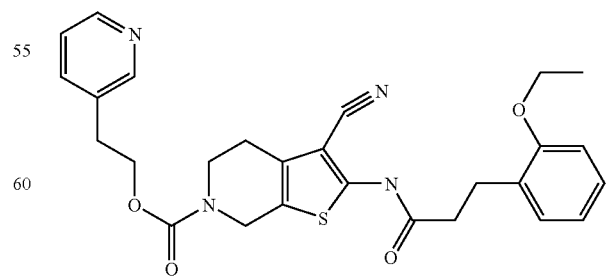

MS: calc.: C,27; H,28; N,4; O,4; S, (504.61) fnd.: 505,0 [M+H].

66. 3-Cyano-2-[3-(2-ethoxy-phenyl)-propanoy-
lamino]-4,7-dihydro-5H-thieno[2,3-c]pyridine-6-
carboxylic acid 2-pyridin-4-yl-ethyl ester

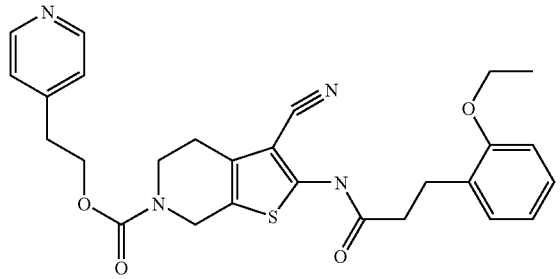

MS: calc.: C,27; H,28; N,4; O,4; S, (504.61) fnd.: 505,0 [M+H].

67. 3-Cyano-2-[3-(3-ethoxy-phenyl)-propanoy-
lamino]-4,7-dihydro-5H-thieno[2,3-c]pyridine-6-
carboxylic acid pyridin-2-ylmethyl ester 68. 3-Cyano-2-[3-(3-ethoxy-phenyl)-propanoy-
lamino]-4,7-dihydro-5H-thieno[2,3-c]pyridine-6-
carboxylic acid pyridin-3-ylmethyl ester 69. 3-Cyano-2-[3-(3-ethoxy-phenyl)-propanoy-
lamino]-4,7-dihydro-5H-thieno[2,3-c]pyridine-6-
carboxylic acid pyridin-4-ylmethyl ester 70. 3-Cyano-2-[3-(3-ethoxy-phenyl)-propanoy-
lamino]-4,7-dihydro-5H-thieno[2,3-c]pyridine-6-
carboxylic acid 2-pyridin-2-yl-ethyl ester 71. 3-Cyano-2-[3-(3-ethoxy-phenyl)-propanoy-
lamino]-4,7-dihydro-5H-thieno[2,3-c]pyridine-6-
carboxylic acid 2-pyridin-3-yl-ethyl ester 72. 3-Cyano-2-[3-(3-ethoxy-phenyl)-propanoy-
lamino]-4,7-dihydro-5H-thieno[2,3-c]pyridine-6-
carboxylic acid 2-pyridin-4-yl-ethyl ester 73. 3-Cyano-2-[3-(2-methoxy-phenyl)-propanoy-
lamino]-4,7-dihydro-5H-thieno[2,3-c]pyridine-6-
carboxylic acid 2-imidazol-1-yl-ethyl ester

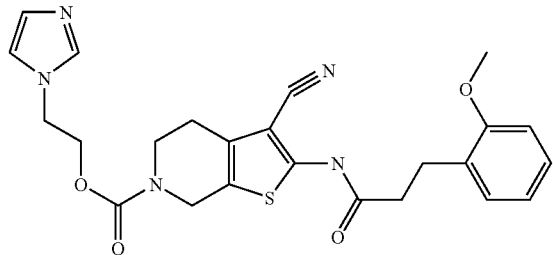

MS: calc.: C,24; H,25; N,5; O,4; S, (479.56) fnd.: 480,0 [M+H].

74. 3-Cyano-2-[3-(2-ethoxy-phenyl)-propanoy-
lamino]-4,7-dihydro-5H-thieno[2,3-c]pyridine-6-
carboxylic acid 2-imidazol-1-yl-ethyl ester

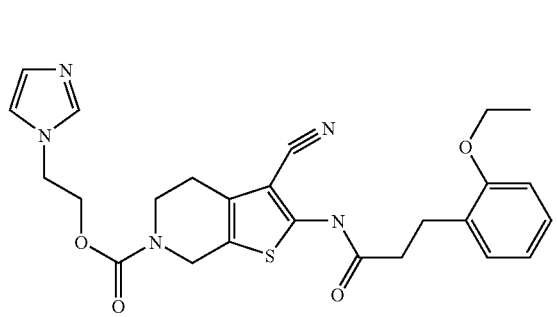

MS: calc.: C,25; H,27; N,5; O,4; S, (493.59) fnd.: 494,0 [M+H].

75. 3-Cyano-2-[3-(3-ethoxy-phenyl)-propanoy-
lamino]-4,7-dihydro-5H-thieno[2,3-c]pyridine-6-
carboxylic acid 2-imidazol-1-yl-ethyl ester 76. 3-Cyano-2-[(RS)-3-(2-methoxy-phenyl)-bu-
tanoylamino]-4,7-dihydro-5H-thieno[2,3-c]pyridine-
6-carboxylic acid 2-pyridin-2-yl-ethyl ester

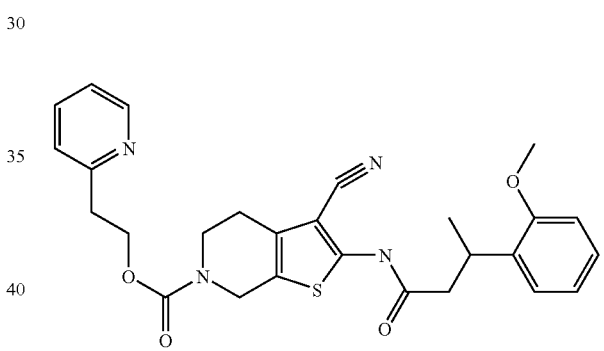

MS: calc.: C,27; H,28; N,4; O,4; S, (504.61) fnd.: 504,7 [M]..

77. 3-Cyano-2-[(RS)-3-(2-methoxy-phenyl)-bu-
tanoylamino]-4,7-dihydro-5H-thieno[2,3-c]pyridine-
6-carboxylic acid 2-pyridin-3-yl-ethyl ester

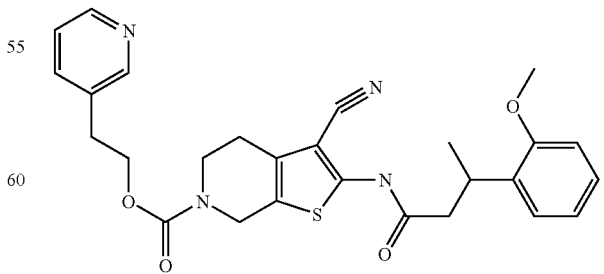

MS: calc.: C,27; H,28; N,4; O,4; S, (504.61) fnd.: 504,7 [M].

78. 3-Cyano-2-[(RS)-3-(2-methoxy-phenyl)-butanoylamino]-4,7-dihydro-5H-thieno[2,3-c]pyridine-6-carboxylic acid 2-pyridin-4-yl-ethyl ester

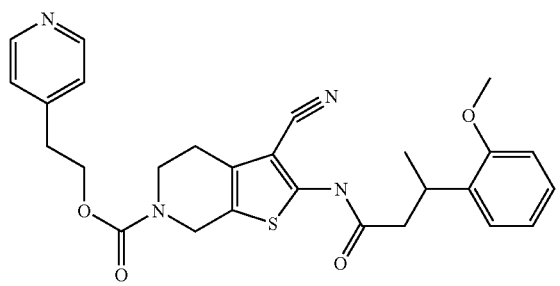

MS: calc.: C,27; H,28; N,4; O,4; S, (504.61) fnd.: 504,5 [M].

79. 3-Cyano-2-[(RS)-3-(3-methoxy-phenyl)-butanoylamino]-4,7-dihydro-5H-thieno[2,3-c]pyridine-6-carboxylic acid 2-pyridin-2-yl-ethyl ester

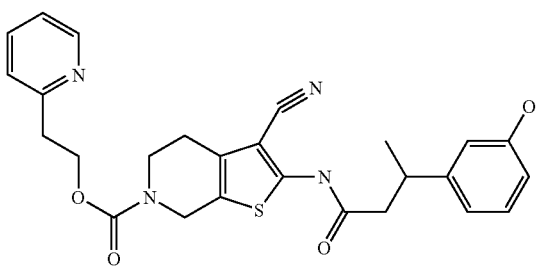

MS: calc.: C,27; H,28; N,4; O,4; S, (504.61) fnd.: 505,1 [M+H].

80. 3-Cyano-2-[(RS)-3-(3-methoxy-phenyl)-butanoylamino]-4,7-dihydro-5H-thieno[2,3-c]pyridine-6-carboxylic acid 2-pyridin-3-yl-ethyl ester

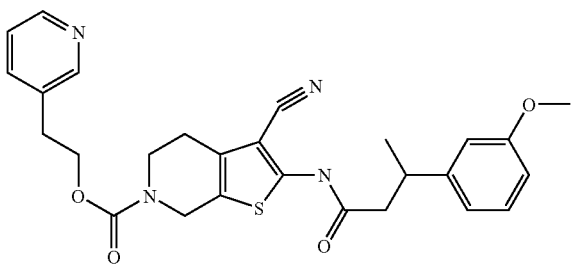

MS: calc.: C,27; H,28; N,4; O,4; S, (504.61) fnd.: 505,1 [M+H].

81. 3-Cyano-2-[(RS)-3-(3-methoxy-phenyl)-butanoylamino]-4,7-dihydro-5H-thieno[2,3-c]pyridine-6-carboxylic acid 2-pyridin-4-yl-ethyl ester

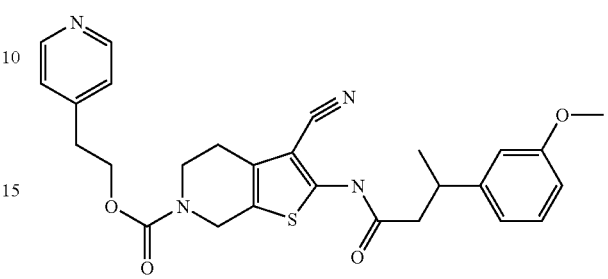

MS: calc.: C,27; H,28; N,4; O,4; S, (504.61) fnd.: 505,1 [M+H].

82. 3-Cyano-2-[(RS)-3-(2-methoxy-phenyl)-butanoylamino]-4,7-dihydro-5H-thieno[2,3-c]pyridine-6-carboxylic acid pyridin-2-ylmethyl ester

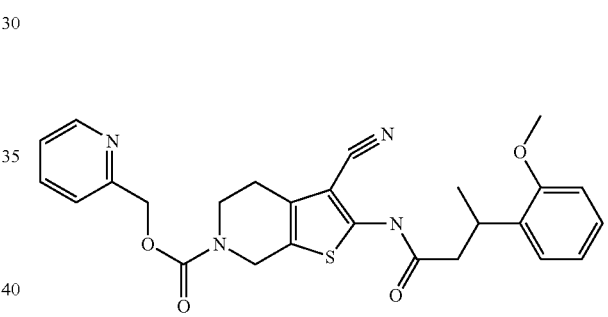

MS: calc.: C,26; H,26; N,4; O,4; S, (490.59) fnd.: 491,1 [M+H].

83. 3-Cyano-2-[(RS)-3-(2-methoxy-phenyl)-butanoylamino]-4,7-dihydro-5H-thieno[2,3-c]pyridine-6-carboxylic acid pyridin-3-ylmethyl ester

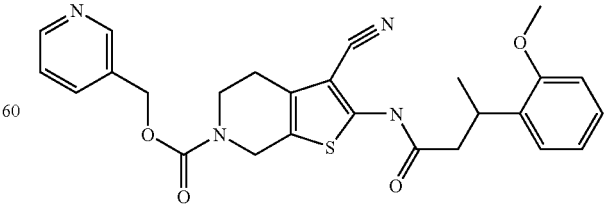

MS: calc.: C,26; H,26; N,4; O,4; S, (490.59) fnd.: 490,7 [M].

84. 3-Cyano-2-[(RS)-3-(2-methoxy-phenyl)-butanoylamino]-4,7-dihydro-5H-thieno[2,3-c]pyridine-6-carboxylic acid pyridin-4-ylmethyl ester

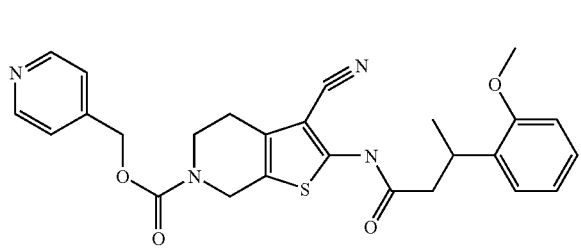

MS: calc.: C,26; H,26; N,4; O,4; S, (490.59) fnd.: 490,7 [M].

85. 3-Cyano-2-[(RS)-3-(3-methoxy-phenyl)-butanoylamino]-4,7-dihydro-5H-thieno[2,3-c]pyridine-6-carboxylic acid pyridin-2-ylmethyl ester

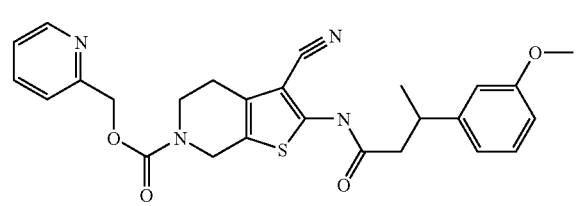

MS: calc.: C,26; H,26; N,4; O,4; S, (490.59) fnd.: 491,1 [M+H].

86. 3-Cyano-2-[(RS)-3-(3-methoxy-phenyl)-butanoylamino]-4,7-dihydro-5H-thieno[2,3-c]pyridine-6-carboxylic acid pyridin-3-ylmethyl ester

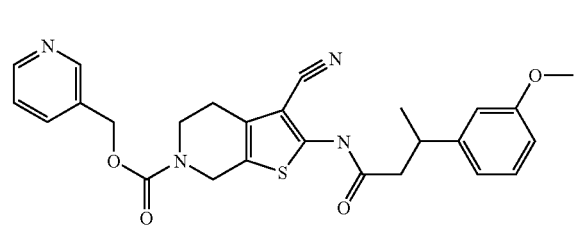

MS: calc.: C,26; H,26; N,4; O,4; S, (490.59) fnd.: 491,1 [M+H].

87. 3-Cyano-2-[(RS)-3-(3-methoxy-phenyl)-butanoylamino]-4,7-dihydro-5H-thieno[2,3-c]pyridine-6-carboxylic acid pyridin-4-ylmethyl ester

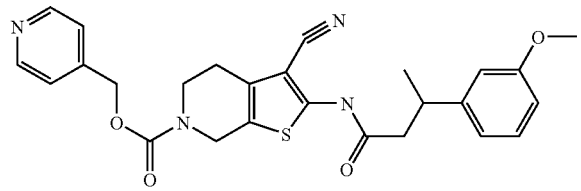

MS: calc.: C,26; H,26; N,4; O,4; S, (490.59) fnd.: 491,1 [M+H].

88. 3-Cyano-2-[(RS)-3-(2-ethoxy-phenyl)-butanoylamino]-4,7-dihydro-5H-thieno[2,3-c]pyridine-6-carboxylic acid 2-pyridin-2-yl-ethyl ester

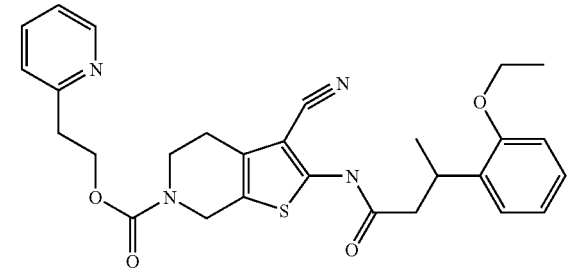

MS: calc.: C,28; H,30; N,4; O,4; S, (518.64) fnd.: 519,2 [M].

89. 3-Cyano-2-[(RS)-3-(2-ethoxy-phenyl)-butanoylamino]-4,7-dihydro-5H-thieno[2,3-c]pyridine-6-carboxylic acid 2-pyridin-3-yl-ethyl ester

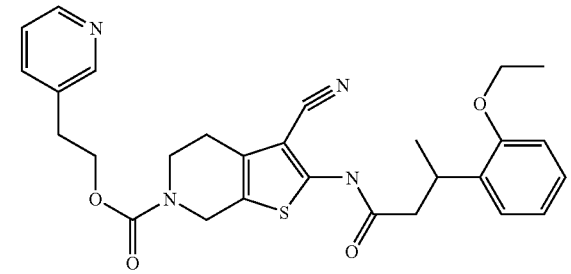

MS: calc.: C,28; H,30; N,4; O,4; S, (518.64) fnd.: 519,2 [M+H].

90. 3-Cyano-2-[(RS)-3-(2-ethoxy-phenyl)-butanoy-
lamino]-4,7-dihydro-5H-thieno[2,3-c]pyridine-6-
carboxylic acid 2-pyridin-4-yl-ethyl ester

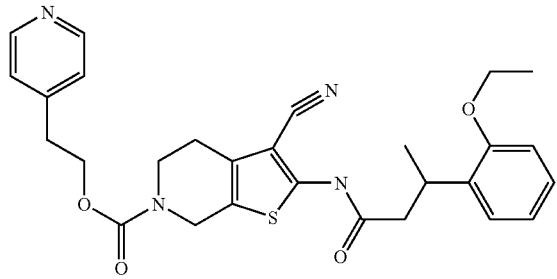

MS: calc.: C,28; H,30; N,4; O,4; S, (518.64) fnd.: 519,2 [M+H].

91. 3-Cyano-2-[(RS)-3-(2-ethoxy-phenyl)-butanoy-
lamino]-4,7-dihydro-5H-thieno[2,3-c]pyridine-6-
carboxylic acid pyridin-2-ylmethyl ester

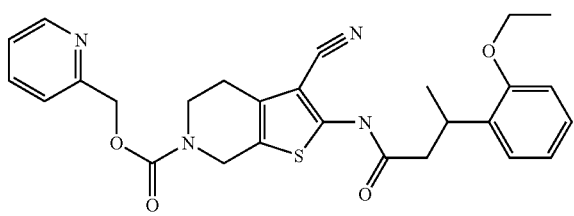

MS: calc.: C,27; H,28; N,4; O,4; S, (504.61) fnd.: 505,1 [M+H].

92. 3-Cyano-2-[(RS)-3-(2-ethoxy-phenyl)-butanoy-
lamino]-4,7-dihydro-5H-thieno[2,3-c]pyridine-6-
carboxylic acid pyridin-3-ylmethyl ester

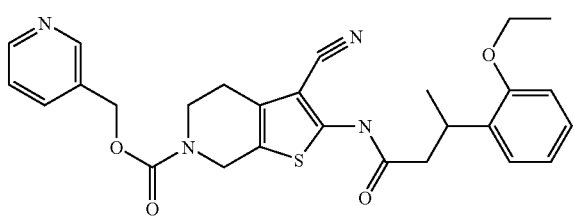

MS: calc.: C,27; H,28; N,4; O,4; S, (504.61) fnd.: 505,1 [M+H].

93. 3-Cyano-2-[(RS)-3-(2-ethoxy-phenyl)-butanoy-
lamino]-4,7-dihydro-5H-thieno[2,3-c]pyridine-6-
carboxylic acid pyridin-4-ylmethyl ester

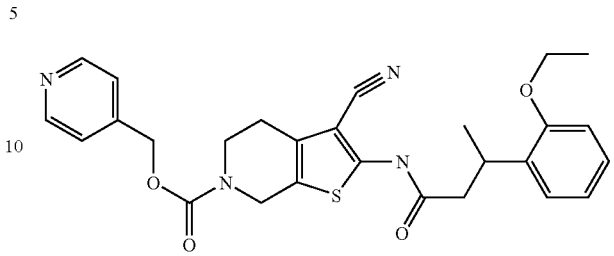

MS: calc.: C,27; H,28; N,4; O,4; S, (504.61) fnd.: 505,1 [M+H].

94. 3-Cyano-2-[(RS)-3-(3-ethoxy-phenyl)-butanoy-
lamino]-4,7-dihydro-5H-thieno[2,3-c]pyridine-6-
carboxylic acid pyridin-2-ylmethyl ester

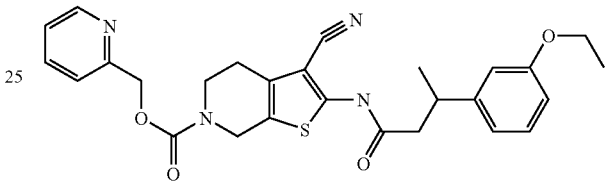

MS: calc.: C,27; H,28; N,4; O,4; S, (504.61) fnd.: 505,1 [M+H].

95. 3-Cyano-2-[(RS)-3-(3-ethoxy-phenyl)-butanoy-
lamino]-4,7-dihydro-5H-thieno[2,3-c]pyridine-6-
carboxylic acid pyridin-3-ylmethyl ester

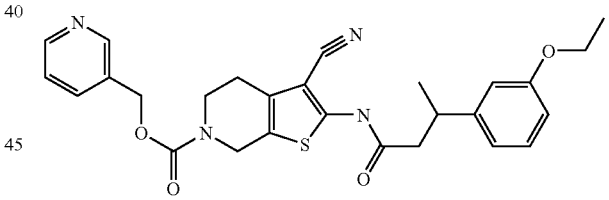

MS: calc.: C,27; H,28; N,4; O,4; S, (504.61) fnd.: 505,1 [M+H].

96. 3-Cyano-2-[(RS)-3-(3-ethoxy-phenyl)-butanoy-
lamino]-4,7-dihydro-5H-thieno[2,3-c]pyridine-6-
carboxylic acid pyridin-4-ylmethyl ester

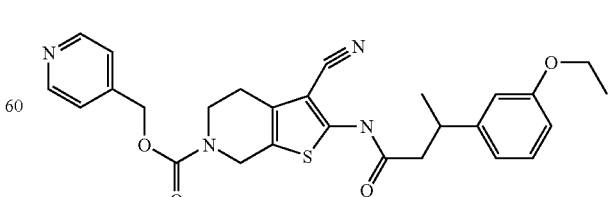

MS: calc.: C,27; H,28; N,4; O,4; S, (504.61) fnd.: 505,1 [M+H].

97. 3-Cyano-2-[(RS)-3-(3-ethoxy-phenyl)-butanoy-lamino]-4,7-dihydro-5H-thieno[2,3-c]pyridine-6-carboxylic acid 2-pyridin-2-yl-ethyl ester

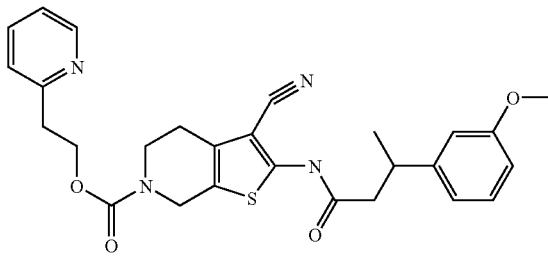

MS: calc.: C,28; H,30; N,4; O,4; S, (518.64) fnd.: 519,2 [M+H].

98. 3-Cyano-2-[(RS)-3-(3-ethoxy-phenyl)-butanoy-lamino]-4,7-dihydro-5H-thieno[2,3-c]pyridine-6-carboxylic acid 2-pyridin-3-yl-ethyl ester

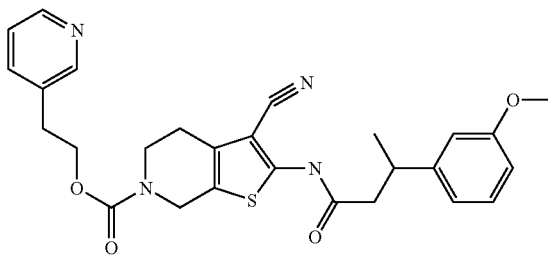

MS: calc.: C,28; H,30; N,4; O,4; S, (518.64) fnd.: 519,2 [M+H].

99. 3-Cyano-2-[(RS)-3-(3-ethoxy-phenyl)-butanoy-lamino]-4,7-dihydro-5H-thieno[2,3-c]pyridine-6-carboxylic acid 2-pyridin-4-yl-ethyl ester

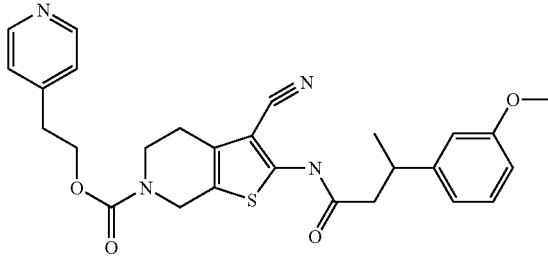

MS: calc.: C,28; H,30; N,4; O,4; S, (518.64) fnd.: 519,2 [M+H].

100. 3-Cyano-2-[(RS)-3-(2-methoxy-phenyl)-bu-tanoylamino]-4,7-dihydro-5H-thieno[2,3-c]pyridine-6-carboxylic acid 2-imidazol-1-yl-ethyl ester

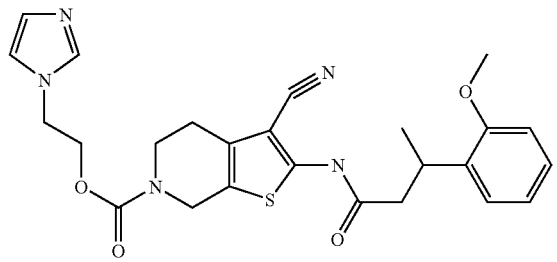

MS: calc.: C,25; H,27; N,5; O,4; S, (493.59) fnd.: 494,1 [M+H].

101. 3-Cyano-2-[(RS)-3-(3-methoxy-phenyl)-bu-tanoylamino]-4,7-dihydro-5H-thieno[2,3-c]pyridine-6-carboxylic acid 2-imidazol-1-yl-ethyl ester

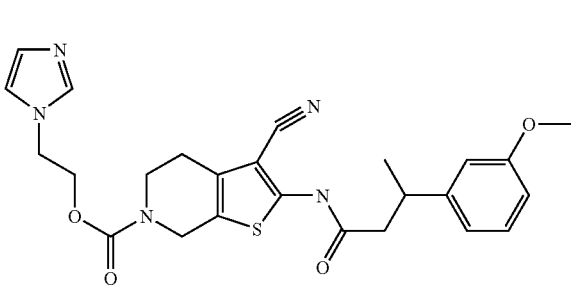

MS: calc.: C,25; H,27; N,5; O,4; S, (493.59) fnd.: 494,1 [M+H].

102. 3-Cyano-2-[(RS)-3-(2-ethoxy-phenyl)-butanoy-lamino]-4,7-dihydro-5H-thieno[2,3-c]pyridine-6-carboxylic acid 2-imidazol-1-yl-ethyl ester

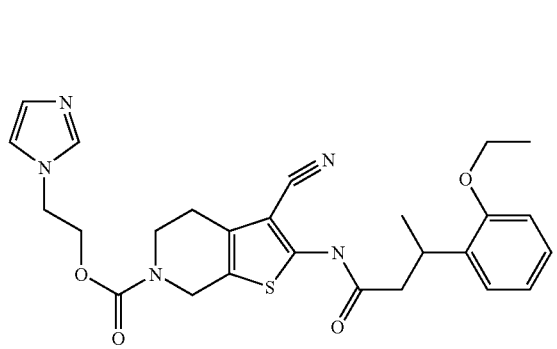

MS: calc.: C,26; H,29; N,5; O,4; S, (507.62) fnd.: 508,2 [M+H].

103. 3-Cyano-2-[(RS)-3-(3-ethoxy-phenyl)-butanoy-lamino]-4,7-dihydro-5H-thieno[2,3-c]pyridine-6-carboxylic acid 2-imidazol-1-yl-ethyl ester

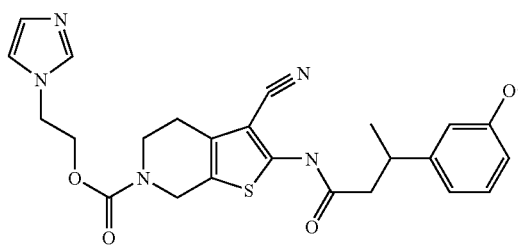

MS: calc.: C,26; H,29; N,5; O,4; S, (507.62) fnd.: 508,1 [M+H].

104. 3-Cyano-2-[3-(2-methoxy-5-methyl-phenyl)-propanoylamino]-4,7-dihydro-5H-thieno[2,3-c]pyridine-6-carboxylic acid pyridin-2-ylmethyl ester

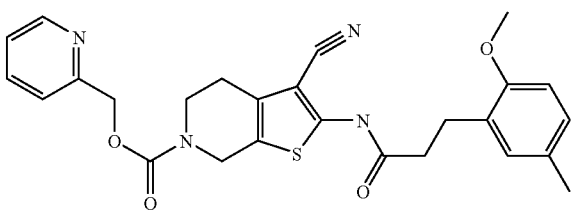

MS: calc.: C,26; H,26; N,4; O,4; S, (490.59) fnd.: 491,1 [M+H].

105. 3-Cyano-2-[3-(2-methoxy-5-methyl-phenyl)-propanoylamino]-4,7-dihydro-5H-thieno[2,3-c]pyridine-6-carboxylic acid pyridin-4-ylmethyl ester

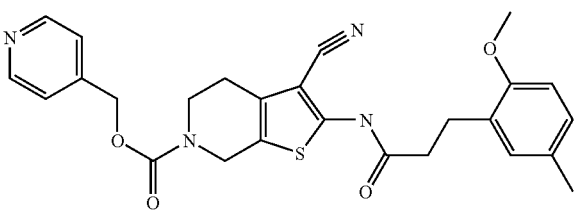

MS: calc.: C,26; H,26; N,4; O,4; S, (490.59) fnd.: 491,0 [M+H].

106. 3-Cyano-2-[3-(2-methoxy-5-methyl-phenyl)-propanoylamino]-4,7-dihydro-5H-thieno[2,3-c]pyridine-6-carboxylic acid 2-pyridin-4-yl-ethyl ester

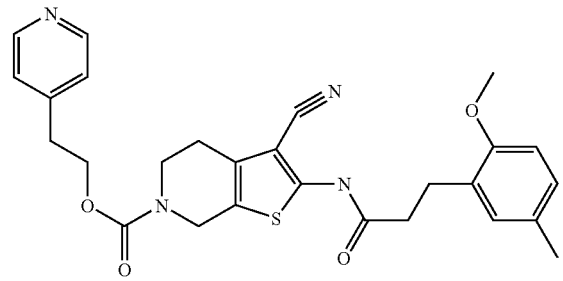

MS: calc.: C,27; H,28; N,4; O,4; S, (504.61) fnd.: 505,1 [M+H].

107. 3-Cyano-2-[(RS)-3-(2-methoxy-phenyl)-butanoylamino]-4,7-dihydro-5H-thieno[2,3-c]pyridine-6-carboxylic acid 1-methyl-1H-imidazol-2-ylmethyl ester

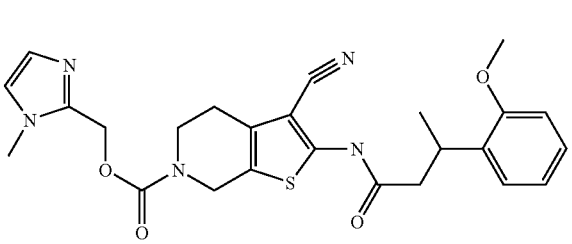

MS: calc.: C,25; H,27; N,5; O,4; S, (493.59) fnd.: 494,1 [M+H].

108. 3-Cyano-2-[(RS)-3-(2-methoxy-phenyl)-butanoylamino]-4,7-dihydro-5H-thieno[2,3-c]pyridine-6-carboxylic acid 3-methyl-3H-imidazol-4-ylmethyl ester

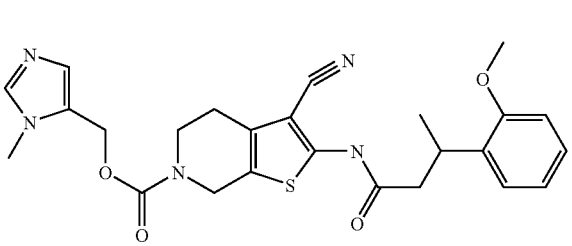

MS: calc.: C,25; H,27; N,5; O,4; S, (493.59) fnd.: 494,1 [M+H].

109. 3-Cyano-2-[(RS)-3-(2-methoxy-phenyl)-butanoylamino]-4,7-dihydro-5H-thieno[2,3-c]pyridine-6-carboxylic acid 2-(2-methyl-imidazol-1-yl)-ethyl ester

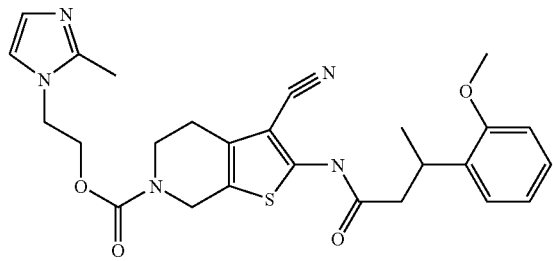

MS: calc.: C,26; H,29; N,5; O,4; S, (507.62) fnd.: 508,2 [M+H].

110. 3-Cyano-2-[(RS)-3-(2-ethoxy-phenyl)-butanoylamino]-4,7-dihydro-5H-thieno[2,3-c]pyridine-6-carboxylic acid 1-methyl-1H-imidazol-2-ylmethyl ester

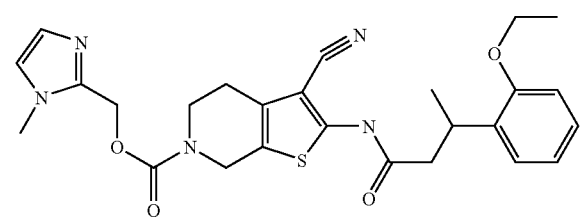

MS: calc.: C,26; H,29; N,5; O,4; S, (507.62) fnd.: 508,2 [M+H].

111. 3-Cyano-2-[(RS)-3-(2-ethoxy-phenyl)-butanoylamino]-4,7-dihydro-5H-thieno[2,3-c]pyridine-6-carboxylic acid 3-methyl-3H-imidazol-4-ylmethyl ester

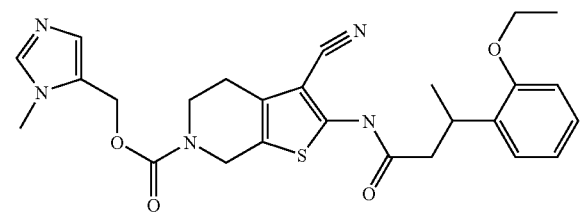

MS: calc.: C,26; H,29; N,5; O,4; S, (507.62)fnd.: 508,1 [M+H].

112. 3-Cyano-2-[(RS)-3-(2-ethoxy-phenyl)-butanoylamino]-4,7-dihydro-5H-thieno[2,3-c]pyridine-6-carboxylic acid 2-(2-methyl-imidazol-1-yl)-ethyl ester

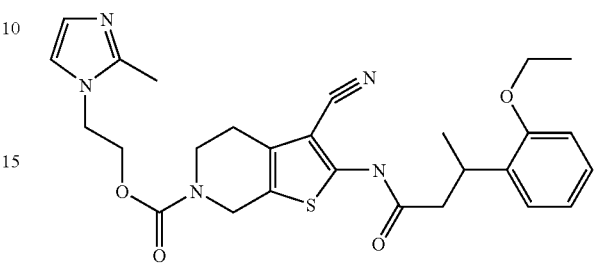

MS: calc.: C,27; H,31; N,5; O,4; S, (521.64) fnd.: 522,2 [M+H].

113. 3-Cyano-2-[(RS)-3-(3-methoxy-phenyl)-butanoylamino]-4,7-dihydro-5H-thieno[2,3-c]pyridine-6-carboxylic acid 1-methyl-1H-imidazol-2-ylmethyl ester

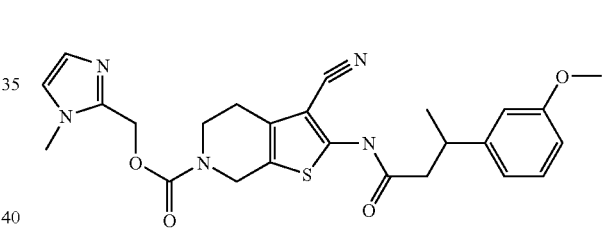

MS: calc.: C,25; H,27; N,5; O,4; S, (493.59) fnd.: 494,1 [M+H].

114. 3-Cyano-2-[(RS)-3-(3-methoxy-phenyl)-butanoylamino]-4,7-dihydro-5H-thieno[2,3-c]pyridine-6-carboxylic acid 3-methyl-3H-imidazol-4-ylmethyl ester

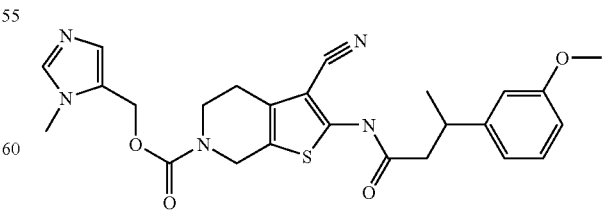

MS: calc.: C,25; H,27; N,5; O,4; S, (493.59) fnd.: 494,1 [M+H].

115. 3-Cyano-2-[(RS)-3-(3-methoxy-phenyl)-butanoylamino]-4,7-dihydro-5H-thieno[2,3-c]pyridine-6-carboxylic acid 2-(2-methyl-imidazol-1-yl)-ethyl ester

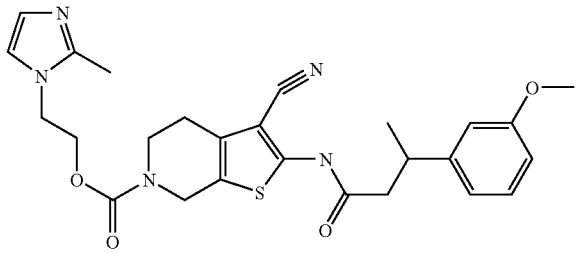

MS: calc.: C,26; H,29; N,5; O,4; S, (507.62) fnd.: 508,2 [M+H].

116. 3-Cyano-2-[(RS)-3-(3-ethoxy-phenyl)-butanoylamino]-4,7-dihydro-5H-thieno[2,3-c]pyridine-6-carboxylic acid 1-methyl-1H-imidazol-2-ylmethyl ester

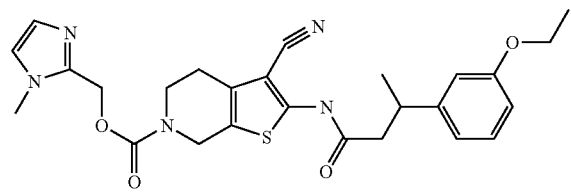

MS: calc.: C,26; H,29; N,5; O,4; S, (507.62) fnd.: 508,1 [M+H].

117. 3-Cyano-2-[(RS)-3-(3-ethoxy-phenyl)-butanoylamino]-4,7-dihydro-5H-thieno[2,3-c]pyridine-6-carboxylic acid 3-methyl-3H-imidazol-4-ylmethyl ester

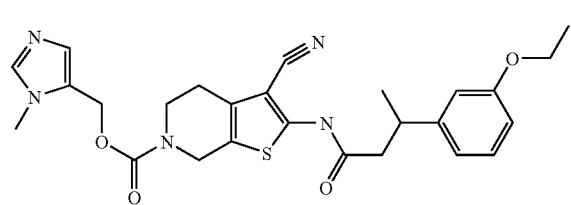

MS: calc.: C,26; H,29; N,5; O,4; S, (507.62)fnd.: 508,1 [M+H].

118. 3-Cyano-2-[(RS)-3-(3-ethoxy-phenyl)-butanoylamino]-4,7-dihydro-5H-thieno[2,3-c]pyridine-6-carboxylic acid 2-(2-methyl-imidazol-1-yl)-ethyl ester

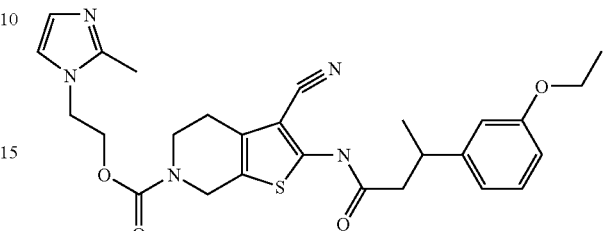

MS: calc.: C,27; H,31; N,5; O,4; S, (521.64) fnd.: 522,2 [M+H].

119. 3-Cyano-2-[3-(3-methoxy-phenyl)-propanoylamino]-4,7-dihydro-5H-thieno[2,3-c]pyridine-6-carboxylic acid 1-methyl-1H-imidazol-2-ylmethyl ester

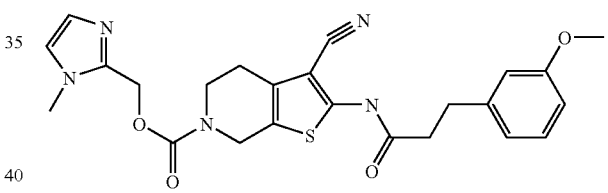

MS: calc.: C,24; H,25; N,5; O,4; S, (479.56) fnd.: 480,0 [M+H].

120. 3-Cyano-2-[3-(3-methoxy-phenyl)-propanoylamino]-4,7-dihydro-5H-thieno[2,3-c]pyridine-6-carboxylic acid 3-methyl-3H-imidazol-4-ylmethyl ester

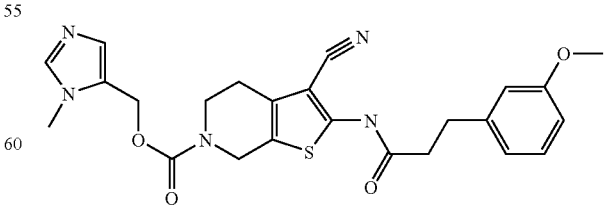

MS: calc.: C,24; H,25; N,5; O,4; S, (479.56) fnd.: 480,0 [M+H].

121. 3-Cyano-2-[3-(3-methoxy-phenyl)-propanoy-lamino]-4,7-dihydro-5H-thieno[2,3-c]pyridine-6-carboxylic acid 2-(2-methyl-imidazol-1-yl)-ethyl ester 124. 3-Cyano-2-[3-(2-methoxy-phenyl)-propanoy-lamino]-4,7-dihydro-5H-thieno[2,3-c]pyridine-6-carboxylic acid 2-(2-methyl-imidazol-1-yl)-ethyl ester

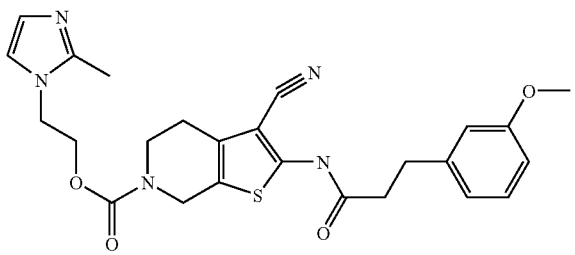

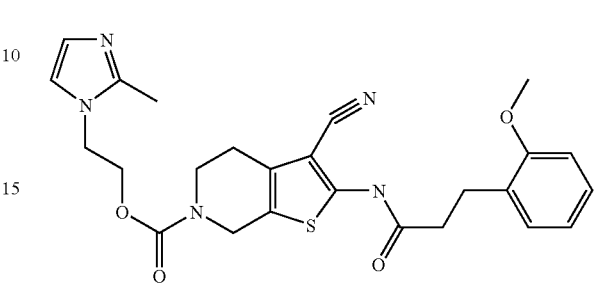

MS: calc.: C,25; H,27; N,5; O,4; SS, (493.59) fnd.: 494,1 [M+H].

MS: calc.: C,25; H,27; N,5; O,4; SS, (493.59) fnd.: 494,0 [M+H].

122. 3-Cyano-2-[3-(2-methoxy-phenyl)-propanoy-lamino]-4,7-dihydro-5H-thieno[2,3-c]pyridine-6-carboxylic acid 1-methyl-1H-imidazol-2-ylmethyl ester 125. 3-Cyano-2-[3-(2-ethoxy-phenyl)-propanoy-lamino]-4,7-dihydro-5H-thieno[2,3-c]pyridine-6-carboxylic acid 1-methyl-1H-imidazol-2-ylmethyl ester

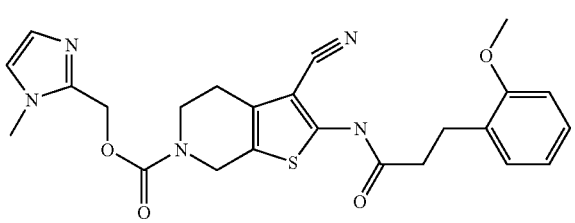

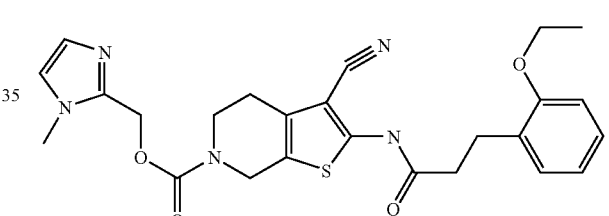

MS: calc.: C,24; H,25; N,5; O,4; S, (479.56) fnd.: 480,0 [M+H].

MS: calc.: C,25; H,27; N,5; O,4; S, (493.59) fnd.: 494,0 [M+H].

123. 3-Cyano-2-[3-(2-methoxy-phenyl)-propanoy-lamino]-4,7-dihydro-5H-thieno[2,3-c]pyridine-6-carboxylic acid 3-methyl-3H-imidazol-4-ylmethyl ester 126. 3-Cyano-2-[3-(2-ethoxy-phenyl)-propanoy-lamino]-4,7-dihydro-5H-thieno[2,3-c]pyridine-6-carboxylic acid 3-methyl-3H-imidazol-4-ylmethyl ester

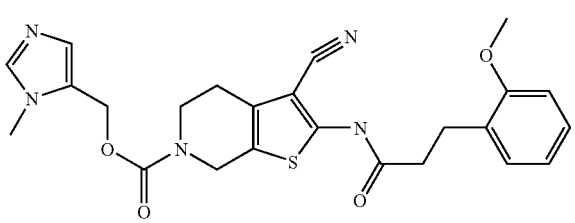

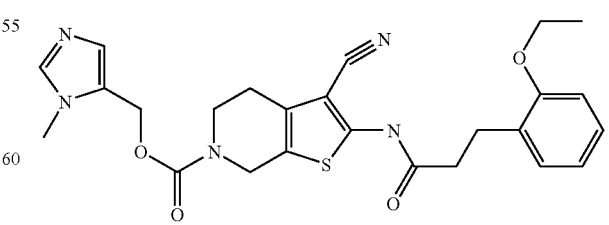

MS: calc.: C,24; H,25; N,5; O,4; S, (479.56) fnd.: 480,2 [M+H].

MS: calc.: C,25; H,27; N,5; O,4; S, (493.59) fnd.: 494,0 [M+H].

127. 3-Cyano-2-[3-(2-ethoxy-phenyl)-propanoylamino]-4,7-dihydro-5H-thieno[2,3-c]pyridine-6-carboxylic acid 2-(2-methyl-imidazol-1-yl)-ethyl ester

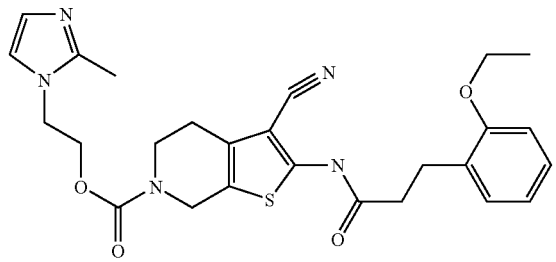

MS: calc.: C,26; H,29; N,5; O,4; S, (507.62) fnd.: 508,0 [M+H].

128. 3-Cyano-2-[3-(2-methoxy-5-methyl-phenyl)-propanoylamino]-4,7-dihydro-5H-thieno[2,3-c]pyridine-6-carboxylic acid 2-pyridin-3-yl-ethyl ester

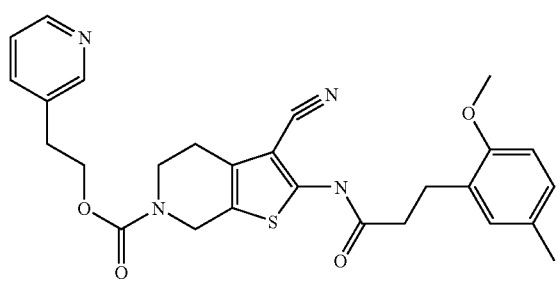

MS: calc.: C,27; H,28; N,4; O,4; S, (504.61) fnd.: 505,2 [M+H].

129. 3-Cyano-2-[3-(2-methoxy-5-methyl-phenyl)-propanoylamino]-4,7-dihydro-5H-thieno[2,3-c]pyridine-6-carboxylic acid 1-methyl-1H-imidazol-2-ylmethyl ester

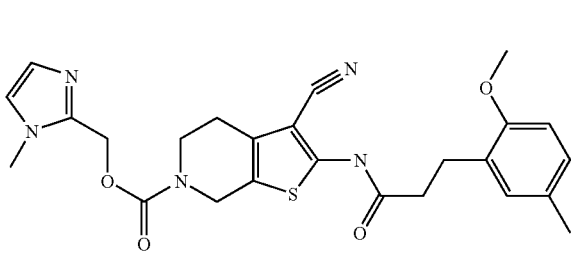

MS: calc.: C,25; H,27; N,5; O,4; S, (493.59) fnd.: 494,0 [M+H].

130. 3-Cyano-2-[3-(2-methoxy-5-methyl-phenyl)-propanoylamino]-4,7-dihydro-5H-thieno[2,3-c]pyridine-6-carboxylic acid 3-methyl-3H-imidazol-4-ylmethyl ester

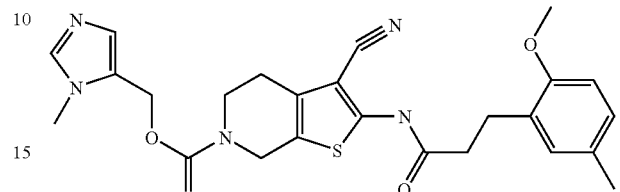

MS: calc.: C,25; H,27; N,5; O,4; S, (493.59) fnd.: 494,1 [M+H].

131. 3-Cyano-2-[3-(2-methoxy-5-methyl-phenyl)-propanoylamino]-4,7-dihydro-5H-thieno[2,3-c]pyridine-6-carboxylic acid 2-(2-methyl-imidazol-1-yl)-ethyl ester

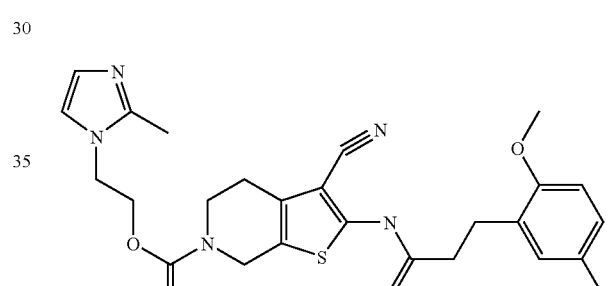

MS: calc.: C,26; H,29; N,5; O,4; S, (507.62) fnd.: 508,3 [M+H].

132. 3-Cyano-2-[3-(2-methoxy-5-methyl-phenyl)-propanoylamino]-4,7-dihydro-5H-thieno[2,3-c]pyridine-6-carboxylic acid 2-imidazol-1-yl-ethyl ester

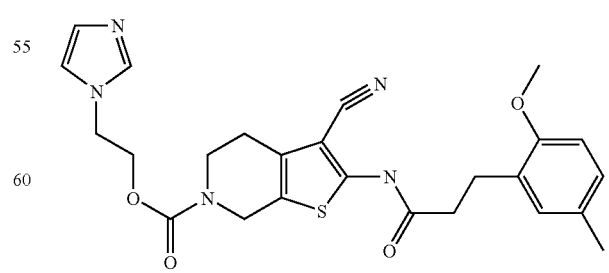

MS: calc.: C,25; H,27; N,5; O,4; S, (493.59) fnd.: 494,1 [M+H].

133. 3-Cyano-2-[(RS)-3-(3-methoxy-phenyl)-bu-tanoylamino]-4,7-dihydro-5H-thieno[2,3-c]pyridine-6-carboxylic acid 2-(2,4-dimethyl-imidazol-1-yl)-ethyl ester

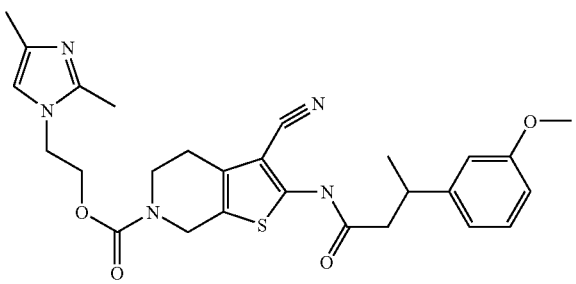

MS: calc.: C,27; H,31; N,5; O,4; S, (521.64) fnd.: 522,2 [M+H].

134. 3-Cyano-2-[(RS)-3-(3-methoxy-phenyl)-bu-tanoylamino]-4,7-dihydro-5H-thieno[2,3-c]pyridine-6-carboxylic acid 2-(4-methyl-imidazol-1-yl)-ethyl ester

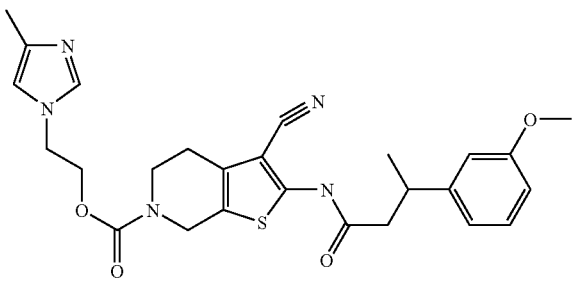

MS: calc.: C,26; H,29; N,5; O,4; S, (507.62) fnd.: 508,2 [M+H].

135. 3-Cyano-2-[(RS)-3-(3-ethoxy-phenyl)-butanoy-lamino]-4,7-dihydro-5H-thieno[2,3-c]pyridine-6-carboxylic acid 2-(2,4-dimethyl-imidazol-1-yl)-ethyl ester

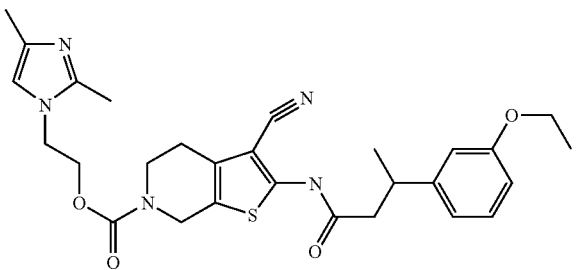

MS: calc.: C,28; H,33; N,5; O,4; S, (535.67) fnd.: 536,2 [M+H].

136. 3-Cyano-2-[(RS)-3-(3-ethoxy-phenyl)-butanoy-lamino]-4,7-dihydro-5H-thieno[2,3-c]pyridine-6-carboxylic acid 2-(4-methyl-imidazol-1-yl)-ethyl ester

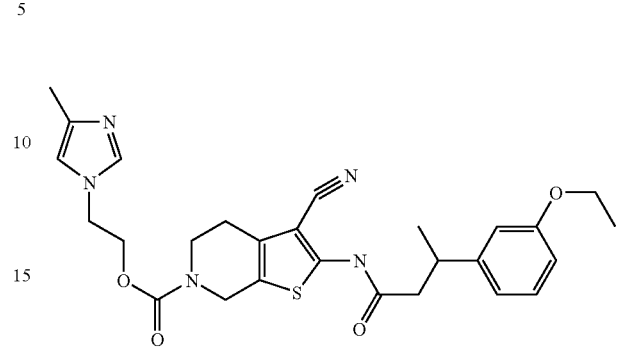

MS: calc.: C,27; H,31; N,5; O,4; S, (521.64) fnd.: 522,2 [M+H].

137. 3-Cyano-2-[(RS)-3-(2-methoxy-phenyl)-bu-tanoylamino]-4,7-dihydro-5H-thieno[2,3-c]pyridine-6-carboxylic acid 2-(2,4-dimethyl-imidazol-1-yl)-ethyl ester

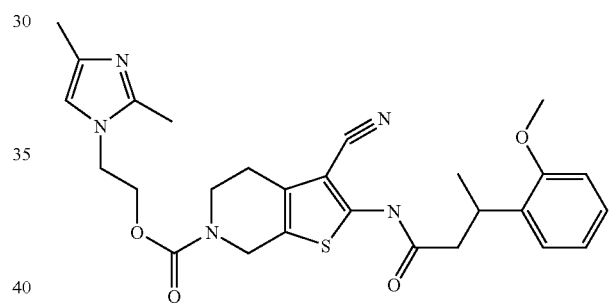

MS: calc.: C,27; H,31; N,5; O,4; S, (521.64) fnd.: 522,2 [M+H].

138. 3-Cyano-2-[(RS)-3-(2-methoxy-phenyl)-bu-tanoylamino]-4,7-dihydro-5H-thieno[2,3-c]pyridine-6-carboxylic acid 2-(4-methyl-imidazol-1-yl)-ethyl ester

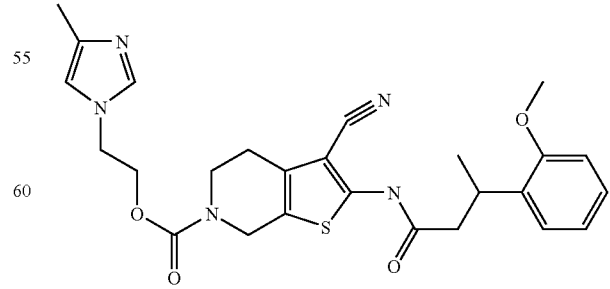

MS: calc.: C,26; H,29; N,5; O,4; S, (507.62) fnd.: 508,1 [M+H].

139. 3-Cyano-2-[(RS)-3-(2-ethoxy-phenyl)-butanoy-
lamino]-4,7-dihydro-5H-thieno[2,3-c]pyridine-6-
carboxylic acid 2-(2,4-dimethyl-imidazol-1-yl)-ethyl
ester 142. 3-Cyano-2-[3-(3-methoxy-phenyl)-propanoy-
lamino]-4,7-dihydro-5H-thieno[2,3-c]pyridine-6-
carboxylic acid 2-(4-methyl-imidazol-1-yl)-ethyl
ester

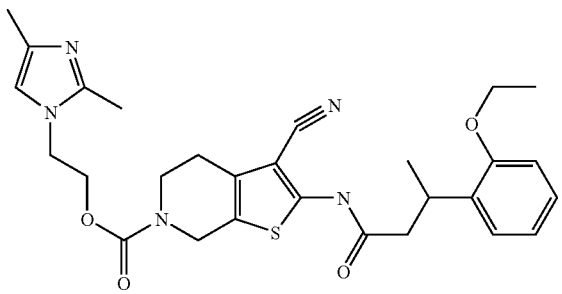

MS: calc.: C,28; H,33; N,5; O,4; S, (535.67) fnd.: 536,2 [M+H].

MS: calc.: C,25; H,27; N,5; O,4; S, (493.59) fnd.: 494,1 [M+H].

140. 3-Cyano-2-[(RS)-3-(2-ethoxy-phenyl)-butanoy-
lamino]-4,7-dihydro-5H-thieno[2,3-c]pyridine-6-
carboxylic acid 2-(4-methyl-imidazol-1-yl)-ethyl
ester 143. 3-Cyano-2-[3-(2-methoxy-phenyl)-propanoy-
lamino]-4,7-dihydro-5H-thieno[2,3-c]pyridine-6-
carboxylic acid 2-(2,4-dimethyl-imidazol-1-yl)-ethyl
ester

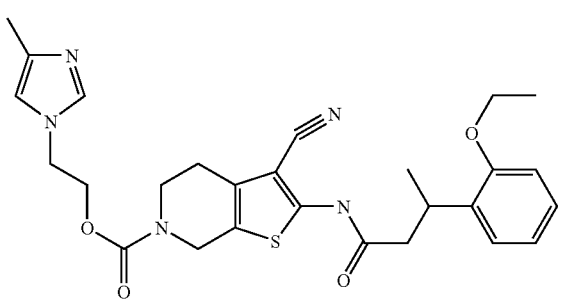

MS: calc.: C,27; H,31; N,5; O,4; S, (521.64) fnd.: 522,2 [M+H].

MS: calc.: C,26; H,29; N,5; O,4; S, (507.62) fnd.: 508,2 [M+H].

141. 3-Cyano-2-[3-(3-methoxy-phenyl)-propanoy-
lamino]-4,7-dihydro-5H-thieno[2,3-c]pyridine-6-
carboxylic acid 2-(2,4-dimethyl-imidazol-1-yl)-ethyl
ester 144. 3-Cyano-2-[3-(2-methoxy-phenyl)-propanoy-
lamino]-4,7-dihydro-5H-thieno[2,3-c]pyridine-6-
carboxylic acid 2-(4-methyl-imidazol-1-yl)-ethyl
ester

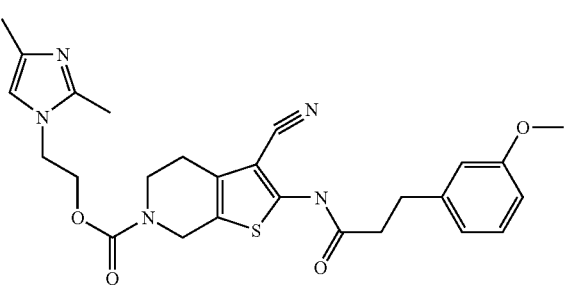

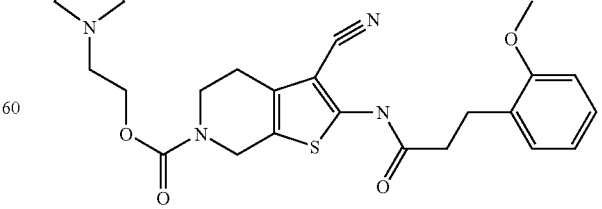

MS: calc.: C,26; H,29; N,5; O,4; S, (507.62) fnd.: 507,7 [M].

MS: calc.: C,25; H,27; N,5; O,4; S, (493.59) fnd.: 494,2 [M+H].

145. 3-Cyano-2-[3-(2-ethoxy-phenyl)-propanoylamino]-4,7-dihydro-5H-thieno[2,3-c]pyridine-6-carboxylic acid 2-(2,4-dimethyl-imidazol-1-yl)-ethyl ester

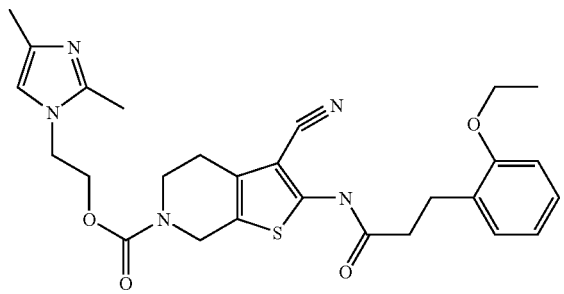

MS: calc.: C,27; H,31; N,5; O,4; S, (521.64) fnd.: 521,7 [M].

146. 3-Cyano-2-[3-(2-ethoxy-phenyl)-propanoylamino]-4,7-dihydro-5H-thieno[2,3-c]pyridine-6-carboxylic acid 2-(4-methyl-imidazol-1-yl)-ethyl ester

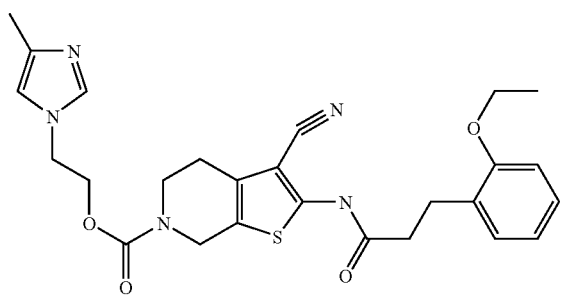

MS: calc.: C,26; H,29; N,5; O,4; S, (507.62) fnd.: 508,2 [M+H].

147. 3-Cyano-2-[3-(2-methoxy-5-methyl-phenyl)-propanoylamino]-4,7-dihydro-5H-thieno[2,3-c]pyridine-6-carboxylic acid 2-(2,4-dimethyl-imidazol-1-yl)-ethyl ester

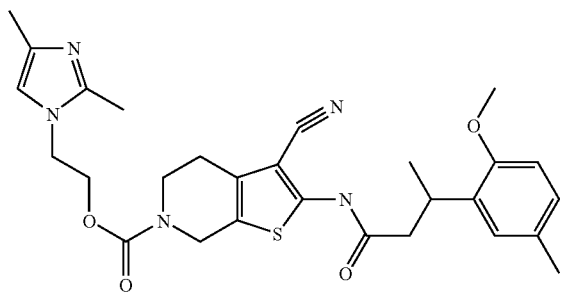

MS: calc.: C,27; H,31; N,5; O,4; S, (521.64) fnd.: 522,2 [M+H].

148. 3-Cyano-2-[3-(2-methoxy-5-methyl-phenyl)-propanoylamino]-4,7-dihydro-5H-thieno[2,3-c]pyridine-6-carboxylic acid 2-(4-methyl-imidazol-1-yl)-ethyl ester

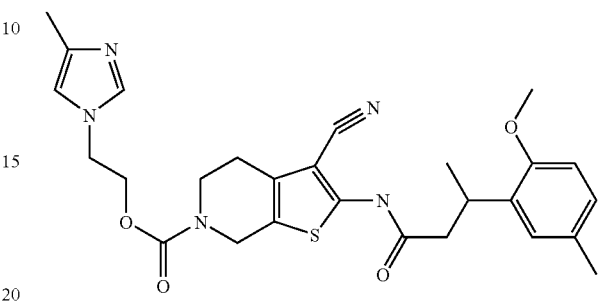

MS: calc.: C,26; H,29; N,5; O,4; S, (507.62) fnd.: 508,1 [M+H].

149. 3-Cyano-2-[(RS)-3-(3-methoxy-phenyl)-butanoylamino]-4,7-dihydro-5H-thieno[2,3-c]pyridine-6-carboxylic acid carboxymethyl ester

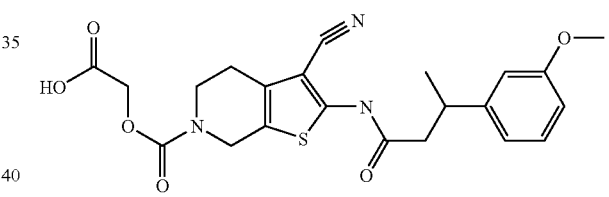

MS: calc.: C,22; H,23; N,3; O,6; S, (457.51) fnd.: 456,0 [M−H].

150. 3-Cyano-2-[(RS)-3-(3-ethoxy-phenyl)-butanoylamino]-4,7-dihydro-5H-thieno[2,3-c]pyridine-6-carboxylic acid carboxymethyl ester

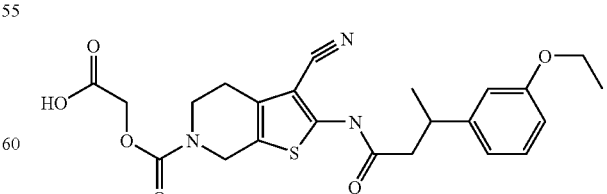

MS: calc.: C,23; H,25; N,3; O,6; S, (471.54) fnd.: 472,0 [M+H].

101

151. 3-Cyano-2-[(RS)-3-(2-methoxy-phenyl)-butanoylamino]-4,7-dihydro-5H-thieno[2,3-c]pyridine-6-carboxylic acid carboxymethyl ester

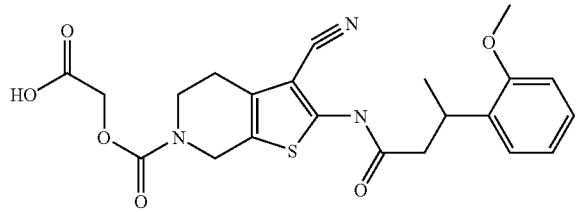

MS: calc.: C,22; H,23; N,3; O,6; S, (457.51) fnd.: 458,0 [M+H].

152. 3-Cyano-2-[(RS)-3-(2-ethoxy-phenyl)-butanoylamino]-4,7-dihydro-5H-thieno[2,3-c]pyridine-6-carboxylic acid carboxymethyl ester

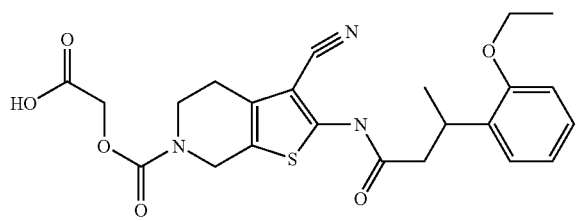

MS: calc.: C,23; H,25; N,3; O,6; S, (471.54) fnd.: 472,0 [M+H].

153. 3-Cyano-2-[3-(2-methoxy-phenyl)-propanoylamino]-4,7-dihydro-5H-thieno[2,3-c]pyridine-6-carboxylic acid carboxymethyl ester

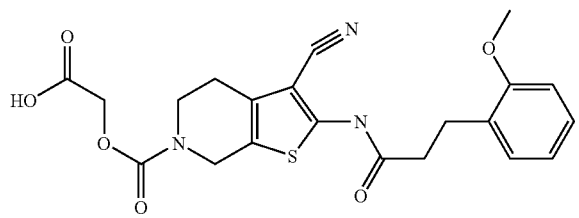

MS: calc.: C,21; H,21; N,3; O,6; S, (443.48) fnd.: 444,0 [M+H].

102

154. 3-Cyano-2-[3-(2-ethoxy-phenyl)-propanoylamino]-4,7-dihydro-5H-thieno[2,3-c]pyridine-6-carboxylic acid carboxymethyl ester

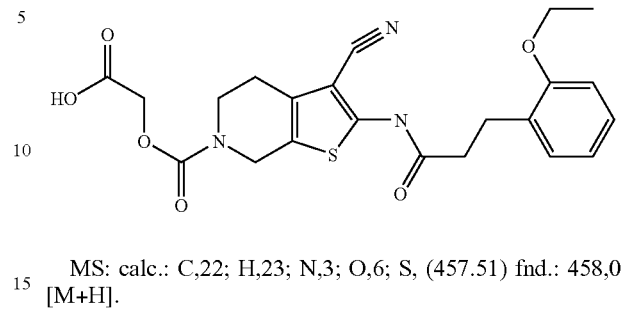

MS: calc.: C,22; H,23; N,3; O,6; S, (457.51) fnd.: 458,0 [M+H].

155. 3-Cyano-2-[3-(2-methoxy-5-methyl-phenyl)-propanoylamino]-4,7-dihydro-5H-thieno[2,3-c]pyridine-6-carboxylic acid carboxymethyl ester

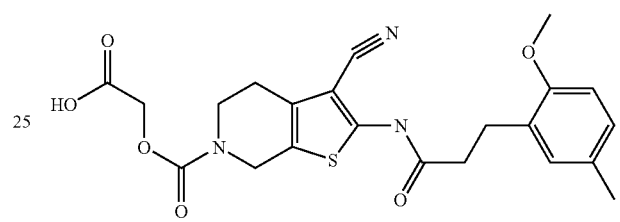

MS: calc.: C,22; H,23; N,3; O,6; S, (457.51) fnd.: 458,0 [M+H].

156. 3-Cyano-2-[(RS)-3-(2-methoxy-5-methyl-phenyl)-propanoylamino]-4,7-dihydro-5H-thieno[2,3-c]pyridine-6-carboxylic acid carboxymethyl ester

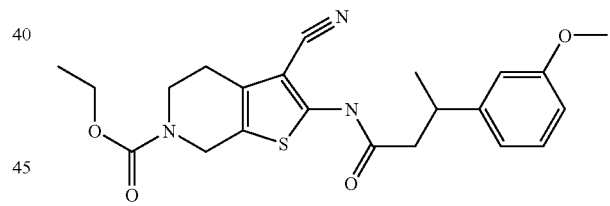

MS: calc.: C,22; H,25; N,3; O,4; S, (427.53) fnd.: 428,0 [M+H].

157. 3-Cyano-2-[(RS)-3-(3-ethoxy-phenyl)-butanoylamino]-4,7-dihydro-5H-thieno[2,3-c]pyridine-6-carboxylic acid ethyl ester

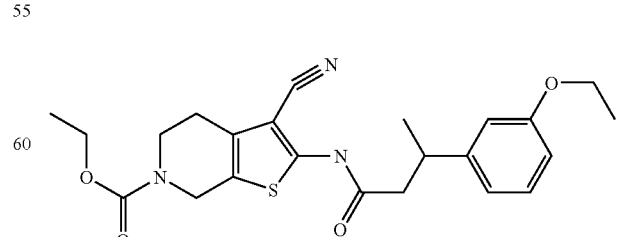

MS: calc.: C,23; H,27; N,3; O,4; S, (441.55) fnd.: 442,1 [M+H].

158. 3-Cyano-2-[(RS)-3-(2-ethoxy-phenyl)-butanoylamino]-4,7-dihydro-5H-thieno[2,3-c]pyridine-6-carboxylic acid ethyl ester

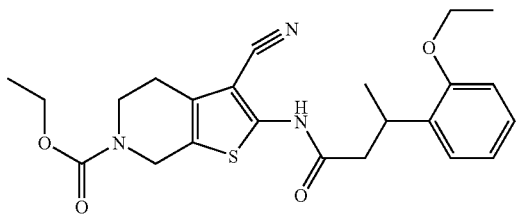

MS: calc.: C,23; H,27; N,3; O,4; S, (441.55) fnd.: 442,0 [M+H].

159. 3-Cyano-2-[(RS)-3-(3-methoxy-phenyl)-butanoylamino]-4,7-dihydro-5H-thieno[2,3-c]pyridine-6-carboxylic acid 2,3-dihydroxy-propyl ester

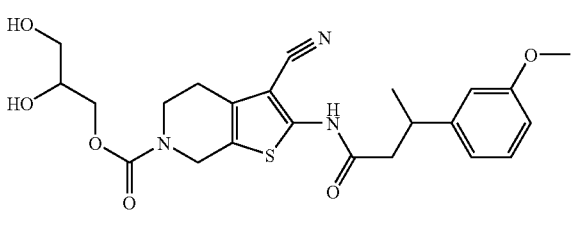

MS: calc.: C,23; H,27; N,3; O,6; S, (473.55) fnd.: 474,0 [M+H].

160. 3-Cyano-2-[(RS)-3-(3-ethoxy-phenyl)-butanoylamino]-4,7-dihydro-5H-thieno[2,3-c]pyridine-6-carboxylic acid 2,3-dihydroxy-propyl ester

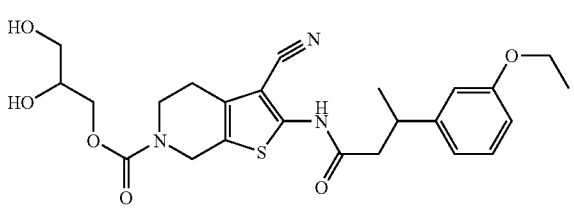

MS: calc.: C,24; H,29; N,3; O,6; S, (487.58) fnd.: 488,1 [M+H].

161. 3-Cyano-2-[(RS)-3-(2-methoxy-phenyl)-butanoylamino]-4,7-dihydro-5H-thieno[2,3-c]pyridine-6-carboxylic acid 2,3-dihydroxy-propyl ester

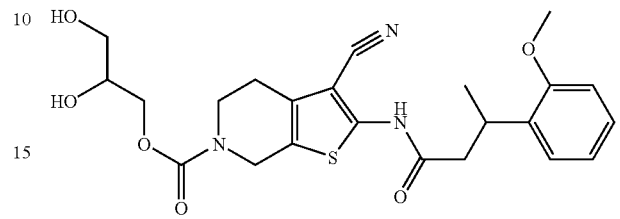

MS: calc.: C,23; H,27; N,3; O,6; S, (473.55) fnd.: 474,0 [M+H].

162. 3-Cyano-2-[(RS)-3-(2-ethoxy-phenyl)-butanoylamino]-4,7-dihydro-5H-thieno[2,3-c]pyridine-6-carboxylic acid 2,3-dihydroxy-propyl ester

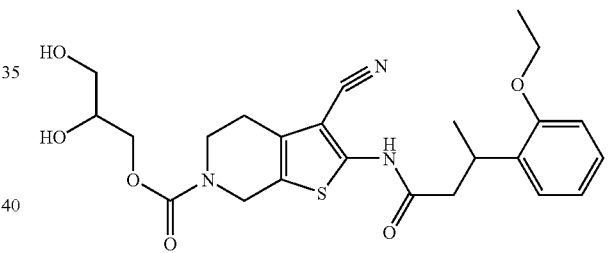

MS: calc.: C,24; H,29; N,3; O,6; S, (487.58) fnd.: 488,1 [M+H].

163. 3-Cyano-2-[3-(3-methoxy-phenyl)-propanoylamino]-4,7-dihydro-5H-thieno[2,3-c]pyridine-6-carboxylic acid 2,3-dihydroxy-propyl ester

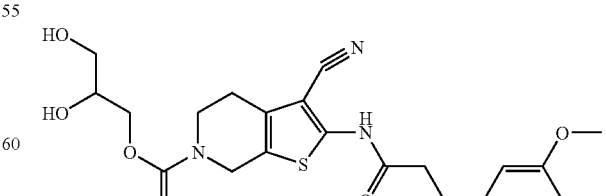

MS: calc.: C,22; H,25; N,3; O,6; S, (459.53) fnd.: 460,2 [M+H].

164. 3-Cyano-2-[3-(2-ethoxy-phenyl)-propanoylamino]-4,7-dihydro-5H-thieno[2,3-c]pyridine-6-carboxylic acid 2,3-dihydroxy-propyl ester 167. 3-Cyano-2-[(RS)-3-(2-methoxy-phenyl)-butanoylamino]-4,7-dihydro-5H-thieno[2,3-c]pyridine-6-carboxylic acid 2-hydroxy-ethyl ester

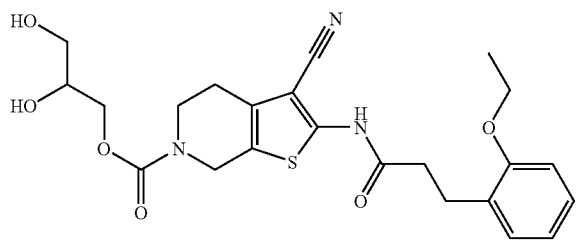

MS: calc.: C,23; H,27; N,3; O,6; S, (473.55) fnd.: 474,0 [M+H].

MS: calc.: C,22; H,25; N,3; O,5; S, (443.53) fnd.: 444,0 [M+H].

165. 3-Cyano-2-[(RS)-3-(3-methoxy-phenyl)-butanoylamino]-4,7-dihydro-5H-thieno[2,3-c]pyridine-6-carboxylic acid 2-hydroxy-ethyl ester 168. 3-Cyano-2-[(RS)-3-(2-ethoxy-phenyl)-butanoylamino]-4,7-dihydro-5H-thieno[2,3-c]pyridine-6-carboxylic acid 2-hydroxy-ethyl ester

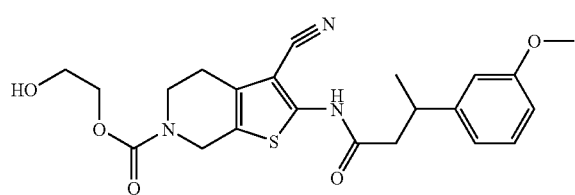

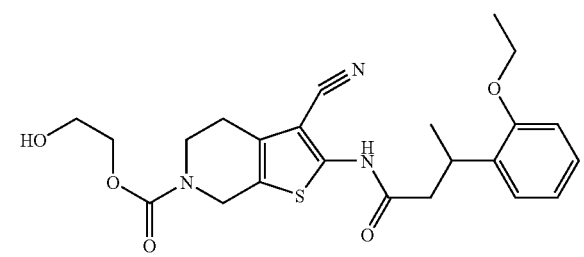

MS: calc.: C,22; H,25; N,3; O,5; S, (443.53) fnd.: 444,0 [M+H].

MS: calc.: C,23; H,27; N,3; O,5; S, (457.55) fnd.: 458,1 [M+H].

166. 3-Cyano-2-[(RS)-3-(3-ethoxy-phenyl)-butanoylamino]-4,7-dihydro-5H-thieno[2,3-c]pyridine-6-carboxylic acid 2-hydroxy-ethyl ester 169. 3-Cyano-2-[(RS)-3-(2-methoxy-5-methyl-phenyl)-butanoylamino]-4,7-dihydro-5H-thieno[2,3-c]pyridine-6-carboxylic acid pyridin-4-ylmethyl ester

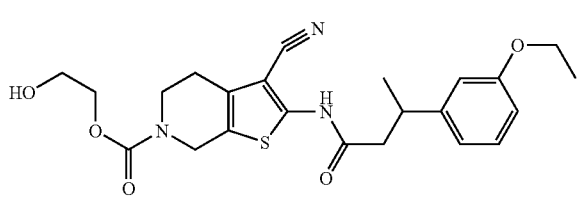

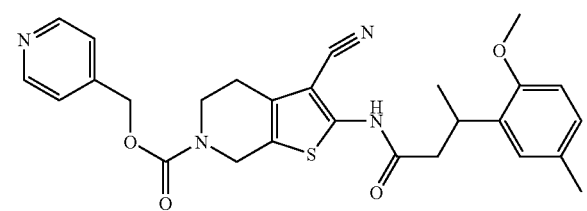

MS: calc.: C,23; H,27; N,3; O,5; S, (457.55) fnd.: 458,1 [M+H].

MS: calc.: C,27; H,28; N,4; O,4; S, (504.61) fnd.: 505,1 [M+H].

170. 3-Cyano-2-[(RS)-3-(2-methoxy-5-methyl-phenyl)-butanoylamino]-4,7-dihydro-5H-thieno[2,3-c]pyridine-6-carboxylic acid pyridin-3-ylmethyl ester

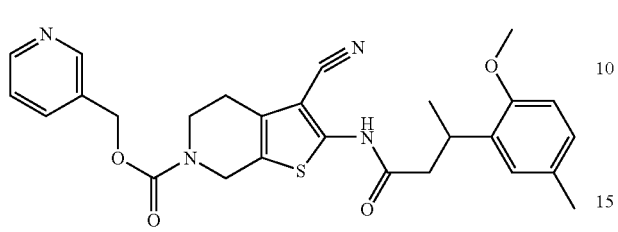

MS: calc.: C,27; H,28; N,4; O,4; S, (504.61) fnd.: 505,1 [M+H].

171. 3-Cyano-2-[(RS)-3-(2-methoxy-5-methyl-phenyl)-butanoylamino]-4,7-dihydro-5H-thieno[2,3-c]pyridine-6-carboxylic acid pyridin-2-ylmethyl ester

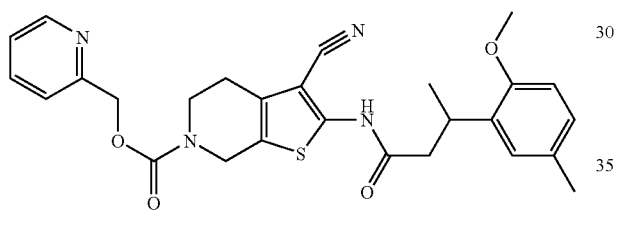

MS: calc.: C,27; H,28; N,4; O,4; S, (504.61) fnd.: 505,1 [M+H].

172. 3-Cyano-2-[(RS)-3-(2-methoxy-5-methyl-phenyl)-butanoylamino]-4,7-dihydro-5H-thieno[2,3-c]pyridine-6-carboxylic acid 2-pyridin-4-yl-ethyl ester

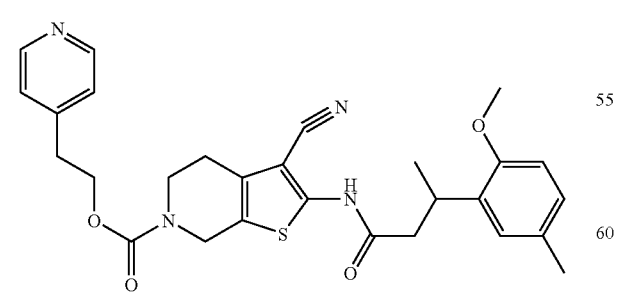

MS: calc.: C,28; H,30; N,4; O,4; S, (518.64) fnd.: 519,1 [M+H].

173. 3-Cyano-2-[(RS)-3-(2-methoxy-5-methyl-phenyl)-butanoylamino]-4,7-dihydro-5H-thieno[2,3-c]pyridine-6-carboxylic acid 2-pyridin-3-yl-ethyl ester

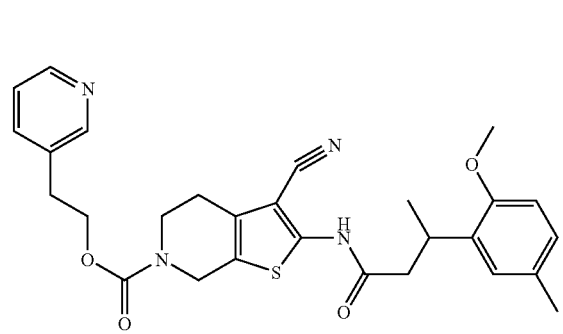

MS: calc.: C,28; H,30; N,4; O,4; S, (518.64) fnd.: 519,1 [M+H].

174. 3-Cyano-2-[(RS)-3-(2-methoxy-5-methyl-phenyl)-butanoylamino]-4,7-dihydro-5H-thieno[2,3-c]pyridine-6-carboxylic acid 2-pyridin-2-yl-ethyl ester

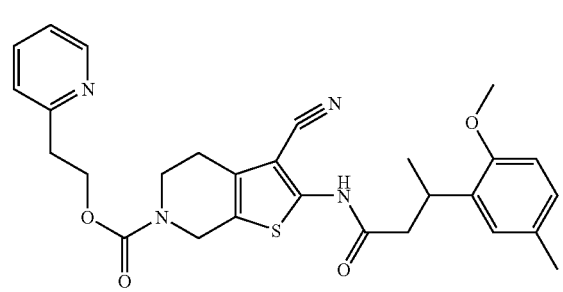

MS: calc.: C,28; H,30; N,4; O,4; S, (518.64) fnd.: 519,1 [M+H].

175. 3-Cyano-2-[(RS)-3-(2-methoxy-5-methyl-phenyl)-butanoylamino]-4,7-dihydro-5H-thieno[2,3-c]pyridine-6-carboxylic acid 1-methyl-1H-imidazol-2-ylmethyl ester

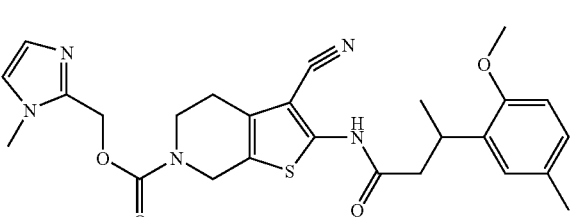

MS: calc.: C,26; H,29; N,5; O,4; S, (507.62) fnd.: 508,1 [M+H].

176. 3-Cyano-2-[(RS)-3-(2-methoxy-5-methyl-phenyl)-butanoylamino]-4,7-dihydro-5H-thieno[2,3-c]pyridine-6-carboxylic acid 3-methyl-3H-imidazol-4-ylmethyl ester

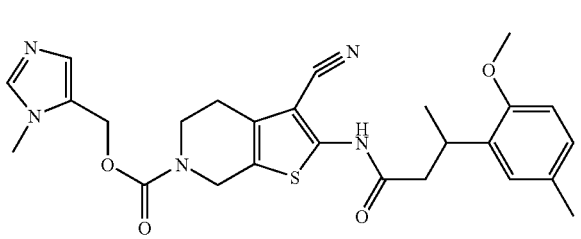

MS: calc.: C,26; H,29; N,5; O,4; S, (507.62) fnd.: 508,1 [M+H].

177. 3-Cyano-2-[(RS)-3-(2-methoxy-5-methyl-phenyl)-butanoylamino]-4,7-dihydro-5H-thieno[2,3-c]pyridine-6-carboxylic acid 2-imidazol-1-yl-ethyl ester

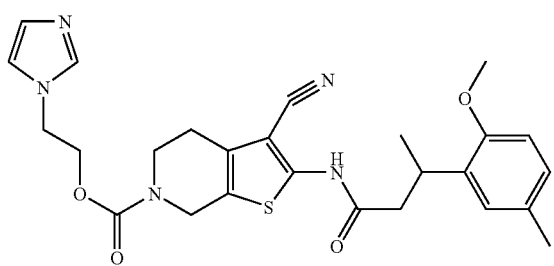

MS: calc.: C,26; H,29; N,5; O,4; S, (507.62) fnd.: 508,1 [M+H].

178. 3-Cyano-2-[(RS)-3-(2-methoxy-5-methyl-phenyl)-butanoylamino]-4,7-dihydro-5H-thieno[2,3-c]pyridine-6-carboxylic acid 2-(2-methyl-imidazol-1-yl)-ethyl ester

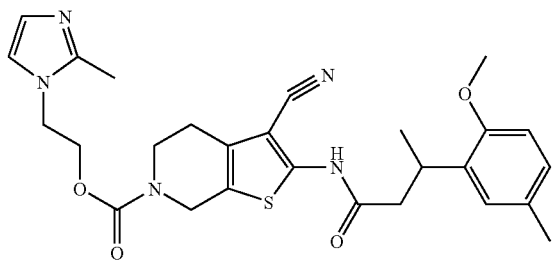

MS: calc.: C,27; H,31; N,5; O,4; S, (521.64) fnd.: 522,1 [M+H].

179. 3-Cyano-2-[(RS)-3-(2-methoxy-5-methyl-phenyl)-butanoylamino]-4,7-dihydro-5H-thieno[2,3-c]pyridine-6-carboxylic acid 2-(2,4-dimethyl-imidazol-1-yl)-ethyl ester MS: calc.: C,28; H,33; N,5; O,4; S, (535.67) fnd.: 536,0 [M+H].

180. 3-Cyano-2-[(RS)-3-(2-methoxy-5-methyl-phenyl)-butanoylamino]-4,7-dihydro-5H-thieno[2,3-c]pyridine-6-carboxylic acid 2-(4-methyl-imidazol-1-yl)-ethyl ester MS: calc.: C,27; H,31; N,5; O,4; S, (521.64) fnd.: 522,1 [M+H].

181. 3-Cyano-2-[(RS)-3-(2-methoxy-5-methyl-phenyl)-butanoylamino]-4,7-dihydro-5H-thieno[2,3-c]pyridine-6-carboxylic acid carboxymethyl ester

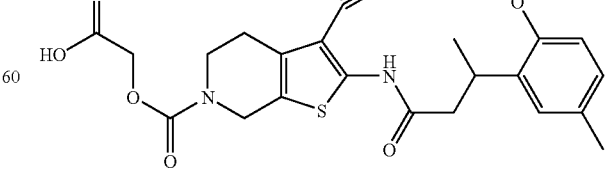

MS: calc.: C,23; H,25; N,3; O,6; S, (471.54) fnd.: 472,0 [M+H].

182. 3-Cyano-2-[(RS)-3-(2-methoxy-5-methyl-phenyl)-butanoylamino]-4,7-dihydro-5H-thieno[2,3-c]pyridine-6-carboxylic acid ethyl ester

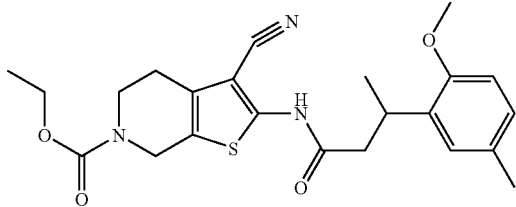

MS: calc.: C,23; H,27; N,3; O,4; S, (441.55) fnd.: 442,0 [M+H].

183. 3-Cyano-2-[(RS)-3-(2-methoxy-5-methyl-phenyl)-butanoylamino]-4,7-dihydro-5H-thieno[2,3-c]pyridine-6-carboxylic acid 2,3-dihydroxy-propyl ester

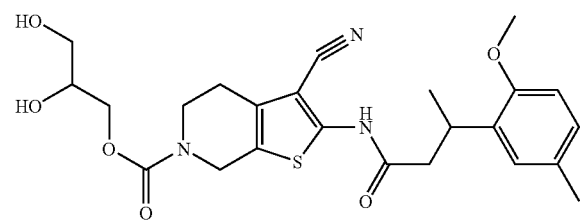

MS: calc.: C,24; H,29; N,3; O,6; S, (487.58) fnd.: 488,1 [M+H].

184. 3-Cyano-2-[(RS)-3-(2-methoxy-5-methyl-phenyl)-butanoylamino]-4,7-dihydro-5H-thieno[2,3-c]pyridine-6-carboxylic acid 2-hydroxy-ethyl ester

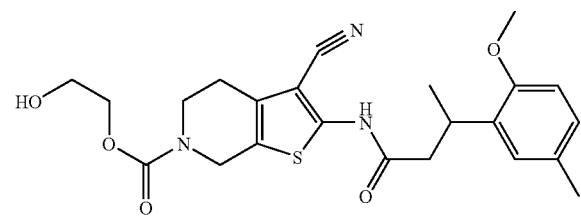

MS: calc.: C,23; H,27; N,3; O,5; S, (457.55) fnd.: 458,1 [M+H].

185. 3-Cyano-2-[(RS)-3-(3-methoxy-phenyl)-butanoylamino]-4,7-dihydro-5H-thieno[2,3-c]pyridine-6-carboxylic acid methoxycarbonylmethyl ester

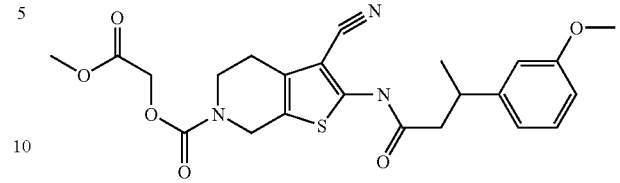

MS: calc.: C,23; H,25; N,3; O,6; S, (471.54) fnd.: 472,0 [M+H].

186. 3-Cyano-2-[(RS)-3-(3-ethoxy-phenyl)-butanoylamino]-4,7-dihydro-5H-thieno[2,3-c]pyridine-6-carboxylic acid methoxycarbonylmethyl ester

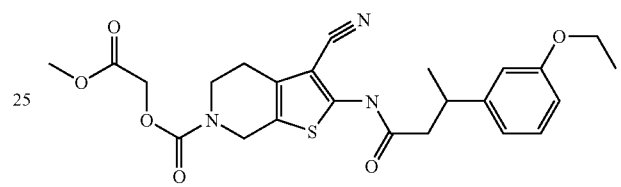

MS: calc.: C,24; H,27; N,3; O,6; S, (485.56) fnd.: 486,0 [M+H].

187. 3-Cyano-2-[(RS)-3-(2-methoxy-phenyl)-butanoylamino]-4,7-dihydro-5H-thieno[2,3-c]pyridine-6-carboxylic acid methoxycarbonylmethyl ester

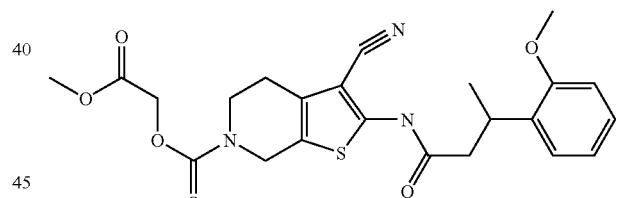

MS: calc.: C,23; H,25; N,3; O,6; S, (471.54) fnd.: 472,0 [M+H].

188. 3-Cyano-2-[(RS)-3-(2-ethoxy-phenyl)-butanoylamino]-4,7-dihydro-5H-thieno[2,3-c]pyridine-6-carboxylic acid methoxycarbonylmethyl ester

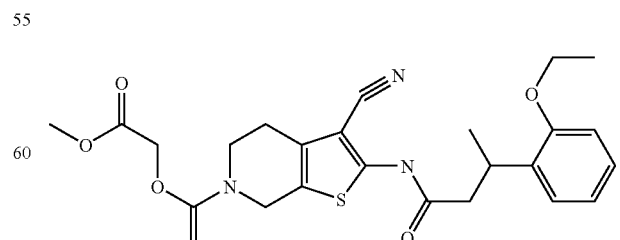

MS: calc.: C,24; H,27; N,3; O,6; S, (485.56) fnd.: 486,0 [M+H].

189. 3-Cyano-2-[3-(2-methoxy-phenyl)-propanoylamino]-4,7-dihydro-5H-thieno[2,3-c]pyridine-6-carboxylic acid methoxycarbonylmethyl ester

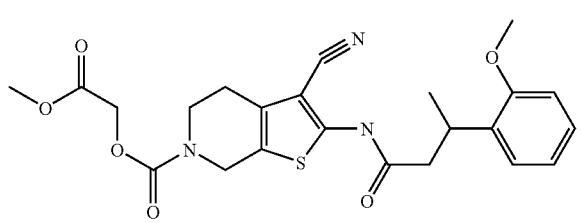

MS: calc.: C,22; H,23; N,3; O,6; S, (457.51) fnd.: 458,0 [M+H].

190. 3-Cyano-2-[3-(2-ethoxy-phenyl)-propanoylamino]-4,7-dihydro-5H-thieno[2,3-c]pyridine-6-carboxylic acid methoxycarbonylmethyl ester

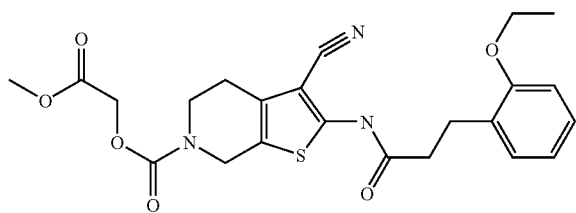

MS: calc.: C,23; H,25; N,3; O,6; S, (471.54) fnd.: 472,0 [M+H].

191. 3-Cyano-2-[3-(2-methoxy-5-methyl-phenyl)-propanoylamino]-4,7-dihydro-5H-thieno[2,3-c]pyridine-6-carboxylic acid methoxycarbonylmethyl ester

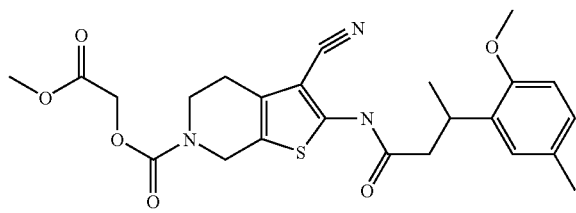

MS: calc.: C,23; H,25; N,3; O,6; S, (471.54) fnd.: 472,0 [M+H].

192. 3-Cyano-2-[(RS)-3-(2-methoxy-5-methyl-phenyl)-butanoylamino]-4,7-dihydro-5H-thieno[2,3-c]pyridine-6-carboxylic acid methoxycarbonylmethyl ester

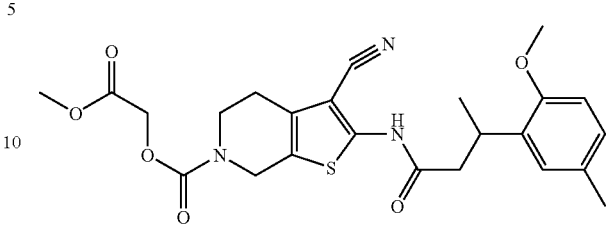

MS: calc.: C,24; H,27; N,3; O,6; S, (485.56) fnd.: 486,0 [M+H].

193. 3-Cyano-2-[(RS)-3-(3-methoxy-phenyl)-butanoylamino]-4,7-dihydro-5H-thieno[2,3-c]pyridine-6-carboxylic acid 2,2-dimethyl-[1,3]dioxolan-4-ylmethyl ester

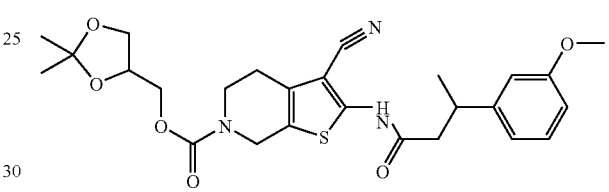

MS: calc.: C,26; H,31; N,3; O,6; S, (513.62) fnd.: 514,1 [M+H].

194. 3-Cyano-2-[(RS)-3-(3-ethoxy-phenyl)-butanoylamino]-4,7-dihydro-5H-thieno[2,3-c]pyridine-6-carboxylic acid 2,2-dimethyl-[1,3]dioxolan-4-ylmethyl ester

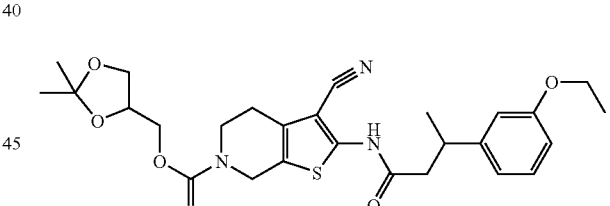

MS: calc.: C,27; H,33; N,3; O,6; S, (527.64) fnd.: 528,1 [M+H].

195. 3-Cyano-2-[(RS)-3-(2-methoxy-phenyl)-butanoylamino]-4,7-dihydro-5H-thieno[2,3-c]pyridine-6-carboxylic acid 2,2-dimethyl-[1,3]dioxolan-4-ylmethyl ester

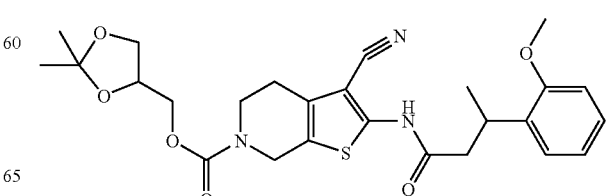

MS: calc.: C,26; H,31; N,3; O,6; S, (513.62) fnd.: 514,1 [M+H].

196. 3-Cyano-2-[(RS)-3-(2-ethoxy-phenyl)-butanoylamino]-4,7-dihydro-5H-thieno[2,3-c]pyridine-6-carboxylic acid 2,2-dimethyl-[1,3]dioxolan-4-ylmethyl ester

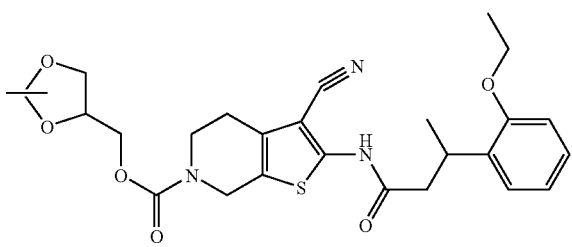

MS: calc.: C,27; H,33; N,3; O,6; S, (527.64) fnd.: 528,1 [M+H].

197. 3-Cyano-2-[3-(3-methoxy-phenyl)-propanoylamino]-4,7-dihydro-5H-thieno[2,3-c]pyridine-6-carboxylic acid 2,2-dimethyl-[1,3]dioxolan-4-ylmethyl ester

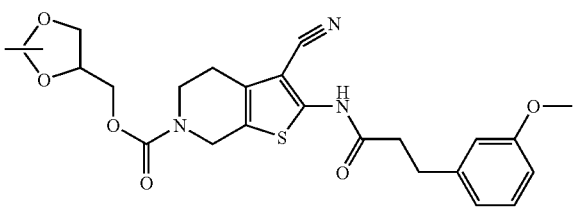

MS: calc.: C,25; H,29; N,3; O,6; S, (499.59) fnd.: 500,2 [M+H].

198. 3-Cyano-2-[3-(2-ethoxy-phenyl)-propanoylamino]-4,7-dihydro-5H-thieno[2,3-c]pyridine-6-carboxylic acid 2,2-dimethyl-[1,3]dioxolan-4-ylmethyl ester

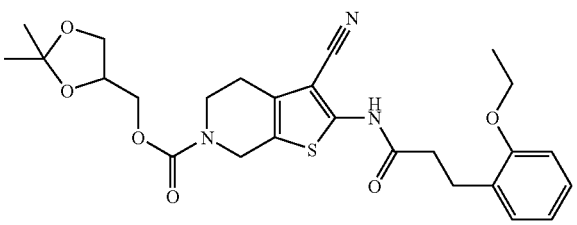

MS: calc.: C,26; H,31; N,3; O,6; S, (513.62) fnd.: 513,8 [M].

199. 3-Cyano-2-[(RS)-3-(3-methoxy-phenyl)-butanoylamino]-4,7-dihydro-5H-thieno[2,3-c]pyridine-6-carboxylic acid 2-acetoxy-ethyl ester

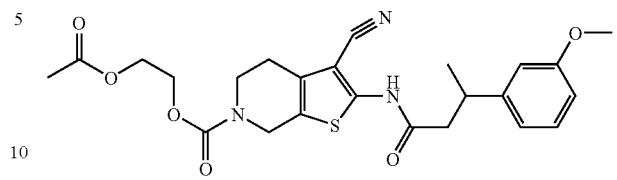

MS: calc.: C,24; H,27; N,3; O,6; S, (485.56) fnd.: 486,1 [M+H].

200. 3-Cyano-2-[(RS)-3-(3-ethoxy-phenyl)-butanoylamino]-4,7-dihydro-5H-thieno[2,3-c]pyridine-6-carboxylic acid 2-acetoxy-ethyl ester

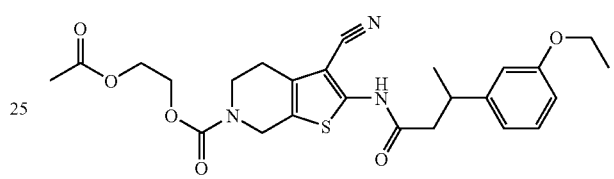

MS: calc.: C,25; H,29; N,3; O,6; S, (499.59) fnd.: 500,0 [M+H].

201. 3-Cyano-2-[(RS)-3-(2-methoxy-phenyl)-butanoylamino]-4,7-dihydro-5H-thieno[2,3-c]pyridine-6-carboxylic acid 2-acetoxy-ethyl ester

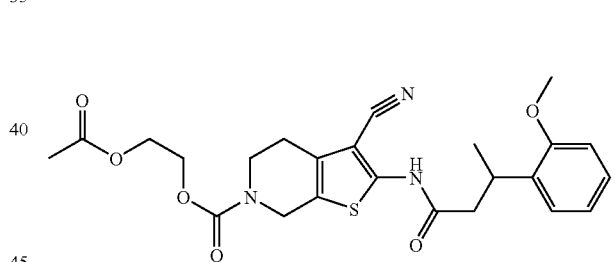

MS: calc.: C,24; H,27; N,3; O,6; S, (485.56) fnd.: 486,1 [M+H].

202. 3-Cyano-2-[(RS)-3-(2-ethoxy-phenyl)-butanoylamino]-4,7-dihydro-5H-thieno[2,3-c]pyridine-6-carboxylic acid 2-acetoxy-ethyl ester

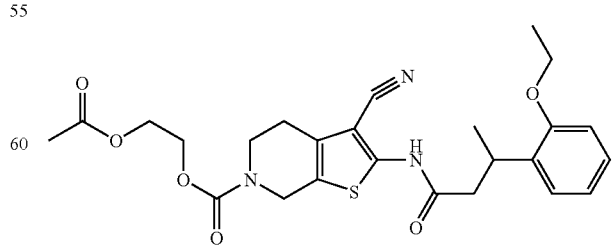

MS: calc.: C,25; H,29; N,3; O,6; S, (499.59) fnd.: 500,1 [M+H].

203. 3-Cyano-2-[(RS)-3-(2-methoxy-5-methyl-phenyl)-butanoylamino]-4,7-dihydro-5H-thieno[2,3-c]pyridine-6-carboxylic acid 2,2-dimethyl-[1,3]dioxolan-4-ylmethyl ester

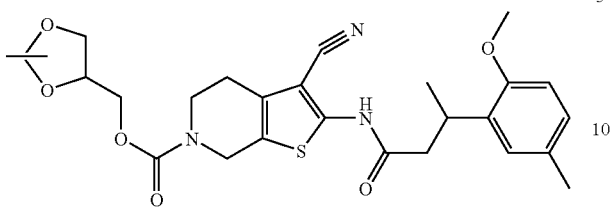

MS: calc.: C,27; H,33; N,3; O,6; S, (527.64) fnd.: 528,1 [M+H].

204. 3-Cyano-2-[(RS)-3-(2-methoxy-5-methyl-phenyl)-butanoylamino]-4,7-dihydro-5H-thieno[2,3-c]pyridine-6-carboxylic acid 2-acetoxy-ethyl ester

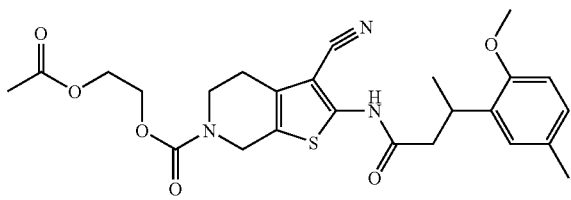

MS: calc.: C,25; H,29; N,3; O,6; S, (499.59) fnd.: 500,0 [M+H].

Starting Materials:

B. General Procedure for Condensed 2-amino-thiophene-3-carbonitrile Derivatives 500 mmol of cyclic ketone and 500 mmol of malononitrile are dissolved in a minimal volume of ethanol and 500 mmol elemental sulfur are added. After addition of 500 mmol diethyl amine, the reaction mixture is heated to 60-70° C. for some minutes and then stirred at room temperature for several hours. The reaction mixture is poured on ice/water and the precipitate filtered off. In case there is no or only some precipitate formed, the aqueous layer is extracted several times with dichloromethane or another appropriate organic solvent, the combined organic layers are dried (e.g. MgSO4) and concentrated in vacuo. Purification of the crude product is achieved by flash chromatography and/or recrystallization from an appropriate solvent (e.g. ethanol).

The following compounds can be prepared according to general procedure B using the appropriate art-known cyclic ketones.

A1. 2-Amino-3-cyano-4,7-dihydro-thieno[2,3-c]pyridine-6(5H)-carboxylic acid ethyl ester

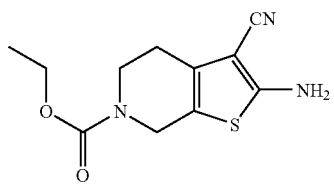

Prepared according to general procedure B using N-carbethoxy-4-piperidinone as cyclic ketone.
MS: calc.: $C_{11}H_{13}N_3O_2S$, (251.31) fnd.: 252.0 [M+H].

A2. 2-Amino-3-cyano-4,7-dihydro-5H-thieno[2,3-c]pyridine-6-carboxylic acid tert-butyl ester

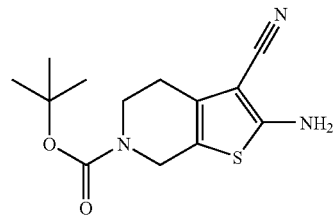

Prepared according to general procedure B using Boc-4-piperidone as cyclic ketone.
MS: calc.: $C_{13}H_{17}N_3O_2S$: (279.36) fnd.: 280.0 [M+H].

C. General Procedure for Removal of Boc Protecting Groups

The Boc protected compound is dissolved in dichloromethane/trifluoroacetic acid (TFA) (2/3) and stirred for several hours at room temperature. After evaporation of the solvent and recrystallization from an appropriate solvent (e.g. ethanol), the desired product is obtained as TFA salt. The TFA salt may be converted into the free base in a manner customary per se to the skilled person.

A3. N-(3-Cyano-4,5,6,7-tetrahydro-thieno[2,3-c]pyridin-2-yl)-3-(2-methoxy-phenyl)-propionamide

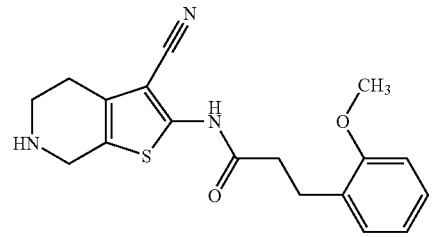

The title compound is prepared according to general procedure C starting from 3-cyano-2-[3-(2-methoxy-phenyl)-propanoylamino]-4,7-dihydro-5H-thieno[2,3-c]pyridine-6-carboxylic acid tert-butyl ester (Example 10).
MS: calc.: C,18; H,19; N,3; O,2; S, (341.44) fnd.: 341.9 [M+H].

Using similar procedures to those described herein, but with suitable choice of starting materials, the following compounds may be prepared.

A4. N-(3-Cyano-4,5,6,7-tetrahydro-thieno[2,3-c]pyridin-2-yl)-3-(2-ethoxyphenyl)-propionamide
A5. N-(3-Cyano-4,5,6,7-tetrahydro-thieno[2,3-c]pyridin-2-yl)-3-(2-methoxy-3-methyl-phenyl)-propionamide
A6. N-(3-Cyano-4,5,6,7-tetrahydro-thieno[2,3-c]pyridin-2-yl)-3-(2-ethoxy-3-methyl-phenyl)-propionamide
A7. N-(3-Cyano-4,5,6,7-tetrahydro-thieno[2,3-c]pyridin-2-yl)-3-(2-methoxy-5-methyl-phenyl)-propionamide
A8. N-(3-Cyano-4,5,6,7-tetrahydro-thieno[2,3-c]pyridin-2-yl)-3-(2-ethoxy-5-methyl-phenyl)-propionamide
A9. N-(3-Cyano-4,5,6,7-tetrahydro-thieno[2,3-c]pyridin-2-yl)-3-(2-ethoxy-3-methoxy-phenyl)-propionamide
A10. N-(3-Cyano-4,5,6,7-tetrahydro-thieno[2,3-c]pyridin-2-yl)-3-(2-ethoxy-5-methoxy-phenyl)-propionamide
A11. N-(3-Cyano-4,5,6,7-tetrahydro-thieno[2,3-c]pyridin-2-yl)-3-(2,3-dimethoxy-phenyl)-propionamide
A12. N-(3-Cyano-4,5,6,7-tetrahydro-thieno[2,3-c]pyridin-2-yl)-3-(2,5-dimethoxy-phenyl)-propionamide A13. N-(3-Cyano-4,5,6,7-tetrahydro-thieno[2,3-c]pyridin-2-yl)-3-(2-methyl-3-methoxy-phenyl)-propionamide
A14. N-(3-Cyano-4,5,6,7-tetrahydro-thieno[2,3-c]pyridin-2-yl)-3-(2-methyl-5-methoxy-phenyl)-propionamide
A15. N-(3-Cyano-4,5,6,7-tetrahydro-thieno[2,3-c]pyridin-2-yl)-3-(2-chloro-3-methoxy-phenyl)-propionamide
A16. N-(3-Cyano-4,5,6,7-tetrahydro-thieno[2,3-c]pyridin-2-yl)-3-(2-chloro-5-methoxy-phenyl)-propionamide
A17. N-(3-Cyano-4,5,6,7-tetrahydro-thieno[2,3-c]pyridin-2-yl)-3-(3-methoxy-phenyl)-propionamide
A18. N-(3-Cyano-4,5,6,7-tetrahydro-thieno[2,3-c]pyridin-2-yl)-3-(3-ethoxy-phenyl)-propionamide
A19. N-(3-Cyano-4,5,6,7-tetrahydro-thieno[2,3-c]pyridin-2-yl)-3-(2-trifluoromethoxy-phenyl)-propionamide
A20. N-(3-Cyano-4,5,6,7-tetrahydro-thieno[2,3-c]pyridin-2-yl)-3-(2-difluoromethoxy-phenyl)-propionamide
A21. N-(3-Cyano-4,5,6,7-tetrahydro-thieno[2,3-c]pyridin-2-yl)-3-(2-ethoxy-6-methyl-phenyl)-propionamide
A22. N-(3-Cyano-4,5,6,7-tetrahydro-thieno[2,3-c]pyridin-2-yl)-3-(2-methoxy-6-methyl-phenyl)-propionamide
A23. (RS)—N-(3-Cyano-4,5,6,7-tetrahydro-thieno[2,3-c]pyridin-2-yl)-3-(2-methoxy-3-methyl-phenyl)-butyramide
A24. (RS)—N-(3-Cyano-4,5,6,7-tetrahydro-thieno[2,3-c]pyridin-2-yl)-3-(2-ethoxy-3-methyl-phenyl)-butyramide
A25. (RS)—N-(3-Cyano-4,5,6,7-tetrahydro-thieno[2,3-c]pyridin-2-yl)-3-(2-methoxy-5-methyl-phenyl)-butyramide
A26. (RS)—N-(3-Cyano-4,5,6,7-tetrahydro-thieno[2,3-c]pyridin-2-yl)-3-(2-ethoxy-5-methyl-phenyl)-butyramide
A27. (RS)—N-(3-Cyano-4,5,6,7-tetrahydro-thieno[2,3-c]pyridin-2-yl)-3-(2-ethoxy-3-methoxy-phenyl)-butyramide
A28. (RS)—N-(3-Cyano-4,5,6,7-tetrahydro-thieno[2,3-c]pyridin-2-yl)-3-(2-ethoxy-5-methoxy-phenyl)-butyramide
A29. (RS)—N-(3-Cyano-4,5,6,7-tetrahydro-thieno[2,3-c]pyridin-2-yl)-3-(2,3-dimethoxy-phenyl)-butyramide
A30. (RS)—N-(3-Cyano-4,5,6,7-tetrahydro-thieno[2,3-c]pyridin-2-yl)-3-(2,5-dimethoxy-phenyl)-butyramide
A31. (RS)—N-(3-Cyano-4,5,6,7-tetrahydro-thieno[2,3-c]pyridin-2-yl)-3-(2-methyl-3-methoxy-phenyl)-butyramide
A32. (RS)—N-(3-Cyano-4,5,6,7-tetrahydro-thieno[2,3-c]pyridin-2-yl)-3-(2-methyl-5-methoxy-phenyl)-butyramide
A33. (RS)—N-(3-Cyano-4,5,6,7-tetrahydro-thieno[2,3-c]pyridin-2-yl)-3-(2-chloro-3-methoxy-phenyl)-butyramide
A34. (RS)—N-(3-Cyano-4,5,6,7-tetrahydro-thieno[2,3-c]pyridin-2-yl)-3-(2-chloro-5-methoxy-phenyl)-butyramide
A35. (RS)—N-(3-Cyano-4,5,6,7-tetrahydro-thieno[2,3-c]pyridin-2-yl)-3-(2-trifluoromethoxy-phenyl)-butyramide
A36. (RS)—N-(3-Cyano-4,5,6,7-tetrahydro-thieno[2,3-c]pyridin-2-yl)-3-(2-difluoromethoxy-phenyl)-butyramide
A37. (RS)—N-(3-Cyano-4,5,6,7-tetrahydro-thieno[2,3-c]pyridin-2-yl)-3-(2-ethoxy-6-methyl-phenyl)-butyramide
A38. (RS)—N-(3-Cyano-4,5,6,7-tetrahydro-thieno[2,3-c]pyridin-2-yl)-3-(2-methoxy-6-methyl-phenyl)-butyramide
A39. (RS)—N-(3-Cyano-4,5,6,7-tetrahydro-thieno[2,3-c]pyridin-2-yl)-3-(2-methoxy-phenyl)-butyramide
Compound A2 is condensed with 3-(2-methoxy-phenyl)-butyric acid as described in general procedure
AA a). Subsequent removal of the Boc protection group is performed according to general procedure C to give the title compound, which is obtained as trifluoroacetic acid salt. M.p.: 113-116° C. (TFA salt)

A40. (RS)—N-(3-Cyano-4,5,6,7-tetrahydro-thieno[2,3-c]pyridin-2-yl)-3-(2-ethoxyphenyl)-butyramide Using the appropriate butyric acid, the title compound is obtained similarly as described for compound A39. M.p.: 111-115° C. (TFA salt)
A41. (RS)—N-(3-Cyano-4,5,6,7-tetrahydro-thieno[2,3-c]pyridin-2-yl)-3-(3-methoxy-phenyl)-butyramide Using the appropriate butyric acid, the title compound is obtained similarly as described for compound A39. M.p.: 197-200° C. (TFA salt)
A42. (RS)—N-(3-Cyano-4,5,6,7-tetrahydro-thieno[2,3-c]pyridin-2-yl)-3-(3-ethoxy-phenyl)-butyramide
Using the appropriate butyric acid, the title compound is obtained similarly as described for compound A39. M.p.: 178-180° C. (TFA salt)

D. General Procedure for the Preparation of carbamates a) Preparation of the imidazole 1-carboxylic ester Reagents:

A solution of the appropriate alcohol (10 mmol), 1,1'-carbonyldiimidazole (10 mmol) in dichloromethane (20 ml) is stirred at room temperature for 2 to 3 h while the reaction is monitored by TLC. Then the reaction mixture is extracted by three portions of 10% sodium hydrogencarbonate solution and once by water. The organic layer is dried over sodium sulfate and evaporated to yield a pale yellow oil or colorless solid.

Synthesis of Carbamates:

To a suspension of the appropriate amine (1 mmol) and abovementioned reagent (1 mmole) in abs. dichloromethane (15 ml), DBU (1.15 mmol) is added and the mixture is stirred for 2 to 7 days, the reaction is monitored by TLC (silica, dichloromethane-methanol 10:1 mixture as an eluent). The reaction mixture is extracted twice by 10% sodium hydrogencarbonate solution, once by water, and the organic layer is dried over sodium sulfate. After evaporation the residue is treated with diethyl ether, the obtained solid is filtered off, washed with a small amount of acetonitrile and finally with diethyl ether. The crude product can be recrystallized from acetonitrile to yield the purified product.

b) In case the appropriate chloroformates are commercially available 1 mmol of the chloroformiate is reacted with 1 mmol of the amino building block in pyridine. After the reaction is completed, the solvent is removed and the remaining crude product purified as described above.

D'. Further General Procedure for the Preparation of Carbamates

Carbamates are prepared in analogy to general procedure D:

A solution of the appropriate alcohol (10 mmol), 1,1'-carbonyldiimidazole (1 mmol) in abs. dichloromethane (20 ml) is stirred at room temperature over night (monitored by TLC). Then the reaction mixture is extracted by three portions of 10% sodium hydrogen carbonate solution and then once by water. The organic layer is dried over sodium or magnesium sulfate and evaporated to yield the desired reagent.

To a suspension of the appropriate amine (1 mmol) and the abovementioned reagent (1 mmol) in abs. dichloromethane (15 ml), DBU (1.15 mmol) is added and the mixture stirred for 1 to 7 days with monitoring by TLC. Then the reaction mixture is evaporated and the remaining residue subjected to flash chromatography (dichloromethane, methanol) or HPLC (AcCN, water at pH 3,75; ammonium formiate buffer). The purified product is then lyophilized from AcCN, water to obtain an amorphous solid. This type of purification (evaporation of the reaction mixture and chromatography) can be performed for most of the final compounds, especially in case recrystallization does not yield pure compounds.

E. General Procedure for the Preparation of Carboxylic Acids

Synthesis of Propionic Acids Starting from Aldehyde:

10 mmol of the appropriate aldehyde are dissolved with 1.1 eq. of triethyl phosphonoacetate in 7 ml THF. At 0° C. 1 eq. of DBU is added and the reaction mixture is stirred over night at room temperature. Then, the reaction mixture is diluted with water, acidified with aq. HCl and extracted with diethyl ether. The organic layer is dried over MgSO$_4$ and the solvent removed. This acrylic acid ester is used without further purification. The crude acrylic acid ester is suspended in 20 ml 1N NaOH and stirred over night. After the reaction is completed, the reaction mixture is acidified with 1N HCl and extracted with diethyl ether. The organic layer is dried over MgSO$_4$ and the solvent evaporated; the desired acrylic acid is obtained in almost pure form. 11 mmol of the acrylic acid are dissolved in 20 ml MeOH, 1 eq. of NAHCO$_3$ and 200 mg Pd/C (10%) are added and the reaction hydrogenated over night at room temperature and normal pressure. Filtration of the reaction mixture over Celite and removal of the solvent affords the desired product in good yield in pure form. In case one of the products is not sufficiently pure, one can also purify them via flash chromatography. According to the above-mentioned procedure, the following compound can be prepared: 2 g of 2-methoxy-5-methyl-benzaldehyde is transformed to 2.2 g of (2-methoxy-5-methyl-phenyl)-acrylic acid. 21 g of the before-mentioned acrylic acid are hydrogenated to yield 20 g of the desired 3-(2-methoxy-5-methyl-phenyl)-propionic acid. Further relevant starting compounds can be prepared similarly.

Synthesis of β-methyl Propionic Acid Starting from Acetophenone:

1.9 mmol of sodium hydride are suspended in 5 ml toluene and 1.6 mmol triethyl phosphonoacetate are added at 0° C. After stirring for 30 min at 0° C., 1.1 mmol of the appropriate acetophenone is dissolved in 1 ml toluene, added to the reaction mixture and the reaction mixture stirred over night at room temperature. After addition of some water, the reaction mixture is extracted with toluene and the combined organic layers are dried over MgSO$_4$. The crude acrylic acid ester is obtained as cis/trans mixture and used without further purification. The acrylic acid ester is suspended in a mixture of EtOH and 1N NaOH and stirred over night at room temperature. After acidification with 1N HCl the acrylic acid crystallizes and can be obtained by filtration. In case no crystallization can be achieved, the acrylic acid can be purified via flash chromatography. The acrylic acid is hydrogenated in MeOH with Pd/C (10%) and 1 eq. NaHCO$_3$ under normal pressure at room temperature. After filtration over Celite, the solvent is removed and the desired β-methyl propionic acid purified via flash chromatography if necessary. According to the above-mentioned procedure, the following compound can be prepared: Starting from 180 mg 2-methoxy-5-methyl-acetophenone, 75 mg of (2-methoxy-5-methyl-phenyl)-crotonic acid can be obtained as cis/trans mixture. Hydrogenation of 200 mg of the crotonic acid affords 190 mg of the 3-(2-methoxy-5-methyl-phenyl)-butyric acid. Further relevant starting compounds can be prepared similarly, such as e.g. 3-(2-ethoxy-phenyl)-butyric acid from 2-ethoxy-acetophenone or 3-(3-ethoxy-phenyl)-butyric acid from 3-ethoxy-acetophenone.

Cyclopropanation:

113 mg of sodium hydride and 1.1 g of trimethyl sulfoxonium iodide are stirred for one hour in 7 ml DMSO at room temperature. 500 mg of trans cinnamic acid ethyl ester are dissolved in 6 ml DMSO/THF (1:1) and added to the reaction mixture. After completion of the reaction (3 h, TLC) 1N HCl is added and the reaction mixture extracted with diethyl ether. The combined organic layers are dried over MgSO$_4$, the solvent removed and the crude product (393 mg) is used without further purification. In case the purity is not sufficient, the product can be purified by flash chromatography. Saponification of the ester to give the corresponding carboxylic acid can be obtained similarly as described in the foregoing procedures. Further relevant starting compounds can be obtained similarly.

Preparation of 2-(2-methyl-imidazol-1-yl)-ethanol

This compound is prepared in analogy to P.Chen et al. J. Med. Chem. 1996, 39, 1991-2007:

A solution of (2-methyl-imidazol-1-yl)-acetic acid methyl ester (2,6 g) in diethyl ether (39 ml) is added drop wise to a suspension of LiAlH4 (1,3 g) in 130 ml diethyl ether (130 ml) at 0° C. After 1 hour 1.3 g water, 1.3 g 15% NaOH and 4 g water is added and the slurry stirred for 1 hour. After addition of MgSO,4;and filtration the filter cake is washed several times with hot ethyl acetate. After removal of the solvent, the crude product is used without further purification.

Preparation of (2-methyl-imidazol-1-yl)-acetic acid methyl ester

This compound is prepared in analogy to US2005/154024:

4 ml of bromo acetic acid methyl ester is dissolved in 30 ml DMF and 5.2 g of 2-methylimidazole and 11.2 g potassium carbonate are added. The reaction mixture is stirred at room temperature for several hours and then subjected to aqueous work up. After removal of the solvent the pure product is obtained by flash chromatography in 47 to 78% yield.

Preparation of 2-(2,4-dimethyl-imidazol-1-yl)-ethanol and 2-(4-methyl-imidazol-1-yl)-ethanol These compounds are prepared in analogy to the above-mentioned 2-(2-methyl-imidazol-1-yl)-ethanol using the below mentioned building blocks. The title compounds can be used as mixture without separation of the components. Separation may be then obtained on the stage of the final compounds by column chromatography (HPLC).

Preparation of (4-methyl-imidazol-1-yl)-acetic acid methyl ester and (2,4-dimethyl-imidazol-1-yl)-acetic acid methyl ester These compounds are prepared in analogy to (2-methyl-imidazol-1-yl)-acetic acid methyl ester and can be obtained as mixture which is used without separation of the components.

Commercial Utility

The compounds according to the present invention have miscellaneous valuable pharmacological properties which can make them commercially applicable.

The compounds according to the invention therefore can be employed as therapeutic agents for the treatment and prophylaxis of diseases in human and veterinary medicine.

Thus, for example, in more embodimental detail, the compounds according to this invention are potent and highly efficacious cell-cycle specific inhibitors of cellular (hyper) proliferation and/or inducers of apoptosis in cancer cells. Therefore, these compounds are expected to be useful for treating (hyper)proliferative diseases and/or disorders responsive to the induction of apoptosis, in particular cancer.

Further on, these compounds can be useful in the treatment of benign or malignant neoplasia.

A "neoplasia" is defined by cells displaying aberrant cell proliferation and/or survival and/or a block in differentiation. A "benign neoplasia" is described by hyperproliferation of cells, incapable of forming an aggressive, metastasizing tumor in-vivo. In contrast, a "malignant neoplasia" is described by cells with multiple cellular and biochemical abnormalities, capable of forming a systemic disease, for example forming tumor metastasis in distant organs.

Various diseases are caused by limitless replicative potential and aberrant cell proliferation ("hyperproliferation") as well as evasion from apoptosis. These diseases include e.g. benign hypoplasia like that of the prostate ("BPH") or colon epithelium, psoriasias, glomerulonephritis or osteoarthritis. Most importantly these diseases include malignant neoplasia commonly described as cancer and characterized by tumor cells finally metastasizing into distinct organs or tissues. Malignant neoplasia include solid and hematological tumors. Solid tumors are exemplified by tumors of the breast, bladder, bone, brain, central and peripheral nervous system, colon, endocrine glands (eg thyroid and adrenal cortex), esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva. Malignant neoplasia include inherited cancers exemplified by retinoblastoma and Wilms tumor. In addition, malignant neoplasia include primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies.

It is to be noted that a cancer disease as well as a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function.

Neoplastic cell proliferation might effect normal cell behaviour and organ function. For example the formation of new blood vessels, a process described as neovascularization, is induced by tumors or tumor metastases. Compounds according to this invention can be commercially applicable for treatment of pathophysiological relevant processes caused by benign or neoplastic cell proliferation, such as but not limited to neovascularization by unphysiological proliferation of vascular endothelial cells.

Drug resistance is of particular importance for the frequent failure of standard cancer therapeutics. This drug resistance is caused by various cellular and molecular mechanisms like overexpression of drug efflux pumps or mutation within the cellular target protein. The commercial applicability of the compounds according to this invention is not limited to $1^{st}$ line treatment of patients. Patients with resistance to defined cancer chemotherapeutics or target specific anti-cancer drugs ($2^{nd}$ or $3^{rd}$ line treatment) can be also amenable for treatment with the compounds according to this invention.

The compounds according to the present invention display a cell cycle dependent cytotoxic activity, more precisely a mitosis confined activity, leading to a mitotic arrest which inevitably results in the onset of apoptosis and/or cell death.

Compounds of the present invention induce a strongly increased phosphorylation of histone H3 when incubated with test cells for more than 8 hours and less than 48 hours at concentrations around the IC50 value of the cytotoxicity or above. Moreover, treatment of cells with compounds of this invention does not induce polyploidy or multinuclearity as primary mode of action.

Compounds according to the present invention can be commercially applicable for treatment, prevention or amelioration of the diseases of benign and malignant behavior as described before, such as e.g. benign or malignant neoplasia, particularly cancer, such as e.g. any of those cancer diseases described above.

In the context of their properties, functions and usabilities mentioned herein, the compounds according to the present invention are expected to be distinguished by valuable and desirable effects related therewith, such as e.g. by low toxicity, superior bioavailability in general (such as e.g. good enteral absorption), superior therapeutic window, absence of significant side effects, and/or further beneficial effects related with their therapeutic and pharmaceutical suitability.

The invention further includes a method for treating (hyper)proliferative diseases and/or disorders responsive to the induction of apoptosis, particularly those diseases, disorders, conditions or illnesses mentioned above, in mammals, including humans, suffering therefrom comprising administering to said mammals in need thereof a pharmacologically active and therapeutically effective and tolerable amount of one or more of the compounds according to this invention.

The present invention further includes a method useful to modulate apoptosis and/or aberrant cell growth in the therapy of benign or malignant neoplastic diseases, such as e.g. cancer, comprising administering to a subject in need of such therapy a therapeutically active and pharmacologically effective and tolerable amount of one or more of the compounds according to this invention.

The present invention further relates to the use of the compounds according to this invention for the production of pharmaceutical compositions which are employed for the treatment, prophylaxis and/or amelioration of the illnesses mentioned.

The present invention further relates to the use of the compounds according to this invention for the production of pharmaceutical compositions which can be used in the treatment, prevention or amelioration of (hyper)proliferative diseases of benign or malignant behaviour and/or disorders responsive to the induction of apoptosis in a mammal, such as, for example, benign or malignant neoplasia, e.g. cancer.

The present invention further relates to the use of the compounds according to this invention for the production of pharmaceutical compositions which can be used use in the treatment, prevention or amelioration of disorders responsive to arresting of aberrant cell growth and/or induction of apoptosis.

The present invention further relates to the use of the compounds according to this invention for the production of pharmaceutical compositions for treating, preventing or ameliorating benign or malignant neoplasia, particularly cancer, such as e.g. any of those cancer diseases described above.

The present invention further relates to pharmaceutical compositions comprising one or more of the compounds according to this invention and a pharmaceutically acceptable carrier or diluent.

The present invention further relates to pharmaceutical compositions made by combining one or more of the compounds according to this invention and a pharmaceutically acceptable carrier or diluent.

The present invention further relates to pharmaceutical compositions comprising one or more of the compounds according to this invention and pharmaceutically acceptable auxiliaries and/or excipients.

The present invention further relates to combinations comprising one or more compounds according to this invention and pharmaceutically acceptable auxiliaries, excipients and/or vehicles, e.g. for treating, preventing or ameliorating benign or malignant neoplasia, particularly cancer, such as e.g. any of those cancer diseases described above.

The present invention further relates to a combination comprising a compound according to this invention and a pharmaceutically acceptable excipient, carrier and/or diluent, e.g. for treating, preventing or ameliorating benign or malignant neoplasia, particularly cancer, such as e.g. any of those cancer diseases described above.

The present invention further relates to a composition consisting essentially of a therapeutically effective and tolerable amount of one or more compounds according to this invention together with the usual pharmaceutically acceptable vehicles, diluents and/or excipients for use in therapy, e.g. for treating, preventing or ameliorating hyperproliferative diseases, such as e.g. cancer, and/or disorders responsive to induction of apoptosis.

The present invention further relates to compounds according to this invention for use in therapy, such as, for example, in the treatment, prevention or amelioration (hyper)proliferative diseases of benign or malignant behaviour and/or disorders responsive to the induction of apoptosis, such as e.g. those diseases mentioned herein, particularly cancer.

The present invention further relates to compounds according to this invention having anti-proliferative and/or apoptosis inducing activity.

The present invention further relates to pharmaceutical compositions according to this invention having anti-proliferative activity.

The present invention further relates to pharmaceutical compositions according to this invention having apoptosis inducing activity.

The invention further relates to the use of a pharmaceutical composition comprising one or more of the compounds according to this invention as sole active ingredient(s) and a pharmaceutically acceptable carrier or diluent in the manufacture of pharmaceutical products for the treatment and/or prophylaxis of the illnesses mentioned above.

Additionally, the invention relates to an article of manufacture, which comprises packaging material and a pharmaceutical agent contained within said packaging material, wherein the pharmaceutical agent is therapeutically effective inhibiting cellular (hyper)proliferation and/or inducing apoptosis, ameliorating the symptoms of a (hyper)proliferative disease and/or a disorder responsive to the induction of apoptosis, and wherein the packaging material comprises a label or package insert which indicates that the pharmaceutical agent is useful for treating, preventing or ameliorating a (hyper)proliferative disease and/or a disorder responsive to the induction of apoptosis, and wherein said pharmaceutical agent comprises one or more compounds according to the invention. The packaging material, label and package insert otherwise parallel or resemble what is generally regarded as standard packaging material, labels and package inserts for pharmaceuticals having related utilities.

The pharmaceutical compositions according to this invention are prepared by processes which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, pre-servatives, solubilizers, colorants, complexing agents or permeation promoters, can be used.

The administration of the compounds, pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of dermatoses, the compounds of the invention can be in particular administered in the form of those pharmaceutical compositions which are suitable for topical application. For the production of the pharmaceutical compositions, the compounds of the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the compounds of the invention (=active compounds) is carried out in the order of magnitude customary for inhibitors of cellular (hyper)proliferation or apoptosis inducers. Topical application forms (such as ointments) for the treatment of dermatoses thus contain the active compounds in a concentration of, for example, 0.1-99%. The customary dose in the case of systemic therapy (p.o.) may be between 0.03 and 60 mg/kg per day, (i. v.) may be between 0.03 and 60 mg/kg/h. In another embodiment, the customary dose in the case of systemic therapy (p.o.) is between 0.3 and 30 mg/kg per day, (i. v.) is between 0.3 and 30 mg/kg/h.

The choice of the optimal dosage regime and duration of medication, particularly the optimal dose and manner of administration of the active compounds necessary in each case can be determined by a person skilled in the art on the basis of his/her expert knowledge.

Depending upon the particular disease, to be treated or prevented, additional therapeutic active agents, which are normally administered to treat or prevent that disease, may optionally be coadministered with the compounds according to this invention. As used herein, additional therapeutic agents that are normally administered to treat or prevent a particular disease are known as appropriate for the disease being treated.

For example, compounds according to this invention may be combined with one or more standard therapeutic agents used for treatment of the diseases as mentioned before.

In one particular embodiment, compounds according to this invention may be combined with one or more art-known anti-cancer agents, such as e.g. with one or more chemotherapeutic and/or target specific anti-cancer agents as described below.

Examples of known chemotherapeutic anti-cancer agents frequently used in combination therapy include, but not are limited to (i) alkylating/carbamylating agents such as Cyclophosphamid (Endoxan®), Ifosfamid (Holoxan®), Thiotepa (Thiotepa Lederle®), Melphalan (Alkeran®), or chloroethylnitrosourea (BCNU); (ii) platinum derivatives like cis-platin (Platinex® BMS), oxaliplatin or carboplatin (Cabroplat® BMS); (iii) antimitotic agents/tubulin inhibitors such as vinca alkaloids (vincristine, vinblastine, vinorelbine), taxanes such as Paclitaxel (Taxol®), Docetaxel (Taxotere®) and analogs as well as new formulations and conjugates thereof, epothilones such as Epothilone B (Patupilone®), Aza-epothilone (Ixabepilone®) or ZK-EPO, a fully synthetic epothilone B analog; (iv) topoisomerase inhibitors such as anthracyclines (exemplified by Doxorubicin/Adriblastin®), epipodophyllotoxines (exemplified by Etoposide/Etopophos®) and camptothecin and camptothecin analogs (exemplified by Irinotecan/Camptosar® or Topotecan/Hycamtin®); (v) pyrimidine antagonists such as 5-fluorouracil (5-FU), Capecitabine (Xeloda®), Arabinosylcytosine/Cyt-arabin (Alexan®) or Gemcitabine (Gemzar®); (vi) purin antagonists such as 6-mercaptopurine (Puri-Nethol®), 6-thioguanine or fludarabine (Fludara®) and finally (vii) folic acid antagonists such as methotrexate (Farmitrexat®) or premetrexed (Alimta®).

Examples of target specific anti-cancer drug classes used in experimental or standard cancer therapy include but are not limited to (i) kinase inhibitors such as e.g. Imatinib (Glivec®), ZD-1839/Gefitinib (Iressa®), Bay43-9006 (Sorafenib), SU1 1248/Sunitinib (Sutent®) or OSI-774/Erlotinib (Tarceva®); (ii) proteasome inhibitors such as PS-341/Bortezumib (Velcade®); (iii) histone deacetylase inhibitors like SAHA, PXD101, MS275, MGCDO103, Depsipeptide/FK228, NVP-LBH589, NVP-LAQ824, Valproic acid (VPA) and butyrates (iv) heat shock protein 90 inhibitors like 17-allylaminogeldanamycin (17-MG); (v) vascular targeting agents (VTAs) like combretastin A4 phosphate or AVE8062/AC7700 and anti-angiogenic drugs like the VEGF antibodies, such as Bevacizumab (Avastin®), or KDR tyrosine kinase inhibitors such as PTK787/ZK222584 (Vatalanib); (vi) monoclonal antibodies such as Trastuzumab (Herceptin®) or Rituximab (MabThera/Rituxan®) or Alemtuzumab (Campath®) or Tositumab (Bexxar®) or C225/Cetuximab (Erbitux®) or Avastin (see above) as well as mutants and conjugates of monoclonal antibodies, e.g. Gemtuzumab ozogamicin (Mylotarg®) or Ibritumomab tiuxetan (Zevalin®), and antibody fragments; (vii) oligonucleotide based therapeutics like G-3139/Oblimersen (Genasense®); (viii) Toll-like receptor/TLR 9 agonists like Promune®, TLR 7 agonists like Imiquimod (Aldara®) or Isatoribine and analogues thereof, or TLR 7/8 agonists like Resiquimod as well as immunostimulatory RNA as TLR 7/8 agonists; (ix) protease inhibitors (x) hormonal therapeutics such as anti-estrogens (e.g. Tamoxifen or Raloxifen), anti-androgens (e.g. Flutamide or Casodex), LHRH analogs (e.g. Leuprolide, Goserelin or Triptorelin) and aromatase inhibitors.

Other known target specific anti-cancer agents which may be used for combination therapy include bleomycin, retinoids such as all-trans retinoic acid (ATRA), DNA methyltransferase inhibitors such as the 2-deoxycytidine derivative Decitabine (Docagen®) and 5-Azacytidine, alanosine, cytokines such as interleukin-2, interferons such as interferon α2 or interferon-γ, death receptor agonists, such as TRAIL, DR4/5 agonistic antibodies, FasL and TNF-R agonists.

As exemplary anti-cancer agents, which may be useful in the combination therapy according to the present invention, any of the following drugs may be mentioned, without being restricted thereto, 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEVACIZUMAB, BEXXAR, BICALUTAMIDE, BLEOMYCIN, BORTEZOMIB, BROXURIDINE, BUSULFAN, CAMPATH, CAPECITABINE, CARBOPLATIN, CARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DAUNORUBICIN, DECITABINE, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ERLOTINIB, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GENASENSE, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, IXABEPILONE, LANREOTIDE, LETROZOLE, LEUPRORELIN, LOBAPLATIN, LOMUSTINE, LUPROLIDE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, MYLOTARG, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PATUPILONE, PEGASPARGASE, PEGFILGRASTIM, PEMETREXED, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALOXIFEN, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SORAFENIB, SPIROMUSTINE, STREPTOZOCIN, SUNITINIB, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRAIL, TRASTUZUMAB, TREOSULFAN, TRIAZIQUONE, TRIMETREXATE, TRIPTORELIN, TROFOSFAMIDE, UREDEPA, VALRUBICIN, VATALANIB, VERTEPORFIN, VINBLASTINE, VINCRISTINE, VINDESINE, VINORELBINE, VOROZOLE and ZEVALIN.

The anti-cancer agents mentioned herein above as combination partners of the compounds according to this invention are meant to include pharmaceutically acceptable derivatives thereof, such as e.g. their pharmaceutically acceptable salts.

The person skilled in the art is aware on the base of his/her expert knowledge of the kind, total daily dosage(s) and administration form(s) of the additional therapeutic agent(s) coadministered. Said total daily dosage(s) can vary within a wide range.

In practicing the present invention, the compounds according to this invention may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics, in particular art-known anti-cancer agents (chemotherapeutic and/or target specific anti-cancer agents), such as e.g. any of those mentioned above.

In this context, the present invention further relates to a combination comprising
a first active ingredient, which is at least one compound according to this invention, and
a second active ingredient, which is at least one art-known anti-cancer agent, such as e.g. one or more of those mentioned herein above,
for separate, sequential, simultaneous, concurrent or chronologically staggered use in therapy, such as e.g. in therapy of any of those diseases mentioned herein.

The term "combination" according to this invention may be present as a fixed combination, a non-fixed combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously, concurrently or chronologically staggered.

The present invention further relates to a pharmaceutical composition comprising
a first active ingredient, which is at least one compound according to this invention, and
a second active ingredient, which is at least one art-known anti-cancer agent, such as e.g. one or more of those mentioned herein above, and, optionally, a pharmaceutically acceptable carrier or diluent,
for separate, sequential, simultaneous, concurrent or chronologically staggered use in therapy.

The present invention further relates to a combination product comprising
a.) at least one compound according to this invention formulated with a pharmaceutically acceptable carrier or diluent, and
b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, concurrent, sequential, separate or chronologically staggered use in therapy. Optionally, said kit comprises instructions for its use in therapy, e.g. to treat (hyper)proliferative diseases and/or disorders responsive to the induction of apoptosis, such as e.g. cancer, more precisely, any of those cancer diseases described above.

The present invention further relates to a combined preparation comprising at least one compound according to this invention and at least one art-known anti-cancer agent for simultaneous, concurrent, sequential or separate administration.

In this connection, the present invention further relates to combinations, compositions, formulations, preparations or kits according to the present invention having anti-proliferative and/or apoptosis inducing properties.

In addition, the present invention further relates to a method for treating in combination therapy (hyper)proliferative diseases and/or disorders responsive to the induction of apoptosis, such as e.g. cancer, in a patient comprising administering a combination, composition, formulation, preparation or kit as described herein to said patient in need thereof.

In addition, the present invention further relates to a method for treating (hyper)proliferative diseases of benign or malignant behaviour and/or disorders responsive to the induction of apoptosis, such as e.g. cancer, in a patient comprising administering in combination therapy separately, simultaneously, concurrently, sequentially or chronologically staggered a pharmaceutically active and therapeutically effective and tolerable amount of a pharmaceutical composition, which comprises a compound according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In further addition, the present invention relates to a method for treating, preventing or ameliorating (hyper)proliferative diseases and/or disorders responsive to induction of apoptosis, such as e.g. benign or malignant neoplasia, e.g. cancer, particularly any of those cancer diseases mentioned herein, in a patient comprising administering separately, simultaneously, concurrently, sequentially or chronologically staggered to said patient in need thereof an amount of a first active compound, which is a compound according to the present invention, and an amount of at least one second active compound, said at least one second active compound being a standard therapeutic agent, particularly at least one art-known anti-cancer agent, such as e.g. one or more of those chemotherapeutic and target-specific anti-cancer agents mentioned herein, wherein the amounts of the first active compound and said second active compound result in a therapeutic effect.

In yet further addition, the present invention relates to a method for treating, preventing or ameliorating (hyper)proliferative diseases and/or disorders responsive to induction of apoptosis, such as e.g. benign or malignant neoplasia, e.g. cancer, particularly any of those cancer diseases mentioned herein, in a patient comprising administering a combination according to the present invention.

In addition, the present invention further relates to the use of a composition, combination, formulation, preparation or kit according to this invention in the manufacture of a pharmaceutical product, such as e.g. a commercial package or a medicament, for treating, preventing, or ameliorating (hyper) proliferative diseases, such as e.g. cancer, and/or disorders responsive to the induction of apoptosis, particularly those diseases mentioned herein, such as e.g. malignant or benign neoplasia.

The present invention further relates to a commercial package comprising one or more compounds of the present invention together with instructions for simultaneous, concurrent, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, concurrent, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, concurrent, sequential or separate use with one or more compounds according to the present invention.

The compositions, combinations, preparations, formulations, kits or packages mentioned in the context of the combination therapy according to this invention may also include more than one of the compounds according to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, concurrent, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a (hyper)proliferative diseases and/or a disorder responsive to the induction of apoptosis, particularly one of those diseases mentioned herein, e.g. benign or malignant neoplasia, especially cancer, like any of those cancer diseases mentioned herein.

In addition, compounds according to the present invention can be used in the pre- or post-surgical treatment of cancer.

In further addition, compounds of the present invention can be used in combination with radiation therapy.

A combination according to this invention can refer to a composition comprising both the compound(s) according to this invention and the other active anti-cancer agent(s) in a fixed combination (fixed unit dosage form), or a medicament pack comprising the two or more active ingredients as discrete separate dosage forms (non-fixed combination). In case of a medicament pack comprising the two or more active ingredients, the active ingredients are preferably packed into blister cards which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

Biological Investigations

The anti-proliferative/cytotoxic activity of the compounds described herein, can be tested on subclones of RKO (RKOp27) human colon adenocarcinoma cells (Schmidt et al., Oncogene 19, 2423-2429; 2000) using the Alamar Blue cell viability assay (described in O'Brien et al. Eur J Biochem 267, 5421-5426, 2000). The compounds are dissolved as 20 mM solutions in dimethylsulfoxide (DMSO) and subsequently diluted in semi-logarithmic steps. DMSO dilutions are further diluted 1:100 into Dulbecco's modified Eagle's medium (DMEM) containing 10% fetal calf serum to a final concentration twice as much as the final concentration in the test. RKO subclones are seeded into 96 well flat bottom plates at a density of 4000 cells per well in a volume of 50 µl per well. 24 hours after seeding the 50 µl each of the compound dilutions in DMEM medium are added into each well of the 96 Well plate. Each compound dilution is tested as quadruplicates. Wells containing untreated control cells are filled with 50 µl DMEM medium containing 1% DMSO. The cells are then incubated with the substances for 72 hours at 37° C. in a humidified atmosphere containing 5% carbon dioxide. To determine the viability of the cells, 10 µl of an Alamar Blue solution (Biosource) are added and the fluorescence is measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values.

The corresponding $IC_{50}$ values of the compounds for anti-proliferative/cytotoxic activity are determined from the concentration-effect curves.

Representative $IC_{50}$ values for anti-proliferation/cytotoxicity determined in the mentioned assay follow from the following table A, in which the numbers of the compound correspond to the numbers of the examples.

TABLE A

| Anti-proliferative/cytotoxic activity | | | |
|---|---|---|---|
| | IC$_{50}$ RKO p27 induced (arrested) >100 μM | IC$_{50}$ RKO p27 induced (arrested) ≧40 μM | IC$_{50}$ RKO p27 induced (arrested) ≧10 μM |
| IC$_{50}$ RKO p27 uninduced (proliferating) ≦0.3 μM | 1-5, 9-12, 14, 15, 17, 19, 20, 25, 28-30, 32-37, 39-42, 44-47, 49, 51, 59, 61, 62, 64, 73, 106, 119, 123, 142, 189-191 | 26, 43, 63, 131, 132 | 122, 124 |
| IC$_{50}$ RKO p27 uninduced (proliferating) ≧0.3 μM but ≦2 μM | 3, 6-8, 16, 18, 21, 24, 38, 46, 48, 50, 52-56, 58, 153, 155 | 57 | 130 |

To determine the cell cycle specific mode of action, subclones of RKO colon adenocarcinoma cells (RKOp27 or RKOp21 as described by Schmidt et al. in Oncogene 19, 2423-2429; 2000) are seeded into 96 well flat bottom plates at a density of 16000 cells per well in a volume of 50 μl per well in DMEM growth medium with 10% FCS containing 10 μM Ponasterone A. 24 hours after seeding the 50 μl each of the compound dilutions in DMEM medium are added into each well of the 96 Well plate. Each compound dilution is tested as quadruplicates. Wells containing untreated control cells are filled with 50 μl DMEM medium containing 1% DMSO. The cells are then incubated with the substances for 72 hours at 37° C. in a humidified atmosphere containing 5% carbon dioxide. To determine the viability of the cells, 10 μl of an Alamar Blue solution (Biosource) are added and the fluorescence was measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values. Viability is compared of proliferating cells grown in the absence of the inducer Ponasterone A, versus viability of cells arrested by the expression of ectopic p27Kip1 induced by Ponasterone A.

To test the anti-proliferative activity/cytotoxicity on cells known to be highly resistant towards distinct classes of chemotherapeutics, HCT15 cells (with P-glycoprotein overexpression) and MCF7 ADR cells, both of them are known to overexpress certain classes of multidrug resistance transporters are used in Alamar Blue assays as described above. Briefly, the compounds are dissolved as 20 mM solutions in dimethylsulfoxide (DMSO) and subsequently diluted in semi-logarithmic steps. DMSO dilutions were further diluted 1:100 into Dulbecco's modified Eagle's medium (DMEM) containing 10% fetal calf serum to a final concentration twice as much as the final concentration in the test. The cells to be tested are seeded into 96 well flat bottom plates at a density of 10000 cells per well in a volume of 50 μl per well. 24 hours after seeding the 50 μl each of the compound dilutions in DMEM medium are added into each well of the 96 Well plate. Each compound dilution is tested as quadruplicates. Wells containing untreated control cells are filled with 50 μl DMEM medium containing 1% DMSO. The cells are then incubated with the substances for 72 hours at 37° C. in a humidified atmosphere containing 5% carbon dioxide. To determine the viability of the cells, 10 μl of an Alamar Blue solution (Biosource) are added and the fluorescence was measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values.

The induction of apoptosis can be measured by using a Cell death detection ELISA (Roche Biochemicals, Mannheim, Germany). RKO subclones are seeded into 96 well flat bottom plates at a density of 10000 cells per well in a volume of 50 μl per well. 24 hours after seeding the 50 μl each of the compound dilutions in DMEM medium are added into each well of the 96 Well plate. Each compound dilution is tested at least as triplicates. Wells containing untreated control cells are filled with 50 μl DMEM medium containing 1% DMSO. The cells are then incubated with the substances for 24 hours at 37° C. in a humidified atmosphere containing 5% carbon dioxide. As a positive control for the induction of apoptosis, cells are treated with 50 μM Cisplatin (Gry Pharmaceuticals, Kirchzarten, Germany). Medium is then removed and the cells are lysed in 200 μl lysis buffer. After centrifugation as described by the manufacturer, 10 μl of cell lysate is processed as described in the protocol. The degree of apoptosis is calculated as follows: The absorbance at 405 nm obtained with lysates from cells treated with 50 μM cisplatin is set as 100 cpu (cisplatin units), while an absorbance at 405 nm of 0.0 was set as 0.0 cpu. The degree of apoptosis is expressed as cpu in relation to the value of 100 cpu reached with the lysates obtained from cells treated with 50 μM cisplatin.

The invention claimed is:

1. A compound of formula I

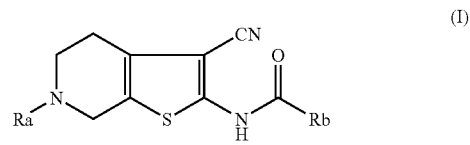

(I)

wherein
Ra is —C(O)OR1,
R1 is 1-7C-alkyl, 3-7C-cycloalkyl, 1-7C-alkyl substituted by Raa, or 2-7C-alkyl substituted by Rab and Rac on different carbon atoms,
Rb is -T-Q,
T is 1-6C-alkylene or 3-7C-cycloalkylene, and
Q is substituted by Rba and Rbb and Rbc, and is phenyl,
Raa is selected from the group consisting of:
  3-7C-cycloalkyl, halogen, trifluoromethyl, cyano, hydroxyl, Har, morpholino, —C(O)R2, —C(O)OR3, —C(O)N(R4)R5, —N(R6)C(O)R7, —OC(O)R8, completely and predominantly fluorine-substituted 1-4C-alkoxy, and —OR9,
wherein said Har may be optionally substituted by one or two substituents independently selected from R10,
R2, R3, R4, R5, R6, R7 and R8 may be the same or different and are independently selected from the group consisting of:
hydrogen and 1-7C-alkyl,
R9 is selected from the group consisting of:
1-4C-alkyl, 3-7C-cycloalkyl, 3-7C-cycloalkyl-1-4C-alkyl, hydroxy-2-4C-alkyl, 1-4C-alkoxy-2-4C-alkyl, phenyl-1-4C-alkyl, pyridyl-1-4C-alkyl, and (1-4C-alkoxy-2-4C-alkoxy)-2-4C-alkyl,
Har is bonded via a ring carbon or a ring nitrogen atom of Har, and is a 5-membered monocyclic unsaturated, aromatic heteroaryl ring comprising one heteroatoms independently selected from the group consisting of nitrogen, oxygen and sulphur,
or
Har is bonded via a ring carbon or a ring nitrogen atom of Har, and is a 6-membered monocyclic unsaturated, aromatic heteroaryl ring comprising one or two nitrogen atoms,
or
Har is bonded via a ring carbon or a ring nitrogen atom of Har, and is a 9- or 10-membered fused bicyclic unsaturated, aromatic heteroaryl ring comprising one to three heteroatoms independently selected from the group consisting of nitrogen, oxygen and sulphur,
each R10 may be the same or different is each independently selected from the group consisting of:
1-4C-alkyl, halogen and 1-4C-alkoxy,
Rab is hydroxyl,
Rac is hydroxyl,
or Rab and Rac bonded to adjacent carbon atoms form together an 1-2C-alkylenedioxy bridge which is optionally substituted by one or two substituents independently selected from the group consisting of fluorine and methyl,
or Rab and Rac bonded to carbon atoms two bonds distant from each other form together a methylenedioxy bridge which is optionally substituted by one or two substituents independently selected from the group consisting of fluorine and methyl,
Rba is selected from the group consisting of:
1-4C-alkoxy, 3-7C-cycloalkoxy, 3-7C-cycloalkyl-1-4C-alkoxy, 1-4C-alkoxy-2-4C-alkoxy, phenyl-1-4C-alkoxy, cyano-1-4C-alkoxy, 3-6C-alkinyloxy, nitro, and completely and predominantly fluorine-substituted 1-4C-alkoxy,
Rbb is selected from the group consisting of:
hydrogen, 1-4C-alkyl, halogen, trifluoromethyl, and 1-4C-alkoxy,
Rbc is selected from the group consisting of:
hydrogen, 1-4C-alkyl, halogen, trifluoromethyl, and 1-4C-alkoxy,
or Rbb and Rbc bounded in ortho position to each other form together an 1-2C-alkylenedioxy bridge, or a completely or partially fluorine-substituted 1-2C-alkylenedioxy bridge;
under the provisio, that those compounds, in which T is methylene substituted by 1-5C-alkyl, are thereof disclaimed;
or a salt thereof.

2. A compound according to claim 1, which is from any one of the formulae Ia, Ib, Ic, Id and Id'

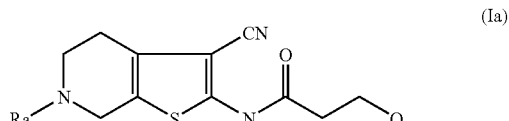

(Ia)

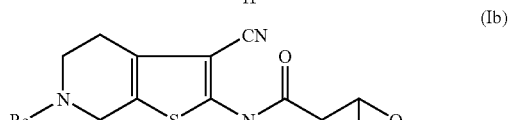

(Ib)

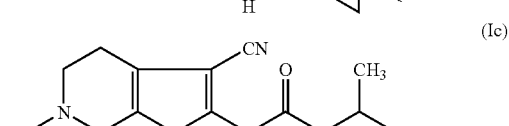

(Ic)

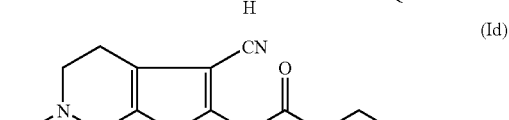

(Id)

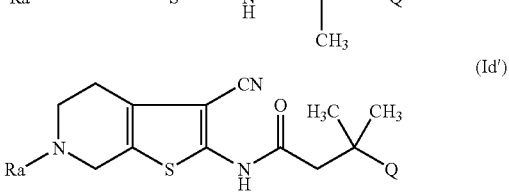

(Id')

wherein
Ra is —C(O)OR1,
R1 is 1-4C-alkyl, 1-7C-alkyl substituted by Raa, or 2-7C-alkyl substituted by Rab and Rac on different carbon atoms, and
Q is substituted by Rba and Rbb and Rbc, and is phenyl,
Raa is selected from the group consisting of:
hydroxyl,
Har, morpholino,
—C(O)R2, —C(O)OR3, —C(O)N(R4)R5, —N(R6)C(O)R7, —OC(O)R8, and
—OR9,
wherein said Har may be optionally substituted by one or two substituents independently selected from R10,
R2, R3, R4, R5, R6, R7 and R8 may be the same or different and are independently selected from the group consisting of:
hydrogen and 1-4C-alkyl,
R9 is selected from the group consisting of:
1-4C-alkyl, hydroxy-2-4C-alkyl, 1-4C-alkoxy-2-4C-alkyl, phenyl-1-4C-alkyl, pyridyl-1-4C-alkyl, and (1-4C-alkoxy-2-4C-alkoxy)-2-4C-alkyl,
Har is bonded via a ring carbon or a ring nitrogen atom of Har, and is a 5-membered monocyclic unsaturated, aromatic heteroaryl ring comprising at least one heteroatom independently selected from the group consisting of nitrogen, oxygen and sulphur, or
Har is bonded via a ring carbon atom of Har, and is a 6-membered monocyclic unsaturated, aromatic heteroaryl ring comprising one or two nitrogen atoms,
each R10 may be the same or different is each independently selected from the group consisting of:
1-4C-alkyl, halogen and 1-4C-alkoxy,
Rab is hydroxyl,
Rac is hydroxyl, or Rab and Rac bonded to adjacent carbon atoms form together a dimethylmethylenedioxy bridge,
Rba is selected from the group consisting of:
1-4C-alkoxy, 3-5C-cycloalkoxy, 3-5C-cycloalkyl-1-4C-alkoxy, cyano-2-4C-alkoxy, 3-5C-alkinyloxy, nitro, and completely and predominantly fluorine-substituted 1-4C-alkoxy,
Rbb is selected from the group consisting of:
hydrogen, 1-4C-alkyl, halogen, trifluoromethyl, and 1-4C-alkoxy,
Rbc is selected from the group consisting of:
hydrogen, halogen, and 1-4C-alkyl,
or Rbb and Rbc bounded in ortho position to each other form together a methylenedioxy, ethylenedioxy, difluoromethylenedioxy or tetrafluoroethylenedioxy bridge;
or a salt thereof.

3. A compound according to claim 1, which is a compound of one of the formulae Ia, Ib, Ic, Id and Id'

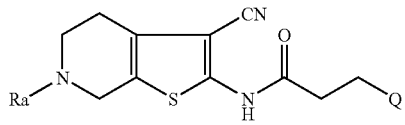
(Ia)

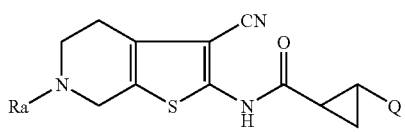
(Ib)

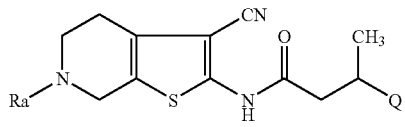
(Ic)

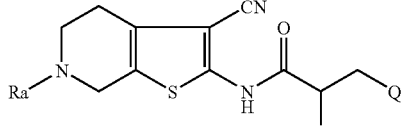
(Id)

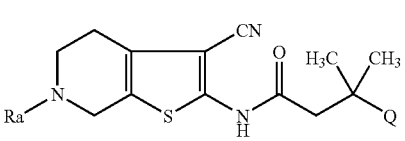
(Id')

wherein
Ra is —C(O)OR1,
R1 is 1-4C-alkyl, 1-4C-alkyl substituted by Raa, or 3-4C-alkyl substituted by Rab and Rac on different carbon atoms,
Q is substituted by Rba and Rbb and Rbc, and is phenyl,
Raa is selected from the group consisting of:
hydroxyl,
Har, morpholino,
—C(O)R2, —C(O)OR3, —C(O)N(R4)R5,
—N(R6)C(O)R7, —OC(O)R8, and
OR9,
wherein said Har may be optionally substituted by one or two substituents independently selected from R10,
R2, R3, R4, R5, R6, R7 and R8 may be the same or different and are independently selected from the group consisting of:
hydrogen and 1-4C-alkyl, R9 is selected from the group consisting of:
1-4C-alkyl, hydroxy-2-4C-alkyl, 1-4C-alkoxy-2-4C-alkyl, phenyl-1-4C-alkyl, pyridyl-1-4C-alkyl, and (1-4C-alkoxy-2-4C-alkoxy)-2-4C-alkyl,
Har is bonded via a ring carbon or a ring nitrogen atom of Har, and is imidazolyl, pyrazolyl or triazolyl,
or
Har is bonded via a ring carbon atom of Har, and is pyridinyl, pyrazinyl or pyrimidinyl,
each R10 may be the same or different is each independently selected from the group consisting of:
1-4C-alkyl and 1-4C-alkoxy,
Rab is hydroxyl,
Rac is hydroxyl,
or Rab and Rae bonded to adjacent carbon atoms form together a dimethylmethylenedioxy bridge,
Rba is selected from the group consisting of:
1-4C-alkoxy, and completely and predominantly fluorine-substituted 1-4C-alkoxy,
Rbb is selected from the group consisting of:
hydrogen, 1-4C-alkyl, and 1-4C-alkoxy,
Rbc is selected from the group consisting of:
hydrogen, and halogen,
or Rbb and Rbc bounded in ortho position to each other form together a methylenedioxy, ethylenedioxy, difluoromethylenedioxy or tetrafluoroethylenedioxy bridge,
or a salt thereof.

4. A compound according to claim 1, which is a compound of one of the formulae Ia, Ib and Ic

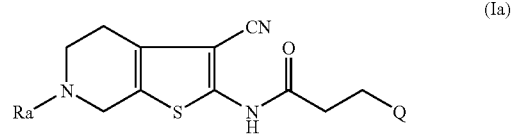
(Ia)

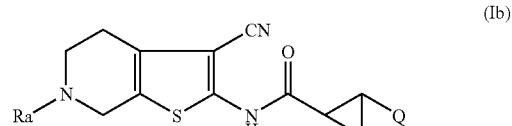
(Ib)

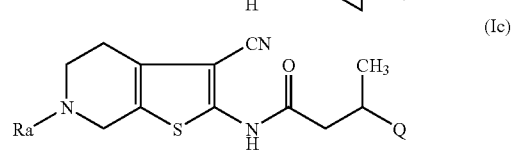
(Ic)

wherein
Ra is —C(O)OR1,
R1 is 1-4C-alkyl,
or
R1 is 1-4C-alkyl which is substituted by Raa, in which
Raa is pyridyl, pyrimidinyl, R101- and/or R102-substituted pyridyl, or R101- and/or R102-substituted pyrimidinyl,
or
R1 is 1-4C-alkyl which is substituted by Raa, in which
Raa is 1N-(1-4C-alkyl)-imidazolyl, 1N-(1-4C-alkyl)-pyrazolyl, R101-substituted 1N-(1-4C-alkyl)-imidazolyl, or R101-substituted 1N-(1-4C-alkyl)-pyrazolyl,
or
R1 is 1-4C-alkyl which is substituted by Raa, in which
Raa is 1N-(H)-imidazolyl, 1N-(H)-pyrazolyl, R101-substituted 1N-(H)-imidazolyl, or R101-substituted 1N-(H)-pyrazolyl, or
R1 is 3-4C-alkyl which is substituted by Rab and Rac on different carbon atoms, in which
Rab is hydroxyl,
Rac is hydroxyl,
or Rab and Rac bonded to adjacent carbon atoms form together a dimethylmethylenedioxy bridge,
or
R1 is 1-4C-alkyl which is substituted by Raa, in which
Raa is —CO )OR3,
or
R1 is 2-4C-alkyl which is substituted by Raa, in which
Raa is hydroxyl, morpholine, —OC(O)R8, or —OR9,
or
R1 is 2-4C-alkyl which is substituted by Raa, in which
Raa is imidazol-1-yl, pyrazol-1-yl, mono- or di-(R101)-substituted imidazol-1-yl, or mono- or di-(R101)-substituted pyrazol-1-yl,
Q is substituted by Rba and Rbb and Rbc, and is phenyl,
R3 is selected from the group consisting of:
hydrogen, and 1-4C-alkyl,
R8 is 1-40-alkyl,
R9 is selected from the group consisting of
1-4C-alkyl,
phenyl-1-2C-alkyl,
1-2C-alkoxy-2-3C-alkyl, and
(1-2C-alkoxy-2-3C-alkoxy)-2-3C-alkyl,
R101 is 1-4C-alkyl,
R102 is 1-4C-alkoxy, or 1-4C-alkyl,
Rba is selected from the group consisting of:
methoxy, ethoxy, trifluoromethoxy, and difluoromethoxy,
Rbb is selected from the group consisting of:
hydrogen, methyl, ethyl, methoxy, and ethoxy,
Rbc is hydrogen;
or a salt thereof.

5. A compound according to claim 1, which is a compound of one of the formulae Ia, Ib and Ic

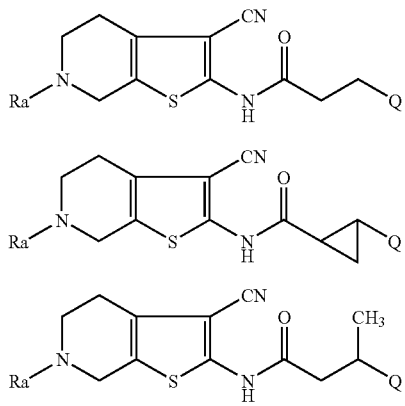

wherein
Ra is —C(O)OR1,
R1 is methyl, ethyl or propyl,
or
R1 is (Raa)-methyl, 2-(Raa)-ethyl, or 3-(Raa)-propyl, in which
Raa is pyridyl, pyrimidinyl, methyl-substituted pyridyl, or methoxy-substituted pyridyl, or
R1 is (Raa)-methyl, 2-(Raa)-ethyl, or 3-(Raa)-propyl, in which
Raa is 1N-methyl-imidazolyl,
or
R1 is 2,3-dihydroxy-propyl,
or
R1 is (Raa)-methyl, 2-(Raa)-ethyl, or 3-(Raa)-propyl, in which
Raa is carboxyl or methoxycarbonyl,
or
R1 is 2-(Raa)-ethyl, or 3-(Raa)-propyl, in which
Raa is hydroxyl, methylcarbonyloxy, methoxy, ethoxy, benzyloxy, or 2methoxyethoxy,
or
R1 is 2-(Raa)-ethyl, or 3-(Raa)-propyl, in which
Raa is imidazol-1-yl, or mono- or di-methyl-substituted imidazol-1-yl;
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
Rba is selected from the group consisting of:
methoxy and ethoxy,
Rbb is selected from the group consisting of:
methyl and methoxy;
or a salt thereof.

6. A compound according to claim 1, which is a compound of one of the formulae Ia, 1b and Ic

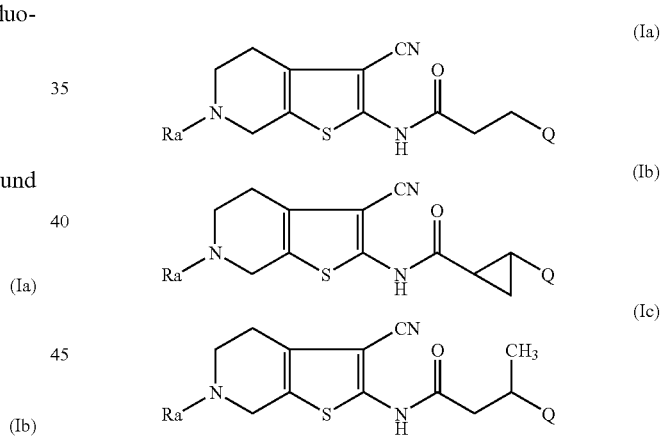

wherein
Ra is —C(O)OR1,
R1 is (Raa)-methyl, or 2-(Raa)-ethyl, in which
Raa is pyridyl,
or
R1 is (Raa)-methyl, in which
Raa is 1N-methyl-imidazolyl,
or
R1 is 2,3-dihydroxy-propyl,
or
R1 is (Raa)-methyl, in which
Raa is carboxyl or methoxycarbonyl,
or
R1 is 2-(Raa)-ethyl, in which
Raa is hydroxyl or methoxy,
or
R1 is 2-(Raa)-ethyl, in which Raa is imidazol-1-yl, or mono- or di-methyl-substituted imidazol-1-yl;
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
Rba is selected from the group consisting of:
    methoxy and ethoxy,
Rbb is methyl;
or a salt thereof.

7. A compound according to claim 1, which is a compound of one of the formulae Ia and Ic

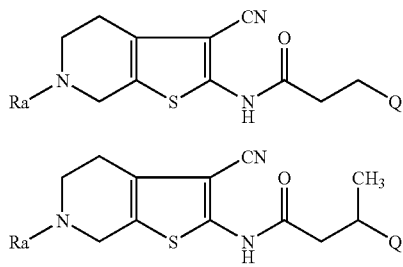

wherein
Ra is —C(O)OR1,
R1 is (Raa)-methyl, or 2-(Raa)-ethyl, in which
Raa is pyridin-2-yl, pyridin-3-yl or pyridin-4-yl,
or
R1 is (Raa)-methyl, in which
Raa is 1-methyl-imidazol-2-yl or 1-methyl-imidazol-5-yl,
or
R1 is 2,3-dihydroxy-propyl,
or
R1 is (Raa)-methyl, in which
Raa is carboxyl or methoxycarbonyl,
or
R1 is 2-(Raa)-ethyl, in which
Raa is hydroxyl or methoxy,
or
R1 is 2-(Raa)-ethyl, in which
Raa is imidazol-1-yl, 2-methyl-imidazol-1-yl or 4-methyl-imidazol-1-yl;
Q is 2-methoxyphenyl,
or
Q is 2-ethoxyphenyl,
or
Q is 3-methoxyphenyl,
or
Q is 3-ethoxyphenyl,
or
Q is 2-(Rba)-3-(Rbb)-phenyl, in which
Rba is methoxy or ethoxy,
Rbb is methyl;
or
Q is 2-(Rba)-5-(Rbb)-phenyl, in which
Rba is methoxy or ethoxy,
Rbb is methyl;
or a salt thereof.

8. A compound according to claim 1, which is a compound of one of the formulae Ia and Ic

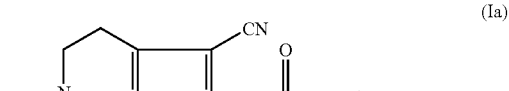

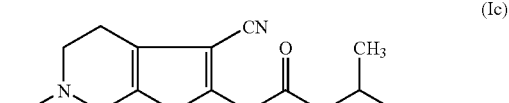

wherein
Ra is —C(O)OR1,
R1 is (Raa)-methyl, or 2-(Raa)-ethyl, in which
Raa is pyridyl,
or
R1 is 2,3-dihydroxy-propyl,
or
R1 is 2-(Raa)-ethyl, in which
Raa is hydroxyl or methoxy,
or
R1 is 2-(Raa)-ethyl, in which
Raa is imidazol-1-yl;
Q is 2-(Rba)-phenyl, 3-(Rba)-phenyl, 2-(Rba)-3-(Rbb)-phenyl, 2-(Rba)-5-(Rbb)-phenyl, 2-(Rba)-6-(Rbb)-phenyl, 2-(Rbb)-3-(Rba)-phenyl or 2-(Rbb)-5-(Rba)-phenyl,
Rba is selected from the group consisting of:
    methoxy and ethoxy,
Rbb is methyl;
or a salt thereof.

9. A compound according to claim 1, which is a compound of one of the formulae Ia and Ic

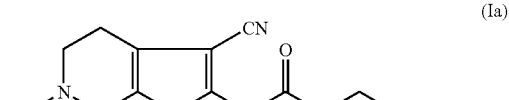

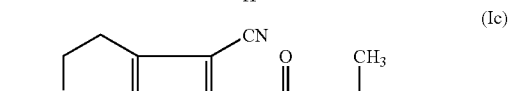

wherein
Ra is —C(O)OR1, in which
either
R1 is (Raa)-methyl, or 2-(Raa)-ethyl, in which
Raa is pyridyl,
or
R1 is 2,3-dihydroxy-propyl,
or
R1 is 2-(Raa)-ethyl, in which
Raa is hydroxyl,
or
R1 is 2-(Raa)-ethyl, in which
Raa is imidazol-1-yl;
Q is 2-methoxyphenyl, or
Q is 2-ethoxyphenyl,
or
Q is 3-methoxyphenyl,
or
Q is 3-ethoxyphenyl,
or
Q is 2-(Rba)-3-(Rbb)-phenyl, in which
Rba is methoxy or ethoxy,
Rbb is methyl;
or
Q is 2-(Rba)-5-(Rbb)-phenyl, in which
Rba is methoxy or ethoxy,
Rbb is methyl;
or a salt thereof.

10. A compound according to claim 1, which is a compound of one of the formulae Ia and Ic

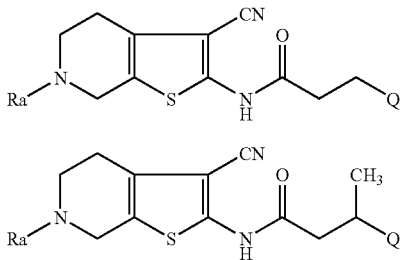

wherein
Q is 2-methoxyphenyl,
or
Q is 2-ethoxyphenyl,
or
Q is 3-methoxyphenyl,
or
Q is 3-ethoxyphenyl,
or
Q is 2-(Rba)-5-(Rbb)-phenyl, in which
Rba is methoxy,
Rbb is methyl;
or a salt thereof.

11. A compound, which is selected from the group consisting of
3-Cyano-2-[3-(4-methoxy-phenyl)-propanoylamino]-4,7-dihydro-5H-thieno[2,3-c]pyridine-6-carboxylic acid ethyl ester,
3-Cyano-2-[3-(3-methoxy-phenyl)-propanoylamino]-4,7-dihydro-5H-thieno[2,3-c]pyridine-6-carboxylic acid ethyl ester,
3-Cyano-2-[3-(2-methoxy-phenyl)-propanoylamino]-4,7-dihydro-5H-thieno[2,3-c]pyridine-6-carboxylic acid ethyl ester,
3-Cyano-2-[3-(3-nitro-phenyl)-propanoylamino]-4,7-dihydro-5H-thieno[2,3-c]pyridine-6-carboxylic acid ethyl ester,
3-Cyano-2-[3-(4-ethoxy-phenyl)-propanoylamino]-4,7-dihydro-5H-thieno[2,3-c]pyridine-6-carboxylic acid ethyl ester.
3-Cyano-2-[3-(2,3-dimethoxy-phenyl)-propanoylamino]-4,7-dihydro-5H-thieno[2,3-c]pyridine-6-carboxylic acid ethyl ester,
3-Cyano-2-[3-(2,5-dimethoxy-phenyl)-propanoylamino]-4,7-dihydro-5H-thieno[2,3-c]pyridine-6-carboxylic acid ethyl ester,
3-Cyano-2-[3-(3-ethoxy-phenyl)-propanoylamino]-4,7-dihydro-5H-thieno[2,3-c]pyridine-6-carboxylic acid ethyl ester,
3-Cyano-2-[3-(2-ethoxy-phenyl)-propanoylamino]-4,7-dihydro-5H-thieno[2,3-c]pyridine-6-carboxylic acid tert-butyl ester,
3-Cyano-2-[3-(2-methoxy-phenyl)-propanoylamino]-4,7-dihydro-5H-thieno[2,3-c]pyridine-6-carboxylic acid tert-butyl ester,
3-Cyano-2-[3-(3-methoxy-phenyl)-propanoylamino]-4,7-dihydro-5H-thieno[2,3-c]pyridine-6-carboxylic acid tert-butyl ester,
3-Cyano-2-{3-[2-(1,1-difluoro-methoxy)-phenyl]-propanoylamino}-4,7-dihydro-5H-thieno[2,3-c]pyridine-6-carboxylic acid ethyl ester,
3-Cyano-2-[3-(3,5-dimethoxy-phenyl)-propanoylamino]-4,7-dihydro-5H-thieno[2,3-c]pyridine-6-carboxylic acid ethyl ester,
2-[3-(5-Bromo-2,3-dimethoxy-phenyl)-propanoylamino]-3-cyano-4,7-dihydro-5H-thieno[2,3-c]pyridine-6-carboxylic acid ethyl ester,
2-[3-(5-Bromo-2-methoxy-phenyl)-propanoylamino]-3-cyano-4,7-dihydro-5H-thieno[2,3-c]pyridine-6-carboxylic acid ethyl ester,
3-Cyano-2-[3-(2,3-diethoxy-phenyl)-propanoylamino]-4,7-dihydro-5H-thieno[2,3-c]pyridine-6-carboxylic acid ethyl ester,
3-Cyano-2-[3-(2-methoxy-5-methyl-phenyl)-propanoylamino]-4,7-dihydro-5H-thieno[2,3-c]pyridine-6-carboxylic acid ethyl ester,
3-Cyano-2-[3-(2,2,3,3-tetrafluoro-6-methoxy-2,3-dihydro-benzo[1,4]dioxin-5-yl)-propanoylamino]-4,7-dihydro-5H-thieno[2,3-c]pyridine-6-carboxylic acid ethyl ester,
3-Cyano-2-[3-(2-ethoxyphenyl)-propanoylamino]-4,7-dihydro-5H-thieno[2,3-c]-pyridine-6-carboxylic acid ethyl ester,
3-Cyano-2-[3-(2-ethoxy-phenyl)-propanoylamino]-4,7-dihydro-5H-thieno[2,3-c]pyridine-6-carboxylic acid 2,2-dimethyl-[1,3]dioxolan-4-ylmethyl ester,
3-Cyano-2-[3-(2-ethoxy-phenyl)-propanoylamino]-4,7-dihydro-5H-thieno [2,3-c]pyridine-6-carboxylic acid 2-benzyloxy-ethyl ester,
3-Cyano-2-[3-(2-ethoxy-phenyl)-propionylamino]-4,7-dihydro-5H-thieno[2,3-c]pyridine-6-carboxylic acid 2-acetoxy-ethyl ester,
3-Cyano-2-[3-(2-methoxy-phenyl)-propanoylamino]-4,7-dihydro-5H-thieno[2,3-c]pyridine-6-carboxylic acid 2-methoxy-ethyl esters
3-Cyano-2-[3-(2-methoxy-phenyl)-propanoylamino]-4,7-dihydro-5H-thieno[2,3-c]pyridine-6-carboxylic acid 2-benzyloxy-ethyl ester,
3-Cyano-2-[3-(2-methoxy-phenyl)-propanoylamino]-4,7-dihydro-5H-thieno[2,3-c]pyridine-6-carboxylic acid 2-pyridin-2-yl-ethyl ester,
3-Cyano-2-[3-(2-methoxy-phenyl)-propanoylamino]-4,7-dihydro-5H-thieno[2,3-c]pyridine-6-carboxylic acid pyridin-2-ylmethyl ester,
3-Cyano-2-[3-(2-methoxy-phenyl)-propanoylamino]-4,7-dihydro-5H-thieno[2,3-c]pyridine-6-carboxylic acid pyridin-3-ylmethyl ester,
3-Cyano-2-[3-(2-methoxy-phenyl)-propanoylamino]-4,7-dihydro-5H-thieno[2,3-c]pyridine-6-carboxylic acid pyridin-4-ylmethyl ester,
3-Cyano-2-[3-(3-methoxy-phenyl)-propanoylamino]-4,7-dihydro-5H-thieno[2,3-c]pyridine-6-carboxylic acid pyridin-2-ylmethyl ester, 3-Cyano-2-[3-(2-methoxy-phenyl)-propanoylamino]-4,7-dihydro-5H-thieno[2,3-c]pyridine-6-carboxylic acid 2,2-dimethyl-[1,3]dioxolan-4-ylmethyl ester,
3-Cyano-2-[3-(2-methoxy-phenyl)-propionylamino]-4,7-dihydro-5H-thieno[2,3-c]pyridine-6-carboxylic acid 2-acetoxy-ethyl ester,
3-Cyano-2-[3-(2-methoxy-phenyl)-propanoylamino]-4,7-dihydro-5H-thieno[2,3-c]pyridine-6-carboxylic acid 2,3-dihydroxy-propyl ester,
3-Cyano-2-[3-(2-ethoxy-phenyl)-propanoylamino]-4,7-dihydro-5H-thieno[2,3-c]pyridine-6-carboxylic acid 2,3-dihydroxy-propyl ester,
3-Cyano-2-[3-(2-methoxy-phenyl)-propanoylamino]-4,7-dihydro-5H-thieno[2,3-c]pyridine-6-carboxylic acid 2-hydroxy-ethyl ester,
3-Cyano-2-[3-(2-ethoxy-phenyl)-propanoylamino]-4,7-dihydro-5H-thieno[2,3-c]pyridine-6-carboxylic acid 2-hydroxy-ethyl ester,
3-Cyano-2-[3-(3-methoxy-phenyl)-propanoylamino]-4,7-dihydro-5H-thieno[2,3-c]pyridine-6-carboxylic acid pyridin-3-ylmethyl ester,
3-Cyano-2-[3-(3-methoxy-phenyl)-propanoylamino]-4,7-dihydro-5H-thieno[2,3-c]pyridine-6-carboxylic acid pyridin-4-ylmethyl ester,
3-Cyano-2-[3-(3-methoxy-phenyl)-propanoylamino]-4,7-dihydro-5H-thieno[2,3-c]pyridine-6-carboxylic acid 2-pyridin-2-yl-ethyl ester,
3-Cyano-2-[3-(2-trifluoromethoxy-phenyl)-propanoylamino]-4,7-dihydro-5H-thieno[2,3-c]pyridine-6-carboxylic acid ethyl ester,
3-Cyano-2-[3-(2-ethoxy-phenyl)-propanoylamino]-4,7-dihydro-5H-thieno[2,3-c]pyridine-6-carboxylic acid 2-methoxy-ethyl ester,
3-Cyano-2-[3-(2-ethoxy-phenyl)-propanoylamino]-4,7-dihydro-5H-thieno[2,3-c]pyridine-6-carboxylic acid pyridin-2-ylmethyl ester,
3-Cyano-2-[3-(2-ethoxy-phenyl)-propanoylamino]-4,7-dihydro-5H-thieno[2,3-c]pyridine-6-carboxylic acid pyridin-3-ylmethyl ester,
3-Cyano-2-[3-(2-ethoxy-phenyl)-propanoylamino]-4,7-dihydro-5H-thieno[2,3-c]pyridine-6-carboxylic acid pyridin-4-ylmethyl ester,
3-Cyano-2-[3-(2-ethoxy-phenyl)-propanoylamino]-4,7-dihydro-5H-thieno[2,3-c]pyridine-6-carboxylic acid 2-pyridin-2-yl-ethyl ester,
3-Cyano-2-[3-(3-methoxy-phenyl)-propanoylamino]-4,7-dihydro-5H-thieno[2,3-c]pyridine-6-carboxylic acid 2-methoxy-ethyl ester,
3-Cyano-2-[3-(2,5-dimethoxy-phenyl)-propanoylamino]-4,7-dihydro-5H-thieno[2,3-c]pyridine-6-carboxylic acid 2-hydroxy-ethyl ester,
3-Cyano-2-[3-(5-methoxy-2-methyl-phenyl)-propanoylamino]-4,7-dihydro-5H-thieno[2,3-c]pyridine-6-carboxylic acid 2-hydroxy-ethyl ester,
3-Cyano-2-[3-(2-methoxy-5-methyl-phenyl)-propanoylamino]-4,7-dihydro-5H-thieno[2,3-c]pyridine-6-carboxylic acid 2-pyridin-2-yl-ethyl ester,
3-Cyano-2-[(RS)-3-(2-methoxy-phenyl)-butanoylamino]-4,7-dihydro-5H-thieno[2,3-c]pyridine-6-carboxylic acid ethyl ester,
3-Cyano-2-[3-(2,5-dimethoxy-phenyl)-propanoylamino]-4,7-dihydro-5H-thieno[2,3-c]pyridine-6-carboxylic acid pyridin-3-ylmethyl ester,
3-Cyano-2-[3-(2-methoxy-5-methyl-phenyl)-propanoylamino]-4,7-dihydro-5H-thieno[2,3-c]pyridine-6-carboxylic acid pyridin-3-ylmethyl ester,
3-Cyano-2-[3-(2-methoxy-5-methyl-phenyl)-propanoylamino]-4,7-dihydro-5H-thieno[2,3-c]pyridine-6-carboxylic acid 2,3-dihydroxy-propyl ester,
3-Cyano-2-[3-(3-methoxy-phenyl)-propanoylamino]-4,7-dihydro-5H-thieno[2,3-c]pyridine-6-carboxylic acid 2-hydroxy-ethyl ester,
3-Cyano-2-({1-[2-(2-methoxy-5-methyl-phenyl)-cyclopropyl]-methanoyl}-amino)-4,7-dihydro-5H-thieno[2,3-c]pyridine-6-carboxylic acid ethyl ester,
3-Cyano-2-[3-(2,5-dimethoxy-phenyl)-propanoylamino]-4,7-dihydro-5H-thieno[2,3-c]pyridine-6-carboxylic acid 2-pyridin-2-yl-ethyl ester,
3-Cyano-2-[3-(2-methoxy-5-methyl-phenyl)-propanoylamino]-4,7-dihydro-5H-thieno[2,3-c]pyridine-6-carboxylic acid 2-morpholin-4-yl-ethyl ester,
3-Cyano-2-[3-(2-methoxy-5-methyl-phenyl)-propanoylamino]-4,7-dihydro-5H-thieno[2,3-c]pyridine-6-carboxylic cid 4-methoxy-pyridin-3-ylmethyl ester.
3-Cyano-2-[3-(3-methoxy-phenyl)-propanoylamino]-4,7-dihydro-5H-thieno[2,3-c]pyridine-6-carboxylic acid 2-imidazol-1-yl-ethyl ester,
3-Cyano-2-[3-(3-ethoxy-phenyl)-propanoylamino]-4,7-dihydro-5H-thieno[2,3-c]pyridine-6-carboxylic acid methoxycarbonylmethyl ester,
3-Cyano-2-[3-(3-ethoxy-phenyl)-propanoylamino]-4,7-dihydro-5H-thieno[2,3-c]pyridine-6-carboxylic acid carboxymethyl ester,
3-Cyano-2-[3-(2-methoxy-phenyl)-propanoylamino]-4,7-dihydro-5H-thieno[2,3-c]pyridine-6-carboxylic acid 2-pyridin-3-yl-ethyl ester,
3-Cyano-2-[3-(2-methoxy-phenyl)-propanoylamino]-4,7-dihydro-5H-thieno[2,3-c]pyridine-6-carboxylic acid 2-pyridin-4-yl-ethyl ester,
3-Cyano-2-[3-(3-methoxy-phenyl)-propanoylamino]-4,7-dihydro-5H-thieno[2,3-c]pyridine-6-carboxylic acid 2-pyridin-3-yl-ethyl ester,
3-Cyano-2-[3-(3-methoxy-phenyl)-propanoylamino]-4,7-dihydro-5H-thieno[2,3-c]pyridine-6-carboxylic acid 2-pyridin-4-yl-ethyl ester,
3-Cyano-2-[3-(2-ethoxy-phenyl)-propanoylamino]-4,7-dihydro-5H-thieno[2,3-c]pyridine-6-carboxylic acid 2-pyridin-3-yl-ethyl ester,
3-Cyano-2-[3-(2-ethoxy-phenyl)-propanoylamino]-4,7-dihydro-5H-thieno[2,3-c]pyridine-6-carboxylic acid 2-pyridin-4-yl-ethyl ester,
3-Cyano-2-[3-(3-ethoxy-phenyl)-propanoylamino]-4,7-dihydro-5H-thieno[2,3-c]pyridine-6-carboxylic acid pyridin-2-ylmethyl ester,
3-Cyano-2-[3-(3-ethoxy-phenyl)-propanoylamino]-4,7-dihydro-5H-thieno[2,3-c]pyridine-6-carboxylic acid pyridin-3-ylmethyl ester,
3-Cyano-2-[3-(3-ethoxy-phenyl)-propanoylamino]-4,7-dihydro-5H-thieno[2,3-c]pyridine-6-carboxylic acid pyridin-4-ylmethyl ester,
3-Cyano-2-[3-(3-ethoxy-phenyl)-propanoylamino]-4,7-dihydro-5H-thieno[2,3-c]pyridine-6-carboxylic acid 2-pyridin-2-yl-ethyl ester,
3-Cyano-2-[3-(3-ethoxy-phenyl)-propanoylamino]-4,7-dihydro-5H-thieno[2,3-c]pyridine-6-carboxylic acid 2-pyridin-3-yl-ethyl ester,
3-Cyano-2-[3-(3-ethoxy-phenyl)-propanoylamino]-4,7-dihydro-5H-thieno[2,3-c]pyridine-6-carboxylic acid 2-pyridin-4-yl-ethyl ester,
3-Cyano-2-[3-(2-methoxy-phenyl)-propanoylamino]-4,7-dihydro-5H-thieno[2,3-c]pyridine-6-carboxylic acid 2-imidazol-1-yl-ethyl ester, 3-Cyano-2-[3-(2-ethoxy-phenyl)-propanoylamino]-4,7-dihydro-5H-thieno[2,3-c]pyridine-6-carboxylic acid 2-imidazol-1-yl-ethyl ester, 3-Cyano-2-[3-(3-ethoxy-phenyl)-propanoylamino]-4,7-dihydro-5H-thieno[2,3-c]pyridine-6-carboxylic acid 2-imidazol-1-yl-ethyl ester, 3-Cyano-2-[(RS)-3-(2-methoxy-phenyl)-butanoylamino]-4,7-dihydro-5H-thieno[2,3-c]pyridine-6-carboxylic acid 2-pyridin-2-yl-ethyl ester, 3-Cyano-2-[(RS)-3-(2-methoxy-phenyl)-butanoylamino]-4,7-dihydro-5H-thieno[2,3-c]pyridine-6-carboxylic acid 2-pyridin-3-yl-ethyl ester, 3-Cyano-2-[(RS)-3-(2-methoxy-phenyl)-butanoylamino]-4,7-dihydro-5H-thieno[2,3-c]pyridine-6-carboxylic acid 2-pyridin-4-yl-ethyl ester, 3-Cyano-2-[(RS)-3-(3-methoxy-phenyl)-butanoylamino]-4,7-dihydro-5H-thieno[2,3-c]pyridine-6-carboxylic acid 2-pyridin-2-yl-ethyl ester, 3-Cyano-2-[(RS)-3-(3-methoxy-phenyl)-butanoylamino]-4,7-dihydro-5H-thieno[2,3-c]pyridine-6-carboxylic acid 2-pyridin-3-yl-ethyl ester, 3-Cyano-2-[(RS)-3-(3-methoxy-phenyl)-butanoylamino]-4,7-dihydro-5H-thieno[2,3-c]pyridine-6-carboxylic acid 2-pyridin-4-yl-ethyl ester, 3-Cyano-2-[(RS)-3-(2-methoxy-phenyl)-butanoylamino]-4,7-dihydro-5H-thieno[2,3-c]pyridine-6-carboxylic acid pyridin-2-ylmethyl ester, 3-Cyano-2-[(RS)-3-(2-methoxy-phenyl)-butanoylamino]-4,7-dihydro-5H-thieno[2,3-c]pyridine-6-carboxylic acid pyridin-3-ylmethyl ester, 3-Cyano-2-[(RS)-3-(2-methoxy-phenyl)-butanoylamino]-4,7-dihydro-5H-thieno[2,3-c]pyridine-6-carboxylic acid pyridin-4-ylmethyl ester, 3-Cyano-2-[(RS)-3-(3-methoxy-phenyl)-butanoylamino]-4,7-dihydro-5H-thieno[2,3-c]pyridine-6-carboxylic acid pyridin-2-ylmethyl ester, 3-Cyano-2-[(RS)-3-(3-methoxy-phenyl)-butanoylamino]-4,7-dihydro-5H-thieno[2,3-c]pyridine-6-carboxylic acid pyridin-3-ylmethyl ester, 3-Cyano-2-[(RS)-3-(3-methoxy-phenyl)-butanoylamino]-4,7-dihydro-5H-thieno[2,3-c]pyridine-6-carboxylic acid pyridin-4-ylmethyl ester, 3-Cyano-2-[(RS)-3-(2-ethoxy-phenyl)-butanoylamino]-4,7-dihydro-5H-thieno[2,3-c]pyridine-6-carboxylic acid 2-pyridin-2-yl-ethyl ester, 3-Cyano-2-[(RS)-3-(2-ethoxy-phenyl)-butanoylamino]-4,7-dihydro-5H-thieno[2,3-c]pyridine-6-carboxylic acid 2-pyridin-3-yl-ethyl ester, 3-Cyano-2-[(RS)-3-(2-ethoxy-phenyl)-butanoylamino]-4,7-dihydro-5H-thieno[2,3-c]pyridine-6-carboxylic acid 2-pyridin-4-yl-ethyl ester, 3-Cyano-2-[(RS)-3-(2-ethoxy-phenyl)-butanoylamino]-4,7-dihydro-5H-thieno[2,3-c]pyridine-6-carboxylic acid pyridin-2-ylmethyl ester, 3-Cyano-2-[(RS)-3-(2-ethoxy-phenyl)-butanoylamino]-4,7-dihydro-5H-thieno[2,3-c]pyridine-6-carboxylic acid pyridin-3-ylmethyl ester, 3-Cyano-2-[(RS)-3-(2-ethoxy-phenyl)-butanoylamino]-4,7-dihydro-5H-thieno[2,3-c]pyridine-6-carboxylic acid pyridin-4-ylmethyl ester, 3-Cyano-2-[(RS)-3-(3-ethoxy-phenyl)-butanoylamino]-4,7-dihydro-5H-thieno[2,3-c]pyridine-6-carboxylic acid pyridin-2-ylmethyl ester, 3-Cyano-2-[(RS)-3-(3-ethoxy-phenyl)-butanoylamino]-4,7-dihydro-5H-thieno[2,3-c]pyridine-6-carboxylic acid pyridin-3-ylmethyl ester;

3-Cyano-2-[(RS)-3-(3-ethoxy-phenyl)-butanoylamino]-4,7-dihydro-5H-thieno[2,3-c]pyridine-6-carboxylic acid pyridin-4-ylmethyl ester;

3-Cyano-2-[(RS)-3-(3-ethoxy-phenyl)-butanoylamino]-4,7-dihydro-5H-thieno[2,3-c]pyridine-6-carboxylic acid 2-pyridin-2-yl-ethyl ester;

3-Cyano-2-[(RS)-3-(3-ethoxy-phenyl)-butanoylamino]-4,7-dihydro-5H-thieno[2,3-c]pyridine-6-carboxylic acid 2-pyridin-3-yl-ethyl ester, 3-Cyano-2-[(RS)-3-(3-ethoxy-phenyl)-butanoylamino]-4,7-dihydro-5H-thieno[2,3-c]pyridine-6-carboxylic acid 2-pyridin-4-yl-ethyl ester;

3-Cyano-2-[(RS)-3-(2-methoxy-phenyl)-butanoylamino]-4,7-dihydro-5H-thieno[2,3-c]pyridine-6-carboxylic acid 2-imidazol-1-yl-ethyl ester, 3-Cyano-2-[(RS)-3-(3-methoxy-phenyl)-butanoylamino]-4,7-dihydro-5H-thieno[2,3-c]pyridine-6-carboxylic acid 2-imidazol-1-yl-ethy ester, 3-Cyano-2-[(RS)-3-(2-ethoxy-phenyl)-butanoylamino]-4,7-dihydro-5H-thieno[2,3-c]pyridine-6-carboxylic acid 2-imidazol-1-yl-ethyl ester, 3-Cyano-2-[(RS)-3-(3-ethoxy-phenyl)-butanoylamino]-4,7-dihydro-5H-thieno[2,3-c]pyridine-6-carboxylic acid 2-imidazol-1-yl-ethyl ester, 3-Cyano-2-[3-(2-methoxy-5-methyl-phenyl)-propanoylamino]-4,7-dihydro-5H-thieno[2,3-c]pyridine-6-carboxylic acid pyridin-2-ylmethyl ester, 3-Cyano-2-[3-(2-methoxy-5-methyl-phenyl)-propanoylamino]-4,7-dihydro-5H-thieno[2,3-c]pyridine-6-carboxylic acid pyridin-4-ylmethyl ester, 3-Cyano-2-[3-(2-methoxy-5-methyl-phenyl)-propanoylamino]-4,7-dihydro-5H-thieno[2,3-c]pyridine-6-carboxylic acid 2-pyridin-4-yl-ethyl ester, 3-Cyano-2-[(RS)-3-(2-methoxy-phenyl)-butanoylamino]-4,7-dihydro-5H-thieno[2,3-c]pyridine-6-carboxylic acid 1'-methyl-1H-imidazol-2-ylmethyl ester, 3-Cyano-2-[(RS)-3-(2-methoxy-phenyl)-butanoylamino]-4,7-dihydro-5H-thieno[2,3-c]pyridine-6-carboxylic acid 3-methyl-3H-imidazol-4-ylmethyl ester, 3-Cyano-2-[(RS)-3-(2-methoxy-phenyl)-butanoylamino]-4,7-dihydro-5H-thieno[2,3-c]pyridine-6-carboxylic acid 2-(2-methyl-imidazol-1-yl)-ethyl ester, 3-Cyano-2-[(RS)-3-(2-ethoxy-phenyl)-butanoylamino]-4,7-dihydro-5H-thieno[2,3-c]pyridine-6-carboxylic acid 1-methyl-1H-imidazol-2-ylmethyl ester, 3-Cyano-2-[(RS)-3-(2-ethoxy-phenyl)-butanoylamino]-4,7-dihydro-5H-thieno[2,3-c]pyridine-6-carboxylic acid 3-methyl-3H-imidazol-4-ylmethyl ester, 3-Cyano-2-[(RS)-3-(2-ethoxy-phenyl)-butanoylamino]-4,7-dihydro-5H-thieno[2,3-c]pyridine-6-carboxylic acid 2-(2-methyl-imidazol-1-yl)-ethyl esters 3-Cyano-2-[(RS)-3-(3-methoxy-phenyl)-butanoylamino]-4,7-dihydro-5H-thieno[2,3-c]pyridine-6-carboxylic acid 1-methyl-1H-imidazol-2-ylmethyl ester, 3-Cyano-2-[(RS)-3-(3-methoxy-phenyl)-butanoylamino]-4,7-dihydro-5H-thieno[2,3-c]pyridine-6-carboxylic acid 3-methyl-3H-imidazol-4-ylmethyl ester, 3-Cyano-2-[(RS)-3-(3-methoxy-phenyl)-butanoylamino]-4,7-dihydro-5H-thieno[2,3-c]pyridine-6-carboxylic acid 2-(2-methyl-imidazol-1-yl)-ethyl ester, 3-Cyano-2-[(RS)-3-(3-ethoxy-phenyl)-butanoylamino]-4,7-dihydro-5H-thieno[2,3-c]pyridine-6-carboxylic acid 1-methyl-1H-imidazol-2-ylmethyl ester, 3-Cyano-2-[(RS)-3-(3-ethoxy-phenyl)-butanoylamino]-4,7-dihydro-5H-thieno[2,3-c]pyridine-6-carboxylic acid 3-methyl-3H-imidazol-4-ylmethyl ester, 3-Cyano-2-[(RS)-3-(3-ethoxy-phenyl)-butanoylamino]-4,7-dihydro-5H-thieno[2,3-c]pyridine-6-carboxylic acid 2-(2-methyl-imidazol-1-yl)-ethyl ester,
3-Cyano-2-[3-(3-methoxy-phenyl)-propanoylamino]-4,7-dihydro-5H-thieno[2,3-c]pyridine-6-carboxylic acid 1-methyl-1H-imidazol-2-ylmethyl ester,
3-Cyano-2-[3-(3-methoxy-phenyl)-propanoylamino]-4,7-dihydro-5H-thieno[2,3-c]pyridine-6-carboxylic acid 3-methyl-3H-imidazol-4-ylmethyl ester,
3-Cyano-2-[3-(3-methoxy-phenyl)-propanoylamino]-4,7-dihydro-5H-thieno[2,3-c]pyridine-6-carboxylic acid 2-(2-methyl-imidazol-1-yl)-ethyl ester,
3-Cyano-2-[3-(2-methoxy-phenyl)-propanoylamino]-4,7-dihydro-5H-thieno[2,3-c]pyridine-6-carboxylic acid 1-methyl-1H-imidazol-2-ylmethyl ester,
3-Cyano-2-[3-(2-methoxy-phenyl)-propanoylamino]-4,7-dihydro-5H-thieno[2,3-c]pyridine-6-carboxylic acid 3-methyl-3H-imidazol-4-ylmethyl ester,
3-Cyano-2-[3-(2-methoxy-phenyl)-propanoylamino]-4,7-dihydro-5H-thieno[2,3-c]pyridine-6-carboxylic acid 2-(2-methyl-imidazol-1-yl)-ethyl esters
3-Cyano-2-[3-(2-ethoxy-phenyl)-propanoylamino]-4,7-dihydro-5H-thieno[2,3-c]pyridine-6-carboxylic acid 1-methyl-1H-imidazol-2-ylmethyl ester,
3-Cyano-2-[3-(2-ethoxy-phenyl)-propanoylamino]-4,7-dihydro-5H-thieno[2,3-c]pyridine-6-carboxylic acid 3-methyl-3H-imidazol-4-ylmethyl ester,
3-Cyano-2-[3-(2-ethoxy-phenyl)-propanoylamino]-4,7-dihydro-5H-thieno[2,3-c]pyridine-6-carboxylic acid 2-(2-methyl-imidazol-1-yl)-ethyl ester,
3-Cyano-2-[3-(2-methoxy-5-methyl-phenyl)-propanoylamino]-4,7-dihydro-5H-thieno[2,3-c]pyridine-6-carboxylic acid 2-pyridin-3-yl-ethyl ester,
3-Cyano-2-[3-(2-methoxy-5-methyl-phenyl)-propanoylamino]-4,7-dihydro-5H-thieno[2,3-c]pyridine-6-carboxylic acid 1-methyl-1H-imidazol-2-ylmethyl ester,
3-Cyano-2-[3-(2-methoxy-5-methyl-phenyl)-propanoylamino]-4,7-dihydro-5H-thieno[2,3-c]pyridine-6-carboxylic acid 3-methyl-3H-imidazol-4-ylmethyl ester,
3-Cyano-2-[3-(2-methoxy-5-methyl-phenyl)-propanoylamino]-4,7-dihydro-5H-thieno[2,3-c]pyridine-6-carboxylic acid 2-(2-methyl-imidazol-1-yl)-ethyl ester,
3-Cyano-2-[3-(2-methoxy-5-methyl-phenyl)-propanoylamino]-4,7-dihydro-5H-thieno[2,3-c]pyridine-6-carboxylic acid 2-imidazol-1-yl-ethyl ester,
3-Cyano-2-[(RS)-3-(3-methoxy-phenyl)-butanoylamino]-4,7-dihydro-5H-thieno[2,3-c]pyridine-6-carboxylic acid 2-(2,4-dimethyl-imidazol-1-yl)-ethyl ester,
3-Cyano-2-[(RS)-3-(3-methoxy-phenyl)-butanoylamino]-4,7-dihydro-5H-thieno[2,3-c]pyridine-6-carboxylic acid 2-(4-methyl-imidazol-1-yl)-ethyl ester,
3-Cyano-2-[(RS)-3-(3-ethoxy-phenyl)-butanoylamino]-4,7-dihydro-5H-thieno[2,3-c]pyridine-6-carboxylic acid 2-(2,4-dimethyl-imidazol-1-yl)-ethyl ester,
3-Cyano-2-[(RS)-3-(3-ethoxy-phenyl)-butanoylamino]-4,7-dihydro-5H-thieno[2,3-c]pyridine-6-carboxylic acid 2-(4-methyl-imidazol-1-yl)-ethyl ester,
3-Cyano-2-[(RS)-3-(2-methoxy-phenyl)-butanoylamino]-4,7-dihydro-5H-thieno[2,3-c]pyridine-6-carboxylic acid 2-(2,4-dimethyl-imidazol-1-yl)-ethyl ester,
3-Cyano-2-[(RS)-3-(2-methoxy-phenyl)-butanoylamino]-4,7-dihydro-5H-thieno[2,3-c]pyridine-6-carboxylic acid 2-(4-methyl-imidazol-1-yl)-ethyl ester,
3-Cyano-2-[(RS)-3-(2-ethoxy-phenyl)-butanoylamino]-4,7-dihydro-5H-thieno[2,3-c]pyridine-6-carboxylic acid 2-(2,4-dimethyl-imidazol-1-yl)-ethyl ester,
3-Cyano-2-[(RS)-3-(2-ethoxy-phenyl)-butanoylamino]-4,7-dihydro-5H-thieno[2,3-c]pyridine-6-carboxylic acid 2-(4-methyl-imidazol-1-yl)-ethyl ester,
3-Cyano-2-[3-(3-methoxy-phenyl)-propanoylamino]-4,7-dihydro-5H-thieno[2,3-c]pyridine-6-carboxylic acid 2-(2,4-dimethyl-imidazol-1-yl)-ethyl ester,
3-Cyano-2-[3-(3-methoxy-phenyl)-propanoylamino]-4,7-dihydro-5H-thieno[2,3-c]pyridine-6-carboxylic acid 2-(4-methyl-imidazol-1-yl)-ethyl ester,
3-Cyano-2-[3-(2-methoxy-phenyl)-propanoylamino]-4,7-dihydro-5H-thieno[2,3-c]pyridine-6-carboxylic acid 2-(2,4-dimethyl-imidazol-1-yl)-ethyl ester,
3-Cyano-2-[3-(2-methoxy-phenyl)-propanoylamino]-4,7-dihydro-5H-thieno[2,3-c]pyridine-6-carboxylic acid 2-(4-methyl-imidazol-1-yl)-ethyl ester,
3-Cyano-2-[3-(2-ethoxy-phenyl)-propanoylamino]-4,7-dihydro-5H-thieno[2,3-c]pyridine-6-carboxylic acid 2-(2,4-dimethyl-imidazol-1-yl)-ethyl ester,
3-Cyano-2-[3-(2-ethoxy-phenyl)-propanoylamino]-4,7-dihydro-5H-thieno[2,3-c]pyridine-6-carboxylic acid 2-(4-methyl-imidazol-1-yl)-ethyl ester,
3-Cyano-2-[3-(2-methoxy-5-methyl-phenyl)-propanoylamino]-4,7-dihydro-5H-thieno[2,3-c]pyridine-6-carboxylic acid 2-(2,4-dimethyl-imidazol-1-yl)-ethyl ester,
3-Cyano-2-[3-(2-methoxy-5-methyl-phenyl)-propanoylamino]-4,7-dihydro-5H-thieno[2,3-c]pyridine-6-carboxylic acid 2-(4-methyl-imidazol-1-yl)-ethyl ester,
3-Cyano-2-[(RS)-3-(3-methoxy-phenyl)-butanoylamino]-4,7-dihydro-5H-thieno[2,3-c]pyridine-6-carboxylic acid carboxymethyl ester,
3-Cyano-2-[(RS)-3-(3-ethoxy-phenyl)-butanoylamino]-4,7-dihydro-5H-thieno[2,3-c]pyridine-6-carboxylic acid carboxymethyl ester,
3-Cyano-2-[(RS)-3-(2-methoxy-phenyl)-butanoylamino]-4,7-dihydro-5H-thieno[2,3-c]pyridine-6-carboxylic acid carboxymethyl ester,
3-Cyano-2-[(RS)-3-(2-ethoxy-phenyl)-butanoylamino]-4,7-dihydro-5H-thieno[2,3-c]pyridine-6-carboxylic acid carboxymethyl ester,
3-Cyano-2-[3-(2-methoxy-phenyl)-propanoylamino]-4,7-dihydro-5H-thieno[2,3-c]pyridine-6-carboxylic acid carboxymethyl ester,
3-Cyano-2-[3-(2-ethoxy-phenyl)-propanoylamino]-4,7-dihydro-5H-thieno[2,3-c]pyridine-6-carboxylic acid carboxymethyl ester,
3-Cyano-2-[3-(2-methoxy-5-methyl-phenyl)-propanoylamino]-4,7-dihydro-5H-thieno[2,3-c]pyridine-6-carboxylic acid carboxymethyl ester,
3-Cyano-2-[(RS)-3-(2-methoxy-5-methyl-phenyl)-ropanoylamino]-4,7-dihydro-5H-thieno[2,3-c]pyridine-6-carboxylic acid carboxymethyl ester,
3-Cyano-2-[(RS)-3-(3-ethoxy-phenyl)-butanoylamino]-4,7-dihydro-5H-thieno[2,3-c]pyridine-6-carboxylic acid ethyl ester,
3-Cyano-2-[(RS)-3-(2-ethoxy-phenyl)-butanoylamino]-4,7-dihydro-5H-thieno[2,3-c]pyridine-6-carboxylic acid ethyl ester,
3-Cyano-2-[(RS)-3-(3-methoxy-phenyl)-butanoylamino]-4,7-dihydro-5H-thieno[2,3-c]pyridine-6-carboxylic acid 2,3-dihydroxy-propyl ester,
3-Cyano-2-[(RS)-3-(3-ethoxy-phenyl)-butanoylamino]-4,7-dihydro-5H-thieno[2,3-c]pyridine-6-carboxylic acid 2,3-dihydroxy-propyl ester,
3-Cyano-2-[(RS)-3-(2-methoxy-phenyl)-butanoylamino]-4,7-dihydro-5H-thieno[2,3-c]pyridine-6-carboxylic acid 2,3-dihydroxy-propyl ester, 3-Cyano-2-[(RS)-3-(2-ethoxy-phenyl)-butanoylamino]-4,7-dihydro-5H-thieno[2,3-c]pyridine-6-carboxylic acid 2,3-dihydroxy-propyl ester, 3-Cyano-2-[3-(3-methoxy-phenyl)-propanoylamino]-4,7-dihydro-5H-thieno[2,3-c]pyridine-6-carboxylic acid 2,3-dihydroxy-propyl ester, 3-Cyano-2-[3-(2-ethoxy-phenyl)-propanoylamino]-4,7-dihydro-5H-thieno[2,3-c]pyridine-6-carboxylic acid 2,3-dihydroxy-propyl ester, 3-Cyano-2-[(RS)-3-(3-methoxy-phenyl)-butanoylamino]-4,7-dihydro-5H-thieno[2,3-c]pyridine-6-carboxylic acid 2-hydroxy-ethyl ester, 3-Cyano-2-[(RS)-3-(3-ethoxy-phenyl)-butanoylamino]-4,7-dihydro-5H-thieno[2,3-c]pyridine-6-carboxylic acid 2-hydroxy-ethyl ester, 3-Cyano-2-[(RS)-3-(2-methoxy-phenyl)-butanoylamino]-4,7-dihydro-5H-thieno[2,3-c]pyridine-6-carboxylic acid 2-hydroxy-ethyl ester, 3-Cyano-2-[(RS)-3-(2-ethoxy-phenyl)-butanoylamino]-4,7-dihydro-5H-thieno[2,3-c]pyridine-6-carboxylic acid 2-hydroxy-ethyl ester, 3-Cyano-2-[(RS)-3-(2-methoxy-5-methyl-phenyl)-butanoylamino]-4,7-dihydro-5H-thieno[2,3-c]pyridine-6-carboxylic acid pyridin-4-ylmethyl ester, 3-Cyano-2-[(RS)-3-(2-methoxy-5-methyl-phenyl)-butanoylamino]-4,7-dihydro-5H-thieno[2,3-c]pyridine-6-carboxylic acid pyridin-3-ylmethyl ester, 3-Cyano-2-[(RS)-3-(2-methoxy-5-methyl-phenyl)-butanoylamino]-4,7-dihydro-5H-thieno[2,3-c]pyridine-6-carboxylic acid pyridin-2-ylmethyl ester, 3-Cyano-2-[(RS)-3-(2-methoxy-5-methyl-phenyl)-butanoylamino]-4,7-dihydro-5H-thieno[2,3-c]pyridine-6-carboxylic acid 2-pyridin-4-yl-ethyl ester, 3-Cyano-2-[(RS)-3-(2-methoxy-5-methyl-phenyl)-butanoylamino]-4,7-dihydro-5H-thieno[2,3-c]pyridine-6-carboxylic acid 2-pyridin-3-yl-ethyl ester, 3-Cyano-2-[(RS)-3-(2-methoxy-5-methyl-phenyl)-butanoylamino]-4,7-dihydro-5H-thieno[2,3-c]pyridine-6-carboxylic acid 2-pyridin-2-yl-ethyl ester, 3-Cyano-2-[(RS)-3-(2-methoxy-5-methyl-phenyl)-butanoylamino]-4,7-dihydro-5H-thieno[2,3-c]pyridine-6-carboxylic acid 1-methyl-1H-imidazol-2-ylmethyl ester, 3-Cyano-2-[(RS)-3-(2-methoxy-5-methyl-phenyl)-butanoylamino]-4,7-dihydro-5H-thieno[2,3-c]pyridine-6-carboxylic acid 3-methyl-3H-imidazol-4-ylmethyl ester, 3-Cyano-2-[(RS)-3-(2-methoxy-5-methyl-phenyl)-butanoylamino]-4,7-dihydro-5H-thieno[2,3-c]pyridine-6-carboxylic acid 2-imidazol-1-yl-ethyl ester, 3-Cyano-2-[(RS)-3-(2-methoxy-5-methyl-phenyl)-butanoylamino]-4,7-dihydro-5H-thieno[2,3-c]pyridine-6-carboxylic acid 2-(2-methyl-imidazol-1-yl)-ethyl ester, 3-Cyano-2-[(RS)-3-(2-methoxy-5-methyl-phenyl)-butanoylamino]-4,7-dihydro-5H-thieno[2,3-c]pyridine-6-carboxylic acid 2-(2,4-dimethyl-imidazol-1-yl)-ethyl ester, 3-Cyano-2-[(RS)-3-(2-methoxy-5-methyl-phenyl)-butanoylamino]-4,7-dihydro-5H-thieno[2,3-c]pyridine-6-carboxylic acid 2-(4-methyl-imidazol-1-yl)-ethyl ester, 3-Cyano-2-[(RS)-3-(2-methoxy-5-methyl-phenyl)-butanoylamino]-4,7-dihydro-5H-thieno[2,3-c]pyridine-6-carboxylic acid carboxymethyl ester, 3-Cyano-2-[(RS)-3-(2-methoxy-5-methyl-phenyl)-butanoylamino]-4,7-dihydro-5H-thieno[2,3-c]pyridine-6-carboxylic acid ethyl ester, 3-Cyano-2-[(RS)-3-(2-methoxy-5-methyl-phenyl)-butanoylamino]-4,7-dihydro-5H-thieno[2,3-c]pyridine-6-carboxylic acid 2,3-dihydroxy-propyl ester, 3-Cyano-2-[(RS)-3-(2-methoxy-5-methyl-phenyl)-butanoylamino]-4,7-dihydro-5H-thieno[2,3-c]pyridine-6-carboxylic acid 2-hydroxy-ethyl ester, 3-Cyano-2-[(RS)-3-(3-methoxy-phenyl)-butanoylamino]-4,7-dihydro-5H-thieno[2,3-c]pyridine-6-carboxylic acid methoxycarbonylmethyl ester, 3-Cyano-2-[(RS)-3-(3-ethoxy-phenyl)-butanoylamino]-4,7-dihydro-5H-thieno[2,3-c]pyridine-6-carboxylic acid methoxycarbonylmethyl ester, 3-Cyano-2-[(RS)-3-(2-methoxy-phenyl)-butanoylamino]-4,7-dihydro-5H-thieno[2,3-c]pyridine-6-carboxylic acid methoxycarbonylmethyl ester, 3-Cyano-2-[(RS)-3-(2-ethoxy-phenyl)-butanoylamino]-4,7-dihydro-5H-thieno[2,3-c]pyridine-6-carboxylic acid methoxycarbonylmethyl ester, 3-Cyano-2-[3-(2-methoxy-phenyl)-propanoylamino]-4,7-dihydro-5H-thieno[2,3-c]pyridine-6-carboxylic acid methoxycarbonyl methyl ester, 3-Cyano-2-[3-(2-ethoxy-phenyl)-propanoylamino]-4,7-dihydro-5H-thieno[2,3-c]pyridine-6-carboxylic acid methoxycarbonylmethyl ester, 3-Cyano-2-[3-(2-methoxy-5-methyl-phenyl)-propanoylamino]-4,7-dihydro-5H-thieno[2,3-c]pyridine-6-carboxylic acid methoxycarbonylmethyl ester, 3-Cyano-2-[(RS)-3-(2-methoxy-5-methyl-phenyl)-butanoylamino]-4,7-dihydro-5H-thieno[2,3-c]pyridine-6-carboxylic acid methoxycarbonylmethyl ester, 3-Cyano-2-[(RS)-3-(3-methoxy-phenyl)-butanoylamino]-4,7-dihydro-5H-thieno[2,3-c]pyridine-6-carboxylic acid 2,2-dimethyl-[1,3]dioxolan-4-ylmethyl ester, 3-Cyano-2-[(RS)-3-(3-ethoxy-phenyl)-butanoylamino]-4,7-dihydro-5H-thieno[2,3-c]pyridine-6-carboxylic acid 2,2-dimethyl-[1,3]dioxolan-4-ylmethyl ester, 3-Cyano-2-[(RS)-3-(2-methoxy-phenyl)-butanoylamino]-4,7-dihydro-5H-thieno[2,3-c]pyridine-6-carboxylic acid 2,2-dimethyl-[1,3]dioxolan-4-ylmethyl ester, 3-Cyano-2-[(RS)-3-(2-ethoxy-phenyl)-butanoylamino]-4,7-dihydro-5H-thieno[2,3-c]pyridine-6-carboxylic acid 2,2-dimethyl-[1,3]dioxolan-4-ylmethyl ester, 3-Cyano-2-[3-(3-methoxy-phenyl)-propanoylamino]-4,7-dihydro-5H-thieno[2,3-c]pyridine-6-carboxylic acid 2,2-dimethyl-[1,3]dioxolan-4-ylmethyl ester, 3-Cyano-2-[3-(2-ethoxy-phenyl)-propanoylamino]-4,7-dihydro-5H-thieno[2,3-c]pyridine-6-carboxylic acid 2,2-dimethyl-[1,3]dioxolan-4-ylmethyl ester, 3-Cyano-2-[(RS)-3-(3-methoxy-phenyl)-butanoylamino]-4,7-dihydro-5H-thieno[2,3-c]pyridine-6-carboxylic acid 2-acetoxy-ethyl ester, 3-Cyano-2-[(RS)-3-(3-ethoxy-phenyl)-butanoylamino]-4,7-dihydro-5H-thieno[2,3-c]pyridine-6-carboxylic acid 2-acetoxy-ethyl ester, 3-Cyano-2-[(RS)-3-(2-methoxy-phenyl)-butanoylamino]-4,7-dihydro-5H-thieno[2,3-c]pyridine-6-carboxylic acid 2-acetoxy-ethyl ester, 3-Cyano-2-[(RS)-3-(2-ethoxy-phenyl)-butanoylamino]-4,7-dihydro-5H-thieno[2,3-c]pyridine-6-carboxylic acid 2-acetoxy-ethyl esters 3-Cyano-2-[(RS)-3-(2-methoxy-5-methyl-phenyl)-butanoylamino]-4,7-dihydro-5H-thieno[2,3-c]pyridine-6-carboxylic acid 2,2-dimethyl-[1,3]dioxolan-4-ylmethyl ester, 3-Cyano-2-[(RS)-3-(2-methoxy-5-methyl-phenyl)-butanoylamino]-4,7-dihydro-5H-thieno[2,3-c]pyridine-6-carboxylic acid 2-acetoxy-ethyl ester,
and salts thereof.

12. A compound of formula Ic according to claim 2, which is from formula Ic*

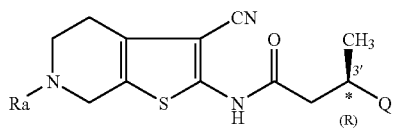

(Ic*)

or a salt thereof.

13. A compound of formula Ic according to claim 2, which is from formula Ic**

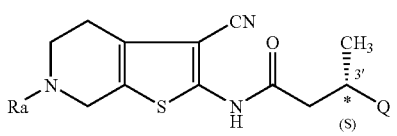

(Ic**)

or a salt thereof.

14. A pharmaceutical composition comprising one or more compounds according to claim 1 or a pharmaceutically acceptable salt thereof, together with a pharmaceutically acceptable excipient, diluent and/or carrier.

15. A combination comprising
a first active ingredient, which is at least one compound according to claim 1 or a pharmaceutically acceptable salt thereof, and
a second active ingredient, which is at least one anti-cancer agent selected from the group consisting of chemotherapeutic anti-cancer agents and target-specific anti-cancer agents,
for separate, sequential, simultaneous, concurrent or chronologically staggered use in therapy.

16. The combination or method according to claim 15, in which said chemotherapeutic anti-cancer agent is selected from the group consisting of (i) alkylating/carbamylating agents; (ii)platinum derivatives(iii)antimitotic agents/tubulin inhibitors; (iv)topoisomerase inhibitors; (v) pyrimidine antagonists; (vi) purin antagonists; and (vii) folic acid antagonists.

17. The combination according to claim 15, in which said target-specific anti-cancer agent is selected from the group consisting of (i) kinase inhibitors; (ii) proteasome inhibitors; (iii) histone deacetylase inhibitors; (iv) heat shock protein 90 inhibitors; (v) vascular targeting agents (VAT), anti-angiogenic drugs or KDR tyrosine kinase inhibitors; (vi) monoclonal antibodies as well as mutants and conjugates of monoclonal antibodies and antibody fragments; (vii) oligonucleotide based therapeutics; (viii) Toll-like receptor/TLR 9 agonists, TLR 7 agonists and analogues thereof, or TLR 7/8 agonists as well as immunostimulatory RNA as TLR 7/8 agonists; (ix) protease inhibitors; (x) hormonal therapeutics; (xi)
bleomycin; (xi) retinoids; (xiii) DNA methyltransferase inhibitors; (xiv) alanosine; (xv) cytokines; (xvi) interferons; and (xvii) death receptor agonists.

* * * * *

UNITED STATES PATENT AND TRADEMARK OFFICE
CERTIFICATE OF CORRECTION

PATENT NO. : 7,741,488 B2
APPLICATION NO. : 11/883624
DATED : June 22, 2010
INVENTOR(S) : Pekari et al.

Page 1 of 1

It is certified that error appears in the above-identified patent and that said Letters Patent is hereby corrected as shown below:

On the first page under (75) Inventors –

Line 2 reads "Schmidt, Constance (DE); Thomas Bär,"
should read --Schmidt, Konstance (DE); Thomas Bär,--.

Line 4 reads "Constance (DE); Bjorn Bartels,"
should read --Konstance (DE), Bjorn Bartels,--.

Column 135, line 21 reads "Har is bonded via a ring carbon or a ring nitrogen atom of
should read --Har is bonded via a ring carbon or a ring carbon atom of--.

Column 136, line 1 reads "2. A compound according to claim 1, which is from any one"
should read --2. A compound according to claim 1, which is a compound of one--.

Column 139, line 23 reads "R8 is 1-40-alkyl,"
should read --R8 is 1-4C-alkyl--.

Column 143, line 51 reads "dihydro-5H-thieno[2,3-c]pyridine$^{-6-}$carboxylic acid"
should read --dihydro-5H-thieno[2,3-c]pyridine-6-carboxylic acid--.

Column 149, line 21 reads "2-(2-methyl-imidazol-1-yl)-ethyl esters"
Should read --2-(2-methyl-imidazol-1-yl)-ethyl ester,--.

Signed and Sealed this
Fourteenth Day of June, 2011

David J. Kappos
*Director of the United States Patent and Trademark Office*